(12) United States Patent
Bertelsen et al.

(10) Patent No.: US 11,129,882 B2
(45) Date of Patent: Sep. 28, 2021

(54) VIRUS LIKE PARTICLE WITH EFFICIENT EPITOPE DISPLAY

(71) Applicant: University of Copenhagen, Copenhagen (DK)

(72) Inventors: Adam Frederik Sander Bertelsen, Dragør (DK); Ali Salanti, Farum (DK); Thor Theander, Greve (DK); Susan Thrane, København N (DK); Christoph Mikkel Janitzek, København S (DK); Mette Ørskov, Agerbaek (DK); Morten Agertoug Nielsen, Birkerød (DK)

(73) Assignee: University of Copenhagen, Copenhagen K (DK)

( * ) Notice: Subject to any disclaimer, the term of this patent is extended or adjusted under 35 U.S.C. 154(b) by 340 days.

(21) Appl. No.: 15/772,186

(22) PCT Filed: Oct. 28, 2016

(86) PCT No.: PCT/DK2016/050342
§ 371 (c)(1),
(2) Date: Apr. 30, 2018

(87) PCT Pub. No.: WO2017/071713
PCT Pub. Date: May 4, 2017

(65) Prior Publication Data
US 2019/0022206 A1   Jan. 24, 2019
US 2020/0171138 A9   Jun. 4, 2020

(30) Foreign Application Priority Data

Oct. 30, 2015  (DK) .............................. PA201570699

(51) Int. Cl.
| | |
|---|---|
| *A61K 39/00* | (2006.01) |
| *A61K 39/015* | (2006.01) |
| *C12N 7/00* | (2006.01) |
| *A61K 39/02* | (2006.01) |

(52) U.S. Cl.
CPC ...... *A61K 39/0011* (2013.01); *A61K 39/0005* (2013.01); *A61K 39/0012* (2013.01); *A61K 39/00115* (2018.08); *A61K 39/001106* (2018.08); *A61K 39/015* (2013.01); *A61K 39/0208* (2013.01); *C12N 7/00* (2013.01); *A61K 2039/5258* (2013.01); *A61K 2039/55505* (2013.01); *A61K 2039/6075* (2013.01); *A61K 2039/625* (2013.01); *C12N 2710/20022* (2013.01); *C12N 2710/20023* (2013.01)

(58) Field of Classification Search
None
See application file for complete search history.

(56) References Cited

U.S. PATENT DOCUMENTS

| | | | |
|---|---|---|---|
| 7,094,409 B2 | 8/2006 | Bachmann et al. | |
| 7,115,266 B2 | 10/2006 | Bachmann | |
| 7,128,911 B2 | 10/2006 | Bachmann et al. | |
| 7,666,408 B2 | 2/2010 | Bachmann | |
| 7,785,873 B2 | 8/2010 | Bachmann et al. | |
| 7,959,928 B2 | 6/2011 | Bachmann et al. | |
| 8,586,708 B2 * | 11/2013 | Ting ..................... | C07K 14/36 530/350 |
| 2009/0155302 A1 | 6/2009 | Bachmann et al. | |
| 2011/0081371 A1 | 4/2011 | Bachmann | |
| 2018/0125954 A1 | 5/2018 | Pedersen et al. | |

FOREIGN PATENT DOCUMENTS

| | | |
|---|---|---|
| EP | 1367166 A1 | 12/2003 |
| EP | 2090319 A2 | 8/2009 |
| EP | 2534484 A1 | 12/2012 |
| GB | 2535753 A | 8/2016 |
| WO | WO-2000/023955 A1 | 4/2000 |
| WO | WO-2002/074243 A2 | 9/2002 |
| WO | WO-2003/024480 A2 | 3/2003 |
| WO | WO-2003/024481 A2 | 3/2003 |
| WO | WO-2003/031466 A2 | 4/2003 |
| WO | WO-2003/039225 A2 | 5/2003 |
| WO | WO-2003/040164 A2 | 5/2003 |
| WO | WO-2003/059386 A2 | 7/2003 |
| WO | WO-2004/007538 A2 | 1/2004 |
| WO | WO-2004/009124 A2 | 1/2004 |
| WO | WO-2004/016282 A1 | 2/2004 |
| WO | WO-2004/084939 A2 | 10/2004 |
| WO | WO-2005/004907 A1 | 1/2005 |
| WO | WO-2005/042695 A2 | 5/2005 |
| WO | WO-2005/068639 A2 | 7/2005 |
| WO | WO-2005/108425 A1 | 11/2005 |
| WO | WO-2005/117963 A1 | 12/2005 |

(Continued)

OTHER PUBLICATIONS

Fairhead et al (Methods. Mol. Biol., 1266:171-184, Jul. 2015).*
Baker et al., Protein Structure Predication and Structural Genomics, Science, 294(5540): 93-96, Oct. 5, 2001.
Attwood, T., The Babel of Bioinformatics, Science, 290(5491): 471-473, Oct. 27, 2000.
GenBank AFD50637.1, 2012.
Asai et al., A human biotin acceptor domain allows site-specific conjugation of an enzyme to an antibody-avidin fusion protein for targeted drug delivery, Biomolecular Engineering 21(6) 1-11, Feb. 1, 2005.

(Continued)

*Primary Examiner* — Brian Gangle
(74) *Attorney, Agent, or Firm* — Julie K. Staple; Dinsmore & Shohl LLP

(57) ABSTRACT

The invention relates to a virus like particle (VLP) based vaccine. The virus-like particle constitutes a non-naturally occurring, ordered and repetitive antigen array display scaffold which can obtain a strong and long-lasting immune response in a subject. The VLP based vaccine may be used for the prophylaxis and/or treatment of a disease including, but is not limited to, cancer, cardiovascular, infectious, asthma, and/or allergy diseases/disorders.

15 Claims, 22 Drawing Sheets

Specification includes a Sequence Listing.

(56) References Cited

FOREIGN PATENT DOCUMENTS

| WO | WO-2005/117983 A2 | 12/2005 |
|---|---|---|
| WO | WO-2006/027300 A2 | 3/2006 |
| WO | WO-2006/032674 A1 | 3/2006 |
| WO | WO-2006/037787 A2 | 4/2006 |
| WO | WO-2006/045796 A2 | 5/2006 |
| WO | WO-2006/045849 A1 | 5/2006 |
| WO | WO-2006/063974 A2 | 6/2006 |
| WO | WO-2006/097530 A2 | 9/2006 |
| WO | WO-2006/134125 A1 | 12/2006 |
| WO | WO-2007/038145 A2 | 4/2007 |
| WO | WO-2007/039552 A1 | 4/2007 |
| WO | WO-2007/067681 A2 | 6/2007 |
| WO | WO-2007/067682 A2 | 6/2007 |
| WO | WO-2007/067683 A2 | 6/2007 |
| WO | WO-2008/024427 A2 | 2/2008 |
| WO | WO-2008/074895 A1 | 6/2008 |
| WO | WO-2008/115631 A2 | 9/2008 |
| WO | WO-2009/080823 A2 | 7/2009 |
| WO | WO-2009/109643 A2 | 9/2009 |
| WO | WO-2009/130261 A1 | 10/2009 |
| WO | WO-2010/012069 A1 | 2/2010 |
| WO | WO-2010/120266 A1 | 10/2010 |
| WO | WO-2010/149752 A2 | 12/2010 |
| WO | WO-2011/082381 A2 | 7/2011 |
| WO | WO-2011/098772 A1 | 8/2011 |
| WO | WO-2011/116226 A2 | 9/2011 |
| WO | WO-2012/033911 A2 | 3/2012 |
| WO | WO-2012/048430 A1 | 4/2012 |
| WO | WO-2012/127060 A1 | 9/2012 |
| WO | WO-2012/142113 A2 | 10/2012 |
| WO | WO-2013/003353 A2 | 1/2013 |
| WO | WO-2014/023947 A1 | 2/2014 |
| WO | WO-2014/088928 A1 | 6/2014 |
| WO | WO-2014/110006 A1 | 7/2014 |
| WO | WO-2014/116730 A2 | 7/2014 |
| WO | WO-2015/004158 A1 | 1/2015 |
| WO | WO-2016/135291 A1 | 9/2016 |
| WO | WO-2016/193746 A1 | 12/2016 |

OTHER PUBLICATIONS

Chen et al., Phage Display Evolution of a Peptide Substrate for Yeast Biotin Ligase and Application to Two-Color Quantum Dot Labeling of Cell Surface Proteins, J. Am. Chem. Soc., 129: 6619-6625, May 2, 2007.

Chen et al., Structure of Small Virus-like Particles Assembled from the L1 Protein of Human Papillomavirus 16, Molecular Cell 5: 557-567, Mar. 2000.

Leneghan et al., Nanoassembly routes stimulate conflicting antibody quantity and quality for transmission-blocking malaria vaccines, Scientific Reports, 7: 3811, pp. 1-14, Jun. 18, 2017.

Tang, S. et al., A Modular Vaccine Development Platform Based on Sortase-Mediated Site-Specific Tagging of Antigens onto Virus-Like Particles, *Scientific Reports*, 6:25741, May 12, 2016.

Dintzis, H. et al., Molecular determinants of immunognicity: The immunon model of immune response, Proc. Natl. Acad. Sci., 73(10): 3671-3675, Oct. 1976.

Tegerstedt, K. et al., A Single Vaccination with Polyomavirus VP1/VP2Her2 Virus-Like Particles Prevents Outgrowth of HER-2 /neu-Expressing Tumors, Cancer Research, 65 (13): 5953-5957, Jul. 1, 2005.

NP_085472.1, coat protein [Acinetobacter phage AP205], Apr. 17, 2009.

Amelung, S. et al., The FbaB-type fibronectin binding protein of *Streptococcus pyogenes* promotes specific invasion into endothelial cell, Cellular Microbiology, 13(8): 1200-1211, 2011.

Andreasson et al., Murine pneumotropic virus chimeric Her2/neu virus-like particles as prophylactic and therapeutic vaccines against Her2/neu expressing tumor, Int. J. Cancer, 124: 150-156, 2009.

Bachmann et al, Therapeutic vaccines for chronic diseases: successes and technical challenges, Phil. Trans. R. Soc. B, 366: 2815-2822, 2011.

Bachmann, M. et al., Neutralizing antiviral B cell responses, Annual Review of Immunology, 15: 235-270, 1997.

Bachmann, M. et al., Virus-like particles: combining innate and adaptive immunity for effective vaccination. In: Kaufmann, P.D.S. H.E. (Ed.),Novel Vaccination Strategies. Wiley-VCH Verlag GmbH & Co, pp. 415-432, 2004.

Bachmann, M. et al., Vaccine delivery: a matter of size, geometry, kinetics and molecular patterns, Nat Rev Immunol, 10(11): 787-796, 2010.

Bachmann, M. et al., The influence of antigen organization on B cell responsiveness, Science, 262(5138): 1448-1451, 1993.

Baneyx; F. et al., Recombinant protein folding and misfolding in *Escherchina coli;* Nature Biotechnology; 22(11):1399-1408, Nov. 2004.

Bian et al., Human papillomavirus type 16 L1E7 chimeric capsomeres have prophylactic and therapeutic efficacy against papillomavirus in mice, Mol Cancer Ther,7(5): 1329-1335, May 2008.

Bishop, B. et al., Crystal Structures of Four Types of Human Papillomavirus L1 Capsid Proteins, J Biol Chem, 282(43): 31803-31811, 2007.

Brown et al., RNA Bacteriophage Capsid-Mediated Drug Delivery and Epitope Presentation, Intervirology 45: 371-380, 2002.

Brune et al., Plug-and-Display: decoration of virus-like particles via isopeptide bonds for modular immunization, Scientific Reports, 6: 19234, Jan. 19, 2016.

Buck, C. et al., Production of Papillomavirus-Based Gene Transfer Vectors, Current Protocols in Cell Biology: 26.1.1-26.1.19, Dec. 2007.

Budzik, J. et al., Intramolecular amide bonds stabilize pili on the surface of bacilli. PNAS USA, 106(47): 19992-19997, 2009.

Chackerian, B., Virus-like particles: flexible platforms for vaccine development, Expert Review of Vaccines 6(3), 381-390. 2007.

Chackerian, B. et al., Determinants of Autoantibody Induction by Conjugated Papillomavirus Virus-Like Particles, J. Immunol, 129: 6120-6126, 2002.

Chackerian, B. et al., Conjugation of a self-antigen to papillomavirus-like particles allows for efficient induction of protective autoantibodies, Journal of Clinical Investigation, 108(3): 415-423, 2001.

Chackerian, B. et al., Virus-Like Display of a Neo-Self Antigen Reverses B Cell Anergy in a B Cell Receptor Transgenic Mouse Model, Journal of immunology, 180(9): 5816-5825, 2008.

Chackerian, B. et al., Induction of autoantibodies to mouse CCR5 with recombinant papillomarivus particles, PNAS, 96(5):2373-2378, 1999.

Cielens, I. et al., Mosaic RNA Phage VLPs Carrying Domain III of the West Nile Virus E Protein, Molecular Biotechnology, 56: 459-469, 2014.

Dias et al., Optimization and Validation of a Multiplexed Luminex Assay to Quantify Antibodies to Neutralizing Epitopes on Human Papillomaviruses 6, 11, 16, and 18, Clinical and Diagnostic Laboratory Immunology, pp. 959-969, Aug. 2005.

Dorn et al., Cellular and Humoral Immunogenicity of Hamster Polyomavirus-Derived Virus-Like Particles Harboring a Mucin 1 Cytotoxic T-Cell Epitope, Viral Immunology, 21(1): 12-26, 2008.

El Mortaji, L. et al., Stability and Assembly of Pilus Subunits of *Streptococcus pneumoniae*\*?, J. Biol. Chem., 285(16): 12405-12415, 2010.

Fairhead, M. et al., SpyAvidin Hubs Enable Precise and Ultrastable Orthogonal Nanoassembly, Journal of American Chemical Society, pp. 12355-12363, Aug. 11, 2014.

Fierer, J. et al., SpyLigase peptide-peptide ligation polymerizes affibodies to enhance magnetic cancer cell capture, PNAS, E1176-1181, Mar. 17, 2014.

Forsgren, N. et al., Two intramolecular isopeptide bonds are identified in the crystal structure of the treptococcus gordonii SSpB C-terminal domain, J Mol Biol, 397(3): 740-751, 2010.

GenBank: AAO18082.1, v-erb-b2 erythroblastic leukemia viral oncogene homolog 2, neuro/glioblastoma derived oncogene homolog (avian) [*Homo sapiens*], Jan. 12, 2013.

Grgacic, E. et al., Virus-like particles: Passport to immune recognition, Particle-based Vaccines, Methods, 40(1): 60-65. 2006.

(56) References Cited

OTHER PUBLICATIONS

Izoré, T. et al., Structural Basis of Host Cell Recognition by the Pilus Adhesin from *Streptococcus neumoniae,* Structure, 18: 106-115, 2010.

Jegerlehner et al, A molecular assembly system that renders antigens of choice highly repetitive for induction of protective B cell responses, Vaccine, pp. 3104-3112, 2002.

Jennings, The coming of age of virus-like particle vaccines, Biol. Chem., 389: 521-536, May 2008.

Kang, H. et al., Stabilizing Isopeptide Bonds Revealed in Gram-Positive Bacterial Pilus Structure, Science, 318: 1625, 2007.

Kang, H. et al., The Corynebacterium diphtheriae shaft pilin SpaA is built of tandem Ig-like modules with stabilizing isopeptide and disulfide bonds, PNAS USA, 106(40): 16967-16971, 2009.

Khan et al., Head-to-Head comparison of soluble vs. QβVLP circumsporozoite protein vaccines reveals selective enhancement of NANP repeat responses, PLOS ONE, 10(11), Nov. 16, 2015.

Kouskoff, V. et al. T Cell-Independent Rescue of B Lymphocytes from Peripheral Immune Tolerance, Science, 287(5462): 2501-2503, 2000.

Li, L. et al., Structural Analysis and Optimization of the Covalent Association between SpyCatcher and a Peptide Tag, J Mol Biol, 426(2): 309-317, 2014.

Liu, Z. et al., A novel method for synthetic vaccine construction based on protein assembly, Scientific Reports, 4: 7266, Dec. 1, 2014.

Liu et al., Polynucleotide viral vaccines: codon optimisation and ubiquitin conjugation enhances prophylactic and therapeutic efficacy, Vaccine 20: 862-869, 2002.

Lv et al., Development of a 2-Plex Luminex-Based Competitive Immunoassay to Quantify Neutralizing Antibodies Induced by Virus-Like Particles for Human Papillomavirus 16 and 18, Journal of Biomedicine and Biotechnology, Article ID 272806, 2011.

Massa, et al., Antitumor Activity of DNA Vaccines Based on the Human Papillomavirus-16 E7 Protein Genetically Fused to a Plant Virus Coat Protein, Human Gene Therapy 19:364-364, Apr. 2008.

Meyer, D et al., Reduced antibody response to streptavidin through site-directed mutagenesis, Protein Science, 10: 491-503, 2001.

Moyle et al., Toward the Development of Prophylactic and Therapeutic Human Papillomavirus Type-16 Lipopeptide Vaccines, J. Med. Chem., 50: 4721-4727, 2007.

Murray, K., Application of recombinant DNA techniques in the development of viral vaccines, Vaccine, 6:164-74, 1988.

Nurkkala et al., Conjugation of HPV16 E7 to cholera toxin enhances the HPV-specific T-cell recall responses to pulsed dendritic cells in vitro in women with cervical dysplasia, Vaccine, 28, 5828-5836, 2010.

Nylander, A. et al,, Structure of the C-terminal domain of the surface antigen SpaP from the caries pathogen *Streptococcus mutans,* Acta Crystallogr Sect F Struct Biol Cryst Commum., F67, 23-26, 2011.

Oke, M. et al., The Scottish Structural Proteomics Facility: targets, methods and outputs, J Struct Funct Geonomics 11: 167-180, 2010.

Palladini, A. et al., Virus-like particle display of HER2 induces potent anti-cancer responses, Oncoimmunology, 7(3), e1408749, 2018.

Patel et al., Surface Functionalization of Virus-Like Particles by Direct Conjugation Using Azide-Alkyne Click Chemistry, Bioconjugate Chemistry, 22(3): 376-387, Mar. 1, 2011.

Paz De La Rosa et al.. An HPV 16 L1-based chimeric human papilloma virus-like particles containing a string of epitopes produced in plants is able to elicit humoral and cytotoxic T-cell activity in mice, Virology Journal, 6:2, 2009.

Peabody, D. et al., Immunogenic Display of Diverse Peptides on Virus-Like Particles of RNA Phage MS2, Journal of Molecular Biology, 380(1): 252-263, 2008.

Peacey et al., Versatile RHDV Virus-Like Particles: Incorporation of Antigens by Genetic Modification and Chemical Conjugation, Biotechnology and Bioengineering, 98(5), 968-977, 2007.

Pejawar-Gaddy et al., Generation of a Tumor Vaccine Candidate Based on Conjugation of a MUC1 Peptide to Polyionic Papillomavirus Virus-Like Particles (VLPs), Cancer Immunol Immunother.; 59(11): 1685-1696, Nov. 2010.

Peng et al., Construction and Production of Flourescent Papillomavirus-like Particles, Journal of Tongji Medical University, 19(3): 170-174, 1999.

Plotkin, S., Vaccines: Past, Present And Future, Nat Med. Supplement, 11(4), pp. S5-S11, Apr. 5, 2005.

Pointon, J. et al., A Highly Unusual Thioester Bond in a Pilus Adhesin Is Required for Efficient Host Cell Interaction, J Bio Chem, 285(44): 33858-33866, 2010.

Powilleit et al., Exploiting the Yeast L-A Viral Capsid for the In Vivo Assembly of Chimeric VLPs as Platform in Vaccine Development and Foreign Protein Expression, PLoS ONE, 2(5):e415, May 2, 2007.

Pumpens, P. et al., HBV Core Particles as a Carrier for B Cell/T Cell Epitopes, Intervirology, 44(2-3): 98-114. 2001.

Pushko, P. et al., Analysis of RNA phage fr coat protein assembly by insertion, deletion and substitution mutagenesis, Protein Eng., 6(8): 883-891, 1993.

Raja, K. et al., Icosahedral Virus Particles as Polyvalent Carbohydrate Display Platforms, ChemBioChem 4(12): 1348-1351. 2003.

Schiller, J. et al., Why HIV Virions Have Low Numbers of Envelope Spikes: Implications for Vaccine Development, PLOS Pathogens, 10(8): e1004254, 2014.

Schwarz-Linek, U. et al., Yet more intramolecular cross-links in Gram-positive surface proteins, PNAS, 11(4): 1229-1230, 2014.

Shishovs, M. et al., Structure of AP205 Coat Protein Reveals Circular Permutation in ssRNA Bacteriophages, J Mol Biol, 428(21): 4267-4279, 2016.

Smith, M. et al., Reengineering viruses and virus-like particles through chemical functionalization strategies; Current Opinion in Biology, 24: 629-626, 2003.

Smith et al., Modified Tobacco mosaic virus particles as scaffolds for display of antigens for vaccine applications, Virology, 348: 475-488, 2006.

Staszczak, M. An in vitro method for selective detection of free monomeric ubiquitin by using a C-terminally biotinylated form of ubiquitin, International Journal of Biochemistry and Cell Biology, 39(2): pp. 319-326, Dec. 8, 2016.

Sun, W. et al., Non-covalent ligand conjugation to biotinylated DNA nanoparticles using TAT pettide genetically fused to monovalent streptavidin; Journal of Drug Targeting, 400A: 251-245, Jan. 1, 1997.

Thrane, S. et al., A Novel Virus-Like Particle Based Vaccine Platform Displaying the Placental Malaria Antigen VAR2CSA, PLOS ONE, 10(11), Nov. 9, 2015.

Tissot, A. et al, Versatile Virus-Like Particle Carrier for Epitope Based Vaccines, Ho PL, ed, PLoS ONE, 5(3): e9809, Mar. 23, 2010.

Veggiani et al., Superglue from bacteria: unbreakable bridges for protein nanotechnology, Trends in Biotechnology, Elsevier Publications, Cambridge, GB. 32(10): 506-512. Aug. 26, 2014.

Zakeri, B., Peptide targeting by spontaneous isopeptide bond formation, Thesis, Department of Biochemistry and St. Peters College, University of Oxford, 2011.

Zakeri, B. et al., Spontaneous intermolecular amide bond formation between side chains for irreversible peptide targeting, J. Am. Chem. Soc., 132(13): 4526-4527, 2010.

Zakeri, B. et al., Peptide tag forming a rapid covalent bond to a protein through engineering a bacerterial adhesion, Proceedings of the National Academy of Sciences, 109(2): E690-E697, 2012.

Zom et al., TLR Ligand-Peptide Conjugate Vaccines: Toward Clinical Application, Advances in Immunology, 114(7): 177-201, 2012.

Andersson, A. et al., SnoopLigase peptide-peptide conjugation enables modular vaccine assembly, Sci Rep., 9(1):4625, Mar. 15, 2019.

Baker, E. et al., Self-generated covalent cross-links in the cell-surface adhesins of Gram-positive bacteria, Biochem Soc Trans., 43(5):787-94, Oct. 2015.

(56) References Cited

OTHER PUBLICATIONS

Brune, K. et al., New Routes and Opportunities for Modular Construction of Particulate Vaccines: Stick, Click, and Glue, Front, Immunology, 9:1432, 2018.

Bruun, T. et al., Engineering a Rugged Nanoscaffold To Enhance Plug-and-Display Vaccination, ACS Nano., 12(9):8855-8866, Sep. 25, 2018, Epub Jul. 26, 2018.

Gomes, A. et al., Harnessing Nanoparticles for Immunomodulation and Vaccines, Vaccines, 5, 6, Feb. 14, 2017; doi:10.3390/vaccines5010006.

Hatlem, D. et al., Catchin a SPY: Using the SpyCatcher-SpyTag and Related Systems for Labeling and Localizing Bacterial Proteins, Int. J. Mol. Sci., 20: 2129, 2019.

Keeble, A. et al., Evolving Accelerated Amidation by SpyTag/SpyCatcher to Analyze Membrane Dynamics, Angew Chem Int Ed Engl., 56(52):16521-16525, Dec. 22, 2017, Epub Dec. 5, 2017.

Keeble, A. et al., Insider information on successful covalent protein coupling with help from SpyBank, Methods Enzymol., 617:443-461, Epub Jan. 25, 2019.

Ma, W. et al., Modular assembly of proteins on nanoparticles, Nat Commun., 9(1):1489, Apr. 16, 2018.

Pröschel, M. et al., Probing the potential of CnaB-type domains for the design of tag/catcher systems, PLoS One, 12(6):e0179740, Jun. 27, 2017.

Schoene, C. et el., SpyRing interrogation; analyzing how enzyme resilience can be achieved with phytase and distinct cyclization chemistries, Sci Rep., 6:21151, Feb. 10, 2016.

Siegmund, V. et al., Spontaneous isopeptide bond formation as a powerful tool for engineering site-specific antibody-drug conjugates, Scientific Reports, 6(39291), Dec. 16, 2016.

Siegmund, V. et al., SpyLigase-Catalyzed Modification of Antibodies, Methods Mol. Biol., 2012:171-192, 2019.

Tan, L. et al., Kinetic Controlled Tag-Catcher Interactions for Directed Covalent Protein Assembly, PLoS One, 11(10):e0165074, Oct. 26, 2016.

Thrane, S. et al., Bacterial superglue enables easy development of efficient virus-like particle based vaccines, Journal of Nanobiotechnology, 14:30: 1-16, 2016.

Veggiani, G., et al., Programmable polyproteams built using twin peptide superglues, Proc Natl Acad Sci. U S A., 113(5)1202-1207, Feb. 2, 2016, Epub Jan. 19, 2016.

Wu, X.. et al., An Intrinsically Disordered Peptide-Peptide Stapler for Highly Efficient Protein Ligation Both in Vivo and in Vitro, J. Am. Chem. Soc., 140; 17474-17483, 2018.

Young, P., et al., Harnessing ester bond chemistry for protein ligation, Chem. Commun., 53: 1502-1505, 2017.

Zlotnick, A., To Build a Virus Capsid; An Equilibrium Model of the Self Assembly of Polyhedral Protein Complexes, J. Mol. Biol., 241, 59-67, 1994.

* cited by examiner a

SEQUENCE LISTING

```
<160> NUMBER OF SEQ ID NOS: 53

<210> SEQ ID NO 1
<211> LENGTH: 525
<212> TYPE: PRT
<213> ORGANISM: Human papillomavirus type 16

<400> SEQUENCE: 1

Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
                20                  25                  30

Ile Tyr Tyr His Ala Gly Thr Ser Arg Leu Leu Ala Val Gly His Pro
            35                  40                  45

Tyr Phe Pro Ile Lys Lys Pro Asn Asn Asn Lys Ile Leu Val Pro Lys
    50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Tyr Ala Ala Asn Ala Gly Val Asp Asn Arg
    130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190
```

```
Thr Val Ile Gln Asp Gly Asp Met Val Asp Thr Gly Phe Gly Ala Met
            195                 200                 205

Asp Phe Thr Thr Leu Gln Ala Asn Lys Ser Glu Val Pro Leu Asp Ile
210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Ala Val Gly Glu Asn Val Pro
            260                 265                 270

Asp Asp Leu Tyr Ile Lys Gly Ser Gly Ser Thr Ala Asn Leu Ala Ser
            275                 280                 285

Ser Asn Tyr Phe Pro Thr Pro Ser Gly Ser Met Val Thr Ser Asp Ala
290                 295                 300

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Ser Leu Cys Ala Ala Ile Ser Thr Ser Glu
            340                 345                 350

Thr Thr Tyr Lys Asn Thr Asn Phe Lys Glu Tyr Leu Arg His Gly Glu
            355                 360                 365

Glu Tyr Asp Leu Gln Phe Ile Phe Gln Leu Cys Lys Ile Thr Leu Thr
370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Pro Gly Gly Thr Leu Glu Asp
                405                 410                 415

Thr Tyr Arg Phe Val Thr Ser Gln Ala Ile Ala Cys Gln Lys His Gly
            420                 425                 430

Leu Asn Asp Ile Phe Glu Ala Gln Lys Ile Glu Trp His Glu Thr Pro
            435                 440                 445

Pro Ala Pro Lys Glu Asp Pro Leu Lys Lys Tyr Thr Phe Trp Glu Val
450                 455                 460

Asn Leu Lys Glu Lys Phe Ser Ala Asp Leu Asp Gln Phe Pro Leu Gly
465                 470                 475                 480

Arg Lys Phe Leu Leu Gln Ala Gly Leu Lys Ala Lys Pro Lys Phe Thr
                485                 490                 495

Leu Gly Lys Arg Lys Ala Thr Pro Thr Thr Ser Ser Thr Ser Thr Thr
            500                 505                 510

Ala Lys Arg Lys Lys Arg Lys Leu Glu Leu Ser Gly Arg
            515                 520                 525

<210> SEQ ID NO 2
<211> LENGTH: 528
<212> TYPE: PRT
<213> ORGANISM: Human papillomavirus type 16
<220> FEATURE:
<221> NAME/KEY: misc_feature
<222> LOCATION: (280)..(281)
<223> OTHER INFORMATION: Xaa can be any naturally occurring amino acid
<220> FEATURE:
<221> NAME/KEY: misc_feature
<222> LOCATION: (285)..(286)
<223> OTHER INFORMATION: Xaa can be any naturally occurring amino acid
<220> FEATURE:
<221> NAME/KEY: misc_feature
```

<222> LOCATION: (288)..(288)
<223> OTHER INFORMATION: Xaa can be any naturally occurring amino acid

<400> SEQUENCE: 2

```
Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
            20                  25                  30

Ile Tyr Tyr His Ala Gly Thr Ser Arg Leu Leu Ala Val Gly His Pro
        35                  40                  45

Tyr Phe Pro Ile Lys Lys Pro Asn Asn Asn Lys Ile Leu Val Pro Lys
    50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Tyr Ala Ala Asn Ala Gly Val Asp Asn Arg
    130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
        195                 200                 205

Asp Phe Thr Thr Leu Gln Ala Asn Lys Ser Glu Val Pro Leu Asp Ile
    210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Ala Val Gly Glu Asn Val Pro
            260                 265                 270

Asp Asp Leu Tyr Ile Lys Gly Xaa Xaa Trp Ile Tyr Xaa Xaa Gln Xaa
        275                 280                 285

Leu Ala Ser Ser Asn Tyr Phe Pro Thr Pro Ser Gly Ser Met Val Thr
    290                 295                 300

Ser Asp Ala Gln Ile Phe Asn Lys Pro Tyr Trp Leu Gln Arg Ala Gln
305                 310                 315                 320

Gly His Asn Asn Gly Ile Cys Trp Gly Asn Gln Leu Phe Val Thr Val
                325                 330                 335

Val Asp Thr Thr Arg Ser Thr Asn Met Ser Leu Cys Ala Ala Ile Ser
            340                 345                 350

Thr Ser Gly Leu Asn Asp Ile Phe Glu Ala Gln Lys Ile Glu Trp His
        355                 360                 365

Glu Glu Thr Thr Tyr Lys Asn Thr Asn Phe Lys Glu Tyr Leu Arg His
    370                 375                 380

Gly Glu Glu Tyr Asp Leu Gln Phe Ile Phe Gln Leu Cys Lys Ile Thr
385                 390                 395                 400
```

Leu Thr Ala Asp Val Met Thr Tyr Ile His Ser Met Asn Ser Thr Ile
            405                 410                 415

Leu Glu Asp Trp Asn Phe Gly Leu Gln Pro Pro Gly Gly Thr Leu
        420                 425                 430

Glu Asp Thr Tyr Arg Phe Val Thr Ser Gln Ala Ile Ala Cys Gln Lys
            435                 440                 445

His Thr Pro Pro Ala Pro Lys Glu Asp Pro Leu Lys Lys Tyr Thr Phe
        450                 455                 460

Trp Glu Val Asn Leu Lys Glu Lys Phe Ser Ala Asp Leu Asp Gln Phe
465                 470                 475                 480

Pro Leu Gly Arg Lys Phe Leu Leu Gln Ala Gly Leu Lys Ala Lys Pro
            485                 490                 495

Lys Phe Thr Leu Gly Lys Arg Lys Ala Thr Pro Thr Thr Ser Ser Thr
            500                 505                 510

Ser Thr Thr Ala Lys Arg Lys Lys Arg Lys Leu Glu Leu Ser Gly Arg
            515                 520                 525

<210> SEQ ID NO 3
<211> LENGTH: 518
<212> TYPE: PRT
<213> ORGANISM: Human papillomavirus type 16

<400> SEQUENCE: 3

Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
            20                  25                  30

Ile Tyr Tyr His Ala Gly Thr Ser Arg Leu Leu Ala Val Gly His Pro
        35                  40                  45

Tyr Phe Pro Ile Lys Lys Pro Asn Asn Asn Lys Ile Leu Val Pro Lys
    50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
            85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Gly Leu Asn Asp Ile Phe Glu Ala Gln Lys
    130                 135                 140

Ile Glu Trp His Glu Ala Gly Val Asp Asn Arg Glu Cys Ile Ser Met
145                 150                 155                 160

Asp Tyr Lys Gln Thr Gln Leu Cys Leu Ile Gly Cys Lys Pro Pro Ile
            165                 170                 175

Gly Glu His Trp Gly Lys Gly Ser Pro Cys Thr Asn Val Ala Val Asn
            180                 185                 190

Pro Gly Asp Cys Pro Pro Leu Glu Leu Ile Asn Thr Val Ile Gln Asp
        195                 200                 205

Gly Asp Met Val Asp Thr Gly Phe Gly Ala Met Asp Phe Thr Thr Leu
    210                 215                 220

Gln Ala Asn Lys Ser Glu Val Pro Leu Asp Ile Cys Thr Ser Ile Cys
225                 230                 235                 240

Lys Tyr Pro Asp Tyr Ile Lys Met Val Ser Glu Pro Tyr Gly Asp Ser

```
                        245                 250                 255
Leu Phe Phe Tyr Leu Arg Arg Glu Gln Met Phe Val Arg His Leu Phe
                260                 265                 270

Asn Arg Ala Gly Ala Val Gly Glu Asn Val Pro Asp Asp Leu Tyr Ile
            275                 280                 285

Lys Gly Ser Gly Ser Thr Ala Asn Leu Ala Ser Ser Asn Tyr Phe Pro
        290                 295                 300

Thr Pro Ser Gly Ser Met Val Thr Ser Asp Ala Gln Ile Phe Asn Lys
305                 310                 315                 320

Pro Tyr Trp Leu Gln Arg Ala Gln Gly His Asn Asn Gly Ile Cys Trp
                325                 330                 335

Gly Asn Gln Leu Phe Val Thr Val Val Asp Thr Thr Arg Ser Thr Asn
            340                 345                 350

Met Ser Leu Cys Ala Ala Ile Ser Thr Ser Glu Thr Thr Tyr Lys Asn
        355                 360                 365

Thr Asn Phe Lys Glu Tyr Leu Arg His Gly Glu Glu Tyr Asp Leu Gln
370                 375                 380

Phe Ile Phe Gln Leu Cys Lys Ile Thr Leu Thr Ala Asp Val Met Thr
385                 390                 395                 400

Tyr Ile His Ser Met Asn Ser Thr Ile Leu Glu Asp Trp Asn Phe Gly
                405                 410                 415

Leu Gln Pro Pro Pro Gly Gly Thr Leu Glu Asp Thr Tyr Arg Phe Val
            420                 425                 430

Thr Ser Gln Ala Ile Ala Cys Gln Lys His Thr Pro Pro Ala Pro Lys
        435                 440                 445

Glu Asp Pro Leu Lys Lys Tyr Thr Phe Trp Glu Val Asn Leu Lys Glu
    450                 455                 460

Lys Phe Ser Ala Asp Leu Asp Gln Phe Pro Leu Gly Arg Lys Phe Leu
465                 470                 475                 480

Leu Gln Ala Gly Leu Lys Ala Lys Pro Lys Phe Thr Leu Gly Lys Arg
                485                 490                 495

Lys Ala Thr Pro Thr Thr Ser Ser Thr Ser Thr Thr Ala Lys Arg Lys
            500                 505                 510

Lys Arg Lys Leu Glu Leu
        515

<210> SEQ ID NO 4
<211> LENGTH: 514
<212> TYPE: PRT
<213> ORGANISM: Human papillomavirus type 16

<400> SEQUENCE: 4

Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
                20                  25                  30

Ile Tyr Tyr His Ala Gly Thr Ser Arg Leu Leu Ala Val Gly His Pro
            35                  40                  45

Tyr Phe Pro Ile Lys Lys Pro Asn Asn Asn Lys Ile Leu Val Pro Lys
        50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                85                  90                  95
```

-continued

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Ala Gly Val Asp Asn Arg Glu Cys Ile Ser
    130                 135                 140

Met Asp Tyr Lys Gln Thr Gln Leu Cys Leu Ile Gly Cys Lys Pro Pro
145                 150                 155                 160

Ile Gly Glu His Trp Gly Lys Gly Ser Pro Cys Thr Asn Val Ala Val
                165                 170                 175

Asn Pro Gly Asp Cys Pro Pro Leu Glu Leu Ile Asn Thr Val Ile Gln
            180                 185                 190

Asp Gly Asp Met Val Asp Thr Gly Phe Gly Ala Met Asp Phe Thr Thr
        195                 200                 205

Leu Gln Ala Asn Lys Ser Glu Val Pro Leu Asp Ile Cys Thr Ser Ile
    210                 215                 220

Cys Lys Tyr Pro Asp Tyr Ile Lys Met Val Ser Glu Pro Tyr Gly Asp
225                 230                 235                 240

Ser Leu Phe Phe Tyr Leu Arg Arg Glu Gln Met Phe Val Arg His Leu
                245                 250                 255

Phe Asn Arg Ala Gly Ala Val Gly Glu Asn Val Pro Asp Asp Leu Tyr
            260                 265                 270

Ile Lys Gly Leu Asn Asp Ile Phe Glu Ala Gln Lys Ile Glu Trp His
        275                 280                 285

Glu Ala Ser Ser Asn Tyr Phe Pro Thr Pro Ser Gly Ser Met Val Thr
290                 295                 300

Ser Asp Ala Gln Ile Phe Asn Lys Pro Tyr Trp Leu Gln Arg Ala Gln
305                 310                 315                 320

Gly His Asn Asn Gly Ile Cys Trp Gly Asn Gln Leu Phe Val Thr Val
                325                 330                 335

Val Asp Thr Thr Arg Ser Thr Asn Met Ser Leu Cys Ala Ala Ile Ser
            340                 345                 350

Thr Ser Glu Thr Thr Tyr Lys Asn Thr Asn Phe Lys Glu Tyr Leu Arg
        355                 360                 365

His Gly Glu Glu Tyr Asp Leu Gln Phe Ile Phe Gln Leu Cys Lys Ile
    370                 375                 380

Thr Leu Thr Ala Asp Val Met Thr Tyr Ile His Ser Met Asn Ser Thr
385                 390                 395                 400

Ile Leu Glu Asp Trp Asn Phe Gly Leu Gln Pro Pro Pro Gly Gly Thr
                405                 410                 415

Leu Glu Asp Thr Tyr Arg Phe Val Thr Ser Gln Ala Ile Ala Cys Gln
            420                 425                 430

Lys His Thr Pro Pro Ala Pro Lys Glu Asp Pro Leu Lys Lys Tyr Thr
        435                 440                 445

Phe Trp Glu Val Asn Leu Lys Glu Lys Phe Ser Ala Asp Leu Asp Gln
450                 455                 460

Phe Pro Leu Gly Arg Lys Phe Leu Leu Gln Ala Gly Leu Lys Ala Lys
465                 470                 475                 480

Pro Lys Phe Thr Leu Gly Lys Arg Lys Ala Thr Pro Thr Thr Ser Ser
                485                 490                 495

Thr Ser Thr Thr Ala Lys Arg Lys Lys Arg Lys Leu Glu Leu Ser Gly
            500                 505                 510

Arg Phe

```
<210> SEQ ID NO 5
<211> LENGTH: 505
<212> TYPE: PRT
<213> ORGANISM: Human papillomavirus type 16

<400> SEQUENCE: 5
```

| | | | | | | | | | | | | | | |
|---|---|---|---|---|---|---|---|---|---|---|---|---|---|---|
|Met|Ser|Leu|Trp|Leu|Pro|Ser|Glu|Ala|Thr|Val|Tyr|Leu|Pro|Pro|
|1| | | |5| | | | |10| | | | |15|
|Val|Pro|Val|Ser|Lys|Val|Val|Ser|Thr|Asp|Glu|Tyr|Val|Ala|Arg|
| | | | |20| | | | |25| | | | |30|
|Thr|Asn|Ile|Tyr|Tyr|His|Ala|Gly|Thr|Ser|Arg|Leu|Leu|Ala|Val|
| | | | |35| | | | |40| | | | |45|
|Gly|His|Pro|Tyr|Phe|Pro|Ile|Lys|Lys|Pro|Asn|Asn|Asn|Lys|Ile|
| | | | |50| | | | |55| | | | |60|
|Leu|Val|Pro|Lys|Val|Ser|Gly|Leu|Gln|Tyr|Arg|Val|Phe|Arg|Ile|
|65| | | | |70| | | | |75| | | | |
|His|Leu|Pro|Asp|Pro|Asn|Lys|Phe|Gly|Phe|Pro|Asp|Thr|Ser|Phe|
| | | |80| | | | |85| | | | |90| |
|Tyr|Asn|Pro|Asp|Thr|Gln|Arg|Leu|Val|Trp|Ala|Cys|Val|Gly|Val|
| | | |95| | | | |100| | | | |105| |
|Glu|Val|Gly|Arg|Gly|Gln|Pro|Leu|Gly|Val|Gly|Ile|Ser|Gly|His|
| | | |110| | | | |115| | | | |120| |
|Pro|Leu|Leu|Asn|Lys|Leu|Asp|Asp|Thr|Glu|Asn|Ala|Ser|Ala|Tyr|
| | | |125| | | | |130| | | | |135| |
|Ala|Ala|Asn|Ala|Gly|Val|Asp|Asn|Arg|Glu|Cys|Ile|Ser|Met|Asp|
| | | |140| | | | |145| | | | |150| |
|Tyr|Lys|Gln|Thr|Gln|Leu|Cys|Leu|Ile|Gly|Cys|Lys|Pro|Pro|Ile|
| | | |155| | | | |160| | | | |165| |
|Gly|Glu|His|Trp|Gly|Lys|Gly|Ser|Pro|Cys|Thr|Asn|Val|Ala|Val|
| | | |170| | | | |175| | | | |180| |
|Asn|Pro|Gly|Asp|Cys|Pro|Pro|Leu|Glu|Leu|Ile|Asn|Thr|Val|Ile|
| | | |185| | | | |190| | | | |195| |
|Gln|Asp|Gly|Asp|Met|Val|His|Thr|Gly|Phe|Gly|Ala|Met|Asp|Phe|
| | | |200| | | | |205| | | | |210| |
|Thr|Thr|Leu|Gln|Ala|Asn|Lys|Ser|Glu|Val|Pro|Leu|Asp|Ile|Cys|
| | | |215| | | | |220| | | | |225| |
|Thr|Ser|Ile|Cys|Lys|Tyr|Pro|Asp|Tyr|Ile|Lys|Met|Val|Ser|Glu|
| | | |230| | | | |235| | | | |240| |
|Pro|Tyr|Gly|Asp|Ser|Leu|Phe|Phe|Tyr|Leu|Arg|Arg|Glu|Gln|Met|
| | | |245| | | | |250| | | | |255| |
|Phe|Val|Arg|His|Leu|Phe|Asn|Arg|Ala|Gly|Thr|Val|Gly|Glu|Asn|
| | | |260| | | | |265| | | | |270| |
|Val|Pro|Asp|Asp|Leu|Tyr|Ile|Lys|Gly|Ser|Gly|Ser|Thr|Ala|Asn|
| | | |275| | | | |280| | | | |285| |
|Leu|Ala|Ser|Ser|Asn|Tyr|Phe|Pro|Thr|Pro|Ser|Gly|Ser|Met|Val|
| | | |290| | | | |295| | | | |300| |
|Thr|Ser|Asp|Ala|Gln|Ile|Phe|Asn|Lys|Pro|Tyr|Trp|Leu|Gln|Arg|
| | | |305| | | | |310| | | | |315| |
|Ala|Gln|Gly|His|Asn|Asn|Gly|Ile|Cys|Trp|Gly|Asn|Gln|Leu|Phe|
| | | |320| | | | |325| | | | |330| |
|Val|Thr|Val|Val|Asp|Thr|Thr|Arg|Ser|Thr|Asn|Met|Ser|Leu|Cys|
| | | |335| | | | |340| | | | |345| |
|Ala|Ala|Ile|Ser|Thr|Ser|Glu|Thr|Thr|Tyr|Lys|Asn|Thr|Asn|Phe|
| | | |350| | | | |355| | | | |360| |
|Lys|Glu|Tyr|Leu|Arg|His|Gly|Glu|Glu|Tyr|Asp|Leu|Gln|Phe|Ile|
| | | |365| | | | |370| | | | |375| |
|Phe|Gln|Leu|Cys|Lys|Ile|Thr|Leu|Thr|
| | | | | | | | | |

```
            370                 375                 380
Ala Asp Val Met Thr Tyr Ile His Ser Met Asn Ser Thr Ile Leu Glu
385                 390                 395                 400

Asp Trp Asn Phe Gly Leu Gln Pro Pro Gly Gly Thr Leu Glu Asp
            405                 410                 415

Thr Tyr Arg Phe Val Thr Gln Ala Ile Ala Cys Gln Lys His Thr Pro
                420                 425                 430

Pro Ala Pro Lys Glu Asp Pro Leu Lys Lys Tyr Thr Phe Trp Glu
            435                 440                 445

Val Asn Leu Lys Glu Lys Phe Ser Ala Asp Leu Asp Gln Phe Pro Leu
450                 455                 460

Gly Arg Lys Phe Leu Leu Gln Ala Gly Leu Lys Ala Lys Pro Lys Phe
465                 470                 475                 480

Thr Leu Gly Lys Arg Lys Ala Thr Pro Thr Thr Ser Ser Thr Ser Thr
                485                 490                 495

Thr Ala Lys Arg Lys Lys Arg Lys Leu
            500                 505

<210> SEQ ID NO 6
<211> LENGTH: 525
<212> TYPE: PRT
<213> ORGANISM: Human papillomavirus type 118

<400> SEQUENCE: 6

Met Ala Val Trp Gln Ala Ala Ser Gly Lys Val Tyr Leu Pro Pro Ser
1               5                   10                  15

Thr Pro Val Ala Arg Val Gln Ser Thr Asp Glu Tyr Val Glu Arg Thr
                20                  25                  30

Asn Ile Tyr Tyr His Ala Phe Thr Asp Arg Leu Leu Thr Val Gly His
            35                  40                  45

Pro Tyr Phe Asn Ile Phe Asn Asn Asp Gly Asn Lys Leu Glu Val Pro
        50                  55                  60

Lys Val Ser Gly Asn Gln His Arg Val Phe Arg Leu Arg Leu Pro Asp
65                  70                  75                  80

Pro Asn Arg Phe Ala Leu Ala Asp Met Ser Val Tyr Asn Pro Asp Lys
                85                  90                  95

Glu Arg Leu Val Trp Ala Ile Thr Gly Leu Glu Ile Gly Arg Gly Gln
            100                 105                 110

Pro Leu Gly Val Gly Thr Ser Gly His Pro Leu Phe Asn Lys Phe Asn
        115                 120                 125

Asp Thr Glu Asn Gly Asn Lys Tyr Thr Asn Thr Ser Thr Asp Asp Arg
130                 135                 140

Gln Asn Ile Ser Phe Asp Pro Lys Gln Leu Gln Met Phe Ile Ile Gly
145                 150                 155                 160

Cys Thr Pro Cys Ile Gly Glu His Trp Asp Arg Ala Pro Ala Cys Val
                165                 170                 175

Glu Asp Glu Gln Leu Gly Arg Cys Pro Pro Ile Glu Leu Val Asn Thr
            180                 185                 190

Phe Ile Gln Asp Asp Asp Met Ala Asp Ile Gly Tyr Gly Asn Leu Asn
        195                 200                 205

Phe Lys Ala Leu Gln Gln Asn Arg Ser Asp Val Ser Leu Asp Ile Val
            210                 215                 220

Asp Glu Ile Cys Lys Tyr Pro Asp Phe Leu Lys Met Gln Asn Asp Val
225                 230                 235                 240
```

Tyr Gly Asp Ala Cys Phe Phe Tyr Ala Arg Arg Glu Gln Cys Tyr Ala
            245                 250                 255

Arg Arg Phe Phe Val Arg Gly Lys Pro Gly Asp Asp Ile Pro Ala
260                 265                 270

Glu Gln Ile Asp Ala Gly Lys Leu Lys Asn Glu Phe Tyr Ile Pro Ala
            275                 280                 285

Ala Gly Gly Gln Ala Gln Gly Gln Leu Gly Asn Ser Met Tyr Phe Pro
            290                 295                 300

Thr Val Ser Gly Ser Leu Val Ser Ser Asp Ala Gln Leu Phe Asn Arg
305                 310                 315                 320

Pro Phe Trp Leu Gln Arg Ala Gln Gly His Asn Asn Gly Ile Leu Trp
            325                 330                 335

Gly Asn Gln Leu Phe Val Thr Val Leu Asp Asn Thr Arg Asn Thr Asn
            340                 345                 350

Phe Ser Ile Ala Val Tyr Ser Glu Gly Leu Asn Asp Ile Phe Glu Ala
            355                 360                 365

Gln Lys Ile Glu Trp His Glu Gln Asp Ile Ala Asn Tyr Asp Ser Ser
            370                 375                 380

Lys Ser Arg Glu Tyr Gln Arg His Val Glu Glu Tyr Glu Val Ser Met
385                 390                 395                 400

Ile Leu Gln Leu Cys Lys Ile Pro Leu Lys Pro Glu Val Leu Ala His
            405                 410                 415

Ile Asn Ala Met Asn Pro Ala Ile Leu Glu Asp Trp Gln Leu Gly Phe
            420                 425                 430

Ile Pro Thr Pro Asp Asn Pro Ile His Asp Thr Tyr Arg Tyr Ile Asp
            435                 440                 445

Ser Leu Ala Thr Arg Cys Pro Asp Lys Val Pro Ala Lys Glu Lys Glu
            450                 455                 460

Asp Pro Tyr Gly Lys Tyr Val Phe Trp Asn Val Asp Leu Ser Glu Arg
465                 470                 475                 480

Leu Ser Leu Asp Leu Asp Gln Tyr Pro Leu Gly Arg Lys Phe Leu Phe
            485                 490                 495

Gln Ala Gly Leu Arg Gln Lys Ser Val Asn Gly Ser Val Thr Arg Thr
            500                 505                 510

Val Ser Arg Gly Ala Lys Arg Lys Arg Lys Ser Gly Arg
            515                 520                 525

<210> SEQ ID NO 7
<211> LENGTH: 522
<212> TYPE: PRT
<213> ORGANISM: Human papillomavirus type 118

<400> SEQUENCE: 7

Met Ala Val Trp Gln Ala Ala Ser Gly Lys Val Tyr Leu Pro Pro Ser
1               5                   10                  15

Thr Pro Val Ala Arg Val Gln Ser Thr Asp Glu Tyr Val Glu Arg Thr
            20                  25                  30

Asn Ile Tyr Tyr His Ala Phe Thr Asp Arg Leu Leu Thr Val Gly His
            35                  40                  45

Pro Tyr Phe Asn Ile Phe Asn Asn Asp Gly Asn Lys Leu Glu Val Pro
            50                  55                  60

Lys Val Ser Gly Asn Gln His Arg Val Phe Arg Leu Arg Leu Pro Asp
65                  70                  75                  80

Pro Asn Arg Phe Ala Leu Ala Asp Met Ser Val Tyr Asn Pro Asp Lys
            85                  90                  95

```
Glu Arg Leu Val Trp Ala Ile Thr Gly Leu Glu Ile Gly Arg Gly Gln
            100                 105                 110

Pro Leu Gly Val Gly Thr Ser Gly His Pro Leu Phe Asn Lys Phe Asn
            115                 120                 125

Asp Thr Glu Asn Gly Asn Gly Leu Asn Asp Ile Phe Glu Ala Gln Lys
            130                 135                 140

Ile Glu Trp His Glu Thr Ser Thr Asp Asp Arg Gln Asn Ile Ser Phe
145                 150                 155                 160

Asp Pro Lys Gln Leu Gln Met Phe Ile Ile Gly Cys Thr Pro Cys Ile
                165                 170                 175

Gly Glu His Trp Asp Arg Ala Pro Ala Cys Val Glu Asp Glu Gln Leu
            180                 185                 190

Gly Arg Cys Pro Pro Ile Glu Leu Val Asn Thr Phe Ile Gln Asp Asp
            195                 200                 205

Asp Met Ala Asp Ile Gly Tyr Gly Asn Leu Asn Phe Lys Ala Leu Gln
            210                 215                 220

Gln Asn Arg Ser Asp Val Ser Leu Asp Ile Val Asp Glu Ile Cys Lys
225                 230                 235                 240

Tyr Pro Asp Phe Leu Lys Met Gln Asn Asp Val Tyr Gly Asp Ala Cys
                245                 250                 255

Phe Phe Tyr Ala Arg Arg Glu Gln Cys Tyr Ala Arg Arg Phe Phe Val
            260                 265                 270

Arg Gly Gly Lys Pro Gly Asp Asp Ile Pro Ala Glu Gln Ile Asp Ala
            275                 280                 285

Gly Lys Leu Lys Asn Glu Phe Tyr Ile Pro Ala Ala Gly Gly Gln Ala
            290                 295                 300

Gln Gly Gln Leu Gly Asn Ser Met Tyr Phe Pro Thr Val Ser Gly Ser
305                 310                 315                 320

Leu Val Ser Ser Asp Ala Gln Leu Phe Asn Arg Pro Phe Trp Leu Gln
                325                 330                 335

Arg Ala Gln Gly His Asn Asn Gly Ile Leu Trp Gly Asn Gln Leu Phe
            340                 345                 350

Val Thr Val Leu Asp Asn Thr Arg Asn Thr Asn Phe Ser Ile Ala Val
            355                 360                 365

Tyr Ser Glu Gln Asp Ile Ala Asn Tyr Asp Ser Ser Lys Ser Arg Glu
            370                 375                 380

Tyr Gln Arg His Val Glu Glu Tyr Glu Val Ser Met Ile Leu Gln Leu
385                 390                 395                 400

Cys Lys Ile Pro Leu Lys Pro Glu Val Leu Ala His Ile Asn Ala Met
                405                 410                 415

Asn Pro Ala Ile Leu Glu Asp Trp Gln Leu Gly Phe Ile Pro Thr Pro
            420                 425                 430

Asp Asn Pro Ile His Asp Thr Tyr Arg Tyr Ile Asp Ser Leu Ala Thr
            435                 440                 445

Arg Cys Pro Asp Lys Val Pro Ala Lys Glu Lys Asp Pro Tyr Gly
            450                 455                 460

Lys Tyr Val Phe Trp Asn Val Asp Leu Ser Glu Arg Leu Ser Leu Asp
465                 470                 475                 480

Leu Asp Gln Tyr Pro Leu Gly Arg Lys Phe Leu Phe Gln Ala Gly Leu
                485                 490                 495

Arg Gln Lys Ser Val Asn Gly Ser Val Thr Arg Thr Val Ser Arg Gly
            500                 505                 510
```

```
Ala Lys Arg Lys Arg Lys Ser Gly Arg Phe
        515                 520

<210> SEQ ID NO 8
<211> LENGTH: 511
<212> TYPE: PRT
<213> ORGANISM: Human papillomavirus type 118

<400> SEQUENCE: 8

Met Ala Val Trp Gln Ala Ser Gly Lys Val Tyr Leu Pro Pro Ser
1               5                   10                  15

Thr Pro Val Ala Arg Val Gln Ser Thr Asp Glu Tyr Val Glu Arg Thr
            20                  25                  30

Asn Ile Tyr Tyr His Ala Phe Thr Asp Arg Leu Leu Thr Val Gly His
                35                  40                  45

Pro Tyr Phe Asn Ile Phe Asn Asn Asp Gly Asn Lys Leu Glu Val Pro
    50                  55                  60

Lys Val Ser Gly Asn Gln His Arg Val Phe Arg Leu Arg Leu Pro Asp
65                  70                  75                  80

Pro Asn Arg Phe Ala Leu Ala Asp Met Ser Val Tyr Asn Pro Asp Lys
                85                  90                  95

Glu Arg Leu Val Trp Ala Ile Thr Gly Leu Glu Ile Gly Arg Gly Gln
            100                 105                 110

Pro Leu Gly Val Gly Thr Ser Gly His Pro Leu Phe Asn Lys Phe Asn
        115                 120                 125

Asp Thr Glu Asn Gly Asn Lys Tyr Thr Asn Thr Ser Thr Asp Asp Arg
    130                 135                 140

Gln Asn Ile Ser Phe Asp Pro Lys Gln Leu Gln Met Phe Ile Ile Gly
145                 150                 155                 160

Cys Thr Pro Cys Ile Gly Glu His Trp Asp Arg Ala Pro Ala Cys Val
                165                 170                 175

Glu Asp Glu Gln Leu Gly Arg Cys Pro Pro Ile Glu Leu Val Asn Thr
            180                 185                 190

Phe Ile Gln Asp Asp Met Ala Asp Ile Gly Tyr Gly Asn Leu Asn
        195                 200                 205

Phe Lys Ala Leu Gln Gln Asn Arg Ser Asp Val Ser Leu Asp Ile Val
    210                 215                 220

Asp Glu Ile Cys Lys Tyr Pro Asp Phe Leu Lys Met Gln Asn Asp Val
225                 230                 235                 240

Tyr Gly Asp Ala Cys Phe Phe Tyr Ala Arg Arg Glu Gln Cys Tyr Ala
                245                 250                 255

Arg Arg Phe Phe Val Arg Gly Gly Lys Pro Gly Asp Asp Ile Pro Ala
            260                 265                 270

Glu Gln Ile Asp Ala Gly Lys Leu Lys Asn Glu Phe Tyr Ile Pro Ala
        275                 280                 285

Ala Gly Gly Gln Ala Gln Gly Gln Leu Gly Asn Ser Met Tyr Phe Pro
    290                 295                 300

Thr Val Ser Gly Ser Leu Val Ser Ser Asp Ala Gln Leu Phe Asn Arg
305                 310                 315                 320

Pro Phe Trp Leu Gln Arg Ala Gln Gly His Asn Asn Gly Ile Leu Trp
                325                 330                 335

Gly Asn Gln Leu Phe Val Thr Val Leu Asp Asn Thr Arg Asn Thr Asn
            340                 345                 350

Phe Ser Ile Ala Val Tyr Ser Glu Ala Gly Lys Ile Gln Asp Ile Ala
        355                 360                 365
```

Asn Tyr Asp Ser Ser Lys Ser Arg Glu Tyr Gln Arg His Val Glu Glu
            370                 375                 380

Tyr Glu Val Ser Met Ile Leu Gln Leu Cys Lys Ile Pro Leu Lys Pro
385                 390                 395                 400

Glu Val Leu Ala His Ile Asn Ala Met Asn Pro Ala Ile Leu Glu Asp
                405                 410                 415

Trp Gln Leu Gly Phe Ile Pro Thr Pro Asp Asn Pro Ile His Asp Thr
            420                 425                 430

Tyr Arg Tyr Ile Asp Ser Leu Ala Thr Arg Cys Pro Asp Lys Val Pro
            435                 440                 445

Ala Lys Glu Lys Glu Asp Pro Tyr Gly Lys Tyr Val Phe Trp Asn Val
450                 455                 460

Asp Leu Ser Glu Arg Leu Ser Leu Asp Leu Asp Gln Tyr Pro Leu Gly
465                 470                 475                 480

Arg Lys Phe Leu Phe Gln Ala Gly Leu Arg Gln Lys Ser Val Asn Gly
            485                 490                 495

Ser Val Thr Arg Thr Val Ser Arg Gly Ala Lys Arg Lys Arg Lys
                500                 505                 510

<210> SEQ ID NO 9
<211> LENGTH: 511
<212> TYPE: PRT
<213> ORGANISM: European elk papillomavirus

<400> SEQUENCE: 9

Met Ala Phe Trp Gln Pro Ser Gln Arg Leu Tyr Leu Pro Pro Thr Pro
1               5                   10                  15

Val Thr Lys Val Leu Cys Ser Glu Gln Tyr Ile Arg Arg Lys Asp Val
                20                  25                  30

Phe Tyr His Gly Glu Thr Glu Arg Met Leu Thr Val Gly His Pro Tyr
            35                  40                  45

Tyr Glu Ile Lys Gln Ser Gly Ser Gly Lys Thr Ile Pro Lys Val Ser
        50                  55                  60

Pro Asn Gln Tyr Arg Val Phe Arg Ile Leu Leu Pro Asp Pro Asn Gln
65                  70                  75                  80

Phe Ala Leu Pro Asp Lys Ala Met Tyr Asp Pro Ser Lys Glu Arg Leu
                85                  90                  95

Val Trp Ala Val Val Gly Val Gln Val Ser Arg Gly Gln Pro Leu Gly
            100                 105                 110

Gly Ser Val Ser Gly His Ser Tyr Gln Asn Thr Leu Ile Asp Ala Glu
        115                 120                 125

Asn Val Ser Gly Leu Asn Asp Ile Phe Glu Ala Gln Lys Ile Glu Trp
130                 135                 140

His Glu Gln Gly Thr Asp Asp Arg Lys Gln Gly Gly Met Asp Val Lys
145                 150                 155                 160

Gln Gln Gln Ile Leu Leu Leu Gly Cys Thr Pro Ala Ile Gly Glu Tyr
                165                 170                 175

Trp Thr Thr Ala Arg Pro Cys Val Thr Asp Arg Pro Glu Thr Gly Ser
            180                 185                 190

Cys Pro Pro Ile Glu Leu Lys Asn Lys Pro Ile Glu Asp Gly Asp Met
        195                 200                 205

Met Asp Ile Gly Phe Gly Ala Ala Asn Phe Lys Glu Leu Asn Ala Thr
    210                 215                 220

Lys Ser Asp Leu Pro Leu Asp Ile Ala Lys Asp Ile Cys Leu Tyr Pro

```
225                 230                 235                 240
Asp Tyr Leu Lys Met Thr Glu Glu Ala Ala Gly Asn Ser Met Phe Phe
                245                 250                 255

Phe Ala Arg Lys Glu Gln Val Tyr Val Arg His Ile Trp Ser Arg Gly
                260                 265                 270

Gly Thr Asp Lys Glu Met Pro Pro Glu Ala Tyr Phe Leu Lys Pro Lys
                275                 280                 285

Gly Gly Asp Gln Thr Gln Lys Met Pro Ser Ile Leu Phe Gly Val Pro
                290                 295                 300

Ser Gly Ser Leu Val Ser Thr Asp Gly Gln Leu Phe Asn Arg Pro Tyr
305                 310                 315                 320

Trp Leu Phe Arg Ala Gln Gly Met Asn Asn Gly Ile Cys Trp Leu Asn
                325                 330                 335

Gln Leu Phe Val Thr Val Gly Asp Asn Thr Arg Gly Thr Thr Leu Thr
                340                 345                 350

Ile Thr Val Pro Thr Ser Gly Ser Pro Leu Thr Glu Tyr Asp Thr Ser
                355                 360                 365

Lys Phe Asn Val Phe Gln Arg His Val Glu Glu Tyr Lys Leu Ala Phe
                370                 375                 380

Val Phe Gln Leu Cys Ser Val Thr Leu Ser Pro Glu Thr Val Ser His
385                 390                 395                 400

Leu Gln Gly Leu Met Pro Ser Ile Leu Glu His Trp Asp Ile Asn Met
                405                 410                 415

Gln Pro Pro Thr Ser Ser Ile Leu Glu Asp Thr Tyr Arg Tyr Leu Glu
                420                 425                 430

Ser Pro Ala Thr Lys Cys Ala Asp Asn Val Thr Pro Met Gly Pro Glu
                435                 440                 445

Asp Pro Tyr Ala Gly Leu Lys Phe Trp Glu Val Asn Leu Lys Glu Arg
                450                 455                 460

Leu Ser Leu Asp Leu Asp Gln Phe Pro Leu Gly Arg Arg Phe Leu Ala
465                 470                 475                 480

Gln Gln Gly Leu Gly Cys Ser Thr Arg Lys Arg Val Ala Pro Val Pro
                485                 490                 495

Lys Val Thr Glu Lys Arg Ile Val Arg Lys Arg Lys Gly Asn
                500                 505                 510

<210> SEQ ID NO 10
<211> LENGTH: 501
<212> TYPE: PRT
<213> ORGANISM: European elk papillomavirus

<400> SEQUENCE: 10

Met Ala Phe Trp Gln Pro Ser Gln Arg Leu Tyr Leu Pro Pro Thr Pro
1               5                   10                  15

Val Thr Lys Val Leu Cys Ser Glu Gln Tyr Ile Arg Arg Lys Asp Val
                20                  25                  30

Phe Tyr His Gly Glu Thr Glu Arg Met Leu Thr Val Gly His Pro Tyr
                35                  40                  45

Tyr Glu Ile Lys Gln Ser Gly Ser Gly Lys Thr Ile Pro Lys Val Ser
                50                  55                  60

Pro Asn Gln Tyr Arg Val Phe Arg Ile Leu Leu Pro Asp Pro Asn Gln
65                  70                  75                  80

Phe Ala Leu Pro Asp Lys Ala Met Tyr Asp Pro Ser Lys Glu Arg Leu
                85                  90                  95
```

```
Val Trp Ala Val Val Gly Val Gln Val Ser Arg Gly Gln Pro Leu Gly
            100                 105                 110

Gly Ser Val Ser Gly His Ser Tyr Gln Asn Thr Leu Ile Asp Ala Glu
        115                 120                 125

Asn Val Ser Lys Lys Val Asn Ala Gln Gly Thr Asp Asp Arg Lys Gln
        130                 135                 140

Gly Gly Met Asp Val Lys Gln Gln Ile Leu Leu Gly Cys Thr
145                 150                 155                 160

Pro Ala Ile Gly Glu Tyr Trp Thr Thr Ala Arg Pro Cys Val Thr Asp
                165                 170                 175

Arg Pro Glu Thr Gly Ser Cys Pro Pro Ile Glu Leu Lys Asn Lys Pro
                180                 185                 190

Ile Glu Asp Gly Asp Met Met Asp Ile Gly Phe Gly Ala Ala Asn Phe
                195                 200                 205

Lys Glu Leu Asn Ala Thr Lys Ser Asp Leu Pro Leu Asp Ile Ala Lys
        210                 215                 220

Asp Ile Cys Leu Tyr Pro Asp Tyr Leu Lys Met Thr Glu Glu Ala Ala
225                 230                 235                 240

Gly Asn Ser Met Phe Phe Phe Ala Arg Lys Glu Gln Val Tyr Val Arg
                245                 250                 255

His Ile Trp Ser Arg Gly Gly Thr Asp Lys Glu Met Pro Pro Glu Ala
                260                 265                 270

Tyr Phe Leu Lys Pro Lys Gly Gly Asp Gln Thr Gln Lys Met Pro Ser
                275                 280                 285

Ile Leu Phe Gly Val Pro Ser Gly Ser Leu Val Ser Thr Asp Gly Gln
290                 295                 300

Leu Phe Asn Arg Pro Tyr Trp Leu Phe Arg Ala Gln Gly Met Asn Asn
305                 310                 315                 320

Gly Ile Cys Trp Leu Asn Gln Leu Phe Val Thr Val Gly Asp Asn Thr
                325                 330                 335

Arg Gly Thr Thr Leu Thr Ile Thr Val Pro Thr Ser Gly Ser Pro Leu
                340                 345                 350

Thr Glu Tyr Asp Thr Ser Lys Phe Asn Val Phe Gln Arg His Val Glu
                355                 360                 365

Glu Tyr Lys Leu Ala Phe Val Phe Gln Leu Cys Ser Val Thr Leu Ser
        370                 375                 380

Pro Glu Thr Val Ser His Leu Gln Gly Leu Met Pro Ser Ile Leu Glu
385                 390                 395                 400

His Trp Asp Ile Asn Met Gln Pro Pro Thr Ser Ser Ile Leu Glu Asp
                405                 410                 415

Thr Tyr Arg Tyr Leu Glu Ser Pro Ala Thr Lys Cys Ala Asp Asn Val
                420                 425                 430

Thr Pro Met Gly Pro Glu Asp Pro Tyr Ala Gly Leu Lys Phe Trp Glu
                435                 440                 445

Val Asn Leu Lys Glu Arg Leu Ser Leu Asp Leu Asp Gln Phe Pro Leu
        450                 455                 460

Gly Arg Arg Phe Leu Ala Gln Gln Gly Leu Gly Cys Ser Thr Arg Lys
465                 470                 475                 480

Arg Val Ala Pro Val Pro Lys Val Thr Glu Lys Arg Ile Val Arg Lys
                485                 490                 495

Arg Arg Lys Gly Asn
                500
```

```
<210> SEQ ID NO 11
<211> LENGTH: 1723
<212> TYPE: DNA
<213> ORGANISM: Human papillomavirus type 16

<400> SEQUENCE: 11
gatatcatgg agataattaa aatgataacc atctcgcaaa taaataagta ttttactgtt      60
ttcgtaacag ttttgtaata aaaaaaccta taaatattcc ggattattca taccgtccca     120
ccatcgggcg cggatctcta ctagtatgtc tctgtggctg ccctctgaag ccaccgtcta     180
cctgccccc gtccctgtct ctaaggtcgt cagcaccgac gaatacgtcg ccaggaccaa      240
catctactac cacgccggaa cctctaggct gctggccgtc ggacacccct acttccccat     300
caagaagccc aacaacaaca agatcctggt ccccaaggtg tccggactgc agtacagggt     360
gttcaggatc cacctccccg accccaacaa gttcggattc cccgcacct ctttctacaa      420
ccccgacacc cagaggctcg tctgggcctg cgtcggagtc gaagtcggaa ggggacagcc     480
cctgggagtc ggaatctctg gacacccct gctgaacaag ctggacgaca ccgaaaacgc      540
ctctgcctac gccgccaacg ccggtgtcga caacagggaa tgcatctcta tggactacaa     600
gcagacccag ctgtgcctga tcggatgcaa gccccccatc ggagaacact ggggaaaggg     660
atctccctgc accaacgtcg ccgtcaaccc cggcgactgc ccccctctgg aactgatcaa     720
caccgtcatc caggacggcg acatggtcga caccggattc ggagccatgg acttcaccac     780
cctgcaggcc aacaagtctg aagtccccct ggacatctgc acctctatct gcaagtaccc     840
cgactacatc aagatggtgt ctgaacccta cggcgactct ctgttcttct acctgaggcg     900
cgaacagatg ttcgtcaggc acctgttcaa ccgcgccggt gccgtcggag aaaacgtccc     960
cgacgacctg tacatcaagg gatctggatc taccgccaac ctggcctctt ctaactactt    1020
ccctacccct tctggatcta tggtcacctc tgacgcccag atcttcaaca gccctactg     1080
gctgcagagg gcccagggac acaacaacgg aatctgctgg ggaaaccagc tgttcgtcac    1140
cgtcgtcgac accaccaggt ctaccaacat gtccctgtgc gccgccatct ctacctctga    1200
aaccacctac aagaacacca acttcaaaga atacctgcgc cacggcgaag aatacgacct    1260
gcagttcatc ttccagctgt gcaagatcac cctgaccgcc gacgtcatga cctacatcca    1320
ctctatgaac tctaccatct ggaggactg aacttcgga ctgcagcccc ctcccggtgg      1380
aacccctcgag gacacctacc gcttcgtcac cagccaggct atcgcctgcc agaagcacgg    1440
actgaacgac atcttcgaag cccaaaagat cgaatggcac gaaaccccc ctgcccccaa     1500
agaggacccc ctgaagaagt acacctttctg ggaagtcaac ctgaaagaaa agttctctgc   1560
cgacctggac cagttccccc tgggacgcaa gttcctgctg caagccggac tgaaggccaa    1620
gcccaagttc accctgggaa agaggaaggc cacccccacc acctcttcta cctctaccac    1680
cgccaagagg aagaagcgca agctggaact gtaaagcggc cgc                      1723

<210> SEQ ID NO 12
<211> LENGTH: 1723
<212> TYPE: DNA
<213> ORGANISM: Human papillomavirus type 16

<400> SEQUENCE: 12
gatatcatgg agataattaa aatgataacc atctcgcaaa taaataagta ttttactgtt      60
ttcgtaacag ttttgtaata aaaaaaccta taaatattcc ggattattca taccgtccca     120
ccatcgggcg cggatctcta ctagtatgtc tctgtggctg ccctctgaag ccaccgtcta     180
```

-continued

```
cctgcccccc gtccctgtct ctaaggtcgt cagcaccgac gaatacgtcg ccaggaccaa      240
catctactac cacgccggaa cctctaggct gctggccgtc ggacacccct acttccccat      300
caagaagccc aacaacaaca agatcctggt ccccaaggtg tccggactgc agtacagggt      360
gttcaggatc cacctccccg accccaacaa gttcggattc cccgacacct ctttctacaa      420
ccccgacacc cagaggctcg tctgggcctg cgtcggagtc gaagtcggaa ggggacagcc      480
cctgggagtc ggaatctctg gacacccccct gctgaacaag ctggacgaca ccgaaaacgc      540
ctctgcctac gccgccaacg ccggtgtcga caacagggaa tgcatctcta tggactacaa      600
gcagacccag ctgtgcctga tcggatgcaa gccccccatc ggagaacact ggggaaaggg      660
atctccctgc accaacgtcg ccgtcaaccc cggcgactgc ccccctctgg aactgatcaa      720
caccgtcatc caggacggcg acatggtcga caccggattc ggagccatgg acttcaccac      780
cctgcaggcc aacaagtctg aagtcccccct ggacatctgc acctctatct gcaagtaccc      840
cgactacatc aagatggtgt ctgaacccta cggcgactct ctgttcttct acctgaggcg      900
cgaacagatg ttcgtcaggc acctcttcaa cagggccggt gccgtcggag aaaacgtccc      960
cgacgacctg tacatcaagg gatctggatc taccgccaac ctggcctctt ctaactactt     1020
ccctacccct tctggatcta tggtcacctc tgacgcccag atcttcaaca gccctactg      1080 gctgcagagg gcccagggac acaacaacgg aatctgctgg ggaaaccagc tgttcgtcac     1140
cgtcgtcgac accaccaggt ctaccaacat gtccctgtgc gccgccatct ctacctctgg     1200
actgaacgac atcttcgagg cccaaaagat cgaatggcac gaggaaacca cctacaagaa     1260
caccaacttc aaagaatacc tgcgccacgg cgaagaatac gacctgcagt tcatcttcca     1320
gctgtgcaag atcaccctga ccgccgacgt catgacctac atccactcta tgaactctac     1380
catcttggag gattgaaact tcggactgca gcccccctcc ggtggaaccc tcgaggacac     1440
ctaccgcttc gtcaccagcc aggctatcgc ctgccagaag cacaccccc ctgcccccaa     1500 agaggacccc ctgaagaagt acaccttctg ggaagtcaac ctgaaagaaa agttctctgc     1560
cgacctggac cagttccccc tgggacgcaa gttcctgctg caagccggac tgaaggccaa     1620
gcccaagttc accctgggaa agaggaaggc cacccccacc acctcttcta cctctaccac     1680
cgccaagagg aagaagcgca agctggaact gtaaagcggc cgc                         1723
```

<210> SEQ ID NO 13
<211> LENGTH: 1711
<212> TYPE: DNA
<213> ORGANISM: Human papillomavirus type 16

<400> SEQUENCE: 13

```
gatatcatgg agataattaa aatgataacc atctcgcaaa taaataagta ttttactgtt       60
ttcgtaacag ttttgtaata aaaaaaccta taaatattcc ggattattca taccgtccca      120
ccatcgggcg cggatctcta ctagtatgtc tctgtggctg ccctctgaag ccaccgtcta      180
cctgcccccc gtccctgtct ctaaggtcgt cagcaccgac gaatacgtcg ccaggaccaa      240
catctactac cacgccggaa cctctaggct gctggccgtc ggacacccct acttccccat      300
caagaagccc aacaacaaca agatcctggt ccccaaggtg tccggactgc agtacagggt      360
gttcaggatc cacctccccg accccaacaa gttcggattc cccgacacct ctttctacaa      420
ccccgacacc cagaggctcg tctgggcctg cgtcggagtc gaagtcggaa ggggacagcc      480
cctgggagtc ggaatctctg gacacccccct gctgaacaag ctggacgaca ccgaaaacgc      540
ctctgccgga ctgaacgaca tcttcgaggc ccaaaagatc gaatggcacg aggccggtgt      600
```

```
cgacaacagg gaatgcatct ctatggacta caagcagacc cagctgtgcc tgatcggatg     660 caagccccc  atcggagaac actggggaaa gggatctccc tgcaccaacg tcgccgtcaa     720
ccccggcgac tgccccctc  tggaactgat caacaccgtc atccaggacg gcgacatggt    780
cgacaccgga ttcggagcca tggacttcac caccctgcag ccaacaagt  ctgaagtccc    840 cctggacatc tgcacctcta tctgcaagta ccccgactac atcaagatgg tgtctgaacc    900
ctacggcgac tctctgttct tctacctgag gcgcgaacag atgttcgtca ggcacctctt    960
caacagggcc ggtgccgtcg agaaaacgt  ccccgacgac ctgtacatca agggatctgg   1020
atctaccgcc aacctggcct cttctaacta cttccctacc ccttctggat ctatggtcac   1080
ctctgacgcc cagatcttca acaagcccta ctggctgcag agggcccagg acacaacaa    1140 cggaatctgc tggggaaacc agctgttcgt caccgtcgtc gacaccacca ggtctaccaa   1200
catgtccctg tgcgccgcca tctctacctc tgaaaccacc tacaagaaca ccaacttcaa   1260
agaatacctg cgccacggcg aagaatacga cctgcagttc atcttccagc tgtgcaagat   1320
caccctgacc gccgacgtca tgacctacat ccactctatg aactctacca tcttggagga   1380
ttggaacttc ggactgcagc cccctcccgg tggaaccctc gaggacacct accgcttcgt   1440
caccagccag gctatcgcct gccagaagca cacccccct  gccccaaag  aggaccccct   1500 gaagaagtac accttctggg aagtcaacct gaaagaaaag ttctctgccg acctggacca   1560
gttccccctg ggacgcaagt tcctgctgca agccggactg aaggccaagc ccaagttcac   1620
cctgggaaag aggaaggcca ccccaccac  ctcttctacc tctaccaccg ccaagaggaa   1680
gaagcgcaag ctggaactgt aaagcggccg c                                   1711

<210> SEQ ID NO 14
<211> LENGTH: 1699
<212> TYPE: DNA
<213> ORGANISM: Human papillomavirus type 16

<400> SEQUENCE: 14
gatatcatgg agataattaa aatgataacc atctcgcaaa taaataagta ttttactgtt     60
ttcgtaacag ttttgtaata aaaaaaccta taaatattcc ggattattca taccgtccca    120
ccatcgggcg cggatctcta ctagtatgtc tctgtggctg ccctctgaag ccaccgtcta    180
cctgcccccc gtccctgtct ctaaggtcgt cagcaccgac gaatacgtcg ccaggaccaa    240
catctactac cacgccggaa cctctaggct gctggccgtc ggacacccct acttccccat    300
caagaagccc aacaacaaca agatcctggt ccccaaggtg tccggactgc agtacagggt    360
gttcaggatc caccteceeg accccaacaa gttcggattc cccgacacct ctttctacaa    420
ccccgacacc cagaggctcg tctgggcctg cgtcggagtc gaagtcggaa ggggacagcc    480
cctgggagtc ggaatctctg gacaccccct gctgaacaag ctggacgaca ccgaaaacgc    540
ctctgcctac gccgccaacg ccggtgtcga acagggaa  tgcatctcta tggactacaa    600
gcagacccag ctgtgcctga tcggatgcaa gcccccatc  ggagaacact ggggaaaggg    660 atctcccctgc accaacgtcg ccgtcaaccc cggcgactgc ccccctctgg aactgatcaa    720
caccgtcatc caggacggcg acatggtcga caccggattc ggagccatgg acttcaccac    780
cctgcaggcc aacaagtctg aagtccccct ggacatctgc acctctatct gcaagtaccc    840
cgactacatc aagatggtgt ctgaacccta cggcgactct ctgttcttct acctgaggcg    900
cgaacagatg ttcgtcaggc acctcttcaa cagggccggt gccgtcggag aaaacgtccc    960
```

| | |
|---|---|
| cgacgacctg tacatcaagg gactgaacga catcttcgag gcccaaaaga tcgaatggca | 1020 |
| cgaggcctct tctaactact tccctacccc ttctggatct atggtcacct ctgacgccca | 1080 |
| gatcttcaac aagccctact ggctgcagag ggcccaggga cacaacaacg gaatctgctg | 1140 |
| gggaaaccag ctgttcgtca ccgtcgtcga caccaccagg tctaccaaca tgtccctgtg | 1200 |
| cgccgccatc tctacctctg aaaccaccta caagaacacc aacttcaaag aatacctgcg | 1260 |
| ccacggcgaa gaatacgacc tgcagttcat cttccagctg tgcaagatca ccctgaccgc | 1320 |
| cgacgtcatg acctacatcc actctatgaa ctctaccatc ttggaggatt ggaacttcgg | 1380 |
| actgcagccc cctcccggtg gaaccctcga ggacacctac cgcttcgtca ccagccaggc | 1440 |
| tatcgcctgc cagaagcaca ccccccctgc ccccaaagag gaccccctga agaagtacac | 1500 |
| cttctgggaa gtcaacctga agaaaaagtt ctctgccgac ctggaccagt tccccctggg | 1560 |
| acgcaagttc ctgctgcaag ccggactgaa ggccaagccc aagttcaccc tgggaaagag | 1620 |
| gaaggccacc cccaccacct cttctaccct taccaccgcc aagaggaaga agcgcaagct | 1680 |
| ggaactgtaa agcggccgc | 1699 |

<210> SEQ ID NO 15
<211> LENGTH: 1723
<212> TYPE: DNA
<213> ORGANISM: Human papillomavirus type 118

<400> SEQUENCE: 15

| | |
|---|---|
| gatatcatgg agataattaa aatgataacc atctcgcaaa taaataagta ttttactgtt | 60 |
| ttcgtaacag ttttgtaata aaaaaaccta taaatattcc ggattattca taccgtccca | 120 |
| ccatcgggcg cggatctcta ctagtatggc cgtctggcag gccgcctctg gaaaggtcta | 180 |
| cctgccccc tctaccccg tcgccaggt ccagtctacc gacgaatacg tcgaaaggac | 240 |
| caacatctac taccacgcct tcaccgacag gctgctgacc gtcggacacc cctacttcaa | 300 |
| catcttcaac aacgacggaa acaagctcga agtccccaag gtgtccggaa accagcacag | 360 |
| ggtgttcagg ctgaggctgc cgacccccaa ccgcttcgcc ctggccgaca tgtctgtcta | 420 |
| caaccccgac aaagaaaggc tcgtctgggc catcaccgga ctggaaatcg aaggggaca | 480 |
| gcccctggga gtcggaacct ctggacaccc cctgttcaac aagttcaacg acaccgaaaa | 540 |
| cggcaacaag tacaccaaca cctccaccga cgacaggcag aacatctctt tcgaccccaa | 600 |
| gcagctgcag atgttcatca tcggatgcac ccctgcatc ggagaacact gggacagggc | 660 |
| ccctgcctgc gtcgaggacg aacagctggg aaggtgcccc cccatcgaac tggtcaacac | 720 |
| cttcatccag gacgacgaca tggccgacat cggatacgga aacctgaact tcaaggccct | 780 |
| gcagcagaac cgctctgacg tgtccctgga catcgtcgac gaaatctgca gtaccccga | 840 |
| cttcctgaag atgcagaacg acgtctacgg cgacgcctgc ttcttctacg ctaggcgcga | 900 |
| acagtgctac gccaggcgct tcttcgtccg cggaggaaag cccggcgacg catcccgc | 960 |
| cgaacagatc gacgccggaa agctgaagaa cgaattctac atccctgccg ccggtggaca | 1020 |
| ggcccaggga cagctcggaa actctatgta cttccccacc gtcagcggat ctctcgtcag | 1080 |
| ctctgacgcc cagctgttca caggcccctt ggctgcag cgcgctcagg acacaacaa | 1140 |
| cggaatcctg tggggaaacc agttgttcgt caccgtcctg acaacaccc gcaacaccaa | 1200 |
| cttctctatc gccgtctact ctgagggact gaacgacatc ttcgaagccc aaaagatcga | 1260 |
| atggcacaga caggacattg ccaactacga ctcttctaag tctagggaat accagcgcca | 1320 |
| cgtcgaagag tacgaagtct ctatgatcct gcagctgtgc aagatccccc tgaagcccga | 1380 |

```
agtcctggcc cacatcaacg ccatgaaccc cgccatcttg gaggactggc agctgggatt    1440
catccccacc cccgacaacc ccatccacga cacctaccgc tacatcgact ccctggccac    1500
caggtgccct gacaaggtcc ccgccaaaga aaagaggac ccctacggca atacgtgtt     1560 ctggaacgtc gacctgtctg aaaggctgtc tctggacctg gaccagtacc ccctgggacg    1620
caagttcctg ttccaagccg gactgaggca gaagtctgtc aacggatctg tcaccaggac    1680
cgtcagcagg ggagccaaga ggaagcgcaa gtaaagcggc cgc                      1723

<210> SEQ ID NO 16
<211> LENGTH: 1723
<212> TYPE: DNA
<213> ORGANISM: Human papillomavirus type 118

<400> SEQUENCE: 16
gatatcatgg agataattaa aatgataacc atctcgcaaa taaataagta ttttactgtt    60
ttcgtaacag ttttgtaata aaaaaaccta taaatattcc ggattattca taccgtccca   120
ccatcgggcg cggatctcta ctagtatggc cgtctggcag gccgcctctg gaaaggtcta   180
cctgcccccc tctaccccg tcgccagggt ccagtctacc gacgaatacg tcgaaaggac    240
caacatctac taccacgcct tcaccgacag gctgctgacc gtcggacacc cctacttcaa   300
catcttcaac aacgacggaa acaagctcga agtccccaag gtgtccggaa accagcacag   360
ggtgttcagg ctgaggctgc cgaccccaa ccgcttcgcc ctggccgaca tgtctgtcta    420
caaccccgac aaagaaaggc tcgtctgggc catcaccgga ctggaaatcg aaggggaca    480 gcccctggga gtcggaacct ctggacaccc cctgttcaac aagttcaacg acaccgaaaa   540
cggcaacgga ctgaacgaca tcttcgaagc caaaagatc gaatggcacg agacctccac    600
cgacgacagg cagaacatct ctttcgaccc caagcagctg cagatgttca tcatcggatg   660 cacccctgc atcggagaac actgggacag ggcccctgcc tgcgtcgagg acgaacagct    720
gggaaggtgc ccccccatcg aactggtcaa caccttcatc caggacgacg acatggccga   780
catcggatac ggaaacctga acttcaaggc cctgcagcag aaccgctctg acgtgtccct   840
ggacatcgtc gacgaaatct gcaagtaccc cgacttcctg aagatgcaga acgacgtcta   900
cggcgacgcc tgcttcttct acgctaggcg cgaacagtgc tacgccaggc gcttcttcgt   960
ccgcggagga aagcccggcg acgacatccc cgccgaacag atcgacgccg aaagctgaa    1020 gaacgaattc tacatccctg ccgccggtgg acaggcccag ggacagctcg aaactctat   1080 gtacttcccc accgtcagcg gatctctcgt cagctctgac gcccagctgt caacaggcc    1140 cttctggctg cagcgcgctc agggacacaa caacggaatc ctgtggggaa accagttgtt    1200
cgtcaccgtc ctggacaaca cccgcaacac caacttctct atcgccgtct actctgaggc    1260
cggaaagatc caggacattg ccaactacga ctcttctaag tctagggaat accagcgcca    1320
cgtcgaagag tacgaagtct ctatgatcct gcagctgtgc aagatccccc tgaagcccga    1380
agtcctggcc cacatcaacg ccatgaaccc cgccatcttg gaggactggc agctgggatt    1440
catccccacc cccgacaacc ccatccacga cacctaccgc tacatcgact ccctggccac    1500
caggtgccct gacaaggtcc ccgccaaaga aaagaggac ccctacggca atacgtgtt     1560 ctggaacgtc gacctgtctg aaaggctgtc tctggacctg gaccagtacc ccctgggacg    1620
caagttcctg ttccaagccg gactgaggca gaagtctgtc aacggatctg tcaccaggac    1680
cgtcagcagg ggagccaaga ggaagcgcaa gtaaagcggc cgc                      1723
```

<210> SEQ ID NO 17
<211> LENGTH: 1693
<212> TYPE: DNA
<213> ORGANISM: European elk papillomavirus

<400> SEQUENCE: 17

```
gatatcatgg agataattaa aatgataacc atctcgcaaa taaataagta ttttactgtt      60
ttcgtaacag ttttgtaata aaaaaaccta taaatattcc ggattattca taccgtccca     120
ccatcgggcg cggatctcta ctagtatggc cttctggcag ccctctcagc gtctgtacct     180
gcccccacc cccgtcacca aggtcctgtg ctctgaacag tacatcaggc gcaaggacgt      240
gttctaccac ggcgaaaccg aaaggatgct gaccgtcgga caccctact acgaaatcaa      300
gcagtctgga tctggaaaga ccatccccaa ggtgtcccc aaccagtaca gggtgttcag      360
gatcctgctg cccgacccta accagttcgc cctgcccgac aaggctatgt acgacccctc      420
taaggaaagg ctcgtctggg ccgtcgtcgg agtccaggtg tcccgtggac agcctctggg     480
aggatctgtc tctggacact cttaccagaa caccctgatc gacgccgaaa acgtgtccgg     540
actgaacgac atcttcgaag cccaaaagat cgaatggcac gaacagggaa ccgacgaccg     600
caagcagggt ggaatggacg tcaagcagca gcagatcctg ctcctgggat gcaccccgc      660
catcggagaa tactggacca ccgccaggcc ctgcgtcacc gacaggcccg aaaccggatc     720
ttgccccccc atcgaactga gaacaagcc catcgaggac ggcgacatga tggacatcgg      780
attcggagcc gccaacttca ggaactgaa cgccaccaag tctgacctgc cctggacat      840
cgccaaggac atctgcctgt accccgacta cctgaagatg accgaagaag ccgccggaaa     900
ctctatgttc ttcttcgccc gcaaggaaca ggtctacgtc cgccacatct ggtcccgcgg     960
aggaaccgac aaggaaatgc ccccgaagc ctacttcctg aagcccaagg gtggcgacca    1020
gacccagaag atgccctcta tcctgttcgg agtccctct ggatctctcg tcagcaccga    1080
cggacagctg ttcaacaggc cctactggct gttcagggcc cagggaatga caacggaat     1140
ctgctggctg aaccagctgt tcgtcaccgt cggagacaac accaggggaa ccaccctgac    1200
catcaccgtc cccacctctg atccccct gaccgaatac gacacctcca gttcaacgt      1260
gttccagagg cacgtcgaag agtacaagct ggccttcgtg ttccagctgt gctctgtcac    1320
cctgtctccc gaaaccgtca gccacctcca gggactgatg ccttccatcc tggaacactg    1380
ggacatcaac atgcagcccc ccacctcttc tatcctcgag gacacctacc gctacctgga    1440
atctcctgcc accaagtgcg ccgacaacgt cacccccatg ggacccgagg accctacgc     1500
cggactgaag ttctgggaag tcaacctgaa ggaacgcctg tccctggacc tggaccagtt    1560
cccccctggga aggcgcttcc tggcccagca gggactggga tgctctaccc gcaagagggt    1620
cgcccccgtc cctaaggtca ccgaaaagag gatcgtccgc aagaggcgca agggaaacta    1680
aagcggccgc taa                                                      1693
```

<210> SEQ ID NO 18
<211> LENGTH: 787
<212> TYPE: PRT
<213> ORGANISM: Artificial sequence
<220> FEATURE:
<223> OTHER INFORMATION: Constructs
<220> FEATURE:
<221> NAME/KEY: MISC_FEATURE
<222> LOCATION: (1)..(787)
<223> OTHER INFORMATION: mSA- Her2-ECD[23]-686

<400> SEQUENCE: 18

```
Ala Glu Ala Gly Ile Thr Gly Thr Trp Tyr Asn Gln His Gly Ser Thr
1               5                   10                  15

Phe Thr Val Thr Ala Gly Ala Asp Gly Asn Leu Thr Gly Gln Tyr Glu
            20                  25                  30

Asn Arg Ala Gln Gly Thr Gly Cys Gln Asn Ser Pro Tyr Thr Leu Thr
        35                  40                  45

Gly Arg Tyr Asn Gly Thr Lys Leu Glu Trp Arg Val Glu Trp Asn Asn
    50                  55                  60

Ser Thr Glu Asn Cys His Ser Arg Thr Glu Trp Arg Gly Gln Tyr Gln
65              70                  75                  80

Gly Gly Ala Glu Ala Arg Ile Asn Thr Gln Trp Asn Leu Thr Tyr Glu
            85                  90                  95

Gly Gly Ser Gly Pro Ala Thr Glu Gln Gly Gln Asp Thr Phe Thr Lys
            100                 105                 110

Val Lys Gly Gly Ser Thr Gln Val Cys Thr Gly Thr Asp Met Lys Leu
            115                 120                 125

Arg Leu Pro Ala Ser Pro Glu Thr His Leu Asp Met Leu Arg His Leu
    130                 135                 140

Tyr Gln Gly Cys Gln Val Val Gln Gly Asn Leu Glu Leu Thr Tyr Leu
145                 150                 155                 160

Pro Thr Asn Ala Ser Leu Ser Phe Leu Gln Asp Ile Gln Glu Val Gln
                165                 170                 175

Gly Tyr Val Leu Ile Ala His Asn Gln Val Arg Gln Val Pro Leu Gln
            180                 185                 190

Arg Leu Arg Ile Val Arg Gly Thr Gln Leu Phe Glu Asp Asn Tyr Ala
    195                 200                 205

Leu Ala Val Leu Asp Asn Gly Asp Pro Leu Asn Asn Thr Thr Pro Val
210                 215                 220

Thr Gly Ala Ser Pro Gly Gly Leu Arg Glu Leu Gln Leu Arg Ser Leu
225                 230                 235                 240

Thr Glu Ile Leu Lys Gly Gly Val Leu Ile Gln Arg Asn Pro Gln Leu
                245                 250                 255

Cys Tyr Gln Asp Thr Ile Leu Trp Lys Asp Ile Phe His Lys Asn Asn
            260                 265                 270

Gln Leu Ala Leu Thr Leu Ile Asp Thr Asn Arg Ser Arg Ala Cys His
    275                 280                 285

Pro Cys Ser Pro Met Cys Lys Gly Ser Arg Cys Trp Gly Glu Ser Ser
    290                 295                 300

Glu Asp Cys Gln Ser Leu Thr Arg Thr Val Cys Ala Gly Gly Cys Ala
305                 310                 315                 320

Arg Cys Lys Gly Pro Leu Pro Thr Asp Cys Cys His Glu Gln Cys Ala
            325                 330                 335

Ala Gly Cys Thr Gly Pro Lys His Ser Asp Cys Leu Ala Cys Leu His
            340                 345                 350

Phe Asn His Ser Gly Ile Cys Glu Leu His Cys Pro Ala Leu Val Thr
        355                 360                 365

Tyr Asn Thr Asp Thr Phe Glu Ser Met Pro Asn Pro Glu Gly Arg Tyr
    370                 375                 380

Thr Phe Gly Ala Ser Cys Val Thr Ala Cys Pro Tyr Asn Tyr Leu Ser
385                 390                 395                 400

Thr Asp Val Gly Ser Cys Thr Leu Val Cys Pro Leu His Asn Gln Glu
            405                 410                 415
```

Val Thr Ala Glu Asp Gly Thr Gln Arg Cys Glu Lys Cys Ser Lys Pro
                420                 425                 430

Cys Ala Arg Val Cys Tyr Gly Leu Gly Met Glu His Leu Arg Glu Val
            435                 440                 445

Arg Ala Val Thr Ser Ala Asn Ile Gln Glu Phe Ala Gly Cys Lys Lys
        450                 455                 460

Ile Phe Gly Ser Leu Ala Phe Leu Pro Glu Ser Phe Asp Gly Asp Pro
465                 470                 475                 480

Ala Ser Asn Thr Ala Pro Leu Gln Pro Glu Gln Leu Gln Val Phe Glu
                485                 490                 495

Thr Leu Glu Glu Ile Thr Gly Tyr Leu Tyr Ile Ser Ala Trp Pro Asp
            500                 505                 510

Ser Leu Pro Asp Leu Ser Val Phe Gln Asn Leu Gln Val Ile Arg Gly
        515                 520                 525

Arg Ile Leu His Asn Gly Ala Tyr Ser Leu Thr Leu Gln Gly Leu Gly
        530                 535                 540

Ile Ser Trp Leu Gly Leu Arg Ser Leu Arg Glu Leu Gly Ser Gly Leu
545                 550                 555                 560

Ala Leu Ile His His Asn Thr His Leu Cys Phe Val His Thr Val Pro
                565                 570                 575

Trp Asp Gln Leu Phe Arg Asn Pro His Gln Ala Leu Leu His Thr Ala
            580                 585                 590

Asn Arg Pro Glu Asp Glu Cys Val Gly Glu Gly Leu Ala Cys His Gln
        595                 600                 605

Leu Cys Ala Arg Gly His Cys Trp Gly Pro Gly Pro Thr Gln Cys Val
610                 615                 620

Asn Cys Ser Gln Phe Leu Arg Gly Gln Glu Cys Val Glu Glu Cys Arg
625                 630                 635                 640

Val Leu Gln Gly Leu Pro Arg Glu Tyr Val Asn Ala Arg His Cys Leu
                645                 650                 655

Pro Cys His Pro Glu Cys Gln Pro Gln Asn Gly Ser Val Thr Cys Phe
            660                 665                 670

Gly Pro Glu Ala Asp Gln Cys Val Ala Cys Ala His Tyr Lys Asp Pro
        675                 680                 685

Pro Phe Cys Val Ala Arg Cys Pro Ser Gly Val Lys Pro Asp Leu Ser
        690                 695                 700

Tyr Met Pro Ile Trp Lys Phe Pro Asp Glu Glu Gly Ala Cys Gln Pro
705                 710                 715                 720

Cys Pro Ile Asn Cys Thr His Ser Cys Val Asp Leu Asp Asp Lys Gly
                725                 730                 735

Cys Pro Ala Glu Gln Arg Ala Ser Pro Leu Thr Ser Ile Ile Ser Ala
            740                 745                 750

Val Val Gly Ile Leu Leu Val Val Leu Gly Val Val Phe Gly Ile
        755                 760                 765

Leu Ile Lys Arg Arg Gln Gln Lys Ile Arg Lys Tyr Thr His His His
        770                 775                 780

His His His
785

<210> SEQ ID NO 19
<211> LENGTH: 236
<212> TYPE: PRT
<213> ORGANISM: Artificial sequence
<220> FEATURE:
<223> OTHER INFORMATION: Constructs

```
<220> FEATURE:
<221> NAME/KEY: MISC_FEATURE
<222> LOCATION: (1)..(236)
<223> OTHER INFORMATION: mSA-IL-5(C63T/C105T)

<400> SEQUENCE: 19

Ala Glu Ala Gly Ile Thr Gly Thr Trp Tyr Asn Gln His Gly Ser Thr
1               5                   10                  15

Phe Thr Val Thr Ala Gly Ala Asp Gly Asn Leu Thr Gly Gln Tyr Glu
            20                  25                  30

Asn Arg Ala Gln Gly Thr Gly Cys Gln Asn Ser Pro Tyr Thr Leu Thr
        35                  40                  45

Gly Arg Tyr Asn Gly Thr Lys Leu Glu Trp Arg Val Glu Trp Asn Asn
    50                  55                  60

Ser Thr Glu Asn Cys His Ser Arg Thr Glu Trp Arg Gly Gln Tyr Gln
65              70                  75                  80

Gly Gly Ala Glu Ala Arg Ile Asn Thr Gln Trp Asn Leu Thr Tyr Glu
                85                  90                  95

Gly Gly Ser Gly Pro Ala Thr Glu Gln Gly Gln Asp Thr Phe Thr Lys
            100                 105                 110

Val Lys Gly Gly Ser Ile Pro Thr Glu Ile Pro Thr Ser Ala Leu Val
        115                 120                 125

Lys Glu Thr Leu Ala Leu Leu Ser Thr His Arg Thr Leu Leu Ile Ala
130                 135                 140

Asn Glu Thr Leu Arg Ile Pro Val Pro Val His Lys Asn His Gln Leu
145                 150                 155                 160

Thr Thr Glu Glu Ile Phe Gln Gly Ile Gly Thr Leu Glu Ser Gln Thr
                165                 170                 175

Val Gln Gly Gly Thr Val Glu Arg Leu Phe Lys Asn Leu Ser Leu Ile
            180                 185                 190

Lys Lys Tyr Ile Asp Gly Gln Lys Lys Lys Thr Gly Glu Glu Arg Arg
        195                 200                 205

Arg Val Asn Gln Phe Leu Asp Tyr Leu Gln Glu Phe Leu Gly Val Met
    210                 215                 220

Asn Thr Glu Trp Ile Ile Glu Ser Ser Gly Arg Lys
225                 230                 235

<210> SEQ ID NO 20
<211> LENGTH: 785
<212> TYPE: PRT
<213> ORGANISM: Artificial sequence
<220> FEATURE:
<223> OTHER INFORMATION: Constructs
<220> FEATURE:
<221> NAME/KEY: MISC_FEATURE
<222> LOCATION: (1)..(785)
<223> OTHER INFORMATION: PCSK9[31]-692[:m]SA:HIS

<400> SEQUENCE: 20

Gln Glu Asp Glu Asp Gly Asp Tyr Glu Glu Leu Val Leu Ala Leu Arg
1               5                   10                  15

Ser Glu Glu Asp Gly Leu Ala Glu Ala Pro Glu His Gly Thr Thr Ala
            20                  25                  30

Thr Phe His Arg Cys Ala Lys Asp Pro Trp Arg Leu Pro Gly Thr Tyr
        35                  40                  45

Val Val Val Leu Lys Glu Glu Thr His Leu Ser Gln Ser Glu Arg Thr
    50                  55                  60

Ala Arg Arg Leu Gln Ala Gln Ala Ala Arg Arg Gly Tyr Leu Thr Lys
```

-continued

```
                65                  70                  75                  80
Ile Leu His Val Phe His Gly Leu Leu Pro Gly Phe Leu Val Lys Met
                    85                  90                  95
Ser Gly Asp Leu Leu Glu Leu Ala Leu Lys Leu Pro His Val Asp Tyr
                    100                 105                 110
Ile Glu Glu Asp Ser Ser Val Phe Ala Gln Ser Ile Pro Trp Asn Leu
                    115                 120                 125
Glu Arg Ile Thr Pro Pro Arg Tyr Arg Ala Asp Glu Tyr Gln Pro Pro
                    130                 135                 140
Asp Gly Gly Ser Leu Val Glu Val Tyr Leu Leu Asp Thr Ser Ile Gln
145                 150                 155                 160
Ser Asp His Arg Glu Ile Glu Gly Arg Val Met Val Thr Asp Phe Glu
                    165                 170                 175
Asn Val Pro Glu Glu Asp Gly Thr Arg Phe His Arg Gln Ala Ser Lys
                    180                 185                 190
Cys Asp Ser His Gly Thr His Leu Ala Gly Val Val Ser Gly Arg Asp
                    195                 200                 205
Ala Gly Val Ala Lys Gly Ala Ser Met Arg Ser Leu Arg Val Leu Asn
210                 215                 220
Cys Gln Gly Lys Gly Thr Val Ser Gly Thr Leu Ile Gly Leu Glu Phe
225                 230                 235                 240
Ile Arg Lys Ser Gln Leu Val Gln Pro Val Gly Pro Leu Val Val Leu
                    245                 250                 255
Leu Pro Leu Ala Gly Gly Tyr Ser Arg Val Leu Asn Ala Ala Cys Gln
                    260                 265                 270
Arg Leu Ala Arg Ala Gly Val Val Leu Val Thr Ala Ala Gly Asn Phe
                    275                 280                 285
Arg Asp Asp Ala Cys Leu Tyr Ser Pro Ala Ser Ala Pro Glu Val Ile
                    290                 295                 300
Thr Val Gly Ala Thr Asn Ala Gln Asp Gln Pro Val Thr Leu Gly Thr
305                 310                 315                 320
Leu Gly Thr Asn Phe Gly Arg Cys Val Asp Leu Phe Ala Pro Gly Glu
                    325                 330                 335
Asp Ile Ile Gly Ala Ser Ser Asp Cys Ser Thr Cys Phe Val Ser Gln
                    340                 345                 350
Ser Gly Thr Ser Gln Ala Ala Ala His Val Ala Gly Ile Ala Ala Met
                    355                 360                 365
Met Leu Ser Ala Glu Pro Glu Leu Thr Leu Ala Glu Leu Arg Gln Arg
                    370                 375                 380
Leu Ile His Phe Ser Ala Lys Asp Val Ile Asn Glu Ala Trp Phe Pro
385                 390                 395                 400
Glu Asp Gln Arg Val Leu Thr Pro Asn Leu Val Ala Ala Leu Pro Pro
                    405                 410                 415
Ser Thr His Gly Ala Gly Trp Gln Leu Phe Cys Arg Thr Val Trp Ser
                    420                 425                 430
Ala His Ser Gly Pro Thr Arg Met Ala Thr Ala Val Ala Arg Cys Ala
                    435                 440                 445
Pro Asp Glu Glu Leu Leu Ser Cys Ser Ser Phe Ser Arg Ser Gly Lys
                    450                 455                 460
Arg Arg Gly Glu Arg Met Glu Ala Gln Gly Gly Lys Leu Val Cys Arg
465                 470                 475                 480
Ala His Asn Ala Phe Gly Gly Glu Gly Val Tyr Ala Ile Ala Arg Cys
                    485                 490                 495
```

```
Cys Leu Leu Pro Gln Ala Asn Cys Ser Val His Thr Ala Pro Pro Ala
            500                 505                 510

Glu Ala Ser Met Gly Thr Arg Val His Cys His Gln Gly His Val
        515                 520                 525

Leu Thr Gly Cys Ser Ser His Trp Glu Val Asp Leu Gly Thr His
    530                 535                 540

Lys Pro Pro Val Leu Arg Pro Arg Gly Gln Pro Asn Gln Cys Val Gly
545                 550                 555                 560

His Arg Glu Ala Ser Ile His Ala Ser Cys Cys His Ala Pro Gly Leu
                565                 570                 575

Glu Cys Lys Val Lys Glu His Gly Ile Pro Ala Pro Gln Glu Gln Val
            580                 585                 590

Thr Val Ala Cys Glu Glu Gly Trp Thr Leu Thr Gly Cys Ser Ala Leu
        595                 600                 605

Pro Gly Thr Ser His Val Leu Gly Ala Tyr Ala Val Asp Asn Thr Cys
    610                 615                 620

Val Val Arg Ser Arg Asp Val Ser Thr Thr Gly Ser Thr Ser Glu Gly
625                 630                 635                 640

Ala Val Thr Ala Val Ala Ile Cys Cys Arg Ser Arg His Leu Ala Gln
                645                 650                 655

Ala Ser Gln Glu Leu Gln Gly Gly Ser Ala Glu Ala Gly Ile Thr Gly
            660                 665                 670

Thr Trp Tyr Asn Gln His Gly Ser Thr Phe Thr Val Thr Ala Gly Ala
        675                 680                 685

Asp Gly Asn Leu Thr Gly Gln Tyr Glu Asn Arg Ala Gln Gly Thr Gly
    690                 695                 700

Cys Gln Asn Ser Pro Tyr Thr Leu Thr Gly Arg Tyr Asn Gly Thr Lys
705                 710                 715                 720

Leu Glu Trp Arg Val Glu Trp Asn Asn Ser Thr Glu Asn Cys His Ser
                725                 730                 735

Arg Thr Glu Trp Arg Gly Gln Tyr Gln Gly Gly Ala Glu Ala Arg Ile
            740                 745                 750

Asn Thr Gln Trp Asn Leu Thr Tyr Glu Gly Gly Ser Gly Pro Ala Thr
        755                 760                 765

Glu Gln Gly Gln Asp Thr Phe Thr Lys Val Lys His His His His His
    770                 775                 780

His
785

<210> SEQ ID NO 21
<211> LENGTH: 763
<212> TYPE: PRT
<213> ORGANISM: Artificial sequence
<220> FEATURE:
<223> OTHER INFORMATION: Constructs
<220> FEATURE:
<221> NAME/KEY: MISC_FEATURE
<222> LOCATION: (1)..(763)
<223> OTHER INFORMATION: mSA-ID1ID2a-HIS

<400> SEQUENCE: 21

Ala Glu Ala Gly Ile Thr Gly Thr Trp Tyr Asn Gln His Gly Ser Thr
1               5                   10                  15

Phe Thr Val Thr Ala Gly Ala Asp Gly Asn Leu Thr Gly Gln Tyr Glu
            20                  25                  30

Asn Arg Ala Gln Gly Thr Gly Cys Gln Asn Ser Pro Tyr Thr Leu Thr
```

```
            35                  40                  45
Gly Arg Tyr Asn Gly Thr Lys Leu Glu Trp Arg Val Glu Trp Asn Asn
 50                  55                  60

Ser Thr Glu Asn Cys His Ser Arg Thr Glu Trp Arg Gly Gln Tyr Gln
 65                  70                  75                  80

Gly Gly Ala Glu Ala Arg Ile Asn Thr Gln Trp Asn Leu Thr Tyr Glu
                 85                  90                  95

Gly Gly Ser Gly Pro Ala Thr Glu Gln Gly Gln Asp Thr Phe Thr Lys
                100                 105                 110

Val Lys Gly Gly Ser Asn Tyr Ile Lys Gly Asp Pro Tyr Phe Ala Glu
                115                 120                 125

Tyr Ala Thr Lys Leu Ser Phe Ile Leu Asn Pro Ser Asp Ala Asn Asn
130                 135                 140

Pro Ser Gly Glu Thr Ala Asn His Asn Asp Glu Ala Cys Asn Cys Asn
145                 150                 155                 160

Glu Ser Gly Ile Ser Ser Val Gly Gln Ala Gln Thr Ser Gly Pro Ser
                165                 170                 175

Ser Asn Lys Thr Cys Ile Thr His Ser Ser Ile Lys Thr Asn Lys Lys
                180                 185                 190

Lys Glu Cys Lys Asp Val Lys Leu Gly Val Arg Glu Asn Asp Lys Asp
                195                 200                 205

Leu Lys Ile Cys Val Ile Glu Asp Thr Ser Leu Ser Gly Val Asp Asn
210                 215                 220

Cys Cys Cys Gln Asp Leu Leu Gly Ile Leu Gln Glu Asn Cys Ser Asp
225                 230                 235                 240

Asn Lys Arg Gly Ser Ser Asn Asp Ser Cys Asp Asn Lys Asn Gln
                245                 250                 255

Asp Glu Cys Gln Lys Lys Leu Glu Lys Val Phe Ala Ser Leu Thr Asn
                260                 265                 270

Gly Tyr Lys Cys Asp Lys Cys Lys Ser Gly Thr Ser Arg Ser Lys Lys
                275                 280                 285

Lys Trp Ile Trp Lys Lys Ser Ser Gly Asn Glu Glu Gly Leu Gln Glu
                290                 295                 300

Glu Tyr Ala Asn Thr Ile Gly Leu Pro Pro Arg Thr Gln Ser Leu Tyr
305                 310                 315                 320

Leu Gly Asn Leu Pro Lys Leu Glu Asn Val Cys Glu Asp Val Lys Asp
                325                 330                 335

Ile Asn Phe Asp Thr Lys Glu Lys Phe Leu Ala Gly Cys Leu Ile Val
                340                 345                 350

Ser Phe His Glu Gly Lys Asn Leu Lys Lys Arg Tyr Pro Gln Asn Lys
                355                 360                 365

Asn Ser Gly Asn Lys Glu Asn Leu Cys Lys Ala Leu Glu Tyr Ser Phe
                370                 375                 380

Ala Asp Tyr Gly Asp Leu Ile Lys Gly Thr Ser Ile Trp Asp Asn Glu
385                 390                 395                 400

Tyr Thr Lys Asp Leu Glu Leu Asn Leu Gln Asn Asn Phe Gly Lys Leu
                405                 410                 415

Phe Gly Lys Tyr Ile Lys Lys Asn Asn Thr Ala Glu Gln Asp Thr Ser
                420                 425                 430

Tyr Ser Ser Leu Asp Glu Leu Arg Glu Ser Trp Trp Asn Thr Asn Lys
                435                 440                 445

Lys Tyr Ile Trp Thr Ala Met Lys His Gly Ala Glu Met Asn Ile Thr
450                 455                 460
```

```
Thr Cys Asn Ala Asp Gly Ser Val Thr Gly Ser Gly Ser Cys Asp
465                 470                 475                 480

Asp Ile Pro Thr Ile Asp Leu Ile Pro Gln Tyr Leu Arg Phe Leu Gln
            485                 490                 495

Glu Trp Val Glu Asn Phe Cys Glu Gln Arg Gln Ala Lys Val Lys Asp
            500                 505                 510

Val Ile Thr Asn Cys Lys Ser Cys Lys Glu Ser Gly Asn Lys Cys Lys
            515                 520                 525

Thr Glu Cys Lys Thr Lys Cys Lys Asp Glu Cys Glu Lys Tyr Lys Lys
            530                 535                 540

Phe Ile Glu Ala Cys Gly Thr Ala Gly Gly Ile Gly Thr Ala Gly
545                 550                 555                 560

Ser Pro Trp Ser Lys Arg Trp Asp Gln Ile Tyr Lys Arg Tyr Ser Lys
                565                 570                 575

His Ile Glu Asp Ala Lys Arg Asn Arg Lys Ala Gly Thr Lys Asn Cys
            580                 585                 590

Gly Thr Ser Ser Thr Thr Asn Ala Ala Ala Ser Thr Asp Glu Asn Lys
            595                 600                 605

Cys Val Gln Ser Asp Ile Asp Ser Phe Phe Lys His Leu Ile Asp Ile
610                 615                 620

Gly Leu Thr Thr Pro Ser Ser Tyr Leu Ser Asn Val Leu Asp Asp Asn
625                 630                 635                 640

Ile Cys Gly Ala Asp Lys Ala Pro Trp Thr Thr Tyr Thr Thr Tyr Thr
                645                 650                 655

Thr Thr Glu Lys Cys Asn Lys Glu Arg Asp Lys Ser Lys Ser Gln Ser
            660                 665                 670

Ser Asp Thr Leu Val Val Val Asn Val Pro Ser Pro Leu Gly Asn Thr
            675                 680                 685

Pro Tyr Arg Tyr Lys Tyr Ala Cys Gln Cys Lys Ile Pro Thr Asn Glu
            690                 695                 700

Glu Thr Cys Asp Asp Arg Lys Glu Tyr Met Asn Gln Trp Ser Cys Gly
705                 710                 715                 720

Ser Ala Arg Thr Met Lys Arg Gly Tyr Lys Asn Asp Asn Tyr Glu Leu
                725                 730                 735

Cys Lys Tyr Asn Gly Val Asp Val Lys Pro Thr Thr Val Arg Ser Asn
            740                 745                 750

Ser Ser Lys Leu Asp His His His His His His
            755                 760

<210> SEQ ID NO 22
<211> LENGTH: 773
<212> TYPE: PRT
<213> ORGANISM: Artificial sequence
<220> FEATURE:
<223> OTHER INFORMATION: Constructs
<220> FEATURE:
<221> NAME/KEY: MISC_FEATURE
<222> LOCATION: (1)..(773)
<223> OTHER INFORMATION: mSA-RO-HIS

<400> SEQUENCE: 22

Ala Glu Ala Gly Ile Thr Gly Thr Trp Tyr Asn Gln His Gly Ser Thr
1               5                   10                  15

Phe Thr Val Thr Ala Gly Ala Asp Gly Asn Leu Thr Gly Gln Tyr Glu
            20                  25                  30

Asn Arg Ala Gln Gly Thr Gly Cys Gln Asn Ser Pro Tyr Thr Leu Thr
```

-continued

```
               35                  40                  45
Gly Arg Tyr Asn Gly Thr Lys Leu Glu Trp Arg Val Glu Trp Asn Asn
 50                  55                  60
Ser Thr Glu Asn Cys His Ser Arg Thr Glu Trp Arg Gly Gln Tyr Gln
 65                  70                  75                  80
Gly Gly Ala Glu Ala Arg Ile Asn Thr Gln Trp Asn Leu Thr Tyr Glu
                 85                  90                  95
Gly Gly Ser Gly Pro Ala Thr Glu Gln Gly Gln Asp Thr Phe Thr Lys
                100                 105                 110
Val Lys Gly Gly Ser Thr Ser Glu Asn Arg Asn Lys Arg Ile Gly Gly
            115                 120                 125
Pro Lys Leu Arg Gly Asn Val Thr Ser Asn Ile Lys Phe Pro Ser Asp
            130                 135                 140
Asn Lys Gly Lys Ile Ile Arg Gly Ser Asn Asp Lys Leu Asn Lys Asn
145                 150                 155                 160
Ser Glu Asp Val Leu Glu Gln Ser Glu Lys Ser Leu Val Ser Glu Asn
                165                 170                 175
Val Pro Ser Gly Leu Asp Ile Asp Ile Pro Lys Glu Ser Ile Phe
            180                 185                 190
Ile Gln Glu Asp Gln Glu Gly Gln Thr His Ser Glu Leu Asn Pro Glu
            195                 200                 205
Thr Ser Glu His Ser Lys Asp Leu Asn Asn Gly Ser Lys Asn Glu
210                 215                 220
Ser Ser Asp Ile Ile Ser Glu Asn Asn Lys Ser Asn Lys Val Gln Asn
225                 230                 235                 240
His Phe Glu Ser Leu Ser Asp Leu Glu Leu Leu Glu Asn Ser Ser Gln
                245                 250                 255
Asp Asn Leu Asp Lys Asp Thr Ile Ser Thr Glu Pro Phe Pro Asn Gln
            260                 265                 270
Lys His Lys Asp Leu Gln Gln Asp Leu Asn Asp Glu Pro Leu Glu Pro
            275                 280                 285
Phe Pro Thr Gln Ile His Lys Asp Tyr Lys Glu Lys Asn Leu Ile Asn
            290                 295                 300
Glu Glu Asp Ser Glu Pro Phe Pro Arg Gln Lys His Lys Lys Val Asp
305                 310                 315                 320
Asn His Asn Glu Glu Lys Asn Val Phe His Glu Asn Gly Ser Ala Asn
                325                 330                 335
Gly Asn Gln Gly Ser Leu Lys Leu Lys Ser Phe Asp Glu His Leu Lys
            340                 345                 350
Asp Glu Lys Ile Glu Asn Glu Pro Leu Val His Glu Asn Leu Ser Ile
            355                 360                 365
Pro Asn Asp Pro Ile Glu Gln Ile Leu Asn Gln Pro Glu Gln Glu Thr
            370                 375                 380
Asn Ile Gln Glu Gln Leu Tyr Asn Glu Lys Gln Asn Val Glu Glu Lys
385                 390                 395                 400
Gln Asn Ser Gln Ile Pro Ser Leu Asp Leu Lys Glu Pro Thr Asn Glu
                405                 410                 415
Asp Ile Leu Pro Asn His Asn Pro Leu Glu Asn Ile Lys Gln Ser Glu
            420                 425                 430
Ser Glu Ile Asn His Val Gln Asp His Ala Leu Pro Lys Glu Asn Ile
            435                 440                 445
Ile Asp Lys Leu Asp Asn Gln Lys Glu His Ile Asp Gln Ser Gln His
            450                 455                 460
```

```
Asn Ile Asn Val Leu Gln Glu Asn Asn Ile Asn Asn His Gln Leu Glu
465                 470                 475                 480

Pro Gln Glu Lys Pro Asn Ile Glu Ser Phe Glu Pro Lys Asn Ile Asp
                485                 490                 495

Ser Glu Ile Ile Leu Pro Glu Asn Val Glu Thr Glu Glu Ile Ile Asp
            500                 505                 510

Asp Val Pro Ser Pro Lys His Ser Asn His Glu Thr Phe Glu Glu Glu
        515                 520                 525

Thr Ser Glu Ser Glu His Glu Glu Ala Val Ser Glu Lys Asn Ala His
    530                 535                 540

Glu Thr Val Glu His Glu Thr Val Ser Gln Glu Ser Asn Pro Glu
545                 550                 555                 560

Lys Ala Asp Asn Asp Gly Asn Val Ser Gln Asn Ser Asn Asn Glu Leu
                565                 570                 575

Asn Glu Asn Glu Phe Val Glu Ser Glu Lys Ser Glu His Glu Ala Arg
            580                 585                 590

Ser Lys Ala Lys Glu Ala Ser Ser Tyr Asp Tyr Ile Leu Gly Trp Glu
        595                 600                 605

Phe Gly Gly Val Pro Glu His Lys Lys Glu Glu Asn Met Leu Ser
610                 615                 620

His Leu Tyr Val Ser Ser Lys Asp Lys Glu Asn Ile Ser Lys Glu Asn
625                 630                 635                 640

Asp Asp Val Leu Asp Glu Lys Glu Glu Ala Glu Glu Thr Glu Glu
                645                 650                 655

Glu Glu Leu Glu Glu Lys Asn Glu Glu Thr Glu Ser Glu Ile Ser
            660                 665                 670

Glu Asp Glu Glu Glu Glu Glu Glu Glu Lys Glu Glu Glu Asn
        675                 680                 685

Asp Lys Lys Lys Glu Gln Glu Lys Glu Gln Ser Asn Glu Asn Asn Asp
        690                 695                 700

Gln Lys Lys Asp Met Glu Ala Gln Asn Leu Ile Ser Lys Asn Gln Asn
705                 710                 715                 720

Asn Asn Glu Lys Asn Val Lys Glu Ala Ala Glu Ser Ile Met Lys Thr
                725                 730                 735

Leu Ala Gly Leu Ile Lys Gly Asn Asn Gln Ile Asp Ser Thr Leu Lys
            740                 745                 750

Asp Leu Val Glu Glu Leu Ser Lys Tyr Phe Lys Asn His Arg Ser His
        755                 760                 765

His His His His
    770

<210> SEQ ID NO 23
<211> LENGTH: 594
<212> TYPE: PRT
<213> ORGANISM: Artificial sequence
<220> FEATURE:
<223> OTHER INFORMATION: Constructs
<220> FEATURE:
<221> NAME/KEY: MISC_FEATURE
<222> LOCATION: (1)..(594)
<223> OTHER INFORMATION: HIS-RO-mSA

<400> SEQUENCE: 23

Gly Ser Thr Ser Glu Asn Arg Asn Lys Arg Ile Gly Gly Pro Lys Leu
1               5                   10                  15

Arg Gly Asn Val Thr Ser Asn Ile Lys Phe Pro Ser Asp Asn Lys Gly
```

```
            20                  25                  30
Lys Ile Ile Arg Gly Ser Asn Asp Lys Leu Asn Lys Asn Ser Glu Asp
        35                  40                  45
Val Leu Glu Gln Ser Glu Lys Ser Leu Val Ser Glu Asn Val Pro Ser
    50                  55                  60
Gly Leu Asp Ile Asp Ile Pro Lys Glu Ser Ile Phe Ile Gln Glu
65                  70                  75                  80
Asp Gln Glu Gly Gln Thr His Ser Glu Leu Asn Pro Glu Thr Ser Glu
                85                  90                  95
His Ser Lys Asp Leu Asn Asn Asn Gly Ser Lys Asn Glu Ser Ser Asp
            100                 105                 110
Ile Ile Ser Glu Asn Asn Lys Ser Asn Lys Val Gln Asn His Phe Glu
        115                 120                 125
Ser Leu Ser Asp Leu Glu Leu Leu Glu Asn Ser Ser Gln Asp Asn Leu
    130                 135                 140
Asp Lys Asp Thr Ile Ser Thr Glu Pro Phe Pro Asn Gln Lys His Lys
145                 150                 155                 160
Asp Leu Gln Gln Asp Leu Asn Asp Glu Pro Leu Glu Pro Phe Pro Thr
                165                 170                 175
Gln Ile His Lys Asp Tyr Lys Glu Lys Asn Leu Ile Asn Glu Glu Asp
            180                 185                 190
Ser Glu Pro Phe Pro Arg Gln Lys His Lys Lys Val Asp Asn His Asn
        195                 200                 205
Glu Glu Lys Asn Val Phe His Glu Asn Gly Ser Ala Asn Gly Asn Gln
    210                 215                 220
Gly Ser Leu Lys Leu Lys Ser Phe Asp Glu His Leu Lys Asp Glu Lys
225                 230                 235                 240
Ile Glu Asn Glu Pro Leu Val His Glu Asn Leu Ser Ile Pro Asn Asp
                245                 250                 255
Pro Ile Glu Gln Ile Leu Asn Gln Pro Glu Gln Glu Thr Asn Ile Gln
            260                 265                 270
Glu Gln Leu Tyr Asn Glu Lys Gln Asn Val Glu Glu Lys Gln Asn Ser
        275                 280                 285
Gln Ile Pro Ser Leu Asp Leu Lys Glu Pro Thr Asn Glu Asp Ile Leu
    290                 295                 300
Pro Asn His Asn Pro Leu Glu Asn Ile Lys Gln Ser Glu Ser Glu Ile
305                 310                 315                 320
Asn His Val Gln Asp His Ala Leu Pro Lys Glu Asn Ile Ile Asp Lys
                325                 330                 335
Leu Asp Asn Gln Lys Glu His Ile Asp Gln Ser Gln His Asn Ile Asn
            340                 345                 350
Val Leu Gln Glu Asn Asn Ile Asn His Gln Leu Glu Pro Gln Glu
        355                 360                 365
Lys Pro Asn Ile Glu Ser Phe Glu Pro Lys Asn Ile Asp Ser Glu Ile
    370                 375                 380
Ile Leu Pro Glu Asn Val Glu Thr Glu Glu Ile Ile Asp Asp Val Pro
385                 390                 395                 400
Ser Pro Lys His Ser Asn His Glu Thr Phe Glu Glu Glu Thr Ser Glu
                405                 410                 415
Ser Glu His Glu Glu Ala Val Ser Glu Lys Asn Ala His Glu Thr Val
            420                 425                 430
Glu His Glu Glu Thr Val Ser Gln Glu Ser Asn Pro Glu Lys Ala Asp
        435                 440                 445
```

-continued

```
Asn Asp Gly Asn Val Ser Gln Asn Ser Asn Asn Glu Leu Asn Glu Asn
        450                 455                 460

Glu Phe Val Glu Ser Glu Lys Ser Glu His Glu Ala Gly Gly Ser Gly
465                 470                 475                 480

Ala Glu Ala Gly Ile Thr Gly Thr Trp Tyr Asn Gln His Gly Ser Thr
                485                 490                 495

Phe Thr Val Thr Ala Gly Ala Asp Gly Asn Leu Thr Gly Gln Tyr Glu
                500                 505                 510

Asn Arg Ala Gln Gly Thr Gly Cys Gln Asn Ser Pro Tyr Thr Leu Thr
            515                 520                 525

Gly Arg Tyr Asn Gly Thr Lys Leu Glu Trp Arg Val Glu Trp Asn Asn
        530                 535                 540

Ser Thr Glu Asn Cys His Ser Arg Thr Glu Trp Arg Gly Gln Tyr Gln
545                 550                 555                 560

Gly Gly Ala Glu Ala Arg Ile Asn Thr Gln Trp Asn Leu Thr Tyr Glu
                565                 570                 575

Gly Gly Ser Gly Pro Ala Thr Glu Gln Gly Gln Asp Thr Phe Thr Lys
            580                 585                 590

Val Lys

<210> SEQ ID NO 24
<211> LENGTH: 768
<212> TYPE: PRT
<213> ORGANISM: Artificial sequence
<220> FEATURE:
<223> OTHER INFORMATION: Constructs
<220> FEATURE:
<221> NAME/KEY: MISC_FEATURE
<222> LOCATION: (1)..(768)
<223> OTHER INFORMATION: HIS-GMZ2ggsmSA

<400> SEQUENCE: 24

Gly Ser Thr Ser Glu Asn Arg Asn Lys Arg Ile Gly Gly Pro Lys Leu
1               5                   10                  15

Arg Gly Asn Val Thr Ser Asn Ile Lys Phe Pro Ser Asp Asn Lys Gly
                20                  25                  30

Lys Ile Ile Arg Gly Ser Asn Asp Lys Leu Asn Lys Asn Ser Glu Asp
            35                  40                  45

Val Leu Glu Gln Ser Glu Lys Ser Leu Val Ser Glu Asn Val Pro Ser
        50                  55                  60

Gly Leu Asp Ile Asp Asp Ile Pro Lys Glu Ser Ile Phe Ile Gln Glu
65                  70                  75                  80

Asp Gln Glu Gly Gln Thr His Ser Glu Leu Asn Pro Glu Thr Ser Glu
                85                  90                  95

His Ser Lys Asp Leu Asn Asn Gly Ser Lys Asn Glu Ser Ser Asp
                100                 105                 110

Ile Ile Ser Glu Asn Asn Lys Ser Asn Lys Val Gln Asn His Phe Glu
            115                 120                 125

Ser Leu Ser Asp Leu Glu Leu Leu Glu Asn Ser Ser Gln Asp Asn Leu
        130                 135                 140

Asp Lys Asp Thr Ile Ser Thr Glu Pro Phe Pro Asn Gln Lys His Lys
145                 150                 155                 160

Asp Leu Gln Gln Asp Leu Asn Asp Glu Pro Leu Glu Pro Phe Pro Thr
                165                 170                 175

Gln Ile His Lys Asp Tyr Lys Glu Lys Asn Leu Ile Asn Glu Glu Asp
            180                 185                 190
```

```
Ser Glu Pro Phe Pro Arg Gln Lys His Lys Val Asp Asn His Asn
    195                 200                 205
Glu Glu Lys Asn Val Phe His Glu Asn Gly Ser Ala Asn Gly Asn Gln
210                 215                 220
Gly Ser Leu Lys Leu Lys Ser Phe Asp Glu His Leu Lys Asp Glu Lys
225                 230                 235                 240
Ile Glu Asn Glu Pro Leu Val His Glu Asn Leu Ser Ile Pro Asn Asp
                245                 250                 255
Pro Ile Glu Gln Ile Leu Asn Gln Pro Gln Glu Thr Asn Ile Gln
            260                 265                 270
Glu Gln Leu Tyr Asn Glu Lys Gln Asn Val Glu Glu Lys Gln Asn Ser
                275                 280                 285
Gln Ile Pro Ser Leu Asp Leu Lys Glu Pro Thr Asn Glu Asp Ile Leu
        290                 295                 300
Pro Asn His Asn Pro Leu Glu Asn Ile Lys Gln Ser Glu Ser Glu Ile
305                 310                 315                 320
Asn His Val Gln Asp His Ala Leu Pro Lys Glu Asn Ile Ile Asp Lys
                325                 330                 335
Leu Asp Asn Gln Lys Glu His Ile Asp Gln Ser Gln His Asn Ile Asn
            340                 345                 350
Val Leu Gln Glu Asn Asn Ile Asn Asn His Gln Leu Glu Pro Gln Glu
                355                 360                 365
Lys Pro Asn Ile Glu Ser Phe Glu Pro Lys Asn Ile Asp Ser Glu Ile
    370                 375                 380
Ile Leu Pro Glu Asn Val Glu Thr Glu Glu Ile Asp Asp Val Pro
385                 390                 395                 400
Ser Pro Lys His Ser Asn His Glu Thr Phe Glu Glu Glu Thr Ser Glu
                405                 410                 415
Ser Glu His Glu Glu Ala Val Ser Glu Lys Asn Ala His Glu Thr Val
            420                 425                 430
Glu His Glu Glu Thr Val Ser Gln Glu Ser Asn Pro Glu Lys Ala Asp
        435                 440                 445
Asn Asp Gly Asn Val Ser Gln Asn Ser Asn Asn Glu Leu Asn Glu Asn
    450                 455                 460
Glu Phe Val Glu Ser Glu Lys Ser Glu His Glu Ala Arg Ser Lys Ala
465                 470                 475                 480
Lys Glu Ala Ser Ser Tyr Asp Tyr Ile Leu Gly Trp Glu Phe Gly Gly
                485                 490                 495
Gly Val Pro Glu His Lys Lys Glu Glu Asn Met Leu Ser His Leu Tyr
            500                 505                 510
Val Ser Ser Lys Asp Lys Glu Asn Ile Ser Lys Glu Asn Asp Asp Val
        515                 520                 525
Leu Asp Glu Lys Glu Glu Glu Ala Glu Glu Thr Glu Glu Glu Glu Leu
    530                 535                 540
Glu Glu Lys Asn Glu Glu Glu Thr Glu Ser Glu Ile Ser Glu Asp Glu
545                 550                 555                 560
Glu Glu Glu Glu Glu Glu Glu Glu Lys Glu Glu Glu Asn Asp Lys Lys
                565                 570                 575
Lys Glu Gln Glu Lys Glu Gln Ser Asn Glu Asn Asn Asp Gln Lys Lys
            580                 585                 590
Asp Met Glu Ala Gln Asn Leu Ile Ser Lys Asn Gln Asn Asn Asn Glu
        595                 600                 605
```

```
Lys Asn Val Lys Glu Ala Ala Glu Ser Ile Met Lys Thr Leu Ala Gly
    610                 615                 620

Leu Ile Lys Gly Asn Asn Gln Ile Asp Ser Thr Leu Lys Asp Leu Val
625                 630                 635                 640

Glu Glu Leu Ser Lys Tyr Phe Lys Asn His Gly Gly Ser Gly Ala Glu
                645                 650                 655

Ala Gly Ile Thr Gly Thr Trp Tyr Asn Gln His Gly Ser Thr Phe Thr
            660                 665                 670

Val Thr Ala Gly Ala Asp Gly Asn Leu Thr Gly Gln Tyr Glu Asn Arg
        675                 680                 685

Ala Gln Gly Thr Gly Cys Gln Asn Ser Pro Tyr Thr Leu Thr Gly Arg
    690                 695                 700

Tyr Asn Gly Thr Lys Leu Glu Trp Arg Val Glu Trp Asn Asn Ser Thr
705                 710                 715                 720

Glu Asn Cys His Ser Arg Thr Glu Trp Arg Gly Gln Tyr Gln Gly Gly
                725                 730                 735

Ala Glu Ala Arg Ile Asn Thr Gln Trp Asn Leu Thr Tyr Glu Gly Gly
            740                 745                 750

Ser Gly Pro Ala Thr Glu Gln Gly Gln Asp Thr Phe Thr Lys Val Lys
        755                 760                 765

<210> SEQ ID NO 25
<211> LENGTH: 691
<212> TYPE: PRT
<213> ORGANISM: Artificial sequence
<220> FEATURE:
<223> OTHER INFORMATION: Constructs

<400> SEQUENCE: 25

Gly Ser Thr Ser Glu Asn Arg Asn Lys Arg Ile Gly Gly Pro Lys Leu
1               5                   10                  15

Arg Gly Asn Val Thr Ser Asn Ile Lys Phe Pro Ser Asp Asn Lys Gly
            20                  25                  30

Lys Ile Ile Arg Gly Ser Asn Asp Lys Leu Asn Lys Asn Ser Glu Asp
        35                  40                  45

Val Leu Glu Gln Ser Glu Lys Ser Leu Val Ser Glu Asn Val Pro Ser
    50                  55                  60

Gly Leu Asp Ile Asp Asp Ile Pro Lys Glu Ser Ile Phe Ile Gln Glu
65                  70                  75                  80

Asp Gln Glu Gly Gln Thr His Ser Glu Leu Asn Pro Glu Thr Ser Glu
                85                  90                  95

His Ser Lys Asp Leu Asn Asn Asn Gly Ser Lys Asn Glu Ser Ser Asp
            100                 105                 110

Ile Ile Ser Glu Asn Asn Lys Ser Asn Lys Val Gln Asn His Phe Glu
        115                 120                 125

Ser Leu Ser Asp Leu Glu Leu Leu Glu Asn Ser Ser Gln Asp Asn Leu
    130                 135                 140

Asp Lys Asp Thr Ile Ser Thr Glu Pro Phe Pro Asn Gln Lys His Lys
145                 150                 155                 160

Asp Leu Gln Gln Asp Leu Asn Asp Glu Pro Leu Glu Pro Phe Pro Thr
                165                 170                 175

Gln Ile His Lys Asp Tyr Lys Glu Lys Asn Leu Ile Asn Glu Glu Asp
            180                 185                 190

Ser Glu Pro Phe Pro Arg Gln Lys His Lys Lys Val Asp Asn His Asn
        195                 200                 205
```

-continued

```
Glu Glu Lys Asn Val Phe His Glu Asn Gly Ser Ala Asn Gly Asn Gln
    210                 215                 220
Gly Ser Leu Lys Leu Lys Ser Phe Asp Glu His Leu Lys Asp Glu Lys
225                 230                 235                 240
Ile Glu Asn Glu Pro Leu Val His Glu Asn Leu Ser Ile Pro Asn Asp
                245                 250                 255
Pro Ile Glu Gln Ile Leu Asn Gln Pro Glu Gln Glu Thr Asn Ile Gln
                260                 265                 270
Glu Gln Leu Tyr Asn Glu Lys Gln Asn Val Glu Lys Gln Asn Ser
                275                 280                 285
Gln Ile Pro Ser Leu Asp Leu Lys Glu Pro Thr Asn Glu Asp Ile Leu
290                 295                 300
Pro Asn His Asn Pro Leu Glu Asn Ile Lys Gln Ser Glu Ser Glu Ile
305                 310                 315                 320
Asn His Val Gln Asp His Ala Leu Pro Lys Glu Asn Ile Ile Asp Lys
                325                 330                 335
Leu Asp Asn Gln Lys Glu His Ile Asp Gln Ser Gln His Asn Ile Asn
                340                 345                 350
Val Leu Gln Glu Asn Asn Ile Asn Asn His Gln Leu Glu Pro Gln Glu
                355                 360                 365
Lys Pro Asn Ile Glu Ser Phe Glu Pro Lys Asn Ile Asp Ser Glu Ile
370                 375                 380
Ile Leu Pro Glu Asn Val Glu Thr Glu Glu Ile Ile Asp Asp Val Pro
385                 390                 395                 400
Ser Pro Lys His Ser Asn His Glu Thr Phe Glu Glu Glu Thr Ser Glu
                405                 410                 415
Ser Glu His Glu Glu Ala Val Ser Glu Lys Asn Ala His Glu Thr Val
                420                 425                 430
Glu His Glu Glu Thr Val Ser Gln Glu Ser Asn Pro Glu Lys Ala Asp
            435                 440                 445
Asn Asp Gly Asn Val Ser Gln Asn Ser Asn Glu Leu Asn Glu Asn
        450                 455                 460
Glu Phe Val Glu Ser Glu Lys Ser Glu His Glu Ala Arg Ser Lys Thr
465                 470                 475                 480
Lys Glu Tyr Ala Glu Lys Ala Lys Asn Ala Tyr Glu Lys Ala Lys Asn
                485                 490                 495
Ala Tyr Gln Lys Ala Asn Gln Ala Val Leu Lys Ala Lys Glu Ala Ser
            500                 505                 510
Ser Tyr Asp Tyr Ile Leu Gly Trp Glu Phe Gly Gly Val Pro Glu
            515                 520                 525
His Lys Lys Glu Glu Asn Met Leu Ser His Leu Tyr Val Ser Ser Lys
        530                 535                 540
Asp Lys Glu Asn Ile Ser Lys Glu Asn Asp Asp Val Leu Asp Glu Lys
545                 550                 555                 560
Glu Glu Glu Ala Glu Glu Thr Glu Glu Glu Leu Glu Gly Gly Ser
                565                 570                 575
Gly Ala Glu Ala Gly Ile Thr Gly Thr Trp Tyr Asn Gln His Gly Ser
            580                 585                 590
Thr Phe Thr Val Thr Ala Gly Ala Asp Gly Asn Leu Thr Gly Gln Tyr
            595                 600                 605
Glu Asn Arg Ala Gln Gly Thr Gly Cys Gln Asn Ser Pro Tyr Thr Leu
        610                 615                 620
Thr Gly Arg Tyr Asn Gly Thr Lys Leu Glu Trp Arg Val Glu Trp Asn
```

```
                625                 630                 635                 640

Asn Ser Thr Glu Asn Cys His Ser Arg Thr Glu Trp Arg Gly Gln Tyr
                    645                 650                 655

Gln Gly Gly Ala Glu Ala Arg Ile Asn Thr Gln Trp Asn Leu Thr Tyr
                660                 665                 670

Glu Gly Gly Ser Gly Pro Ala Thr Glu Gln Gly Gln Asp Thr Phe Thr
            675                 680                 685

Lys Val Lys
        690

<210> SEQ ID NO 26
<211> LENGTH: 627
<212> TYPE: PRT
<213> ORGANISM: Artificial sequence
<220> FEATURE:
<223> OTHER INFORMATION: Constructs
<220> FEATURE:
<221> NAME/KEY: MISC_FEATURE
<222> LOCATION: (1)..(627)
<223> OTHER INFORMATION: mSA-PfRH5-HIS

<400> SEQUENCE: 26

Ala Glu Ala Gly Ile Thr Gly Thr Trp Tyr Asn Gln His Gly Ser Thr
1               5                   10                  15

Phe Thr Val Thr Ala Gly Ala Asp Gly Asn Leu Thr Gly Gln Tyr Glu
                20                  25                  30

Asn Arg Ala Gln Gly Thr Gly Cys Gln Asn Ser Pro Tyr Thr Leu Thr
            35                  40                  45

Gly Arg Tyr Asn Gly Thr Lys Leu Glu Trp Arg Val Glu Trp Asn Asn
        50                  55                  60

Ser Thr Glu Asn Cys His Ser Arg Thr Glu Trp Arg Gly Gln Tyr Gln
65                  70                  75                  80

Gly Gly Ala Glu Ala Arg Ile Asn Thr Gln Trp Asn Leu Thr Tyr Glu
                85                  90                  95

Gly Gly Ser Gly Pro Ala Thr Glu Gln Gly Gln Asp Thr Phe Thr Lys
            100                 105                 110

Val Lys Gly Gly Ser Leu Ser Phe Glu Asn Ala Ile Lys Lys Thr Lys
        115                 120                 125

Asn Gln Glu Asn Asn Leu Thr Leu Leu Pro Ile Lys Ser Thr Glu Glu
    130                 135                 140

Glu Lys Asp Asp Ile Lys Asn Gly Lys Asp Ile Lys Lys Glu Ile Asp
145                 150                 155                 160

Asn Asp Lys Glu Asn Ile Lys Thr Asn Asn Ala Lys Asp His Ser Thr
                165                 170                 175

Tyr Ile Lys Ser Tyr Leu Asn Thr Asn Val Asn Asp Gly Leu Lys Tyr
            180                 185                 190

Leu Phe Ile Pro Ser His Asn Ser Phe Ile Lys Lys Tyr Ser Val Phe
        195                 200                 205

Asn Gln Ile Asn Asp Gly Met Leu Leu Asn Glu Lys Asn Asp Val Lys
    210                 215                 220

Asn Asn Glu Asp Tyr Lys Asn Val Asp Tyr Lys Asn Val Asn Phe Leu
225                 230                 235                 240

Gln Tyr His Phe Lys Glu Leu Ser Asn Tyr Asn Ile Ala Asn Ser Ile
                245                 250                 255

Asp Ile Leu Gln Glu Lys Glu Gly His Leu Asp Phe Val Ile Ile Pro
            260                 265                 270
```

His Tyr Thr Phe Leu Asp Tyr Lys His Leu Ser Tyr Asn Ser Ile
            275                 280                 285

Tyr His Lys Tyr Ser Thr Tyr Gly Lys Tyr Ile Ala Val Asp Ala Phe
290                 295                 300

Ile Lys Lys Ile Asn Glu Thr Tyr Asp Lys Val Lys Ser Lys Cys Asn
305                 310                 315                 320

Asp Ile Lys Asn Asp Leu Ile Ala Thr Ile Lys Lys Leu Glu His Pro
                325                 330                 335

Tyr Asp Ile Asn Asn Lys Asn Asp Ser Tyr Arg Tyr Asp Ile Ser
            340                 345                 350

Glu Glu Ile Asp Asp Lys Ser Glu Glu Thr Asp Asp Glu Thr Glu Glu
355                 360                 365

Val Glu Asp Ser Ile Gln Asp Thr Asp Ser Asn His Thr Pro Ser Asn
370                 375                 380

Lys Lys Lys Asn Asp Leu Met Asn Arg Thr Phe Lys Lys Met Met Asp
385                 390                 395                 400

Glu Tyr Asn Thr Lys Lys Lys Leu Ile Lys Cys Ile Lys Asn His
            405                 410                 415

Glu Asn Asp Phe Asn Lys Ile Cys Met Asp Met Lys Asn Tyr Gly Thr
            420                 425                 430

Asn Leu Phe Glu Gln Leu Ser Cys Tyr Asn Asn Asn Phe Cys Asn Thr
            435                 440                 445

Asn Gly Ile Arg Phe His Tyr Asp Glu Tyr Ile His Lys Leu Ile Leu
            450                 455                 460

Ser Val Lys Ser Lys Asn Leu Asn Lys Asp Leu Ser Asp Met Thr Asn
465                 470                 475                 480

Ile Leu Gln Gln Ser Glu Leu Leu Thr Asn Leu Asn Lys Lys Met
                485                 490                 495

Gly Ser Tyr Ile Tyr Ile Asp Thr Ile Lys Phe Ile His Lys Glu Met
            500                 505                 510

Lys His Ile Phe Asn Arg Ile Glu Tyr His Thr Lys Ile Ile Asn Asp
            515                 520                 525

Lys Thr Lys Ile Ile Gln Asp Lys Ile Lys Leu Asn Ile Trp Arg Thr
530                 535                 540

Phe Gln Lys Asp Glu Leu Leu Lys Arg Ile Leu Asp Met Ser Asn Glu
545                 550                 555                 560

Tyr Ser Leu Phe Ile Thr Ser Asp His Leu Arg Gln Met Leu Tyr Asn
                565                 570                 575

Thr Phe Tyr Ser Lys Lys His Leu Asn Asn Ile Phe His His Leu
            580                 585                 590

Ile Tyr Val Leu Gln Met Lys Phe Asn Asp Val Pro Ile Lys Met Glu
            595                 600                 605

Tyr Phe Gln Thr Tyr Lys Lys Asn Lys Pro Leu Thr Gln His His His
610                 615                 620

His His His
625

<210> SEQ ID NO 27
<211> LENGTH: 333
<212> TYPE: PRT
<213> ORGANISM: Artificial sequence
<220> FEATURE:
<223> OTHER INFORMATION: Constructs
<220> FEATURE:
<221> NAME/KEY: MISC_FEATURE
<222> LOCATION: (1)..(333)

<223> OTHER INFORMATION: mSA-Pfs25-HIS

<400> SEQUENCE: 27

```
Ala Glu Ala Gly Ile Thr Gly Thr Trp Tyr Asn Gln His Gly Ser Thr
1               5                   10                  15

Phe Thr Val Thr Ala Gly Ala Asp Gly Asn Leu Thr Gly Gln Tyr Glu
            20                  25                  30

Asn Arg Ala Gln Gly Thr Gly Cys Gln Asn Ser Pro Tyr Thr Leu Thr
        35                  40                  45

Gly Arg Tyr Asn Gly Thr Lys Leu Glu Trp Arg Val Glu Trp Asn Asn
    50                  55                  60

Ser Thr Glu Asn Cys His Ser Arg Thr Glu Trp Arg Gly Gln Tyr Gln
65                  70                  75                  80

Gly Gly Ala Glu Ala Arg Ile Asn Thr Gln Trp Asn Leu Thr Tyr Glu
                85                  90                  95

Gly Gly Ser Gly Pro Ala Thr Glu Gln Gly Gln Asp Thr Phe Thr Lys
            100                 105                 110

Val Lys Gly Gly Ser Asn Lys Leu Tyr Ser Leu Phe Leu Phe Leu Phe
        115                 120                 125

Ile Gln Leu Ser Ile Lys Tyr Asn Asn Ala Lys Val Thr Val Asp Thr
    130                 135                 140

Val Cys Lys Arg Gly Phe Leu Ile Gln Met Ser Gly His Leu Glu Cys
145                 150                 155                 160

Lys Cys Glu Asn Asp Leu Val Leu Val Asn Glu Thr Cys Glu Glu
                165                 170                 175

Lys Val Leu Lys Cys Asp Glu Lys Thr Val Asn Lys Pro Cys Gly Asp
            180                 185                 190

Phe Ser Lys Cys Ile Lys Ile Asp Gly Asn Pro Val Ser Tyr Ala Cys
        195                 200                 205

Lys Cys Asn Leu Gly Tyr Asp Met Val Asn Asn Val Cys Ile Pro Asn
    210                 215                 220

Glu Cys Lys Asn Val Thr Cys Gly Asn Gly Lys Cys Ile Leu Asp Thr
225                 230                 235                 240

Ser Asn Pro Val Lys Thr Gly Val Cys Ser Cys Asn Ile Gly Lys Val
                245                 250                 255

Pro Asn Val Gln Asp Gln Asn Lys Cys Ser Lys Asp Gly Glu Thr Lys
            260                 265                 270

Cys Ser Leu Lys Cys Leu Lys Glu Asn Glu Thr Cys Lys Ala Val Asp
        275                 280                 285

Gly Ile Tyr Lys Cys Asp Cys Lys Asp Gly Phe Ile Ile Asp Asn Glu
    290                 295                 300

Ser Ser Ile Cys Thr Ala Phe Ser Ala Tyr Asn Ile Leu Asn Leu Ser
305                 310                 315                 320

Ile Met Phe Ile Leu Phe Ser Val Cys Phe Phe Ile Met
                325                 330
```

<210> SEQ ID NO 28
<211> LENGTH: 422
<212> TYPE: PRT
<213> ORGANISM: Artificial sequence
<220> FEATURE:
<223> OTHER INFORMATION: Constructs
<220> FEATURE:
<221> NAME/KEY: MISC_FEATURE
<222> LOCATION: (1)..(422)
<223> OTHER INFORMATION: HIS-PfCSP(aa92-397)-mSA -continued

```
<400> SEQUENCE: 28

Lys Leu Lys Gln Pro Ala Asp Gly Asn Pro Asp Pro Asn Ala Asn Pro
1               5                   10                  15

Asn Val Asp Pro Asn Ala Asn Pro Asn Val Asp Pro Asn Ala Asn Pro
            20                  25                  30

Asn Val Asp Pro Asn Ala Asn Pro Asn Ala Asn Pro Asn Ala Asn Pro
        35                  40                  45

Asn Ala Asn Pro Asn Ala Asn Pro Asn Ala Asn Pro Asn Ala Asn Pro
50                  55                  60

Asn Ala Asn Pro Asn Ala Asn Pro Asn Ala Asn Pro Asn Ala Asn Pro
65                  70                  75                  80

Asn Ala Asn Pro Asn Ala Asn Pro Asn Ala Asn Pro Asn Ala Asn Pro
                85                  90                  95

Asn Ala Asn Pro Asn Ala Asn Pro Asn Val Asp Pro Asn Ala Asn Pro
            100                 105                 110

Asn Ala Asn Pro Asn Ala Asn Pro Asn Ala Asn Pro Asn Ala Asn Pro
        115                 120                 125

Asn Ala Asn Pro Asn Ala Asn Pro Asn Ala Asn Pro Asn Ala Asn Pro
    130                 135                 140

Asn Ala Asn Pro Asn Ala Asn Pro Asn Ala Asn Pro Asn Ala Asn Pro
145                 150                 155                 160

Asn Ala Asn Pro Asn Ala Asn Pro Asn Ala Asn Pro Asn Ala Asn Pro
                165                 170                 175

Asn Ala Asn Pro Asn Lys Asn Asn Gln Gly Asn Gly Gln Gly His Asn
            180                 185                 190

Met Pro Asn Asp Pro Asn Arg Asn Val Asp Glu Asn Ala Asn Ala Asn
        195                 200                 205

Ser Ala Val Lys Asn Asn Asn Glu Glu Pro Ser Asp Lys His Ile
    210                 215                 220

Lys Glu Tyr Leu Asn Lys Ile Gln Asn Ser Leu Ser Thr Glu Trp Ser
225                 230                 235                 240

Pro Cys Ser Val Thr Cys Gly Asn Gly Ile Gln Val Arg Ile Lys Pro
                245                 250                 255

Gly Ser Ala Asn Lys Pro Lys Asp Glu Leu Asp Tyr Ala Asn Asp Ile
            260                 265                 270

Glu Lys Lys Ile Cys Lys Met Glu Lys Cys Ser Ser Val Phe Asn Val
        275                 280                 285

Val Asn Ser Ser Ile Gly Leu Ile Met Val Leu Ser Phe Leu Phe Leu
    290                 295                 300

Asn Gly Gly Ser Ala Glu Ala Gly Ile Thr Gly Thr Trp Tyr Asn Gln
305                 310                 315                 320

His Gly Ser Thr Phe Thr Val Thr Ala Gly Ala Asp Gly Asn Leu Thr
                325                 330                 335

Gly Gln Tyr Glu Asn Arg Ala Gln Gly Thr Gly Cys Gln Asn Ser Pro
            340                 345                 350

Tyr Thr Leu Thr Gly Arg Tyr Asn Gly Thr Lys Leu Glu Trp Arg Val
        355                 360                 365

Glu Trp Asn Asn Ser Thr Glu Asn Cys His Ser Arg Thr Glu Trp Arg
    370                 375                 380

Gly Gln Tyr Gln Gly Gly Ala Glu Ala Arg Ile Asn Thr Gln Trp Asn
385                 390                 395                 400

Leu Thr Tyr Glu Gly Gly Ser Gly Pro Ala Thr Glu Gln Gly Gln Asp
                405                 410                 415
```

Thr Phe Thr Lys Val Lys
            420

<210> SEQ ID NO 29
<211> LENGTH: 2973
<212> TYPE: DNA
<213> ORGANISM: Artificial sequence
<220> FEATURE:
<223> OTHER INFORMATION: Constructs
<220> FEATURE:
<221> NAME/KEY: misc_feature
<222> LOCATION: (1)..(2973)
<223> OTHER INFORMATION: PCSK9[31]-692[:m]SA:HIS DNA

<400> SEQUENCE: 29

| | | | | | |
|---|---|---|---|---|---|
| tttcatatgc | caagtacgcc | ccctattgac | gtcaatgacg | gtaaatggcc | cgcctggcat | 60 |
| tatgcccagt | acatgacctt | atgggacttt | cctacttggc | agtacatcta | cgtattagtc | 120 |
| atcgctatta | ccatggtgat | gcggttttgg | cagtacatca | atgggcgtgg | atagcggttt | 180 |
| gactcacggg | gatttccaag | tctccacccc | attgacgtca | atgggagttt | gttttggcac | 240 |
| caaaatcaac | gggactttcc | aaaatgtcgt | aacaactccg | ccccattgac | gcaaatgggc | 300 |
| ggtaggcgtg | tacggtggga | ggtctatata | agcagagctc | tctggctaac | tagagaaccc | 360 |
| actgcttact | ggcttatcga | aattaatacg | actcactata | gggagaccca | agctggctag | 420 |
| cgtttaaact | taagcttagc | gcagaggctt | ggggcagccg | agcggcagcc | aggccccggc | 480 |
| ccgggcctcg | gttccagaag | ggagaggagc | ccgccaaggc | gcgcaagaga | gcgggctgcc | 540 |
| tcgcagtccg | agccgagag | ggagcgcgag | ccgcgccggc | cccggacggc | ctccgaaacc | 600 |
| atgcaggaag | atgaggacgg | cgactacgag | gaactggtgc | tggccctgcg | gagcgaagag | 660 |
| gatggactgg | ccgaggcccc | tgagcacggc | accaccgcca | ccttccacag | atgcgccaag | 720 |
| gacccttggc | ggctgcccgg | cacatacgtg | gtggtgctga | agaggaaac | ccacctgagc | 780 |
| cagagcgagc | ggaccgccag | aaggctgcag | gcccaggccg | ccagaagagg | ctacctgacc | 840 |
| aagatcctgc | acgtgttcca | cggcctgctg | cccggcttcc | tggtgaaaat | gagcggcgac | 900 |
| ctgctggaac | tgcccctgaa | gctgcccac | gtggactaca | tcgaagagga | cagcagcgtg | 960 |
| ttcgcccaga | gcatcccctg | gaacctggaa | cggatcaccc | ccccccagata | ccgggccgac | 1020 |
| gagtaccagc | ctcctgacgg | cggcagcctg | gtggaagtgt | acctgctgga | caccagcatc | 1080 |
| cagagcgacc | accgcgagat | cgagggcaga | gtgatggtga | cagacttcga | aacgtgccc | 1140 |
| gaagaggacg | gcacccggtt | ccacagacag | gccagcaagt | gcgacagcca | cggcacacat | 1200 |
| ctggccggcg | tggtgtctgg | cagagatgcc | ggcgtggcca | agggcgccag | catgagaagc | 1260 |
| ctgcgggtgc | tgaactgcca | gggcaagggc | accgtgtccg | gcaccctgat | cggcctggaa | 1320 |
| ttcatccgga | agtcccagct | ggtgcagccc | gtgggccctc | tggtggtgct | gctgcctctg | 1380 |
| gctggcggct | acagcagagt | gctgaacgcc | gcctgccaga | gactggccag | agctggcgtg | 1440 |
| gtgctggtga | cagccgccgg | aaacttccgg | gacgacgcct | gcctgtacag | ccccgcctct | 1500 |
| gcccccgaag | tgatcaccgt | gggcgccacc | aacgcccagg | accagcctgt | gacactgggc | 1560 |
| accctgggca | caaacttcgg | cagatgcgtg | gacctgttcg | ccctggcga | ggacatcatc | 1620 |
| ggcgccagca | gcgactgcag | cacctgtttc | gtgtcccaga | gcggcaccag | ccaggccgct | 1680 |
| gcccatgtgg | ccggaatcgc | cgccatgatg | ctgagcgccg | agcctgagct | gaccctggcc | 1740 |
| gagctgcggc | agcggctgat | ccacttctcc | gccaaggaca | tgatcaacga | ggcctggttc | 1800 |
| cccgaggacc | agagagtgct | gacccccaac | ctggtggccg | ccctgcctcc | ttctacacac | 1860 |

```
ggcgctggct ggcagctgtt ctgcaggaca gtgtggtccg cccacagcgg ccccaccaga    1920
atggccacag ccgtggccag atgcgcccct gatgaggaac tgctgagctg cagcagcttc    1980
tccagaagcg gcaagcggag aggcgagcgg atggaagccc agggcggcaa gctcgtgtgc    2040
agagcccaca atgccttcgg cggcgagggc gtgtacgcca ttgccagatg ctgcctgctg    2100
cctcaggcca actgcagcgt gcacacagcc cctccagccg aggccagcat gggcaccaga    2160
gtgcactgcc accagcaggg ccacgtgctg accggctgta gcagccactg ggaggtggaa    2220
gatctgggca cccacaagcc ccccgtgctg aggcccagag ccagcctaa tcagtgcgtg     2280 ggccacagag aggcctccat ccacgccagc tgttgccacg cccctggcct ggaatgcaaa    2340
gtgaaagagc acggcatccc tgcccccag gaacaggtca cagtggcctg cgaggaaggc     2400
tggaccctga caggctgttc cgccctgcca ggcacctctc acgtgctggg cgcctacgcc    2460
gtggacaata cctgcgtcgt gcgcagccgg gacgtgtcca caaccggctc tacaagcgag    2520
ggcgccgtga ccgccgtggc catctgctgc agaagcagac acctggccca ggcctcccag    2580
gaactgcagg gcggatctgc cgaggccggc atcaccggca cctggtacaa tcagcacggc    2640
agcaccttca ccgtgaccgc tggcgccgac ggcaacctga ccggccagta cgagaacaga    2700
gcccagggca ccggctgcca gaacagccct tacaccctga ccggcagata caacggcacc    2760
aagctggaat ggcgggtgga atggaacaac agcaccgaga actgccacag ccggaccgag    2820
tggcggggac agtatcaggg cggagccgag gcccggatca cacccagtg gaacctgacc    2880 tacgagggcg gctctggccc tgccacagag cagggacagg acaccttcac caaagtgaag    2940
caccaccacc atcaccacta gcggccgct ttt                                  2973
```

<210> SEQ ID NO 30
<211> LENGTH: 2309
<212> TYPE: DNA
<213> ORGANISM: Artificial sequence
<220> FEATURE:
<223> OTHER INFORMATION: Constructs
<220> FEATURE:
<221> NAME/KEY: misc_feature
<222> LOCATION: (1)..(2309)
<223> OTHER INFORMATION: mSA-ID1ID2a-HIS DNA

<400> SEQUENCE: 30

```
ccatgggcgg tgcagaagca ggtattaccg gcacctggta taatcagcat ggtagcacct      60
ttaccgttac cgcaggcgca gatggtaatc tgacaggtca gtatgaaaat cgtgcacagg    120
gcaccggttg tcagaatagc ccgtataccc tgaccggtcg ttataatggc accaaactgg    180
aatggcgtgt tgaatggaat aatagcaccg aaaattgtca tagccgtacc gaatggcgtg    240
gtcagtatca gggtggtgca gaagcccgta ttaataccca gtggaatctg acctatgaag    300
gtggtagcgg tccggcaacc gaacagggtc aggatacctt taccaaagtt aaaggtggca    360
gcaactatat caaaggcgat cgtatttttg cagagtatgc aaccaaactg agctttattc    420
tgaatccgag tgatgcaaat aatccgagcg gtgaaaccgc aaatcacaat gatgaagcct    480
gtaattgtaa cgaaagcggt attagcagcg ttggtcaggc acagaccagc ggtccgagca    540
gcaataaaac ctgtattacc catagcagca ttaaaaccaa taaaagaaa gaatgcaaag     600 atgtgaaact gggcgtgcgc gaaaatgata agatctgaa atttgcgtg atcgaggata       660 ccagcctgag cggtgttgat aattgttgtt gtcaggatct gctgggtatt ctgcaagaaa    720
attgcagcga taataaacgt ggtagcagca gcaatgatag ctgcgataac aaaaatcagg    780
```

-continued

```
atgaatgcca gaaaaaactg gaaaaagttt tgccagcct gacgaatggt tacaaatgcg      840
ataaatgtaa aagcggcacc agccgcagca aaaagaaatg gatttggaaa aaaagcagcg      900
gcaatgaaga aggtctgcaa gaggaatatg caaataccat tggtctgcct ccgcgtaccc      960
agagcctgta tctgggtaat ctgccgaaac tggaaaatgt gtgtgaagat gtgaaagata     1020
tcaattttga taccaaagaa aaatttctgg caggctgcct gattgtgagc tttcatgaag     1080
gtaaaaacct gaaaaaacgc tatccgcaga ataaaaacag cggtaacaaa gaaaatctgt     1140
gcaaagcact ggaatacagc tttgcagatt atggcgatct gattaaaggc accagcattt     1200
gggataacga gtataccaaa gatctggaac tgaatctgca gaacaatttc ggtaaactgt     1260
tcggcaaata tatcaaaaaa aacaataccg cagagcagga taccagctat agcagcctgg     1320
atgaactgcg tgaaagttgg tggaatacca acaaaaaata catttggacc gccatgaaac     1380
atggtgccga aatgaatatt accacctgta atgcagatgg tagcgttacc ggtagcggta     1440
gcagctgtga tgatattccg accattgatc tgattccgca gtatctgcgt tttctgcaag     1500
aatgggttga aaacttttgt gaacagcgtc aggcgaaagt gaaagatgtt attaccaatt     1560
gcaaaagctg caaagaaagc ggcaataaat gcaaaaccga gtgcaaaacc aaatgcaaag     1620
acgagtgcga gaaatacaaa aaattcattg aagcatgtgg tacagccggt ggtggtattg     1680
gcaccgcagg tagcccgtgg tcaaaacgtt gggatcagat ctataaacgc tacagcaaac     1740
acatcgaaga tgccaaacgt aatcgtaaag caggcaccaa aaattgtggc accagcagca     1800
ccaccaatgc agcagcaagc accgatgaaa acaaatgtgt tcagagcgat atcgatagct     1860
tcttcaaaca tctgattgat attggtctga ccaccccgag cagctatctg agcaatgttc     1920
tggatgataa catttgcggt gcagataaag caccgtggac cacctatacc acatatacca     1980
ccacagaaaa atgcaacaaa gagcgcgata aaagcaaaag ccagagcagc gataccctgg     2040
ttgttgttaa tgttccgagt ccgctgggta taccccgta tcgttataag tatgcctgcc      2100
agtgtaaaat cccgaccaat gaagaaacct gtgatgatcg caaagaatac atgaatcagt     2160
ggtcatgtgg tagcgcacgt accatgaaac gtggctataa aacgataat tatgaactgt      2220
gcaaatataa cggcgtggat gttaaaccga ccaccgttcg tagcaatagc agcaaactgg     2280
atcatcatca tcaccatcat taaggatcc                                       2309
```

<210> SEQ ID NO 31
<211> LENGTH: 2342
<212> TYPE: DNA
<213> ORGANISM: Artificial sequence
<220> FEATURE:
<223> OTHER INFORMATION: Constructs
<220> FEATURE:
<221> NAME/KEY: misc_feature
<222> LOCATION: (1)..(2342)
<223> OTHER INFORMATION: mSA-RO-HIS DNA

<400> SEQUENCE: 31

```
ccatgggcgg tgcagaagca ggtattaccg gcacctggta taatcagcat ggtagcacct       60
ttaccgttac cgcaggcgca gatggtaatc tgacaggtca gtatgaaaat cgtgcacagg      120
gcaccggttg tcagaatagc ccgtataccc tgaccggtcg ttataatggc accaaactgg      180
aatggcgtgt tgaatggaat aatagcaccg aaaattgtca tagccgtacc gaatggcgtg      240
gtcagtatca gggtggtgca gaagcccgta ttaatcccca gtggaatctg acctatgaag      300
gtggtagcgc tccggcaacc gaacagggtc aggataccct taccaaagtt aaaggtggca      360
gcacaagtga aatagaaat aaacgaatcg ggggtcctaa attaaggggt aatgttacaa       420
```

```
gtaatataaa gttcccatca gataacaaag gtaaaattat aagaggttcg aatgataaac    480
ttaataaaaa ctctgaagat gttttagaac aaagcgaaaa atcgcttgtt tcagaaaatg    540
ttcctagtgg attagatata gatgatatcc ctaagaatc tattttttatt caagaagatc    600 aagaaggtca aactcattct gaattaaatc ctgaaacatc agaacatagt aaagatttaa    660
ataataatgg ttcaaaaaat gaatctagtg atattatttc agaaataat aaatcaaata    720 aagtacaaaa tcattttgaa tcattatcag atttagaatt acttgaaaat tcctcacaag    780
ataatttaga caaagataca atttcaacag aacctttttcc taatcaaaaa cataaagact    840
tacaacaaga tttaaatgat gaacctttag accccttttcc tacacaaata cataaagatt    900 ataagaaaa aaatttaata aatgaagaag attcagaacc atttcccaga caaaagcata    960 aaaggtaga caatcataat gaagaaaaaa acgtatttca tgaaaatggt tctgcaaatg    1020
gtaatcaagg aagtttgaaa cttaaatcat tcgatgaaca tttaaaagat gaaaaaatag    1080
aaaatgaacc acttgttcat gaaaatttat ccataccaaa tgatccaata gaacaaatat    1140
taaatcaacc tgaacaagaa acaaatatcc aggaacaatt gtataatgaa aaacaaaatg    1200
ttgaagaaaa acaaaattct caaataccct cgttagattt aaaagaacca acaaatgaag    1260
atattttacc aaatcataat ccattagaaa atataaaaca aagtgaatca gaaataaatc    1320
atgtacaaga tcatgcgcta ccaaaagaga atataataga caaacttgat aatcaaaaag    1380
aacacatcga tcaatcacaa cataatataa atgtattaca agaaaataac ataaacaatc    1440
accaattaga acctcaagag aaacctaata ttgaatcgtt tgaacctaaa aatatagatt    1500
cagaaattat tcttcctgaa aatgttgaaa cagaagaaat aatagatgat gtgccttccc    1560
ctaaacattc taaccatgaa acatttgaag aagaaacaag tgaatctgaa catgaagaag    1620
ccgtatctga aaaaaatgcc cacgaaactg tcgaacatga agaaactgtg tctcaagaaa    1680
gcaatcctga aaaagctgat aatgatggaa atgtatctca aacagcaac aacgaattaa    1740 atgaaaatga attcgttgaa tcggaaaaaa gcgagcatga agcaagatcc aaagcaaaag    1800
aagcttctag ttatgattat attttaggtt gggaatttgg aggaggcgtt ccagaacaca    1860
aaaaagaaga aaatatgtta tcacatttat atgtttcttc aaaggataag gaaaatatat    1920
ctaaggaaaa tgatgatgta ttagatgaga aggaagaaga ggcagaagaa acagaagaag    1980
aagaacttga agaaaaaaat gaagaagaaa cagaatcaga aataagtgaa gatgaagaag    2040
aagaagaaga agaagaagaa aaggaagaag aaaatgacaa aaaaaaagaa caagaaaaag    2100
aacaaagtaa tgaaaataat gatcaaaaaa aagatatgga agcacagaat ttaatttcta    2160 aaaccagaa taataatgag aaaaacgtaa aagaagctgc tgaaagcatc atgaaaactt    2220
tagctggttt aatcaaggga aataatcaaa tagattctac cttaaaagat ttagtagaag    2280
aattatccaa atattttaaa aatcatagat ctcatcacca tcatcaccat tagggatcct    2340
tt                                                                  2342

<210> SEQ ID NO 32
<211> LENGTH: 1791
<212> TYPE: DNA
<213> ORGANISM: Artificial sequence
<220> FEATURE:
<223> OTHER INFORMATION: Constructs
<220> FEATURE:
<221> NAME/KEY: misc_feature
<222> LOCATION: (1)..(1791)
<223> OTHER INFORMATION: HIS-RO-mSA DNA
```

<400> SEQUENCE: 32

```
ggatccacaa gtgagaatag aaataaacga atcggggtc ctaaattaag gggtaatgtt    60
acaagtaata taaagttccc atcagataac aaaggtaaaa ttataagagg ttcgaatgat   120
aaacttaata aaaactctga agatgtttta gaacaaagcg aaaaatcgct tgtttcagaa   180
aatgttccta gtggattaga tatagatgat atccctaaag aatctatttt tattcaagaa   240
gatcaagaag gtcaaactca ttctgaatta aatcctgaaa catcagaaca tagtaaagat   300
ttaaataata atggttcaaa aaatgaatct agtgatatta tttcagaaaa taataaatca   360
aataaagtac aaaatcattt tgaatcatta tcagatttag aattacttga aaattcctca   420
caagataatt tagacaaaga tacaatttca acagaacctt ttcctaatca aaaacataaa   480
gacttacaac aagatttaaa tgatgaacct ttagaaccct ttcctacaca aatacataaa   540
gattataaag aaaaaaattt aataaatgaa gaagattcag aaccatttcc cagacaaaag   600
cataaaaagg tagacaatca taatgaagaa aaaaacgtat ttcatgaaaa tggttctgca   660
aatggtaatc aaggaagttt gaaacttaaa tcattcgatg aacatttaaa agatgaaaaa   720
atagaaaatg aaccacttgt tcatgaaaat ttatccatac caaatgatcc aatagaacaa   780
atattaaatc aacctgaaca agaaacaaat atccaggaac aattgtataa tgaaaaacaa   840
aatgttgaag aaaaacaaaa ttctcaaata ccttcgttag atttaaaaga accaacaaat   900
gaagatattt taccaaatca taatccatta gaaaatataa acaaagtga atcagaaata   960
aatcatgtac aagatcatgc gctaccaaaa gagaatataa tagacaaact tgataatcaa  1020
aaagaacaca tcgatcaatc acaacataat ataaatgtat tacaagaaaa taacataaac  1080
aatcaccaat tagaacctca agagaaacct aatattgaat cgtttgaacc taaaaatata  1140
gattcagaaa ttattcttcc tgaaaatgtt gaaacagaag aaataataga tgatgtgcct  1200
tcccctaaac attctaacca tgaaacattt gaagaagaaa caagtgaatc tgaacatgaa  1260
gaagccgtat ctgaaaaaaa tgcccacgaa actgtcgaac atgaagaaac tgtgtctcaa  1320
gaaagcaatc ctgaaaaagc tgataatgat ggaaatgtat ctcaaaacag caacaacgaa  1380
ttaaatgaaa atgaattcgt tgaatcggaa aaaagcgagc atgaagcagg tggtagcggt  1440
gcagaagcag gtattaccgg cacctggtat aatcagcatg gtagcacctt taccgttacc  1500
gcaggcgcag atggtaatct gacaggtcag tatgaaaatc gtgcacaggg caccggttgt  1560
cagaatagcc cgtatacccT gaccggtcgt tataatggca ccaaactgga atggcgtgtt  1620
gaatggaata atagcaccga aaattgtcat agccgtaccg aatggcgtgg tcagtatcag  1680
ggtggtgcag aagcccgtat taatacccag tggaatctga cctatgaagg tggtagtggt  1740
ccggcaaccg aacagggtca ggatacctt accaaagtga ataacatat g             1791
```

<210> SEQ ID NO 33
<211> LENGTH: 2313
<212> TYPE: DNA
<213> ORGANISM: Artificial sequence
<220> FEATURE:
<223> OTHER INFORMATION: Constructs
<220> FEATURE:
<221> NAME/KEY: misc_feature
<222> LOCATION: (1)..(2313)
<223> OTHER INFORMATION: HIS-GMZ2ggsmSA3

<400> SEQUENCE: 33

```
ggatccacaa gtgagaatag aaataaacga atcggggtc ctaaattaag gggtaatgtt    60
acaagtaata taaagttccc atcagataac aaaggtaaaa ttataagagg ttcgaatgat   120
```

```
aaacttaata aaaactctga agatgtttta gaacaaagcg aaaaatcgct tgtttcagaa      180
aatgttccta gtggattaga tatagatgat atccctaaag aatctatttt tattcaagaa      240
gatcaagaag gtcaaactca ttctgaatta aatcctgaaa catcagaaca tagtaaagat      300
ttaaataata atggttcaaa aatgaatcta gtgatatta tttcagaaaa taataaatca       360
aataaagtac aaaatcattt tgaatcatta tcagatttag aattacttga aaattcctca      420
caagataatt tagacaaaga tacaatttca acagaacctt ttcctaatca aaacataaaa      480
gacttacaac aagatttaaa tgatgaacct ttagaaccct ttcctacaca aatacataaa      540
gattataaag aaaaaaattt aataaatgaa gaagattcag aaccatttcc cagacaaaag      600
cataaaaagg tagacaatca taatgaagaa aaaaacgtat tcatgaaaaa tggttctgca      660
aatggtaatc aaggaagttt gaaacttaaa tcattcgatg aacatttaaa agatgaaaaa      720
atagaaaatg aaccacttgt tcatgaaaat ttatccatac caaatgatcc aatagaacaa      780
atattaaatc aacctgaaca agaaacaaat atccaggaac aattgtataa tgaaaaacaa      840
aatgttgaag aaaaacaaaa ttctcaaata ccttcgttag atttaaaaga accaacaaat      900
gaagatattt taccaaatca taatccatta gaaaatataa aacaaagtga atcagaaata      960
aatcatgtac aagatcatgc gctaccaaaa gagaatataa tagacaaact tgataatcaa     1020
aaagaacaca tcgatcaatc acaacataat ataaatgtat tacaagaaaa taacataaac     1080
aatcaccaat tagaacctca agagaaacct aatattgaat cgtttgaacc taaaaatata     1140
gattcagaaa ttattcttcc tgaaaatgtt gaaacagaag aaataataga tgatgtgcct     1200
tcccctaaac attctaacca tgaaacattt gaagaagaaa caagtgaatc tgaacatgaa     1260
gaagccgtat ctgaaaaaaa tgcccacgaa actgtcgaac atgaagaaac tgtgtctcaa     1320
gaaagcaatc ctgaaaaagc tgataatgat ggaaatgtat ctcaaaacag caacaacgaa     1380
ttaaatgaaa atgaattcgt tgaatcggaa aaaagcgagc atgaagcaag atccaaagca     1440
aaagaagctt ctagttatga ttatatttta ggttgggaat ttggaggagg cgttccagaa     1500
cacaaaaaag aagaaaatat gttatcacat ttatatgttt cttcaaagga taaggaaaat     1560
atatctaagg aaaatgatga tgtattagat gagaaggaag aagaggcaga agaaacagaa     1620
gaagaagaac ttgaagaaaa aaatgaagaa gaaacagaat cagaaataag tgaagatgaa     1680
gaagaagaag aagaagaaga agaaaaggaa gaagaaatg acaaaaaaaa agaacaagaa      1740
aaagaacaaa gtaatgaaaa taatgatcaa aaaaagagata tggaagcaca gaatttaatt     1800
tctaaaaacc agaataataa tgagaaaaac gtaaagaag ctgctgaaag catcatgaaa       1860
actttagctg gtttaatcaa gggaaataat caaatagatt ctaccttaaa agatttagta     1920
gaagaattat ccaaatattt taaaaatcat ggtggtagcg gtgcagaagc aggtattacc     1980
ggcacctggt ataatcagca tggtagcacc tttaccgtta ccgcaggcgc agatggtaat     2040
ctgacaggtc agtatgaaaa tcgtgcacag ggcaccggtt gtcagaatag cccgtatacc     2100
ctgaccggtc gttataatgg caccaaactg gaatggcgtg ttgaatggaa taatagcacc     2160
gaaaattgtc atagccgtac cgaatggcgt ggtcagtatc agggtggtgc agaagcccgt     2220
attaatacccc agtggaatct gacctatgaa ggtggtagtg gtccggcaac cgaacagggt     2280
caggatacct ttaccaaagt gaaataacat atg                                  2313
```

<210> SEQ ID NO 34
<211> LENGTH: 2082
<212> TYPE: DNA

<213> ORGANISM: Artificial sequence
<220> FEATURE:
<223> OTHER INFORMATION: Constructs
<220> FEATURE:
<221> NAME/KEY: misc_feature
<222> LOCATION: (1)..(2082)
<223> OTHER INFORMATION: HIS-GMZ2T:ggsmSA DNA

<400> SEQUENCE: 34

```
ggatccacaa gtgagaatag aaataaacga atcggggtc ctaaattaag gggtaatgtt      60
acaagtaata taaagttccc atcagataac aaaggtaaaa ttataagagg ttcgaatgat    120
aaacttaata aaaactctga agatgtttta gaacaaagcg aaaaatcgct tgtttcagaa    180
aatgttccta gtggattaga tatagatgat atccctaaag aatctatttt tattcaagaa    240
gatcaagaag gtcaaactca ttctgaatta aatcctgaaa catcagaaca tagtaaagat    300
ttaaataata atggttcaaa aaatgaatct agtgatatta tttcagaaaa taataaatca    360
aataaagtac aaaatcattt tgaatcatta tcagatttag aattacttga aaattcctca    420
caagataatt tagacaaaga tacaatttca acagaacctt ttcctaatca aaaacataaa    480
gacttacaac aagatttaaa tgatgaacct ttagaaccct ttcctacaca aatacataaa    540
gattataaag aaaaaaattt aataaatgaa gaagattcag aaccatttcc cagacaaaag    600
cataaaaagg tagacaatca taatgaagaa aaaaacgtat ttcatgaaaa tggttctgca    660
aatggtaatc aaggaagttt gaaacttaaa tcattcgatg aacatttaaa agatgaaaaa    720
atagaaaatg aaccacttgt tcatgaaaat ttatccatac caaatgatcc aatagaacaa    780
atattaaatc aacctgaaca agaaacaaat atccaggaac aattgtataa tgaaaaacaa    840
aatgttgaag aaaaacaaaa ttctcaaata ccttcgttag atttaaaaga accaacaaat    900
gaagatattt taccaaatca taatccatta gaaaatataa aacaaagtga atcagaaata    960
aatcatgtac aagatcatgc gctaccaaaa gagaatataa tagacaaact tgataatcaa   1020
aaagaacaca tcgatcaatc acaacataat ataaatgtat tacaagaaaa taacataaac   1080
aatcaccaat tagaacctca agagaaacct aatattgaat cgtttgaacc taaaaatata   1140
gattcagaaa ttattcttcc tgaaaatgtt gaaacagaag aaataataga tgatgtgcct   1200
tcccctaaac attctaacca tgaaacattt gaagaagaaa caagtgaatc tgaacatgaa   1260
gaagccgtat ctgaaaaaaa tgcccacgaa actgtcgaac atgaagaaac tgtgtctcaa   1320
gaaagcaatc ctgaaaaagc tgataatgat ggaaatgtat ctcaaaacag caacaacgaa   1380
ttaaatgaaa atgaattcgt tgaatcggaa aaaagcgagc atgaagcaag atccaaaaca   1440
aaagaatatg ctgaaaaagc aaaaaatgct tatgaaaagg caaaaaatgc ttatcaaaaa   1500
gcaaaccaag ctgttttaaa agcaaaagaa gcttctagtt atgattatat tttaggttgg   1560
gaatttggag gaggcgttcc agaacacaaa aaagaagaaa atatgttatc acatttatat   1620
gtttcttcaa aggataagga aaatatatct aaggaaaatg atgatgtatt agatgagaag   1680
gaagaagagg cagaagaaac agaagaagaa gaacttgaag gtggtagcgg tgcagaagca   1740
ggtattaccg gcacctggta atcagcat ggtagcacct ttaccgttac cgcaggcgca   1800
gatggtaatc tgacaggtca gtatgaaaat cgtgcacagg gcaccggttg tcagaatagc   1860
ccgtataccc tgaccggtcg ttataatggc accaaactgg aatggcgtgt tgaatggaat   1920
aatagcaccg aaaattgtca tagccgtacc gaatggcgtg gtcagtatca gggtggtgca   1980
gaagcccgta ttaatacccca gtggaatctg acctatgaag gtggtagtgg tccggcaacc   2040
gaacagggtc aggataccctt taccaaagtg aaataacata tg                     2082
```

<210> SEQ ID NO 35
<211> LENGTH: 1890
<212> TYPE: DNA
<213> ORGANISM: Artificial sequence
<220> FEATURE:
<223> OTHER INFORMATION: Constructs
<220> FEATURE:
<221> NAME/KEY: misc_feature
<222> LOCATION: (1)..(1890)
<223> OTHER INFORMATION: mSA-PfRH5-HIS DNA

<400> SEQUENCE: 35

```
gaattcggtg cagaagcagg tattaccggc acctggtata atcagcatgg tagcaccttt      60
accgttaccg caggcgcaga tggtaatctg acaggtcagt atgaaaatcg tgcacagggc     120
accggttgtc agaatagccc gtataccctg accggtcgtt ataatggcac caaactggaa     180
tggcgtgttg aatggaataa tagcaccgaa aattgtcata gccgtaccga atggcgtggt     240
cagtatcagg gtggtgcaga agcccgtatt aatacccagt ggaatctgac ctatgaaggt     300
ggtagcggtc cggcaaccga acagggtcag gatacccttta ccaaagttaa aggtggcagc     360
ctgtccttcg agaacgccat caagaagacc aagaaccagg aaaacaacct gaccctgctg     420
cccatcaagt ccaccgagga agagaaggac gacatcaaga acggcaagga tatcaagaag     480
gaaatcgaca cgacaaggga aaacatcaag accaacaacg ccaaggacca ctccaccctac     540 atcaagtctt acctgaacac caacgtgaac gacggcctga agtacctgtt catcccatcc     600
cacaacagct tcatcaagaa gtactccgtt tcaaccaga tcaacgacgg catgctgctg     660
aacgagaaga cgacgtgaa gacaacgag gactacaaga acgtcgacta caagaacgtg     720
aacttcctgc agtaccactt caaggaactg tccaactaca catcgccaa ctccatcgac     780 atcctgcaag aaaaggaagg ccacctggac ttcgtgatca tcccccacta cactttcttg     840
gactactaca gcacctgtc ctacaacagc atctaccaca gtacagcac ctacggcaag     900 tacatcgctg tggacgcttt catcaagaag atcaacgaga cttacgacaa agtgaagtcc     960
aagtgtaacg atatcaagaa cgacctgatc gccaccatca agaagctcga gcaccctac    1020 gacatcaaca acaagaacga cgacagctac cgctacgaca tctccgaaga gatcgacgac    1080
aagtccgagg aaaccgacga cgagactgag gaagtcgagg actccatcca ggacaccgac    1140
tccaaccaca ccccctccaa caagaagaag aacgatctga tgaaccgcac cttcaagaag    1200
atgatggacg agtacaacac taagaagaag aagctgatca agtgcatcaa gaaccacgag    1260
aacgacttca caagatctg catggacatg aagaactacg caccaacct gttcgagcag    1320 ctgtcctgct acaacaacaa cttctgcaac actaacggca tccgcttcca ctacgatgag    1380
tacatccaca gctgatcct gtccgtcaag agcaagaacc tgaacaagga cctgagcgac    1440
atgaccaaca tcctccagca gtccgagctg ctgctgacca acttgaacaa gaagatgggc    1500
tcctacatct acatcgacac tatcaagttc atccacaagg aaatgaagca catcttcaac    1560
cgcatcgagt accacaccaa gatcatcaac gataagacta agatcatcca agacaagatc    1620
aagctgaaca tctggcgcac ttttccaaaag gacgaactgc tgaagcgtat cctggacatg    1680
tctaacgagt actccctctt catcacctcc gaccacctga ggcagatgct gtacaacacc    1740
ttctactcca aggaaaagca cctcaacaac atcttccacc acctgatcta cgtgctgcag    1800
atgaagttca acgacgtccc catcaagatg gaatacttcc agacctacaa gaagaacaag    1860
cccctgaccc agcatcatca ccaccaccac                                     1890
```

```
<210> SEQ ID NO 36
<211> LENGTH: 15
<212> TYPE: PRT
<213> ORGANISM: Artificial sequence
<220> FEATURE:
<223> OTHER INFORMATION: Constructs
<220> FEATURE:
<221> NAME/KEY: BINDING
<222> LOCATION: (1)..(15)
<223> OTHER INFORMATION: biotin acceptor site

<400> SEQUENCE: 36

Gly Leu Asn Asp Ile Phe Glu Ala Gln Lys Ile Glu Trp His Glu
1               5                   10                  15

<210> SEQ ID NO 37
<211> LENGTH: 114
<212> TYPE: PRT
<213> ORGANISM: Artificial sequence
<220> FEATURE:
<223> OTHER INFORMATION: Constructs
<220> FEATURE:
<221> NAME/KEY: PEPTIDE
<222> LOCATION: (1)..(114)
<223> OTHER INFORMATION: Monovalent streptaviding

<400> SEQUENCE: 37

Ala Glu Ala Gly Ile Thr Gly Thr Trp Tyr Asn Gln His Gly Ser Thr
1               5                   10                  15

Phe Thr Val Thr Ala Gly Ala Asp Gly Asn Leu Thr Gly Gln Tyr Glu
                20                  25                  30

Asn Arg Ala Gln Gly Thr Gly Cys Gln Asn Ser Pro Tyr Thr Leu Thr
            35                  40                  45

Gly Arg Tyr Asn Gly Thr Lys Leu Glu Trp Arg Val Glu Trp Asn Asn
        50                  55                  60

Ser Thr Glu Asn Cys His Ser Arg Thr Glu Trp Arg Gly Gln Tyr Gln
65                  70                  75                  80

Gly Gly Ala Glu Ala Arg Ile Asn Thr Gln Trp Asn Leu Thr Tyr Glu
                85                  90                  95

Gly Gly Ser Gly Pro Ala Thr Glu Gln Gly Gln Asp Thr Phe Thr Lys
            100                 105                 110

Val Lys

<210> SEQ ID NO 38
<211> LENGTH: 321
<212> TYPE: PRT
<213> ORGANISM: Artificial sequence
<220> FEATURE:
<223> OTHER INFORMATION: Constructs
<220> FEATURE:
<221> NAME/KEY: MISC_FEATURE
<222> LOCATION: (1)..(321)
<223> OTHER INFORMATION: BirA OS=Escherichia coli (strain K12) GN=birA
      PE=1 SV=1

<400> SEQUENCE: 38

Met Lys Asp Asn Thr Val Pro Leu Lys Leu Ile Ala Leu Leu Ala Asn
1               5                   10                  15

Gly Glu Phe His Ser Gly Glu Gln Leu Gly Glu Thr Leu Gly Met Ser
                20                  25                  30

Arg Ala Ala Ile Asn Lys His Ile Gln Thr Leu Arg Asp Trp Gly Val
            35                  40                  45

Asp Val Phe Thr Val Pro Gly Lys Gly Tyr Ser Leu Pro Glu Pro Ile
```

-continued

```
                 50                  55                  60

Gln Leu Leu Asn Ala Lys Gln Ile Leu Gly Gln Leu Asp Gly Ser
 65                  70                  75                  80

Val Ala Val Leu Pro Val Ile Asp Ser Thr Asn Gln Tyr Leu Leu Asp
                 85                  90                  95

Arg Ile Gly Glu Leu Lys Ser Gly Asp Ala Cys Ile Ala Glu Tyr Gln
                100                 105                 110

Gln Ala Gly Arg Gly Arg Arg Gly Arg Lys Trp Phe Ser Pro Phe Gly
                115                 120                 125

Ala Asn Leu Tyr Leu Ser Met Phe Trp Arg Leu Glu Gln Gly Pro Ala
                130                 135                 140

Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Gly Ile Leu Val Glu Leu Thr
                180                 185                 190

Gly Lys Thr Gly Asp Ala Ala Gln Ile Val Ile Gly Ala Gly Ile Asn
                195                 200                 205

Met Ala Met Arg Arg Val Glu Glu Ser Val Val Asn Gln Gly Trp Ile
210                 215                 220

Thr Leu Gln Glu Ala Gly Ile Asn Leu Asp Arg Asn Thr Leu Ala Ala
225                 230                 235                 240

Met Leu Ile Arg Glu Leu Arg Ala Ala Leu Glu Leu Phe Glu Gln Glu
                245                 250                 255

Gly Leu Ala Pro Tyr Leu Ser Arg Trp Glu Lys Leu Asp Asn Phe Ile
                260                 265                 270

Asn Arg Pro Val Lys Leu Ile Ile Gly Asp Lys Glu Ile Phe Gly Ile
                275                 280                 285

Ser Arg Gly Ile Asp Lys Gln Gly Ala Leu Leu Leu Glu Gln Asp Gly
                290                 295                 300

Ile Ile Lys Pro Trp Met Gly Gly Glu Ile Ser Leu Arg Ser Ala Glu
305                 310                 315                 320

Lys

<210> SEQ ID NO 39
<211> LENGTH: 45
<212> TYPE: DNA
<213> ORGANISM: Artificial sequence
<220> FEATURE:
<223> OTHER INFORMATION: Constructs
<220> FEATURE:
<221> NAME/KEY: misc_feature
<222> LOCATION: (1)..(45)
<223> OTHER INFORMATION: DNA sequence of the biotin binding site

<400> SEQUENCE: 39
ggtctgaacg acatcttcga ggctcagaaa atcgaatggc acgaa            45

<210> SEQ ID NO 40
<211> LENGTH: 260
<212> TYPE: PRT
<213> ORGANISM: Artificial sequence
<220> FEATURE:
<223> OTHER INFORMATION: Constructs
<220> FEATURE:
<221> NAME/KEY: MISC_FEATURE
<222> LOCATION: (1)..(260)
<223> OTHER INFORMATION: Survivin:mSA (Homo Sapiens)
```

```
<400> SEQUENCE: 40

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Pro Ile Glu Glu His Lys Lys His
65                  70                  75                  80

Ser Ser Gly Cys Ala Phe Leu Ser Val Lys Lys Gln Phe Glu Glu Leu
                85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Glu Phe Glu Glu Thr Ala
        115                 120                 125

Lys Lys Val Arg Arg Ala Ile Glu Gln Leu Ala Ala Met Asp Gly Gly
    130                 135                 140

Ser Gly Ala Glu Ala Gly Ile Thr Gly Thr Trp Tyr Asn Gln His Gly
145                 150                 155                 160

Ser Thr Phe Thr Val Thr Ala Gly Ala Asp Gly Asn Leu Thr Gly Gln
                165                 170                 175

Tyr Glu Asn Arg Ala Gln Gly Thr Gly Cys Gln Asn Ser Pro Tyr Thr
            180                 185                 190

Leu Thr Gly Arg Tyr Asn Gly Thr Lys Leu Glu Trp Arg Val Glu Trp
        195                 200                 205

Asn Asn Ser Thr Glu Asn Cys His Ser Arg Thr Glu Trp Arg Gly Gln
    210                 215                 220

Tyr Gln Gly Gly Ala Glu Ala Arg Ile Asn Thr Gln Trp Asn Leu Thr
225                 230                 235                 240

Tyr Glu Gly Gly Ser Gly Pro Ala Thr Glu Gln Gly Gln Asp Thr Phe
                245                 250                 255

Thr Lys Val Lys
            260

<210> SEQ ID NO 41
<211> LENGTH: 259
<212> TYPE: PRT
<213> ORGANISM: Artificial sequence
<220> FEATURE:
<223> OTHER INFORMATION: Constructs
<220> FEATURE:
<221> NAME/KEY: MISC_FEATURE
<222> LOCATION: (1)..(259)
<223> OTHER INFORMATION: mSA:Survivin (Homo Sapiens)

<400> SEQUENCE: 41

Met Ala Glu Ala Gly Ile Thr Gly Thr Trp Tyr Asn Gln His Gly Ser
1               5                   10                  15

Thr Phe Thr Val Thr Ala Gly Ala Asp Gly Asn Leu Thr Gly Gln Tyr
            20                  25                  30

Glu Asn Arg Ala Gln Gly Thr Gly Cys Gln Asn Ser Pro Tyr Thr Leu
        35                  40                  45

Thr Gly Arg Tyr Asn Gly Thr Lys Leu Glu Trp Arg Val Glu Trp Asn
    50                  55                  60
```

Asn Ser Thr Glu Asn Cys His Ser Arg Thr Glu Trp Arg Gly Gln Tyr
65                  70                  75                  80

Gln Gly Gly Ala Glu Ala Arg Ile Asn Thr Gln Trp Asn Leu Thr Tyr
                85                  90                  95

Glu Gly Gly Ser Gly Pro Ala Thr Glu Gln Gly Gln Asp Thr Phe Thr
            100                 105                 110

Lys Val Lys Gly Gly Ser Gly Ala Pro Thr Leu Pro Pro Ala Trp Gln
        115                 120                 125

Pro Phe Leu Lys Asp His Arg Ile Ser Thr Phe Lys Asn Trp Pro Phe
    130                 135                 140

Leu Glu Gly Cys Ala Cys Thr Pro Glu Arg Met Ala Glu Ala Gly Phe
145                 150                 155                 160

Ile His Cys Pro Thr Glu Asn Glu Pro Asp Leu Ala Gln Cys Phe Phe
                165                 170                 175

Cys Phe Lys Glu Leu Glu Gly Trp Glu Pro Asp Asp Pro Ile Glu
            180                 185                 190

Glu His Lys Lys His Ser Ser Gly Cys Ala Phe Leu Ser Val Lys Lys
        195                 200                 205

Gln Phe Glu Glu Leu Thr Leu Gly Glu Phe Leu Lys Leu Asp Arg Glu
    210                 215                 220

Arg Ala Lys Asn Lys Ile Ala Lys Glu Thr Asn Asn Lys Lys Lys Glu
225                 230                 235                 240

Phe Glu Glu Thr Ala Lys Lys Val Arg Arg Ala Ile Glu Gln Leu Ala
                245                 250                 255

Ala Met Asp

<210> SEQ ID NO 42
<211> LENGTH: 260
<212> TYPE: PRT
<213> ORGANISM: Artificial sequence
<220> FEATURE:
<223> OTHER INFORMATION: Constructs
<220> FEATURE:
<221> NAME/KEY: MISC_FEATURE
<222> LOCATION: (1)..(260)
<223> OTHER INFORMATION: Survivin(F101A/L102A):mSA (Homo Sapiens)

<400> SEQUENCE: 42

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Pro Ile Glu Glu His Lys Lys His
65                  70                  75                  80

Ser Ser Gly Cys Ala Phe Leu Ser Val Lys Lys Gln Phe Glu Glu Leu
                85                  90                  95

Thr Leu Gly Glu Ala Ala Lys Leu Asp Arg Glu Arg Ala Lys Asn Lys
            100                 105                 110

Ile Ala Lys Glu Thr Asn Asn Lys Lys Lys Glu Phe Glu Glu Thr Ala
        115                 120                 125

Lys Lys Val Arg Arg Ala Ile Glu Gln Leu Ala Ala Met Asp Gly Gly
    130                 135                 140

```
Ser Gly Ala Glu Ala Gly Ile Thr Gly Thr Trp Tyr Asn Gln His Gly
145                 150                 155                 160

Ser Thr Phe Thr Val Thr Ala Gly Ala Asp Gly Asn Leu Thr Gly Gln
            165                 170                 175

Tyr Glu Asn Arg Ala Gln Gly Thr Gly Cys Gln Asn Ser Pro Tyr Thr
        180                 185                 190

Leu Thr Gly Arg Tyr Asn Gly Thr Lys Leu Glu Trp Arg Val Glu Trp
            195                 200                 205

Asn Asn Ser Thr Glu Asn Cys His Ser Arg Thr Glu Trp Arg Gly Gln
210                 215                 220

Tyr Gln Gly Gly Ala Glu Ala Arg Ile Asn Thr Gln Trp Asn Leu Thr
225                 230                 235                 240

Tyr Glu Gly Gly Ser Gly Pro Ala Thr Glu Gln Gly Gln Asp Thr Phe
                245                 250                 255

Thr Lys Val Lys
            260

<210> SEQ ID NO 43
<211> LENGTH: 259
<212> TYPE: PRT
<213> ORGANISM: Artificial sequence
<220> FEATURE:
<223> OTHER INFORMATION: Constructs
<220> FEATURE:
<221> NAME/KEY: MISC_FEATURE
<222> LOCATION: (1)..(259)
<223> OTHER INFORMATION: mSA:Survivin(F101A/L102A) (Homo Sapiens)

<400> SEQUENCE: 43

Met Ala Glu Ala Gly Ile Thr Gly Thr Trp Tyr Asn Gln His Gly Ser
1               5                   10                  15

Thr Phe Thr Val Thr Ala Gly Ala Asp Gly Asn Leu Thr Gly Gln Tyr
            20                  25                  30

Glu Asn Arg Ala Gln Gly Thr Gly Cys Gln Asn Ser Pro Tyr Thr Leu
        35                  40                  45

Thr Gly Arg Tyr Asn Gly Thr Lys Leu Glu Trp Arg Val Glu Trp Asn
    50                  55                  60

Asn Ser Thr Glu Asn Cys His Ser Arg Thr Glu Trp Arg Gly Gln Tyr
65                  70                  75                  80

Gln Gly Gly Ala Glu Ala Arg Ile Asn Thr Gln Trp Asn Leu Thr Tyr
                85                  90                  95

Glu Gly Gly Ser Gly Pro Ala Thr Glu Gln Gly Gln Asp Thr Phe Thr
            100                 105                 110

Lys Val Lys Gly Gly Ser Gly Ala Pro Thr Leu Pro Pro Ala Trp Gln
        115                 120                 125

Pro Phe Leu Lys Asp His Arg Ile Ser Thr Phe Lys Asn Trp Pro Phe
    130                 135                 140

Leu Glu Gly Cys Ala Cys Thr Pro Glu Arg Met Ala Glu Ala Gly Phe
145                 150                 155                 160

Ile His Cys Pro Thr Glu Asn Glu Pro Asp Leu Ala Gln Cys Phe Phe
                165                 170                 175

Cys Phe Lys Glu Leu Glu Gly Trp Glu Pro Asp Asp Pro Ile Glu
            180                 185                 190

Glu His Lys Lys His Ser Ser Gly Cys Ala Phe Leu Ser Val Lys Lys
        195                 200                 205

Gln Phe Glu Glu Leu Thr Leu Gly Glu Ala Ala Lys Leu Asp Arg Glu
```

-continued

```
              210                 215                 220
Arg Ala Lys Asn Lys Ile Ala Lys Glu Thr Asn Asn Lys Lys Glu
225                 230                 235                 240

Phe Glu Glu Thr Ala Lys Lys Val Arg Arg Ala Ile Glu Gln Leu Ala
                245                 250                 255

Ala Met Asp

<210> SEQ ID NO 44
<211> LENGTH: 261
<212> TYPE: PRT
<213> ORGANISM: Artificial sequence
<220> FEATURE:
<223> OTHER INFORMATION: Constructs
<220> FEATURE:
<221> NAME/KEY: MISC_FEATURE
<222> LOCATION: (1)..(261)
<223> OTHER INFORMATION: mSA:Survivin(F101A/L102A) (Mus Musculus)

<400> SEQUENCE: 44

Met Ala Glu Ala Gly Ile Thr Gly Thr Trp Tyr Asn Gln His Gly Ser
1               5                   10                  15

Thr Phe Thr Val Thr Ala Gly Ala Asp Gly Asn Leu Thr Gly Gln Tyr
                20                  25                  30

Glu Asn Arg Ala Gln Gly Thr Gly Cys Gln Asn Ser Pro Tyr Thr Leu
            35                  40                  45

Thr Gly Arg Tyr Asn Gly Thr Lys Leu Glu Trp Arg Val Glu Trp Asn
        50                  55                  60

Asn Ser Thr Glu Asn Cys His Ser Arg Thr Glu Trp Arg Gly Gln Tyr
65                  70                  75                  80

Gln Gly Gly Ala Glu Ala Arg Ile Asn Thr Gln Trp Asn Leu Thr Tyr
                85                  90                  95

Glu Gly Gly Ser Gly Pro Ala Thr Glu Gln Gly Gln Asp Thr Phe Thr
            100                 105                 110

Lys Val Lys Gly Gly Ser Gly Ala Pro Ala Leu Pro Gln Ile Trp Gln
        115                 120                 125

Leu Tyr Leu Lys Asn Tyr Arg Ile Ala Thr Phe Lys Asn Trp Pro Phe
    130                 135                 140

Leu Glu Asp Cys Ala Cys Thr Pro Glu Arg Met Ala Glu Ala Gly Phe
145                 150                 155                 160

Ile His Cys Pro Thr Glu Asn Glu Pro Asp Leu Ala Gln Cys Phe Phe
                165                 170                 175

Cys Phe Lys Glu Leu Glu Gly Trp Glu Pro Asp Asp Asn Pro Ile Glu
            180                 185                 190

Glu His Arg Lys His Ser Pro Gly Cys Ala Phe Leu Thr Val Lys Lys
        195                 200                 205

Gln Met Glu Glu Leu Thr Val Ser Glu Ala Ala Lys Leu Asp Arg Gln
    210                 215                 220

Arg Ala Lys Asn Lys Ile Ala Lys Glu Thr Asn Asn Lys Gln Lys Glu
225                 230                 235                 240

Phe Glu Glu Thr Ala Lys Thr Thr Arg Gln Ser Ile Glu Gln Leu Ala
                245                 250                 255

Ala Ser Gly Arg Phe
            260

<210> SEQ ID NO 45
<211> LENGTH: 256
<212> TYPE: PRT
```

<213> ORGANISM: Artificial sequence
<220> FEATURE:
<223> OTHER INFORMATION: Constructs
<220> FEATURE:
<221> NAME/KEY: MISC_FEATURE
<222> LOCATION: (1)..(256)
<223> OTHER INFORMATION: Survivin (F101A/L102A):mSA (Mus Musculus)

<400> SEQUENCE: 45

```
Gly Ala Pro Ala Leu Pro Gln Ile Trp Gln Leu Tyr Leu Lys Asn Tyr
1               5                   10                  15

Arg Ile Ala Thr Phe Lys Asn Trp Pro Phe Leu Glu Asp Cys Ala Cys
            20                  25                  30

Thr Pro Glu Arg Met Ala Glu Ala Gly Phe Ile His Cys Pro Thr Glu
        35                  40                  45

Asn Glu Pro Asp Leu Ala Gln Cys Phe Phe Cys Phe Lys Glu Leu Glu
    50                  55                  60

Gly Trp Glu Pro Asp Asp Asn Pro Ile Glu Glu His Arg Lys His Ser
65                  70                  75                  80

Pro Gly Cys Ala Phe Leu Thr Val Lys Lys Gln Met Glu Glu Leu Thr
                85                  90                  95

Val Ser Glu Ala Ala Lys Leu Asp Arg Gln Arg Ala Lys Asn Lys Ile
            100                 105                 110

Ala Lys Glu Thr Asn Asn Lys Gln Lys Glu Phe Glu Glu Thr Ala Lys
        115                 120                 125

Thr Thr Arg Gln Ser Ile Glu Gln Leu Ala Ala Gly Gly Ser Ala Glu
130                 135                 140

Ala Gly Ile Thr Gly Thr Trp Tyr Asn Gln His Gly Ser Thr Phe Thr
145                 150                 155                 160

Val Thr Ala Gly Ala Asp Gly Asn Leu Thr Gly Gln Tyr Glu Asn Arg
                165                 170                 175

Ala Gln Gly Thr Gly Cys Gln Asn Ser Pro Tyr Thr Leu Thr Gly Arg
            180                 185                 190

Tyr Asn Gly Thr Lys Leu Glu Trp Arg Val Glu Trp Asn Asn Ser Thr
        195                 200                 205

Glu Asn Cys His Ser Arg Thr Glu Trp Arg Gly Gln Tyr Gln Gly Gly
    210                 215                 220

Ala Glu Ala Arg Ile Asn Thr Gln Trp Asn Leu Thr Tyr Glu Gly Gly
225                 230                 235                 240

Ser Gly Pro Ala Thr Glu Gln Gly Gln Asp Thr Phe Thr Lys Val Lys
                245                 250                 255
```

<210> SEQ ID NO 46
<211> LENGTH: 261
<212> TYPE: PRT
<213> ORGANISM: Artificial sequence
<220> FEATURE:
<223> OTHER INFORMATION: Constructs
<220> FEATURE:
<221> NAME/KEY: MISC_FEATURE
<222> LOCATION: (1)..(261)
<223> OTHER INFORMATION: mSA:Survivin (Mus Musculus)

<400> SEQUENCE: 46

```
Met Ala Glu Ala Gly Ile Thr Gly Thr Trp Tyr Asn Gln His Gly Ser
1               5                   10                  15

Thr Phe Thr Val Thr Ala Gly Ala Asp Gly Asn Leu Thr Gly Gln Tyr
            20                  25                  30

Glu Asn Arg Ala Gln Gly Thr Gly Cys Gln Asn Ser Pro Tyr Thr Leu
```

```
            35                  40                  45
Thr Gly Arg Tyr Asn Gly Thr Lys Leu Glu Trp Arg Val Glu Trp Asn
 50                  55                  60

Asn Ser Thr Glu Asn Cys His Ser Arg Thr Glu Trp Arg Gly Gln Tyr
 65                  70                  75                  80

Gln Gly Gly Ala Glu Ala Arg Ile Asn Thr Gln Trp Asn Leu Thr Tyr
                 85                  90                  95

Glu Gly Gly Ser Gly Pro Ala Thr Glu Gln Gly Gln Asp Thr Phe Thr
            100                 105                 110

Lys Val Lys Gly Gly Ser Gly Ala Pro Ala Leu Pro Gln Ile Trp Gln
        115                 120                 125

Leu Tyr Leu Lys Asn Tyr Arg Ile Ala Thr Phe Lys Asn Trp Pro Phe
130                 135                 140

Leu Glu Asp Cys Ala Cys Thr Pro Glu Arg Met Ala Glu Ala Gly Phe
145                 150                 155                 160

Ile His Cys Pro Thr Glu Asn Glu Pro Asp Leu Ala Gln Cys Phe Phe
                165                 170                 175

Cys Phe Lys Glu Leu Glu Gly Trp Glu Pro Asp Asp Asn Pro Ile Glu
            180                 185                 190

Glu His Arg Lys His Ser Pro Gly Cys Ala Phe Leu Thr Val Lys Lys
        195                 200                 205

Gln Met Glu Glu Leu Thr Val Ser Glu Phe Leu Lys Leu Asp Arg Gln
210                 215                 220

Arg Ala Lys Asn Lys Ile Ala Lys Glu Thr Asn Asn Lys Gln Lys Glu
225                 230                 235                 240

Phe Glu Glu Thr Ala Lys Thr Thr Arg Gln Ser Ile Glu Gln Leu Ala
                245                 250                 255

Ala Ser Gly Arg Phe
            260

<210> SEQ ID NO 47
<211> LENGTH: 256
<212> TYPE: PRT
<213> ORGANISM: Artificial sequence
<220> FEATURE:
<223> OTHER INFORMATION: Constructs
<220> FEATURE:
<221> NAME/KEY: MISC_FEATURE
<222> LOCATION: (1)..(256)
<223> OTHER INFORMATION: Survivin:mSA (Mus Musculus)

<400> SEQUENCE: 47

Gly Ala Pro Ala Leu Pro Gln Ile Trp Gln Leu Tyr Leu Lys Asn Tyr
 1               5                  10                  15

Arg Ile Ala Thr Phe Lys Asn Trp Pro Phe Leu Glu Asp Cys Ala Cys
                20                  25                  30

Thr Pro Glu Arg Met Ala Glu Ala Gly Phe Ile His Cys Pro Thr Glu
            35                  40                  45

Asn Glu Pro Asp Leu Ala Gln Cys Phe Phe Cys Phe Lys Glu Leu Glu
 50                  55                  60

Gly Trp Glu Pro Asp Asp Asn Pro Ile Glu Glu His Arg Lys His Ser
 65                  70                  75                  80

Pro Gly Cys Ala Phe Leu Thr Val Lys Lys Gln Met Glu Glu Leu Thr
                85                  90                  95

Val Ser Glu Phe Leu Lys Leu Asp Arg Gln Arg Ala Lys Asn Lys Ile
            100                 105                 110
```

```
Ala Lys Glu Thr Asn Asn Lys Gln Lys Glu Phe Glu Thr Ala Lys
            115                 120                 125

Thr Thr Arg Gln Ser Ile Glu Gln Leu Ala Ala Gly Ser Ala Glu
130                 135                 140

Ala Gly Ile Thr Gly Thr Trp Tyr Asn Gln His Gly Ser Thr Phe Thr
145                 150                 155                 160

Val Thr Ala Gly Ala Asp Gly Asn Leu Thr Gly Gln Tyr Glu Asn Arg
                165                 170                 175

Ala Gln Gly Thr Gly Cys Gln Asn Ser Pro Tyr Thr Leu Thr Gly Arg
            180                 185                 190

Tyr Asn Gly Thr Lys Leu Glu Trp Arg Val Glu Trp Asn Asn Ser Thr
        195                 200                 205

Glu Asn Cys His Ser Arg Thr Glu Trp Arg Gly Gln Tyr Gln Gly Gly
    210                 215                 220

Ala Glu Ala Arg Ile Asn Thr Gln Trp Asn Leu Thr Tyr Glu Gly Gly
225                 230                 235                 240

Ser Gly Pro Ala Thr Glu Gln Gly Gln Asp Thr Phe Thr Lys Val Lys
                245                 250                 255

<210> SEQ ID NO 48
<211> LENGTH: 783
<212> TYPE: DNA
<213> ORGANISM: Artificial sequence
<220> FEATURE:
<223> OTHER INFORMATION: Constructs
<220> FEATURE:
<221> NAME/KEY: misc_feature
<222> LOCATION: (1)..(783)
<223> OTHER INFORMATION: mSA:Survivin(F101A/L102A) (Mus Musculus) DNA

<400> SEQUENCE: 48
atggcagaag caggtattac cggcacctgg tataatcagc atggtagcac ctttaccgtt    60
accgcaggcg cagatggtaa tctgacaggt cagtatgaaa atcgtgcaca gggcaccggt   120
tgtcagaata gcccgtatac cctgaccggt cgttataatg gcaccaaact ggaatggcgt   180
gttgaatgga ataatagcac cgaaaattgt catagccgta ccgaatggcg tggtcagtat   240
cagggtggtg cagaagcccg tattaatacc cagtggaatc tgacctatga aggtggtagc   300
ggtccggcaa ccgaacaggg tcaggatacc tttaccaaag ttaaaggtgg cagcggtgca   360
ccggcactgc cgcagatttg cagctgtat ctgaaaaact atcgtatcgc cacctttaaa   420
aactggccgt ttctggaaga ttgtgcatgt acaccggaac gtatggcaga agcaggtttt   480
attcattgtc cgaccgaaaa tgaaccggat ctggcacagt gtttttttg ctttaaagaa   540 ctggaaggtt gggagccgga tgataatccg attgaagaac atcgtaaaca tagtccgggt   600
tgtgcatttc tgaccgtgaa aaaacaaatg gaagaactga ccgttagcga ggcagcaaaa   660
ctggatcgtc agcgtgccaa aaacaaaatt gcaaagaaa ccaataacaa acagaaagaa   720
ttcgaagaaa ccgccaaaac cacccgtcag agcattgaac agctggcagc aagcggccgc   780
ttt                                                                 783

<210> SEQ ID NO 49
<211> LENGTH: 768
<212> TYPE: DNA
<213> ORGANISM: Artificial sequence
<220> FEATURE:
<223> OTHER INFORMATION: Constructs
<220> FEATURE:
<221> NAME/KEY: misc_feature
<222> LOCATION: (1)..(768)
```

<223> OTHER INFORMATION: Survivin (F101A/L102A):mSA (Mus Musculus) DNA

<400> SEQUENCE: 49

```
ggtgcaccgg cactgccgca gatttggcag ctgtatctga aaaactatcg tatcgccacc       60
tttaaaaact ggccgtttct ggaagattgt gcatgtacac cggaacgtat ggcagaagca      120
ggttttattc attgtccgac cgaaaatgaa ccggatctgg cacagtgttt ttttttgcttt    180
aaagaactgg aaggttggga gccggatgat aatccgattg aagaacatcg taaacatagt     240
ccgggttgtg catttctgac cgtgaaaaaa caaatggaag aactgaccgt tagcgaggca     300
gcaaaactgg atcgtcagcg tgccaaaaac aaaattgcaa agaaaccaa taacaaacag      360
aaagaattcg aagaaccgc caaaaccacc cgtcagagca ttgaacagct ggcagcaggt      420
ggcagcgcag aagcaggtat taccggcacc tggtataatc agcatggtag caccctttacc   480
gttaccgcag gcgcagatgg taatctgaca ggtcagtatg aaaatcgtgc acagggcacc    540
ggttgtcaga atagcccgta ccctgaccg gtcgttata atggcaccaa actggaatgg      600
cgtgttgaat ggaataatag caccgaaaat tgtcatagcc gtaccgaatg gcgtggtcag    660
tatcagggtg gtgcagaagc ccgtattaat acccagtgga atctgaccta tgaaggtggt    720
agcggtccgg caaccgaaca gggtcaggat acctttacca aagttaaa                 768
```

<210> SEQ ID NO 50
<211> LENGTH: 783
<212> TYPE: DNA
<213> ORGANISM: Artificial sequence
<220> FEATURE:
<223> OTHER INFORMATION: Constructs
<220> FEATURE:
<221> NAME/KEY: misc_feature
<222> LOCATION: (1)..(783)
<223> OTHER INFORMATION: mSA:Survivin (Mus Musculus) DNA

<400> SEQUENCE: 50

```
atggcagaag caggtattac cggcacctgg tataatcagc atggtagcac ctttaccgtt       60
accgcaggcg cagatggtaa tctgacaggt cagtatgaaa atcgtgcaca gggcaccggt     120
tgtcagaata gcccgtatac cctgaccggt cgttataatg gcaccaaact ggaatggcgt     180
gttgaatgga ataatagcac cgaaaattgt catagccgta ccgaatggcg tggtcagtat     240
cagggtggtg cagaagcccg tattaatacc cagtggaatc tgacctatga aggtggtagc    300
ggtccggcaa ccgaacaggg tcaggatacc tttaccaaag ttaaaggtgg cagcggtgca    360
ccggcactgc cgcagatttg gcagctgtat ctgaaaaact atcgtatcgc cacctttaaa    420
aactggccgt ttctggaaga ttgtgcatgt acaccggaac gtatggcaga agcaggtttt    480
attcattgtc cgaccgaaaa tgaaccggat ctggcacagt gtttttttg ctttaaagaa     540
ctggaaggtt gggagccgga tgataatccg attgaagaac atcgtaaaca tagtccgggt    600
tgtcatttc tgaccgtgaa aaaacaaatg gaagaactga ccgttagcga ggcagcaaaa    660
ctggatcgtc agcgtgccaa aaacaaaatt gcaaagaaa ccaataacaa acagaaagaa    720
ttcgaagaaa ccgccaaaac cacccgtcag agcattgaac agctggcagc aagcggccgc   780
ttt                                                                 783
```

<210> SEQ ID NO 51
<211> LENGTH: 768
<212> TYPE: DNA
<213> ORGANISM: Artificial sequence
<220> FEATURE:
<223> OTHER INFORMATION: Constructs

```
<220> FEATURE:
<221> NAME/KEY: misc_feature
<222> LOCATION: (1)..(768)
<223> OTHER INFORMATION: Survivin:mSA (Mus Musculus) DNA

<400> SEQUENCE: 51
ggtgcaccgg cactgccgca gatttggcag ctgtatctga aaaactatcg tatcgccacc      60
tttaaaaact ggccgtttct ggaagattgt gcatgtacac cggaacgtat ggcagaagca     120
ggttttattc attgtccgac cgaaaatgaa ccggatctgg cacagtgttt ttttgctttt     180
aaagaactgg aaggttggga gccggatgat aatccgattg aagaacatcg taaacatagt     240
ccgggttgtg catttctgac cgtgaaaaaa caaatggaag aactgaccgt tagcgagttt     300
ctgaaactgg atcgtcagcg tgccaaaaac aaaattgcaa agaaaccaa taacaaacag      360 aaagaattcg aagaaaccgc caaaaccacc cgtcagagca ttgaacagct ggcagcaggt     420
ggcagcgcag aagcaggtat taccggcacc tggtataatc agcatggtag cacctttacc     480
gttaccgcag cgcagatgg taatctgaca ggtcagtatg aaaatcgtgc acagggcacc      540
ggttgtcaga atagcccgta taccctgacc ggtcgttata tggcaccaa actggaatgg      600 cgtgttgaat ggaataatag caccgaaaat tgtcatagcc gtaccgaatg cgtggtcag     660 tatcagggtg gtgcagaagc ccgtattaat acccagtgga atctgaccta tgaaggtggt     720
agcggtccgg caaccgaaca gggtcaggat acctttacca aagttaaa                 768

<210> SEQ ID NO 52
<211> LENGTH: 268
<212> TYPE: PRT
<213> ORGANISM: Artificial sequence
<220> FEATURE:
<223> OTHER INFORMATION: Constructs
<220> FEATURE:
<221> NAME/KEY: MISC_FEATURE
<222> LOCATION: (1)..(268)
<223> OTHER INFORMATION: mSA:CIDR1a-HIS

<400> SEQUENCE: 52

Gly Ala Glu Ala Gly Ile Thr Gly Thr Trp Tyr Asn Gln His Gly Ser
1               5                   10                  15

Thr Phe Thr Val Thr Ala Gly Ala Asp Gly Asn Leu Thr Gly Gln Tyr
                20                  25                  30

Glu Asn Arg Ala Gln Gly Thr Gly Cys Gln Asn Ser Pro Tyr Thr Leu
            35                  40                  45

Thr Gly Arg Tyr Asn Gly Thr Lys Leu Glu Trp Arg Val Glu Trp Asn
        50                  55                  60

Asn Ser Thr Glu Asn Cys His Ser Arg Thr Glu Trp Arg Gly Gln Tyr
65                  70                  75                  80

Gln Gly Gly Ala Glu Ala Arg Ile Asn Thr Gln Trp Asn Leu Thr Tyr
                85                  90                  95

Glu Gly Gly Ser Gly Pro Ala Thr Glu Gln Gly Gln Asp Thr Phe Thr
            100                 105                 110

Lys Val Lys Gly Gly Ser Lys Ile Thr Ser Phe Asp Glu Phe Phe Asp
        115                 120                 125

Phe Trp Val Arg Lys Leu Leu Ile Asp Thr Ile Lys Trp Glu Thr Glu
    130                 135                 140

Leu Thr Tyr Cys Ile Asn Asn Thr Asp Val Thr Asp Cys Asn Lys Cys
145                 150                 155                 160

Asn Lys Asn Cys Val Cys Phe Asp Lys Trp Val Lys Gln Lys Glu Asp
                165                 170                 175
```

```
Glu Trp Thr Asn Ile Met Lys Leu Phe Thr Asn Lys His Asp Ile Pro
                180                 185                 190
Lys Lys Tyr Tyr Leu Asn Ile Asn Asp Leu Phe Asp Ser Phe Phe Phe
            195                 200                 205
Gln Val Ile Tyr Lys Phe Asn Glu Gly Glu Ala Lys Trp Asn Glu Leu
        210                 215                 220
Lys Glu Asn Leu Lys Lys Gln Ile Ala Ser Ser Lys Ala Asn Asn Gly
225                 230                 235                 240
Thr Lys Asp Ser Glu Ala Ala Ile Lys Val Leu Phe Asn His Ile Lys
                245                 250                 255
Glu Ile Ala Thr Ile Cys Lys Asp Asn Asn Thr Asn
                260                 265

<210> SEQ ID NO 53
<211> LENGTH: 801
<212> TYPE: DNA
<213> ORGANISM: Artificial sequence
<220> FEATURE:
<223> OTHER INFORMATION: Constructs
<220> FEATURE:
<221> NAME/KEY: misc_feature
<222> LOCATION: (1)..(801)
<223> OTHER INFORMATION: mSA:CIDR1a-HIS DNA

<400> SEQUENCE: 53
gcagaagcag gtattaccgg cacctggtat aatcagcatg gtagcacctt taccgttacc      60
gcaggcgcag atggtaatct gacaggtcag tatgaaaatc gtgcacaggg caccggttgt     120
cagaatagcc cgtataccct gaccggtcgt tataatggca ccaaactgga atggcgtgtt     180
gaatggaata atagcaccga aaattgtcat agccgtaccg aatggcgtgg tcagtatcag     240
ggtggtgcag aagcccgtat taatacccag tggaatctga cctatgaagg tggtagcggt     300
ccggcaaccg aacagggtca ggatacccttt accaaagtta aggtggcag caaaataacg     360 tcatttgatg aattttttga ttttgggtt agaaaattat taatagacac tataaagtgg     420
gaaaccgaac ttacgtattg tataaataat actgatgtca cggattgtaa taaatgtaac     480
aaaaattgcg tatgttttga caaatgggtt aaacaaaaag aagacgaatg gacaaatata     540
atgaaactat tcacaaacaa acacgatata ccgaaaaaat attatcttaa tattaatgat     600 cttttttgata gtttttttt ccaagttata tataagttta acgaaggaga agcaaaatgg     660
aatgaactta agaaaatttt aaaaaagcaa attgcgtctt ccaaagcaaa taacggaacc     720
aaagattcag aagctgcaat aaaagtgttg tttaatcaca taaaagaaat tgcaacaata     780
tgcaaagata taatacaaa c                                                 801
```

VIRUS LIKE PARTICLE WITH EFFICIENT EPITOPE DISPLAY

FIELD OF INVENTION

The present invention relates to a technology and method for making a virus like particle based vaccine with efficient epitope display and capable of inducing a strong and long-term protective immune response. The present invention solves the key challenge of obtaining a virus like particle which presents a larger antigen on the particle surface at high density, while being regularly spaced, and with consistent orientation; three critical factors for obtaining optimal activation of the immune system.

BACKGROUND OF INVENTION

Vaccines have played, and still play, a major role in reducing the impact of infectious diseases on global health. The first generation of vaccines was based on attenuated or inactivated pathogens. These full-pathogen-based vaccines have proven extremely effective and, in some cases, have (e.g. small pox) led to the complete eradication of the target pathogen. There are however serious concerns associated with using full-pathogens for immunization as these have been seen to induce severe side effects at some frequency in populations, underscoring the need to develop safer vaccines (Plotkin S A et. al 2005). Along with the recent advances in recombinant DNA technology and genetic engineering, modern vaccine research has put effort into identifying critical antigenic targets of neutralizing antibodies with the aim of developing so called 'subunit vaccines' composed solely of well-defined, purified antigen components (Murray K. et al. 1988). The immunogenicity of subunit vaccines based on soluble protein is, unfortunately, low compared to that of full pathogen-based vaccines. To induce a high-titer antibody response it is thus often necessary to use high antigen doses, booster administrations, and co-administration of adjuvants and even so these subunit vaccines are generally not capable of inducing long-term protective immunity. This is indeed exemplified by the many vaccine failures observed with soluble proteins during the past several years and point to an important fact: that the size and the spatial assembly of the vaccine antigen component is critical for proper activation of the immune system, demonstrating the importance of qualitative immune responses beyond quantitative ones.

Virus-like particles (VLPs), which are both highly immunogenic and safe, represent a major advancement in the development of subunit vaccines, combining many of the advantages of full pathogen-based vaccines and recombinant subunit vaccines. VLPs are composed of one or several recombinantly expressed viral proteins which spontaneously assemble into macromolecular particulate structures mimicking the morphology of the native virus coat—but lacking infectious genetic material. The particulate nature and size of VLPs (22-150 nm) appears to be optimal for efficient uptake by professional antigen presenting cells, particularly dendritic cells (DCs) as well as for entry into lymph vessels (Bachmann, M F, Jennings, G T. 2010). Furthermore, surface structures presenting an antigen at high density, while being regularly spaced, and with consistent orientation are characteristic of microbial surface antigens for which the mammalian immune system has evolved to respond vigorously to. At the molecular level, the presentation of an epitope at high density, while being regularly spaced, and with consistent orientation enables efficient cross-linking of B-cell receptors (Bachmann, M F and Zinkernagel, R M. 1997) leading to strong B-cell responses, even in the absence of T-cell help (Bachmann, M F et al., 1993; Chackerian et al., 1999; Kouskoff, V. et al., 2000) and cumulative data from several studies indicate that B-cells, in fact, discriminate antigen patterns via the degree of surface Ig-cross-linking and use antigen repetitiveness as a self/nonself discriminator.

It has long been an attractive goal to exploit the VLPs as an immunogenicity-boosting platform for inducing immune responses against heterologous antigens by using them as molecular scaffolds for antigen presentation. Traditionally this has been achieved either by incorporation of antigenic epitopes into VLPs by genetic fusion (chimeric VLPs) or by conjugating antigens to preassembled VLPs. The chimeric VLP approach is to date the most common method for displaying heterologous epitopes on VLPs (Pumpens, P and Grens, E. 2001; Bachmann, M F and Jennings, G T, 2004a; Chackerian, 2007; Grgacic, E V L. and Anderson, D A. 2006). However, this strategy is severely limited by both the size and nature of epitopes that can be inserted into VLPs, especially in their immunodominant regions, and it has in general not been possible to insert peptides longer than 20 amino acids without disrupting the fragile self-assembly process of the VLPs. In addition, this approach requires that critical epitopes have already been identified in the target antigen and that these can be presented in an immunodominant region on the VLP surface while maintaining its native conformation. Therefore, despite a still growing understanding of the VLP structure/assembly process, generating chimeric VLPs is still a trial-and-error process and it remains impossible to predict whether individual peptides will be compatible with VLP assembly or whether insertions will be immunogenic. Finally, due to the small size of inserted peptide sequences the induced antibody response will essentially be monoclonal, which in some cases will set a limit to the potency of protection.

On the other hand chemical conjugation e.g. through chemical biotinylation of exposed lysine residues allows the attachment of diverse kinds of target antigens (incl. non-protein targets) to VLPs and this approach is generally not restricted by the size of the antigen (Raja K S. Et al. 2003 and others). However with this approach it is very challenging, if not impossible, to control the orientation and the total amount/stoichiometry of the coupled antigen, affecting both the density and regularity of displayed epitopes, and thus potentially limiting the immune response. In addition to this, chemical coupling procedures are rarely compatible with large scale vaccine production. As a result the current technologies are not sufficient to ensure VLP display of antigens at high density, while being regularly spaced, and with consistent orientation, which are three critical factors for obtaining strong and long lasting activation of the immune system.

In brief:
Induction of a strong and long lasting immune response to pathogens as well as disease associated antigens is very difficult to obtain with subunit vaccines.
Virus like particle (VLP) presentation of antigens has proven to be very efficient in inducing the highly functional long-term immune responses.
Coupling of an antigen onto the surface of a VLP, to ensure a high density display of regularly spaced epitopes, pose a major biotechnological challenge.
Specifically, the main challenge of current VLP delivery platforms is to present an antigen on the surface of the VLP, at high density, and with a consistent orientation to enable a regular, high density, spacing of displayed epitopes, which is important for inducing long-term protective immunity.

SUMMARY OF INVENTION

The present invention solves the challenges of obtaining a VLP which presents densely and regularly spaced surface antigens with consistent orientation, capable of efficiently displaying epitopes and to induce long-term protective immunity in a subject. The general concept of the present invention is illustrated in FIG. 1. The present inventors have identified regions of the Papilloma Virus (PV) VLP where the inventors can insert a biotin acceptor site, without compromising the self-assembly of the particle. In addition, the inventors have managed to setup a system to produce antigens fused to a monovalent streptavidin, which ensures control of the orientation of the coupled antigen. Enzymatical biotinylation of the human papilloma virus (HPV) VLPs facilitate linkage to the monovalent streptavidin/antigen and ensure control of the overall amount/stoichiometry as well as display of antigens in a densely and repetitive ordered manner with consistent orientation which is important for yielding efficient epitope display and consequently a potent immune response. The described antigen display scaffold is unique as it for the first time enables coupling of virtually any antigen at high density on a VLP surface, thereby presenting ordered arrays of the particular antigens which are all held in the same orientation, thereby solving three key issues of mounting an efficient immune response. The system can both be used to target self-antigens (i.e. break tolerance) as well as to efficiently target infectious organisms.

The problems described above are solved by the aspects and embodiments of the present invention characterized in the claims. As illustrated in FIG. 1, a main aspect of the present invention concerns a vaccine for use in the prophylaxis and/or treatment of a disease wherein the vaccine comprises:
  i. a papilloma virus (PV) L1 protein containing a biotin acceptor site, and
  ii. a biotin molecule enzymatically conjugated to said biotin acceptor site, and
  iii. an antigen fused to a monovalent streptavidin,
wherein the antigen and PV L1 protein are linked via the interaction between the monovalent streptavidin and the biotin molecule enzymatically conjugated to the biotin acceptor site of the PV L1 protein, and wherein i-iii form a virus like particle displaying said antigen.

In another aspect the present invention concerns a vector comprising at least one polynucleotide encoding
  i. a PV L1 protein containing a biotin acceptor site, and
  ii. a biotin ligase capable of biotinylating the biotin acceptor site, and
  iii. an antigen fused to a monovalent streptavidin as illustrated on FIG. 1.

In another aspect the present invention concerns a host cell expressing at least one polypeptide encoded by said polynucleotide.

In another aspect the present invention concerns a composition comprising said vaccine.

A further aspect of the present invention concerns a method of manufacturing a pharmaceutical composition comprising said vaccine, wherein the method comprises the steps of
  i. obtaining a first polypeptide; a PV L1 protein containing a biotin acceptor site, and
  ii. obtaining a second polypeptide; a biotin ligase, capable of biotinylating the biotin acceptor site, and
  iii. obtaining a third polypeptide; an antigen fused to a monovalent streptavidin, and
  iv. subjecting the first polypeptide to conditions which enable formation of virus like particles, and
  v. enable enzymatic biotinylating of the biotin acceptor site of said virus like particles using said second polypeptide, and
  vi. obtaining a vaccine by linkage of the third polypeptide and said virus like particles via the interaction between the monovalent streptavidin and the biotin molecule enzymatically conjugated to the biotin acceptor site of said virus like particles, and
  vii. generating a composition comprising said vaccine, thereby obtaining a pharmaceutical composition.

Yet an aspect of the present invention concerns a method of administering said vaccine to treat and/or prevent a clinical condition in a subject in need thereof comprising the steps of:
  i. obtaining a composition comprising at least one vaccine, and/or
  ii. administering said composition to a subject at least once for prophylaxis and/or treatment of a disease.

In another aspect the present invention concerns a kit of parts comprising
  i. a composition comprising a vaccine, and
  ii. a medical instrument or other means for administering the vaccine, and
  iii. instructions on how to use the kit of parts.

An aspect of the invention relates to a method for inducing an immune response in a subject, the method comprising the steps of
  i. obtaining a composition comprising at least one vaccine, and
  ii. administering said composition to a subject at least once for prophylaxis and/or treatment of a disease.

DETAILED DESCRIPTION OF THE INVENTION

The present invention solves the challenge of conjugating larger proteins (e.g. full length antigens) at high density and in a consistent orientation onto the surface of a VLP, thereby obtaining VLPs presenting densely and repetitive arrays of heterologous epitopes. The solution of the present invention represents a novel approach for making a versatile VLP-based vaccine delivery platform capable of efficiently displaying antigen epitopes and of inducing long-term protective immunity.

Figure 1A:
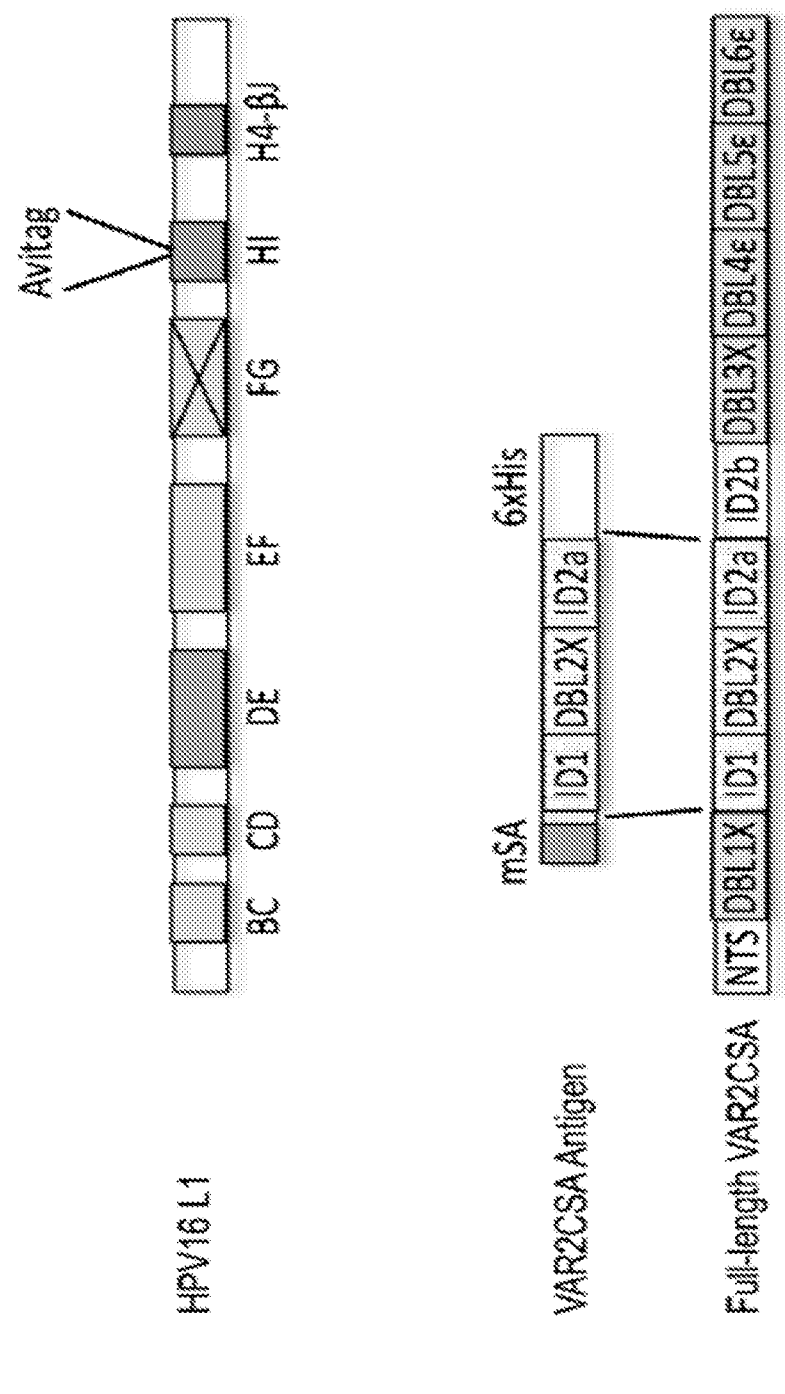
FIG. 1. Schematic representation of the VAR2CSA VLP-vaccine components and the assembly system. a. Structure of HPV16 L1 major capsid protein. The biotin acceptor sequence (AviTag™) was successfully inserted into the protruding DE and HI loops and the H4-βJ coil (blue boxes) of the HPV16 L1. Gray boxes represent regions (loops and coils) of the L1 protein where the AviTag™ could not be inserted (FG loop) or has not been investigated. The VAR2CSA antigen encompasses the extracellular ID1-ID2a (ID1—Interdomain 1, DBL2X—Duffy binding like 2X and ID2a—Interdomain 2a) domains of the full-length VAR2CSA fused at the N-terminus to a previously described monovalent streptavidin (mSA) (Lim et al., 2011). b. Production process of HPV16 Avi-L1 VLPs displaying consistently oriented mSA-VAR2 antigens in a high-density repetitive manner. The HPV16 Avi-L1 and the mSA-vaccine antigen are separately expressed. The HPV16 Avi-VLPs are subsequently in vitro biotinylated (the triangle represents BirA ligase) and finally mixed with the soluble mSA-vaccine antigen. The HPV16 Avi-L1 VLP is theoretically expected to bind one mSA-VAR2CSA antigen per Avi-L1.
Figure 1B:
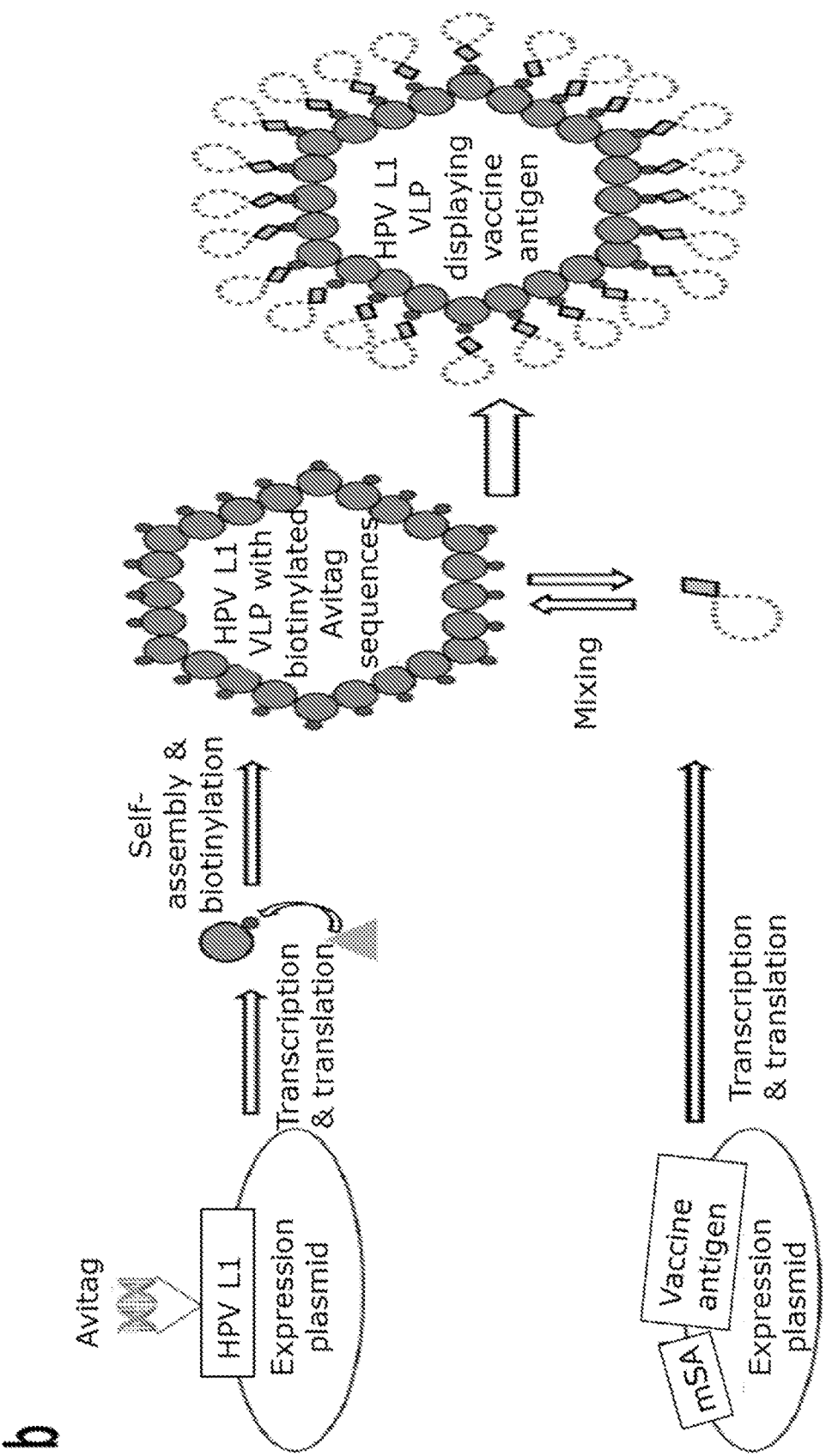

A general aspect of the present invention is illustrated in FIG. 1b.

Definitions

The term "PV" refers to papillomavirus.

The term "L1 protein" refers to the major capsid L1 protein from papillomavirus, which has the ability to spontaneously self-assemble into virus-like particles (VLPs). The L1 proteins of the present invention are displaying antigens.

The term "virus like particle" or "VLP" refers to one or several recombinantly expressed viral proteins which spontaneously assemble into macromolecular particulate structures mimicking the morphology of a virus coat, but lacking infectious genetic material.

The term "self-assembly" refers to a process in which a system of pre-existing components, under specific conditions, adopts a more organised structure through interactions between the components themselves. In the present context, self-assembly refers to the intrinsic capacity of L1, the major capsid protein of papillomavirus to self-assemble into virus-like particles in the absence of L2 or other papillomavirus proteins, when subjected to specific conditions. The self-assembly process may be sensitive and fragile and may be influenced by factors such as, but not limited to, choice of expression host, choice of expression conditions, and conditions for maturing the virus-like particles.

The term "consistent orientation", as used herein, refers to the orientation of the monomeric streptavidin/antigen constructs of the present invention and their spatial orientation to the major capsid protein of papillomavirus (PV L1) of the present invention. When linking an antigen fused to a monomeric streptavidin to a PV L1 protein VLP comprising a biotin acceptor site with a biotin molecule enzymatically conjugated to the biotin acceptor site, the monomeric streptavidin can only be linked to a single PV L1 protein, thus creating a uniform and/or consistent presentation of said antigen with a consistent orientation. In contrast a streptavidin homo-tetramer may crosslink several PV L1 proteins on the surface of a VLP, thus creating an irregular and non-consistent orientation of said antigen. Besides, it is highly challenging to use a homo-tetramer streptavidin as a bridging molecule e.g. for conjugating biotinylated antigens onto biotinylated VLPs, since the multiple biotin binding sites will allow cross-linking and aggregation of the biotinylated VLPs.

The term "regularly spaced" as used herein, refers to antigens of the present invention which forms a pattern on the surface of a VLP. Such pattern may be symmetric, circle-like, and/or bouquet like pattern of antigens.

The term "treatment" refers to the remediation of a health problem. Treatment may also be preventive and/or prophylactic or reduce the risk of the occurrence of a disease and/or infection. Treatment may also be curative or ameliorate a disease and/or infection.

The term "prophylaxis" refers to the reduction of risk of the occurrence of a disease and/or infection. Prophylaxis may also refer to the prevention of the occurrence of a disease and/or infection.

The term "loop" refers to a secondary structure of a polypeptide where the polypeptide chain reverses its overall direction and may also be referred to as a turn.

The term "vaccine cocktail" refers to a mixture of antigens administered together. A vaccine cocktail may be administered as a single dose or as several doses administered over a period of time. Time intervals may be, but not limited to administration within the same year, month, week, day, hour and/or minute. Co-vaccination and vaccine cocktail may be used interchangeably.

The term "self-antigens" refers to endogenous antigens that have been generated within previously normal cells as a result of normal cell metabolism, or because of viral or intracellular bacterial infection.

The term "biotin acceptor site" refers to a peptide sequence capable of binding a biotin molecule. Biotin acceptor site and AviTag are interchangeably used herein.

The term "sequence variant" refers to a polypeptide and/or polynucleotide sequence with at least 70%, such as 75%, such as 80%, such as 85%, such as 90%, such as 95%, such as 96%, such as, 97%, such as 98%, such as 99%, such as 99.5%, such as 100% sequence identity to said polypeptide and/or polynucleotide sequence.

VLP Based Vaccine

The expression of viral structural proteins, such as Envelope or Capsid proteins, can result in the self-assembly of virus-like particles (VLPs). VLPs resemble viruses, but are non-infectious as they do not contain any viral genetic material. For the purpose of active immunization VLPs have proven highly immunogenic and provide a safer alternative to attenuated viruses since they lack genetic material. Besides, VLPs are a useful tool for the development of vaccines and can be used as molecular scaffolds for efficient antigen epitope display. This has been achieved by either genetic insertion or by chemical conjugation approaches. However, it has generally not been possible to incorporate peptides longer than 20 amino acids without disrupting the self-assembly process of the chimeric VLP. At the same time the current technologies using chemical conjugation are not sufficient to enable VLP-presentation of larger proteins at high density and with a consistent orientation to ensure an orderly, high density, display of repetitive antigen epitopes, which are critical factors for obtaining strong and long-lasting immune responses.

The present inventors have solved these problems by a novel approach to linking antigens to a PV L1 VLP using a biotin acceptor site, a biotin molecule and a monovalent streptavidin tag without disrupting the self-assembly of the VLP. Thus in a main aspect, as illustrated in FIG. 1b, the present invention concerns a vaccine for use in the prophylaxis and/or treatment of a disease wherein the vaccine comprises:
 i. a papilloma virus (PV) L1 protein containing a biotin acceptor site, and
 ii. a biotin molecule enzymatically conjugated to said biotin acceptor site, and
 iii. an antigen fused to a monovalent streptavidin,
wherein the antigen and PV L1 protein are linked via the interaction between the monovalent streptavidin and the biotin molecule enzymatically conjugated to the biotin acceptor site of the PV L1 protein, and wherein i-iii form a virus like particle displaying said antigen.

In an embodiment the PV L1 protein containing a biotin acceptor site is able to form a virus like particle.

The inventors of the present invention have demonstrated formation of VLP's using insect cells, such as High Five of Sf9 cells incubated at 28° C. In vitro maturation may occur for 18-24 hours at 30° C.-37° C. Other conditions and expression hosts (such as *Pichia Pastoris*) may work as well.

In an embodiment the antigen is capable of eliciting an immune reaction in an animal, such as a mammal, such as a cow, pig, horse, sheep, goat, llama, mouse, rat, monkey, most preferably such as a human being; or bird such as a chicken, or fish such as a Salmon.

It has long been an attractive goal to exploit the VLPs as an immunogenicity-boosting platform for inducing immune responses against heterologous antigens by using them as molecular scaffolds for antigen display. Thus another aspect of the present invention relates to an antigen display scaffold, comprising an assembled virus-like particle comprising:
  i. a papilloma virus (PV) L1 protein containing a biotin acceptor site, and
  ii. a biotin molecule enzymatically conjugated to said biotin acceptor site, and
  iii. an antigen fused to a monovalent streptavidin,
wherein the antigen and PV L1 protein are linked via the interaction between the monovalent streptavidin and the biotin molecule enzymatically conjugated to the biotin acceptor site of the PV L1 protein, and wherein i-iii form an antigen display scaffold.

Another aspect of the present invention relates to a method of producing a non-naturally occurring, ordered and repetitive antigen array comprising
  i. a papilloma virus (PV) L1 protein containing a biotin acceptor site, and
  ii. a biotin molecule enzymatically conjugated to said biotin acceptor site, and
  iii. an antigen fused to a monovalent streptavidin,
wherein the antigen and PV L1 protein are linked via the interaction between the monovalent streptavidin and the biotin molecule enzymatically conjugated to the biotin acceptor site of the PV L1 protein, and wherein i-iii form a non-naturally occurring, ordered and repetitive antigen array.

Diseases and Medical Indications

The present invention is a novel, generic, and easy-to-use-approach to conjugate various antigens to a VLP. Depending on the antigen the VLP-based vaccines of the present invention can be used for prophylaxis and/or treatment of a wide range of diseases. The diseases which the present invention may be used for prophylaxis and/or treatment of include but are not limited to cancers, cardiovascular diseases, allergic diseases, and/or infectious diseases.

In an embodiment an antigen which is associated with at least one cancer disease is linked to the PV L1 protein via the interaction between the monovalent streptavidin and the biotin molecule enzymatically conjugated to the biotin acceptor site of the PV L1 protein. In a further embodiment the present VLP vaccine may be used for prophylaxis and/or treatment of the cancer and/or cancers which the antigen is associated with.

In an embodiment an antigen which is associated with at least one cardiovascular disease is linked to the PV L1 protein via the interaction between the monovalent streptavidin and the biotin molecule enzymatically conjugated to the biotin acceptor site of the PV L1 protein. In a further embodiment the present VLP vaccine can be used for prophylaxis and/or treatment of the cardiovascular disease and/or cardiovascular diseases which the antigen is associated with.

In an embodiment an antigen which is associated with at least one allergic disease is linked to the PV L1 protein via the interaction between the monovalent streptavidin and the biotin molecule enzymatically conjugated to the biotin acceptor site of the PV L1 protein. In a further embodiment the present VLP vaccine can be used for prophylaxis and/or treatment of the allergic disease and/or allergic diseases which the antigen is associated with.

In an embodiment an antigen which is associated with at least one infectious disease is linked to the PV L1 protein via the interaction between the monovalent streptavidin and the biotin molecule enzymatically conjugated to the biotin acceptor site of the PV L1 protein. In a further embodiment the present VLP vaccine can be used for prophylaxis and/or treatment of the infectious disease and/or infectious diseases which the antigen is associated with.

A non-exhaustive list of antigens which may be used by the present invention is outlined in table 1 and table 2. In addition table 1 show examples of specific diseases the antigens are associated with as well as examples of patient groups which may be in need of prophylaxis and/or treatment using the antigen-VLP vaccines of the present invention.

TABLE 1

Non-exhaustive list of antigens or parts hereof that could be used in treatment of specific diseases/medical indications in various patient groups.

| Examples of antigens (non-exhaustive) | Examples of a specific disease (non-exhaustive) | Examples of patient group (non-exhaustive) |
| --- | --- | --- |
| Her2/Neu (ERBB2) | Breast cancer | Females overexpressing Her2 |
| Her2/Neu (ERBB2) | Gastric cancer | Males and Females overexpressing Her2 |
| Her2/Neu (ERBB2) | Ovarian cancer | Females overexpressing Her2 |
| Her2/Neu (ERBB2) | Uterine serous carcinoma | Postmenopausal Females overexpressing Her2 |
| Survivin | Cancer types overexpressing Survivin | Males and non-pregnant Females overexpressing Survivin |
| PCSK9 | cardiovascular disease | Males and Females with dyslipidemia |
| PCSK9 | cardiovascular disease | Males and Females with atherosclerosis |
| PCSK9 | cardiovascular disease | Males and Females with hypercholesterolemia |
| Interleukin-5 | Asthma | Males and Females with eosinophilia |
| Interleukin-5 | nasal polyposis | Males and Females with eosinophilia |
| Interleukin-5 | atopic dermatitis | Males and Females with eosinophilia |
| Interleukin-5 | eosinophilic esophagitis | Males and Females with eosinophilia |
| Interleukin-5 | Hypereosinophilic syndrome | Males and Females with eosinophilia |

TABLE 1-continued

Non-exhaustive list of antigens or parts hereof that could be used in
treatment of specific diseases/medical indications in various patient groups.

| Examples of antigens (non-exhaustive) | Examples of a specific disease (non-exhaustive) | Examples of patient group (non-exhaustive) |
|---|---|---|
| Interleukin-5 | Churg-Strauss syndrome | Males and Females with eosinophilia |
| Ag85A | Tuberculosis | Males and Females with tuberculosis |
| PfRH5 | Malaria | Males and Females with malaria |
| VAR2CSA | Malaria | Females with malaria |
| PfEMP1, CIDR1a | Malaria | Males and Females with malaria |
| GLURP | Malaria | Males and Females with malaria |
| MSP3 | Malaria | Males and Females with malaria |
| Pfs25 | Malaria | Males and Females with malaria |
| CSP | Malaria | Males and Females with malaria |
| PfSEA-1 | Malaria | Males and Females with malaria |

The disclosed antigens may as well be relevant for the use in other patient groups and/or against other specific or related diseases. In an embodiment at least two such as three, four, and/or five antigens may be combined.

TABLE 2

Non-exhaustive list of diseases/medical indications and target antigen/organisms of the present VLP vaccine.

| Disease: | Target antigen/Organism: |
|---|---|
| Cancer: | Her2/Neu (ERBB2)/*Homo Sapiens* |
| | Survivin (Baculoviral IAP repeat-containing protein 5)/*Homo Sapiens* |
| Cardiovascular disease: | PCSK9 (Proprotein convertase subtilisin/kexin type 9)/*Homo Sapiens* |
| Asthma/Allergies: | IL-5 (Interleukin-5)/*Homo Sapiens* |
| Tuberculosis: | Ag85A (Diacylglycerol cyltransferase/mycolyltransferase)/*Mycobacterium tuberculosis* |
| Malaria: | Reticulocyte-binding protein homologue 5 (PfRH5)/*Plasmodium falciparum* |
| | VAR2CSA (domain, ID1-ID2a)/*Plasmodium falciparum* |
| | CIDR1a domain of PfEMP1, *Plasmodium falciparum* |
| | Glutamate rich protein (GLURP)/*Plasmodium falciparum* |
| | Merozoite surface protein 3 (MSP3)/*Plasmodium falciparum* |
| | 25 kDa ookinete surface antigen (Pfs25)/*Plasmodium falciparum* |
| | Circumsporozoite protein (CSP)/*Plasmodium falciparum* |
| | Schizont egress antigen-1 (PfSEA-1)/*Plasmodium falciparum* |

The vaccine of the present invention may as well be used against other diseases and/or use other antigens.

In an embodiment of the present invention the medical indication is selected from the group consisting of a cancer, a cardiovascular disease, an allergy, and/or an infectious disease. In a particular embodiment the medical indication is an allergy. In another particular embodiment the medical indication is a cardiovascular disease. In a most preferred embodiment the medical indication is a cancer.

In another embodiment the antigen is a polypeptide, peptide and/or an antigenic fragment of a polypeptide associated with an abnormal physiological response such as a cardiovascular disease and/or an allergic reaction/disease. In a particular embodiment the abnormal physiological response is a cancer.

In a further embodiment the antigen is a protein, peptide and/or an antigenic fragment associated with a medical indication disclosed in the present invention.

Cancer and Associated Antigens

In 2012 more than 14 million adults were diagnosed with cancer and there were more than 8 million deaths from cancer, globally. Consequently, there is a need for efficient cancer therapeutics.

One characteristic of cancer cells is abnormal expression levels of genes and proteins. One example of a cancer associated gene is HER2, which is overexpressed in 20% of all breast cancers and is associated with increased metastatic potential and poor patient survival. Although cancer cells express cancer associated antigens in a way that immunologically distinguishes them from normal cells, most cancer associated antigens are only weakly immunogenic because most cancer associated antigens are "self" proteins which are generally tolerated by the host. The present invention has solved this problem by an effective antigen-VLP based vaccine which is capable of activating the immune system to react against for example cancer associated antigens and overcome the immunological tolerance to such antigens. Different cancers are characterized by having different cancer associated antigens. Survivin is regarded to be overexpressed in most cancer cells and could also be used in the present invention. Therefore the present invention may be used in treatment/prophylaxis of most types of cancers that overexpress a tumor associated antigen.

The antigen is linked to the PV L1 protein of the present invention via the interaction between the monovalent streptavidin and the biotin molecule enzymatically conjugated to the biotin acceptor site of the PV L1 protein (see FIG. 1b for the general concept of the present invention). Thereby the present invention provides effective antigen-VLP based vaccine which is capable of activating the immune system to react against for example cancer associated antigens and overcome immunological tolerance to such antigens. In an embodiment the VLP vaccine of the present invention can be used for prophylaxis and/or treatment of the cancer which the antigen is associated with.

An embodiment of the present invention comprises a cancer associated antigen linked to the PV L1 protein via the interaction between the monovalent streptavidin and the biotin molecule enzymatically conjugated to the biotin acceptor site of the PV L1 protein. In a further embodiment the present VLP vaccine can be used for prophylaxis and/or treatment of the cancer which the antigen is associated with.

In another embodiment the present invention is used in treatment/prophylaxis of any type of cancer which overexpresses an antigen. The type of cancer which the invention may be used against is determined by the choice of antigen.

It is known that oncovirus can cause cancer. Therefore in an embodiment the vaccine of the present invention comprises an oncovirus associated antigen linked to the PV L1 protein via the interaction between the monovalent streptavidin and the biotin molecule enzymatically conjugated to the biotin acceptor site of the PV L1 protein.

In a further embodiment the present vaccine can be used for prophylaxis and/or treatment of the cancer which the antigen is associated with.

In an embodiment the antigen is a protein or peptide or an antigenic fragment of a polypeptide associated with a cancer selected from the group comprising of Adrenal Cancer, Anal Cancer, Bile Duct Cancer, Bladder Cancer, Bone Cancer, Brain/CNS Tumors in adults, Brain/CNS Tumors In Children, Breast Cancer, Breast Cancer In Men, Cancer in Adolescents, Cancer in Children, Cancer in Young Adults, Cancer of Unknown Primary, Castleman Disease, Cervical Cancer, Colon/Rectum Cancer, Endometrial Cancer, Esophagus Cancer, Ewing Family Of Tumors, Eye Cancer, Gallbladder Cancer, Gastrointestinal Carcinoid Tumors, Gastrointestinal Stromal Tumor, Gestational Trophoblastic Disease, Hodgkin Disease, Kaposi Sarcoma, Kidney Cancer, Laryngeal and Hypopharyngeal Cancer, Leukemia, Acute Lymphocytic in Adults, Leukemia, Acute Myeloid Leukemia, Chronic Lymphocytic Leukemia, Chronic Myeloid Leukemia, Chronic Myelomonocytic Leukemia, Leukemia in Children, Liver Cancer, Lung Cancer, Non-Small Cell Lung Cancer, Small Cell Lung Cancer, Lung Carcinoid Tumor, Lymphoma, Lymphoma of the Skin, Malignant Mesothelioma, Multiple Myeloma, Myelodysplastic Syndrome, Nasal Cavity and Paranasal Sinus Cancer, Nasopharyngeal Cancer, Neuroblastoma, Non-Hodgkin Lymphoma, Non-Hodgkin Lymphoma In Children, Oral Cavity and Oropharyngeal Cancer, Osteosarcoma, Ovarian Cancer, Pancreatic Cancer, Penile Cancer, Pituitary Tumors, Prostate Cancer, Retinoblastoma, Rhabdomyosarcoma, Salivary Gland Cancer, Adult Soft Tissue Cancer Sarcoma, Skin Cancer, Basal and Squamous Cell Skin Cancer, Melanoma Skin Cancer, Merkel Cell Skin cancer, Small Intestine Cancer, Stomach Cancer, Testicular Cancer, Thymus Cancer, Thyroid Cancer, Uterine Sarcoma, Vaginal Cancer, Vulvar Cancer, Waldenstrom Macroglobulinemia, and Wilms Tumor.

In a preferred embodiment the cancer is selected from the group consisting of breast cancer, gastric cancer, ovarian cancer, and uterine serous carcinoma.

Linking the Her2/Neu (ERBB2) and/or Survivin or an antigenic fragment hereof to the VLP forms a VLP based vaccine which is capable of activating the immune system to react against for example cells with high Her2/Neu (ERBB2) and/or Survivin expression and overcome immunological tolerance. In an embodiment the Her2/Neu (ERBB2) and/or Survivin VLP vaccine of the present invention can be used for prophylaxis and/or treatment of the herein disclosed cancer disease and/or other cancer diseases. Using a similar reasoning other cancer disease associated antigen-VLP based vaccines may be used against any cancer disease.

In an embodiment the antigen of the present invention is Her2/Neu (ERBB2) and/or Survivin or an antigenic fragment hereof, wherein the antigen is associated with and directed against at least one of the herein disclosed types of cancers.

In a most preferred embodiment the present invention concerns a vaccine for use in the prophylaxis and/or treatment of one of the herein disclosed cancers wherein the vaccine comprises:

i. a papilloma virus (PV) L1 protein containing a biotin acceptor site, and
   ii. a biotin molecule enzymatically conjugated to said biotin acceptor site, and
   iii. a cancer associated antigen such as Her2/Neu (ERBB2) and/or Survivin or an antigenic fragment of Her2/Neu (ERBB2) and/or Survivin fused to a monovalent streptavidin, wherein the antigen and the PV L1 protein are linked via the interaction between the monovalent streptavidin and the biotin molecule enzymatically conjugated to the biotin acceptor site of the PV L1 protein, and wherein i-iii form a virus like particle displaying said antigen.

In an embodiment the antigen fused to a monovalent streptavidin is selected from the group comprising SEQ ID NO: 18, SEQ ID NO: 40, SEQ ID NO: 41, SEQ ID NO: 42, SEQ ID NO: 43, SEQ ID NO: 44, SEQ ID NO: 45, SEQ ID NO: 46, and/or SEQ ID NO: 47 and/or a sequence variant hereof.

Cardiovascular Diseases and Associated Antigens

An estimated 17.3 million people died from cardiovascular diseases in 2008, representing 30% of all global deaths. Addressing risk factors such as tobacco use, unhealthy diet and obesity, physical inactivity, high blood pressure, diabetes and raised lipids are important for prevention of cardiovascular diseases. However, the need for preventive pharmaceutical measures is increasingly important. The present invention may be used in treatment/prophylaxis of most types of cardiovascular diseases. The type of cardiovascular disease which the invention may be used against is decided by the choice of antigen.

In an embodiment of the invention the antigen is a protein or peptide or an antigenic fragment of a polypeptide associated with a disease selected from the group comprising a lipid disorder such as hyperlipidemia, type I, type II, type III, type IV, or type V hyperlipidemia, secondary hypertriglyceridemia, hypercholesterolemia, familial hypercholesterolemia, xanthomatosis, cholesterol acetyltransferase deficiency, an ateriosclerotic condition (e.g., atherosclerosis), a coronary artery disease, a cardiovascular disease, and Alzheimer's disease.

In an embodiment of the invention the antigen is a protein or peptide or an antigenic fragment of a polypeptide associated with a cardiovascular disease. In a further embodiment the cardiovascular disease is selected from the group consisting of dyslipidemia, atherosclerosis, and hypercholesterolemia.

One example of a polypeptide associated with a cardiovascular disease is PCSK9 which acts in cholesterol homeostasis. Blockage of PCSK9 has medical significance and can lower the plasma and/or serum low-density lipoprotein cholesterol (LDL-C) levels. Reducing LDL-C reduces the risk of for example heart attacks.

Linking the PCSK9 antigen to the VLP forms a PCSK9-VLP based vaccine which is capable of activating the immune system to react against for example cells with high PCSK9 expression and overcome immunological PCSK9 tolerance, thereby lowering the LDL-C levels and the risk of heart attacks. In an embodiment the PCSK9-VLP vaccine of the present invention can be used for prophylaxis and/or treatment of the herein disclosed cardiovascular disease and/or other cardiovascular diseases. Using a similar reasoning other cardiovascular disease associated antigen-VLP based vaccines may be used against any cardiovascular disease.

In a preferred embodiment the antigen comprises PCSK9 or an antigenic fragment hereof, wherein the antigen is associated with and directed against at least one of the herein disclosed cardiovascular disease and/or other cardiovascular diseases.

In a most preferred embodiment the present invention concerns a vaccine for use in the prophylaxis and/or treatment of at least one of the herein disclosed cardiovascular diseases wherein the vaccine comprises:
  i. a papilloma virus (PV) L1 protein containing a biotin acceptor site, and
  ii. a biotin molecule enzymatically conjugated to said biotin acceptor site, and
  iii. a cardiovascular disease associated antigen such as PCSK9 or an antigenic fragment hereof fused to a monovalent streptavidin, wherein the antigen and the PV L1 protein are linked via the interaction between the monovalent streptavidin and the biotin molecule enzymatically conjugated to the biotin acceptor site of the PV L1 protein, and wherein i-iii form a virus like particle displaying said antigen.

In an embodiment the antigen fused to a monovalent streptavidin comprise SEQ ID NO: 20 and/or a sequence variant hereof.

Asthma or Allergy Diseases and Associated Antigens

The prevalence of allergic diseases worldwide is rising dramatically in both developed and developing countries. According to World Health Organization statistics, hundreds of millions of subjects in the world suffer from allergic rhinitis and it is estimated that 300 million have asthma markedly affecting the quality of life of these individuals and negatively impacting the socio-economic welfare of society.

Interleukin 5 (IL-5) has been shown to play an instrumental role in eosinophilic inflammation in various types of allergies, including severe eosinophilic asthma. Eosinophils are regulated in terms of their recruitment, activation, growth, differentiation and survival by IL-5 which, consequently, has identified this cytokine as a primary target for therapeutic interventions. Linking an IL-5 antigen or a fragment hereof to the VLP of the present invention forms an IL-5-VLP based vaccine which is capable of activating the immune system to react against IL-5. Consequently an IL-5-VLP based vaccine described in the present invention may be used in the treatment/prophylaxis of eosinophilic asthma or allergy. Other allergy-associated antigens (e.g. IgE) may be used by the present invention using a similar reasoning. The type of asthma or allergy disease which the invention may be used against is decided by the choice of antigen. In an embodiment the antigen is a protein or peptide or an antigenic fragment of a polypeptide associated with one or more asthma or allergy diseases disclosed herein. In a preferred embodiment the asthma or allergy is selected from the group consisting of eosinophilic asthma, allergy, nasal polyposis, atopic dermatitis, eosinophilic esophagitis, hypereosinophilic syndrome, and Churg-Strauss syndrome.

In a preferred embodiment the antigen comprises IL-5 or an antigenic fragment hereof, wherein the antigen is associated with and directed against at least one of the herein disclosed asthma or allergy diseases and/or other asthma or allergy diseases.

In a most preferred embodiment the present invention concerns a vaccine for use in the prophylaxis and/or treatment of one of the herein disclosed asthma or allergy diseases wherein the vaccine comprises:
  i. a papilloma virus (PV) L1 protein containing a biotin acceptor site, and
  ii. a biotin molecule enzymatically conjugated to said biotin acceptor site, and
  iii. an allergy associated antigen such as IL-5 or an antigenic fragment hereof fused to a monovalent streptavidin, wherein the antigen and the PV L1 protein are linked via the interaction between the monovalent streptavidin and the biotin molecule enzymatically conjugated to the biotin acceptor site of the PV L1 protein, and wherein i-iii form a virus like particle displaying said antigen.

In an embodiment the antigen fused to a monovalent streptavidin comprises SEQ ID NO: 19 and/or a sequence variant hereof.

Infectious Diseases and Associated Antigens

Tuberculosis and malaria are two major infectious diseases. In 2012, an estimated 207 million cases of malaria occurred which resulted in more than 500.000 deaths. Also in 2012, an estimated 8.6 million people developed tuberculosis and 1.3 million died from the disease. The current methods of treatment are insufficient and some have resulted in drug resistance. Consequently there is a need for new and efficient drugs for treatment/prophylaxis of tuberculosis and malaria. Linking a malaria or tuberculosis associated-antigen or a fragment hereof to the VLP of the present invention forms a VLP based vaccine which is capable of activating the immune system to react against for example malaria or tuberculosis. Using a similar line of reasoning the present invention may be used in treatment/prophylaxis of most infectious disease. The type of infectious disease which the invention may be used against is decided by the choice of antigen.

In an embodiment the antigen fused to the monovalent streptavidin of the present invention is a protein or peptide or an antigenic fragment of a polypeptide associated with an infectious disease such as tuberculosis and/or malaria.

In a further embodiment an antigen from *Plasmodium falciparum* is fused to the monovalent streptavidin of the present invention for use in treatment/prophylaxis of malaria.

In a further embodiment an antigen from *Mycobacterium tuberculosis* is fused to the monovalent streptavidin of the present invention for use in treatment/prophylaxis of tuberculosis.

In a further embodiment the antigen is selected from the group consisting of Ag85A from *Mycobacterium tuberculosis*, PfRH5 from *Plasmodium falciparum*, VAR2CSA (domain, ID1-ID2a) from *Plasmodium falciparum*, CIDR1a domain, of PfEMP1 from *Plasmodium falciparum*, GLURP from *Plasmodium falciparum*, MSP3 from *Plasmodium falciparum*, Pfs25 from *Plasmodium falciparum*, CSP from *Plasmodium falciparum*, and PfSEA-1 from *Plasmodium falciparum* or an antigenic fragment of the disclosed antigens. In another embodiment the antigen comprises a fusion construct between MSP3 and GLURP (GMZ2) from *Plasmodium falciparum*.

In another embodiment the antigen of the present invention comprises a protein, or an antigenic fragment hereof, from the pathogenic organism which causes the infectious disease.

In a most preferred embodiment the present invention concerns a vaccine for use in the prophylaxis and/or treatment of one of the herein disclosed infectious diseases wherein the vaccine comprises:
  i. a papilloma virus (PV) L1 protein containing a biotin acceptor site, and
  ii. a biotin molecule enzymatically conjugated to said biotin acceptor site, and
  iii. an antigen associated with an infectious disease such as Ag85A from *Mycobacterium tuberculosis*, PfRH5 from *Plasmodium falciparum*, VAR2CSA (domain, ID1-ID2a) from *Plasmodium falciparum*, CIDR1a domain, of PfEMP1 from *Plasmodium falciparum*, GLURP from *Plasmodium falciparum*, MSP3 from *Plasmodium falciparum*, Pfs25 from *Plasmodium falciparum*, CSP from *Plasmodium falciparum*, and/or PfSEA-1 from *Plasmodium falciparum* or an antigenic fragment hereof fused to a monovalent streptavidin, wherein the antigen and the PV L1 protein are linked via the interaction between the monovalent streptavidin and the biotin molecule enzymatically conjugated to the biotin acceptor site of the PV L1 protein, and wherein i-iii form a virus like particle displaying said antigen.

In a preferred embodiment, the antigen is VAR2CSA and the vaccine is for use in the prophylaxis and/or treatment of placental malaria.

In another preferred embodiment, the antigen is surviving and the vaccine is for use in the prophylaxis and/or treatment of cancer.

In an embodiment the antigen fused to a monovalent streptavidin comprises SEQ ID NO: 21, SEQ ID NO: 22, SEQ ID NO: 23, SEQ ID NO: 24, SEQ ID NO: 25, SEQ ID NO: 26, SEQ ID NO: 27, or SEQ ID NO: 28 and/or a sequence variant hereof. In a preferred embodiment the antigen fused to a monovalent streptavidin comprises SEQ ID NO: 21. In a more preferred embodiment the antigen fused to a monovalent streptavidin comprises SEQ ID NO: 24. In a most preferred embodiment the antigen fused to a monovalent streptavidin comprises SEQ ID NO: 28.

Induction of an Immune Response in a Subject

Active vaccination (immunization), by delivering small doses of an antigen into a subject, is a way to activate a subject's immune system to develop adaptive immunity to the antigen. This allows a subjects body to react quickly and efficiently to future exposures.

An aspect of the invention relates to a method for inducing an immune response in a subject, the method comprising the steps of i. obtaining a composition comprising at least one vaccine of the present invention and/or
ii. administering said composition to a subject at least once for prophylaxis and/or treatment of a disease, thereby inducing an immune response in the subject.

Another aspect of the present invention relates to a method of immunizing a subject in need thereof, said method comprises the steps of:

i. obtaining a composition comprising at least one vaccine of the present invention, and/or
ii. administering said composition to a subject at least once for prophylaxis and/or treatment of a disease.

thereby immunizing the subject in need thereof.

Another aspect of the present invention relates to a method for obtaining a strong and long-lasting immune response in a subject in need thereof, said method comprising the steps of:

i. obtaining composition comprising a vaccine of the present invention, and/or
ii. administering the vaccine to treat and/or prevent a clinical condition in an subject in need thereof, wherein the vaccine obtain a strong and long-lasting immune response in the subject.

In an embodiment the method of inducing an immune response in a subject, immunizing a subject in need thereof, and/or obtaining a strong and long-lasting immune response further comprising at least one booster vaccine and/or a second active ingredient.

Origin of the PV L1 Protein

An important element of the present VLP based vaccine is the major capsid L1 protein from papillomavirus (PV), which has the ability to spontaneously self-assemble into virus-like particles (VLPs). The use of papillomavirus L1 proteins in the present invention is illustrated in FIG. 1*b*. Several hundred species of papillomaviruses, traditionally referred to as "types", are known to infect most mammals, as well as birds, snakes, and turtles. In principle the major capsid protein L1 from most papillomavirus, capable of forming a VLP, may be used to carry out the present invention.

In an embodiment the PV L1 protein of the present invention is from a mammal such as but not limited to: *Alces* genus, *Homo sapiens*, cow, pig, horse, sheep, goat, llama, mouse, rat, monkey, and chicken.

In a most preferred embodiment the PV L1 protein of the present invention is from the human PV genotype 16 and/or 118. In yet a particular embodiment the PV L1 protein is from the *Alces alces*.

Biotin Acceptor Site and its Position in the PV L1 Protein

The biotin acceptor site of the present invention comprises a sequence of 15 amino acids encoded by a polynucleotide sequence. It is extremely difficult, if not impossible, to predict the consequence of modifications to VLP forming proteins, such as PV L1 proteins. Such modifications often lead to disruption of the delicate and sensitive self-assembly process of the VLPs. Successful modification of the VLP forming process is at least dependent on three factors 1) the amino acid sequence of the biotin acceptor site, 2) the insertion site, and 3) deletion/removal of amino acid residues to make room for the biotin acceptor site. The inventors have demonstrated several successful modifications to PV L1 loops without disrupting the delicate self-assembly process.

In an embodiment the biotin acceptor site is fused into a loop of the PV L1 protein.

In an embodiment the present invention concerns a vaccine for use in the prophylaxis and/or treatment of a disease wherein the vaccine comprises:

i. a papilloma virus (PV) L1 protein containing a biotin acceptor site in a loop of the PV L1 protein, and
ii. a biotin molecule enzymatically conjugated to said biotin acceptor site, and
iii. an antigen fused to a monovalent streptavidin, wherein the antigen and PV L1 protein are linked via the interaction between the monovalent streptavidin and the biotin molecule enzymatically conjugated to the biotin acceptor site of the PV L1 protein, and wherein i-iii form a virus like particle displaying said antigen.

In another embodiment the loop is selected from the group consisting of the DE-loop, and the HI-loop of the PV L1 protein. The PV L1 protein starts with a methionine residue which is cleaved off after translation. There are thus two ways of numbering the amino acid residues of the PV L1 protein: either the methionine residue is the first, or the methionine residue is not counted and the following serine residue is the first. The positions given in the present disclosure are numbered using the first numbering, i.e. where the methionine is counted.

In an embodiment the biotin acceptor site is inserted into the HI-loop of the L1 protein from the human PV genotype 16 at position 351/352 (SEQ ID NO: 2). In another embodiment the biotin acceptor site, is inserted into the H4-loop of the L1 protein from the human PV genotype 16 at position 431/432 (SEQ ID NO: 1). In an embodiment the biotin acceptor site is inserted into the HI-loop of the L1 protein from the human PV genotype 118 at position 360/365 where the residues 361-364 (AGKI) are deleted (SEQ ID NO: 6). In a most preferred embodiment the biotin acceptor site is inserted into the DE-loop of the L1 protein from the human PV genotype 16 at position 134/139 where the residues 135-137 (YAAN) are deleted (SEQ ID NO: 3).

In an embodiment the PV L1 protein containing the biotin acceptor site comprises the amino acid sequences selected from the group consisting of SEQ ID NO: 3, SEQ ID NO: 2, and SEQ ID NO: 6 or a biologically active sequence variant that has at least 95%, such as 96%, such as, 97%, such as 98%, such as 99%, such as 99.5%, such as 100% sequence identity to any of the herein disclosed PV L1 proteins containing the biotin acceptor site sequences. By "biological active" is meant the ability to form a virus like particle.

In an embodiment the biotin acceptor site of the present invention comprises the amino acid sequence GLNDIFEAQKIEWHE (SEQ ID NO 36).

Enzymatic Biotinylation

In general, two approaches for biotinylation of proteins exists; chemical biotinylation and enzymatic biotinylation. Chemical biotinylation such as biotinylation of exposed lysine residues allows the attachment to VLPs of diverse kinds of target antigens (incl. non-protein targets) and this approach is generally not restricted by the size of the antigen (Raja K S. et al., 2003). However, with this strategy it is very challenging to control the overall amount/stoichiometry as well as the orientation of the coupled antigen. Finally, chemical coupling procedures are rarely compatible with large scale vaccine production. The main challenge of current VLP platforms is to present the antigen on the surface of the VLP, at high density, in a regularly spaced order with a consistent orientation for an efficient epitope display which are capable of inducing long-term protective immunity.

In order to solve these challenges the VLPs of the present invention are made by enzymatic biotinylation. Enzymatic biotinylation ensures that only a single biotin molecule is conjugated to each L1 in the VLP thus controlling the overall ratio/stoichiometry and placement of VLP proteins and biotin molecules. This control will enable display of an antigen at high density i.e. in theory one antigen per L1 protein, while being regularly spaced, and with consistent orientation on the surface of the VLPs of the present invention.

Thus, in an embodiment the biotin molecule is enzymatically conjugated to the biotin acceptor site. In another embodiment the biotin molecule is enzymatically conjugated to the biotin acceptor site by a biotin ligase from a prokaryote, such as from a bacteria, such as from *E. coli*. The biotin ligase is in a preferred embodiment BirA from *E. coli*.

Antigen Fused to a Monovalent Streptavidin

Streptavidin from *Streptomyces avidinii* forms streptavidin homo-tetramers and binds up to four biotin molecules. The monovalent streptavidin of the present invention forms monomers and binds a single biotin molecule. Thus when linking the antigen fused to a monovalent streptavidin to the VLP of the present invention, the monovalent streptavidin ensures a uniform presentation of said antigens. Using monovalent streptavidin further ensures control of the overall amount/stoichiometry as well as the orientation of the coupled antigen. This control will enable display of an antigen at high density, while being regularly spaced, and with consistent orientation on the surface of a VLP, thus solving three major critical factors for obtaining prober activation of the immune system. In contrast a streptavidin homo-tetramer may crosslink several PV L1 proteins on the surface of a VLP, thus creating an irregular presentation of said antigen, which may hamper the immune response of an antigen. It is thus an aspect of the present invention to use monovalent streptavidin fused to the antigen for linking the antigen to the PV L1 protein via the interaction between the monovalent streptavidin and the biotin molecule enzymatically conjugated to the biotin acceptor site of the PV L1 protein.

In an embodiment the monovalent streptavidin used by the present invention comprises or consists of the amino acid sequence of SEQ ID NO: 37.

In another embodiment each antigen is presented in immediate continuation of each PV L1 protein in a consistent orientation.

In another embodiment the ratio of PV L1 protein:biotin molecule:antigen is 1:1:1.

Changing the position where the monomeric streptavidin tag is fused to the antigen will allow changing the orientation of the antigen. This may be performed to enable the best possible display of the most immunogenic epitopes of the antigen. The best possible orientation may be different from antigen to antigen.

In another embodiment the antigen fused to a monovalent streptavidin further comprises a tag. Such tags may be used for purification techniques known to the skilled person. The tag may be selected from the group comprising polyhistidine tag, Calmodulin-tag, polyglutamate tag, E-tag, FLAG-tag, HA-tag, Myc-tag, S-tag, SBP-tag, Softag 1, Softag 3, Strep-tag, Strep-tag II, TC tag, V5 tag, VSV-tag, and Xpress tag. Other peptide or non-peptide tags may be used instead or in combination with the above mentioned peptide tags. In a particular embodiment the tag is a polyhistidine tag, such as a 4×His, 5×His, 6×His, 7×His, 8×His, 9×His, or 10×His tag.

In an embodiment the monovalent streptavidin is fused to the antigen in any position. In another embodiment the monovalent streptavidin is fused to the antigen in the N-terminal, C-terminal, and/or is fused to the antigen into the coding sequence of the antigen. A person of skill will know how to fuse the antigen and the monovalent streptavidin, without introducing stop-codons or causing frame shift or any other mutations.

In another embodiment the monovalent streptavidin fused to the antigen comprises
   i. a polypeptide sequence selected from the group consisting of SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, and SEQ ID NO: 28, or
   ii. a sequence variant of said polypeptide sequence, wherein the sequence variant has at least 70%, such as 75%, such as 80%, such as 85%, such as 90%, such as 95%, such as 96%, such as, 97%, such as 98%, such as 99%, such as 99.5%, such as 100% sequence identity to the sequences of the group comprising SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, and SEQ ID NO: 28.

In a preferred embodiment the monovalent streptavidin fused to the antigen comprises
   i. a polypeptide sequence comprising SEQ ID NO: 19, and/or
   ii. a sequence variant of said polypeptide sequence, wherein the sequence variant has at least 70%, such as 75%, such as 80%, such as 85%, such as 90%, such as 95%, such as 96%, such as, 97%, such as 98%, such as 99%, such as 99.5%, such as 100% sequence identity to SEQ ID NO: 19.

In a most preferred embodiment the monovalent streptavidin fused to the antigen comprises
  i. a polypeptide sequence comprising SEQ ID NO: 18, and/or
  ii. a sequence variant of said polypeptide sequence, wherein the sequence variant has at least 70%, such as 75%, such as 80%, such as 85%, such as 90%, such as 95%, such as 96%, such as, 97%, such as 98%, such as 99%, such as 99.5%, such as 100% sequence identity to SEQ ID NO: 18.

Vector and Polynucleotide/Polypeptide Sequences

In molecular cloning, a vector is a DNA molecule used as a vehicle to artificially carry foreign genetic material into a cell, where it can be replicated and/or expressed. The four major types of vectors are plasmids, viral vectors, cosmids, and artificial chromosomes. The vector itself is generally a DNA sequence that consists of an insert (transgene) and a larger sequence that serves as the "backbone" of the vector. The purpose of a vector which transfers genetic information to another cell is typically to isolate, multiply, or express the insert in the target cell. Expression vectors (expression constructs) specifically are for the expression of transgenes in target cells, and generally have a promoter sequence that drives expression of the transgene.

The heterologous expression/production of the vaccine of the present invention comprises 3 peptide components 1) a PV L1 protein containing a biotin acceptor site 2) a biotin ligase capable of biotinylating the biotin acceptor site, and 3) an antigen fused to a monovalent streptavidin. Thus in an embodiment of the present invention each of the peptide components are encoded by a polynucleotide sequence and each of the polynucleotide sequences may be expressed on one, two, or three different plasmids.

To enable heterologous expression/production of the vaccine one aspect of the present invention is a vector comprising at least one polynucleotide encoding
  i. a PV L1 protein containing a biotin acceptor site, and/or
  ii. a biotin ligase capable of biotinylating the biotin acceptor site, and/or
  iii. an antigen fused to a monovalent streptavidin.

In another embodiment the vector comprises at least two, such as at least three polynucleotides of the following polypeptides:
  i. a PV L1 protein containing a biotin acceptor site, and/or
  ii. a biotin ligase capable of biotinylating the biotin acceptor site, and/or
  iii. an antigen fused to a monovalent streptavidin.

In a further embodiment the PV L1 protein containing the biotin acceptor site is encoded by a polynucleotide sequence comprising:
  i. a polynucleotide sequence selected from the group comprising SEQ ID 11, SEQ ID 12, SEQ ID 13, SEQ ID 14, SEQ ID 15, SEQ ID 16, SEQ ID 17, and/or
  ii. a sequence variant of said polynucleotide sequence, wherein the sequence variant has at least 70%, such as 75%, such as 80%, such as 85%, such as 90%, such as 95%, such as 96%, such as, 97%, such as 98%, such as 99%, such as 99.5%, such as 100% sequence identity to said SEQ ID 11, SEQ ID 12, SEQ ID 13, SEQ ID 14, SEQ ID 15, SEQ ID 16, SEQ ID 17, and/or
  iii. a sequence variant of said polynucleotide, wherein the codon usage is altered.

In a preferred embodiment the PV L1 protein containing the biotin acceptor site is encoded by a polynucleotide sequence comprising:
  i. a polynucleotide sequence selected from the group comprising, SEQ ID 12, and/or SEQ ID 13, and/or
  ii. a sequence variant of said polynucleotide sequence, wherein the sequence variant has at least 70%, such as 75%, such as 80%, such as 85%, such as 90%, such as 95%, such as 96%, such as, 97%, such as 98%, such as 99%, such as 99.5%, such as 100% sequence identity to said, SEQ ID 12, and/or SEQ ID 13, and/or
  iii. a sequence variant of said polynucleotide, wherein the codon usage is altered.

In a further embodiment the antigen fused to the monovalent streptavidin has a polynucleotide sequence comprising:
  i. a polynucleotide sequence selected from the group consisting of SEQ ID 29, SEQ ID 30, SEQ ID 31, SEQ ID 32, SEQ ID 33, SEQ ID 34, SEQ ID 35, and/or
  ii. a sequence variant of said polynucleotide sequence, wherein the sequence variant has at least 70%, such as 75%, such as 80%, such as 85%, such as 90%, such as 95%, such as 96%, such as, 97%, such as 98%, such as 99%, such as 99.5%, such as 100% sequence identity to said SEQ ID 11, SEQ ID 12, SEQ ID 13, SEQ ID 14, SEQ ID 15, SEQ ID 16, SEQ ID 17, and/or
  iii. a sequence variant of said polynucleotide, wherein the codon usage is altered.

In an embodiment the biotin acceptor site, comprises the nucleotide sequence SEQ ID NO: 39.

Another aspect of the present invention relates to polynucleotide sequences encoding
  i. a PV L1 protein containing a biotin acceptor site, and/or
  ii. a biotin ligase capable of biotinylating the biotin acceptor site, and/or
  iii. an antigen fused to a monovalent streptavidin.

In a preferred embodiment the present invention relates to polynucleotide sequences encoding
  i. a PV L1 protein containing a biotin acceptor site comprising SEQ ID NO: 2, and/or
  ii. a biotin ligase capable of biotinylating the biotin acceptor site comprising SEQ ID 38, and/or
  iii. an antigen fused to a monovalent streptavidin comprising SEQ ID NO: 19.

In a more preferred embodiment the present invention relates to polynucleotide sequences encoding
  i. a PV L1 protein containing a biotin acceptor site comprising SEQ ID NO: 2, and/or
  ii. a biotin ligase capable of biotinylating the biotin acceptor site comprising SEQ ID 38, and/or
  iii. an antigen fused to a monovalent streptavidin comprising SEQ ID NO: 20.

In a most preferred embodiment the present invention relates to polynucleotide sequences encoding
  i. a PV L1 protein containing a biotin acceptor site comprising SEQ ID NO: 2, and/or
  ii. a biotin ligase capable of biotinylating the biotin acceptor site comprising SEQ ID 38, and/or
  iii. an antigen fused to a monovalent streptavidin comprising SEQ ID NO: 18.

Host Cell

The invention further relates to a host cell comprising a polynucleotide and/or a vector. The polynucleotide may have a sequence that is codon-optimised. Codon optimisation methods are known in the art and allow optimised expression in a heterologous host organism or cell. In an embodiment the host cell may be selected from the group comprising bacteria, yeast, fungi, plant, mammalian and/or insect cells. Methods for expressing a first polypeptide: a PV L1 protein containing a biotin acceptor site, and/or a second polypeptide; a biotin ligase, capable of biotinylating the biotin acceptor site, and/or a third polypeptide: an antigen fused to a monovalent streptavidin in a host cell are known in the art. The first, second or third polypeptide may be heterologously expressed from corresponding polynucleotide sequences cloned into the genome of the host cell or they may be comprised within a vector. For example, a first and/or second and/or third polynucleotide coding for the first and/or second and/or third polypeptide is cloned into the genome, and a first and/or second and/or third polynucleotide coding for the first and/or second and/or third polypeptide is comprised within a vector transformed or transfected into the host cell. Alternatively, the first and/or second and/or third polynucleotide is comprised within a first vector and the first and/or second and/or third polynucleotide is comprised within a second vector and the first and/or second and/or third is comprised within a third vector.

Expression of the first, second, and third polypeptides in the host cell may occur in a transient manner. When the polynucleotide encoding one of the polypeptides is cloned into the genome, an inducible promoter may be cloned as well to control expression of the polypeptides. Such inducible promoters are known in the art. Alternatively, genes coding for suppressors of gene silencing may also be cloned into the genome or into a vector transfected within the host cell.

In a particular embodiment the host cell may be selected from the group comprising *Escherichia coli*, *Spodoptera frugiperda* (sf9), *Trichoplusia ni* (BTI-TN-5B1-4), *Pichia Pastoris*, *Saccharomyces cerevisiae*, *Hansenula polymorpha*, *Drosophila* Schneider 2 (S2), *Lactococcus lactis*, Chinese hamster ovary (CHO), Human Embryonic Kidney 293, *Nicotiana tabacum* cv. Samsun NN and *Solanum tuberosum* cv. Solara. Thus in an embodiment, the host cell is *Escherichia coli*. In another embodiment, the host cell is *Spodoptera frugiperda*. In another embodiment, the host cell is *Pichia Pastoris*. In another embodiment, the host cell is *Saccharomyces cerevisiae*. In another embodiment, the host cell is *Hansenula polymorpha*. In another embodiment, the host cell is *Drosophila* Schneider 2. In another embodiment, the host cell is *Lactococcus lactis*. In another embodiment, the host cell is Chinese hamster ovary (CHO). In another embodiment, the host cell is Human Embryonic Kidney 293. In another embodiment, the host cell is *Trichoplusia ni* (BTI-TN-5B1-4). In another embodiment, the host cell is *Nicotiana tabacum* cv. Samsun NN. In another embodiment, the host cell is *Solanum tuberosum* cv. Solara.

In another aspect the present invention relates to a host cell expressing at least one polypeptide encoded by any of the polynucleotides disclosed by the present invention.

In an embodiment the host cell expresses:
i. a first polypeptide; a PV L1 protein containing a biotin acceptor site, and/or
ii. a second polypeptide; a biotin ligase, capable of biotinylating the biotin acceptor site, and/or
iii. a third polypeptide; an antigen fused to a monovalent streptavidin,
wherein the cell is selected from the group comprising bacteria, yeast, fungi, plant, mammalian and/or insect cells.
In a further embodiment the host cell, expresses
i. a first polypeptide having a sequence at least 70%, such as 75%, such as 80%, such as 85%, such as 90%, such as 95%, such as 96%, such as, 97%, such as 98%, such as 99%, such as 99.5%, such as 100% identical to SEQ ID NO: 3 [DE-loop, HPV genotype 16], SEQ ID NO: 2 [HI-loop, HPV genotype 16], SEQ ID NO: 6 [HI-loop, HPV118]; and/or
ii. a second polypeptide having a sequence at least 70%, such as 75%, such as 80%, such as 85%, such as 90%, such as 95%, such as 96%, such as, 97%, such as 98%, such as 99%, such as 99.5%, such as 100% identical to SEQ ID NO: 38, and/or
iii. a third polypeptide having a sequence at least 70%, such as 75%, such as 80%, such as 85%, such as 90%, such as 95%, such as 96%, such as, 97%, such as 98%, such as 99%, such as 99.5%, such as 100% identical to SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, and SEQ ID NO: 28,
wherein the cell is selected from the group comprising bacteria, yeast, fungi, plant, mammalian and/or insect cells.
In a preferred embodiment the host cell expresses:
i. a first polypeptide; a PV L1 protein containing a biotin acceptor site comprising SEQ ID NO: 2, and/or
ii. a second polypeptide; a biotin ligase, capable of biotinylating the biotin acceptor site comprising SEQ ID NO: 38, and/or
iii. a third polypeptide; an antigen fused to a monovalent streptavidin comprising SEQ ID NO:18,
wherein the cell is selected from the group comprising bacteria, yeast, fungi, plant, mammalian and/or insect cells.

The inventors of the present invention have demonstrated formation of VLP's using insect cells, such as High Five (*Trichoplusia ni*) of Sf9 cells incubated at 28° C. Other conditions and expression hosts may work as well.

In a particular embodiment *Trichoplusia ni* cells are used as host cell for expression of any of the disclosed polynucleotides and/or polypeptides. In another embodiment *Trichoplusia ni* cells are used to express a polypeptide having a sequence at least 70%, such as 75%, such as 80%, such as 85%, such as 90%, such as 95%, such as 96%, such as, 97%, such as 98%, such as 99%, such as 99.5%, such as 100% identical any of the polypeptides disclosed herein.

Composition Comprising the Vaccine

The vaccine of the present invention is to be used in the prophylaxis and/or treatment of a disease. Thus, one aspect of the present invention relates to a composition comprising the vaccine of the present invention. Such compositions may further comprise for example an adjuvant, a buffer, and/or salts or a combination hereof.

An adjuvant is a pharmacological and/or immunological agent that modifies the effect of other agents. Adjuvants may be added to a vaccine to modify the immune response by boosting it such as to give a higher amount of antibodies and/or a longer lasting protection, thus minimizing the amount of injected foreign material. Adjuvants may also be used to enhance the efficacy of a vaccine by helping to subvert the immune response to particular cell types of the immune system, for example by activating the T cells instead of antibody-secreting B cells dependent on the type of the vaccine. Thus in an embodiment the composition comprises at least one adjuvant. In an embodiment the adjuvant is aluminium based. Alluminumum adjuvants may be aluminum phosphate, aluminum hydroxide, amorphous aluminum hydroxyphosphate sulfate and/or a combination hereof. Other adjuvants may be included as well.

In another embodiment the composition described above comprises at least one buffer. In an embodiment the buffer is PBS and/or histidine based. In another embodiment the buffer has a pH between pH 6-pH 7.5. In an embodiment the buffer, is isotonic such as has 0.6%-1.8% NaCl.

An emulsifier (also known as an "emulgent") is a substance that stabilizes an emulsion by increasing its kinetic stability. One class of emulsifiers is known as "surface active agents", or surfactants. Polysorbates are a class of emulsifiers used in some pharmaceuticals and food preparation. Common brand names for polysorbates include Alkest, Canarcel, and Tween. Some examples of polysorbates are Polysorbate 20, Polysorbate 40, Polysorbate 60, Polysorbate 80. In an embodiment the composition of the present invention comprises an emulsifier such as one of the above described polysorbates. In a particular embodiment the composition comprises 0.001-0.02% polysorbate 80. Other polysorbates or emulsifiers may be used in the present invention as well.

A Pharmaceutical Composition Comprising the Vaccine

The vaccine of the present invention is intended to be used in the prophylaxis and/or treatment of a disease. Accordingly, the present invention further provides a pharmaceutical formulation, which comprises the vaccine of the present invention and a pharmaceutically acceptable carrier therefor. The pharmaceutical formulations may be prepared by conventional techniques, e.g. as described in Remington: The Science and Practice of Pharmacy 2005, Lippincott, Williams & Wilkins.

The pharmaceutically acceptable carriers can be either solid or liquid. Solid form preparations include powders, tablets, pills, capsules, cachets, suppositories, and dispersible granules. A solid carrier can be one or more excipients which may also act as diluents, flavoring agents, solubilizers, lubricants, suspending agents, binders, preservatives, wetting agents, tablet disintegrating agents, or an encapsulating material.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like. 3

The compounds of the present invention may be formulated for parenteral administration and may be presented in unit dose form in ampoules, pre-filled syringes, small volume infusion or in multi-dose containers, optionally with an added preservative. The compositions may take such forms as suspensions, solutions, or emulsions in oily or aqueous vehicles, for example solutions in aqueous polyethylene glycol. Examples of oily or non-aqueous carriers, diluents, solvents or vehicles include propylene glycol, polyethylene glycol, vegetable oils, and injectable organic esters, and may contain agents such as preserving, wetting, emulsifying or suspending, stabilizing and/or dispersing agents. Preferably, the formulation will comprise about 0.5% to 75% by weight of the active ingredient(s) with the remainder consisting of suitable pharmaceutical excipients as described herein.

The vaccine of the invention may be administered concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount.

Thus, one aspect of the present invention relates to a pharmaceutical composition comprising a vaccine. Such pharmaceutical composition may comprise an adjuvant, a buffer, and/or salts or a combination hereof.

In an embodiment the pharmaceutical composition, further comprises a composition comprising a vaccine as described by the present invention.

A Method of Manufacture a Pharmaceutical Composition Comprising a Vaccine

The present invention further relates to a method of manufacturing a pharmaceutical composition comprising a vaccine. In one aspect the VLP based vaccine of the present invention, may at least be manufactured by the following steps:

i. obtaining a first polypeptide comprising: a PV L1 protein containing a biotin acceptor site, and/or
ii. obtaining a second polypeptide: a biotin ligase capable of biotinylating the biotin acceptor site, and/or
iii. obtaining a third polypeptide: an antigen fused to a monovalent streptavidin, and
iv. subjecting the first polypeptide to conditions which enable formation of virus like particles, and/or
v. enabling enzymatic biotinylation of the biotin acceptor site of said virus like particles using said second polypeptide, and/or
vi. obtaining a vaccine by linkage of the third polypeptide and said virus like particles via the interaction between the monovalent streptavidin and the biotin molecule enzymatically conjugated to the biotin acceptor site of said virus like particles, and/or
vii. generating a composition comprising said vaccine.

thereby obtaining a pharmaceutical composition.

In the manufacture of the pharmaceutical composition other steps may be included for example a) isolation/purification of the VLP to yield a high purity/quality product. This will be accomplished using different techniques for protein purification. For this purpose several separation steps will be carried out using the differences in for instance protein size, physico-chemical properties, binding affinity or biological activity b) formulation by adding stabilizers to prolong the storage life or preservatives to allow multi-dose vials to be used safely as needed c) all components that constitute the final vaccine are combined and mixed uniformly e.g. in a single vial or syringe d) the vaccine is put in recipient vessel (e.g. a vial or a syringe) and sealed with sterile stoppers.

All the processes described above will have to comply with the standards defined for Good Manufacturing Practices (GMP) that will involve several quality controls and an adequate infrastructure and separation of activities to avoid cross-contamination. Finally, the vaccine may be labeled and distributed worldwide.

Method of Administering a Vaccine

Routes of Administration

Systemic treatment. The main routes of administration are oral and parenteral in order to introduce the agent into the blood stream to ultimately target the sites of desired action. Appropriate dosage forms for such administration may be prepared by conventional techniques.

Oral administration. Oral administration is normally for enteral drug delivery, wherein the agent is delivered through the enteral mucosa.

Parenteral administration. Parenteral administration is any administration route not being the oral/enteral route whereby the medicament avoids first-pass degradation in the liver. Accordingly, parenteral administration includes any injections and infusions, for example bolus injection or continuous infusion, such as intravenous administration, intramuscular administration, subcutaneous administration. Furthermore, parenteral administration includes inhalations and topical administration.

Accordingly, the agent may be administered topically to cross any mucosal membrane of an animal to which the biologically active substance is to be given, e.g. in the nose, vagina, eye, mouth, genital tract, lungs, gastrointestinal tract, or rectum, preferably the mucosa of the nose, or mouth, and accordingly, parenteral administration may also include buccal, sublingual, nasal, rectal, vaginal and intraperitoneal administration as well as pulmonal and bronchial administration by inhalation or installation. Also, the agent may be administered topically to cross the skin.

The subcutaneous and intramuscular forms of parenteral administration are generally preferred.

Local treatment. The agent according to the invention may be used as a local treatment, ie. be introduced directly to the site(s) of action as will be described below.

Thus one agent may be applied to the skin or mucosa directly, or the agent may be injected into the diseased tissue or to an end artery leading directly to the diseased tissue.

Thus another aspect of the present invention relates to a method of administering a vaccine to treat and/or prevent a clinical condition in a subject in need thereof, comprising the steps of
  i. obtaining a composition comprising at least one vaccine according to the present invention, and/or
  ii. administering said composition to a subject at least once for prophylaxis and/or treatment of a disease.

A preferred embodiment relates to a method of administering a vaccine to treat and/or prevent cancer, as disclosed herein, in a subject in need thereof, comprising the steps of
  i. obtaining a composition comprising at least one vaccine as disclosed herein, and/or
  ii. administering said composition to a subject intramuscular and/or intravenous at least once for prophylaxis and/or treatment of a cancer.

A preferred embodiment relates to a method of administering a vaccine to treat and/or prevent a cardiovascular disease, as disclosed herein, in a subject in need thereof, comprising the steps of
  i. obtaining a composition comprising at least one vaccine as disclosed herein, and/or
  ii. administering said composition to a subject intramuscular and/or intravenous at least once for prophylaxis and/or treatment of a cardiovascular disease.

In another embodiment the vaccine of the present invention is administered by any type of injections or infusions selected from the group of bolus injection, continuous infusion, intravenous administration, intramuscular administration, subcutaneous administration, inhalation or topical administration or a combination hereof. In a particular embodiment the vaccine is administered by intramuscular administration and/or intravenous administration.

In medicine, a booster dose is an extra administration of a vaccine after an earlier dose. After initial immunization, a booster injection or booster dose is a re-exposure to the immunizing antigen cell. It is intended to increase immunity against that antigen back to protective levels after it has been shown to have decreased or after a specified period. In an embodiment the vaccine of the present invention is administered any number of times from one, two, three, four times or more.

In a further embodiment the vaccine is boosted by administration in a form and/or body part different from the previous administration. In another embodiment the vaccine is administered to the area most likely to be the receptacle of a given disease or infection which the vaccine is intended to prevent/reduce the risk of.

In another embodiment the recipient of the vaccine (the subject) of the present invention is an animal, for example a mammal, such as a *Homo sapiens*, cow, pig, horse, sheep, goat, llama, mouse, rat, monkey, and/or chicken. In a particular embodiment the subject is a *Homo sapiens*.

Administration of more than one vaccine is known in the art and refers to this concept as co-vaccination or to give a vaccine cocktail. Thus, in an embodiment of the vaccine, is co-administered with any other vaccine. In another embodiment the vaccine forms a part of a vaccine cocktail.

A Kit of Parts

In another aspect of the present invention relates to a kit of parts comprising
  i. a composition comprising a vaccine of the present invention, and/or
  ii. a medical instrument or other means for administering the vaccine, and/or
  iii. instructions on how to use the kit of parts.

In an embodiment the kit of parts comprises a second active ingredient or vaccine component for therapeutic use in the treatment or prevention of one or more of the diseased disclosed in the present invention.

In an embodiment the vaccine of the invention is administered separate, sequential, or simultaneously with at least one other pharmaceutical active ingredient and/or vaccine component.

Dosages and Dosing Regimes

The dosage requirements will vary with the particular drug composition employed, the route of administration and the particular subject being treated. It will also be recognized by one of skill in the art that the optimal quantity and spacing of individual dosages of a compound will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound given per day for a defined number of days, can be ascertained using conventional course of treatment determination tests.

The daily oral dosage regimen will preferably be from about 0.01 to about 80 mg/kg of total body weight. The daily parenteral dosage regimen about 0.001 to about 80 mg/kg of total body weight. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day.

The term "unit dosage form" refers to physically discrete units suitable as unitary dosages for human and animal subjects, each unit containing a predetermined quantity of a compound, alone or in combination with other agents, calculated in an amount sufficient to produce the desired effect in association with a pharmaceutically acceptable diluent, carrier, or vehicle. The specifications for the unit dosage forms of the present invention depend on the particular compound or compounds employed and the effect to be achieved, as well as the pharmacodynamics associated with each compound in the host. The dose administered should be an "effective amount" or an amount necessary to achieve an "effective level" in the individual patient.

When the "effective level" is used as the preferred endpoint for dosing, the actual dose and schedule can vary, depending on inter-individual differences in pharmacokinetics, drug distribution, age, gender, size, health and metabolism. The "effective level" can be defined, for example, as the blood or tissue level desired in the patient that corresponds to a concentration of one or more compounds according to the invention.

EXAMPLES

Modification of VLPs without disrupting the delicate and sensitive self-assembly process is challenging. The inventors have below shown several examples of successful introduction of a biotin acceptor site into various VLP loops without disrupting the self-assembly process. In addition the inventors have shown enzymatic biotinylation of the biotin acceptor site as well as coupled several antigen/monovalent streptavidin fusion proteins to the VLPs. Immunological testing of the VLP vaccines have been initiated. The examples below are non-limiting to the scope of the invention.

Example 1—Design of Chimeric HPV16 Avi-L1 Coat Proteins

The chimeric HPV16 Avi-L1 gene sequences were constructed by insertion of the biotin acceptor sequence (Avi-Tag™), GLNDIFEAQKIEWHE (SEQ ID NO: 36), into the DE- (aa positions 134-139), FG- (aa positions 279-286), HI- (aa positions 351-352) or H4-βJ coil (aa positions 431-432) after having deleted any intervening amino acids (HPV16 L1 accession number DQ155283.1). Gene sequences were further modified to contain an EcoRV restriction site followed by a polyhedrin promotor sequence at the N-terminus and a stop-codon followed by a NotI restriction site at the C-terminus. The synthetic gene sequences were finally codon-optimized for recombinant expression in *Trichoplusia ni* cells and synthesized by Geneart (Life Technologies).

Example 2—Expression and Purification of Chimeric HPV16 Avi-L1-VLPs

The HPV16 Avi-L1 gene fragments were cloned into the EcoRV/NotI sites of the pAcGP67A vector (BD Biosciences) deleting the gp67 secretion signal sequence. To generate recombinant virus particles, linearized BakPak viral DNA (BD Biosciences) was co-transfected with pAcGP67A/Avi-L1 into Sf9 insect cells using Lipofectamine 2000 10 Reagent (Invitrogen, 11668-019) and incubated at 28° C. for 3-5 days. Recombinant Baculovirus was harvested from the supernatant and used to generate a high-titer virus stock, which was used for infection of High-Five insect cells. Infected High-Five cells were incubated for 48 hours at 28° C. with shaking. In vitro maturation and purification of HPV16 Avi-L1 VLPs were performed as previously described (Buck et al., 2005, Buck et al., 2007). In brief, cell lysates were harvested and VLPs were allowed to mature in maturation-buffer (0.5% Triton-X-100, 0.1% Benzonase® Nuclease (Sigma-Aldrich), 25 mM $(NH_4)_2SO_4$ and 4 mM $MgCl_2$) for 18 h at 37° C. Matured VLPs were subsequently purified by ultracentrifugation through an Optiprep™ step gradient (27%/33%/39%) as previously described (22). VLPs were dialyzed in PBS (0.02% PS80) and incubated for 30 min at 30° C. with biotin and Biotin ligase (BirA) according to instructions from Avidity (Aurora, Colo.). Excess biotin was removed by dialysis in PBS (0.32 M NaCl, 0.02% PS80) and protein concentration was determined using BCA analysis. Collected ultracentrifugation fractions were analyzed with NuPAGE® Bis-Tris Protein gels (Life Technologies) or blotted onto a nitrocellulose membrane (GE-Healthcare, RPN203E) for detection of L1 or biotin with CamVir-1 (AbD Serotec, Bio-Rad, 7135-2804) or Streptavidin-HRP (Life Technologies, 43-4323), respectively. Densitometric analysis of SDS-PAGE gels was done using ImageJ.

Example 3—Gene Design and Recombinant Expression of Biotin-Binding Vaccine Antigens Heterologous vaccine antigens were genetically fused with a GGS linker at either their C- or N-terminus to a previously described (refs)/patented (U.S. Pat. No. 8,586, 708 B2) engineered monovalent streptavidin (mSA) (SEQ ID NO: 37), thereby introducing biotin binding capability to the expressed mSA-antigen fusion proteins. mSA-antigen fusion genes expressed in *E. coli* were designed with a 6×Histidine tag and NcoI/BamHI restriction sites for subcloning into pET-15b vector. mSA-antigen fusion genes expressed in either S2 cells, Human Embryonic Kidney 293 (HEK293) cells or in Baculovirus infected insect cells were designed with flanking EcoRI/BamHI (N-terminal) and NotI (C-terminal) sites and a 6×Histidine tag and were subcloned into the pHP34s, pcDNA™4/HisMax or pAcGP67A (BD Biosciences) vector, respectively.

Example 4—Characterisation of Particles

Figure 2:
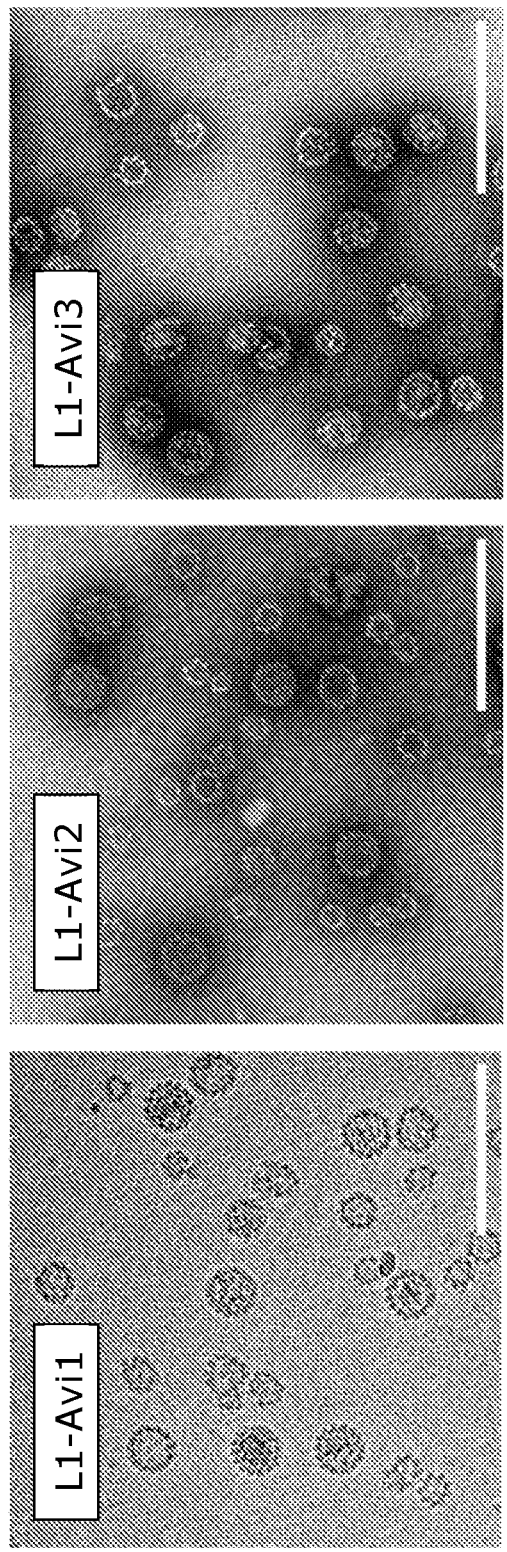
FIG. 2: Transmission electron microscopy of HPV Avi-Tag-L1 virus-like particles. The TEM pictures shows non-aggregated VLPs (size range: 28-60 nm) assembled from biotinylated HPV16 L1-Avi (SEQ ID NO. 1-3) constructs, respectively. Scale bar=200 nm.

Electron Microscopy—Negative Staining
An aliquot of diluted VLPs was adsorbed to 200-mesh mica carbon-coated grids and negatively stained with 2% phosphotungstic acid (pH=7.0). The sample was examined with a CM 100 BioTWIN electron microscope (Phillips, Amsterdam) at an accelerating voltage of 80 kV. Photographic records were performed on an Olympus Veleta camera. Particle sizes were estimated using ImageJ. Representative pictures are shown in FIG. 2.

Example 5—Particle Size Measurement by Dynamic Light Scattering (DLS)

The hydrodynamic diameter (referred to as size) of the VLP was measured using a particle analyzer, DynaPro NanoStar (WYATT Technology), equipped with a 658 nm laser. VLP samples were diluted to 0.2 mg/mL with PBS (0.32 M NaCl, 0.02% PS80) and 70 μl of each VLP sample was loaded into a disposable low volume cuvette and mounted into the DLS chamber. After 1 min equilibration, the size distribution was obtained by DLS measurement at 25° C. Each sample was measured 2 times with 20 runs in each measurement. The most predominant average sizes of particles in the population were calculated from the measurements and recorded together with the % polydispersity (% Pd).

Example 6—Determination of the Extent of Biotinylation of AviTag-VLPs

The degree of biotinylation of the AviTag-VLPs is estimated by comparison with known quantities of fully biotinylated C-terminal AviTag Maltose Binding Protein (MBP-AviTag protein) using a typical ELISA setup. Briefly, the standard MBP-AviTag protein and AviTag-VLPs are adsorbed to the wells of a 96-well maxisorb plate (Nunc 456537) at known protein quantities (1-45 ng, 5 ng increments). Extraneous biotin is removed by washing with TBST buffer (10 mM Tris, pH 7.5, 150 mM NaCl, 0.05% Tween 20) and the plate is blocked by adding 300 μl blocking solution (PBS plus 40 μg/ml BSA) to each well.

The streptavidin-horseradish peroxidase solution is then added into each well and incubated with gentle shaking for 1 hour at room temperature. Finally, the biotin associated with the biotin acceptor site is detected by its interaction with streptavidin-conjugated horseradish peroxidase by monitoring the absorption at 490 nm after adding the developing solution (3 OPD tablets dissolved in 12 ml d-water with 10 µl H2O2).

Figure 3:
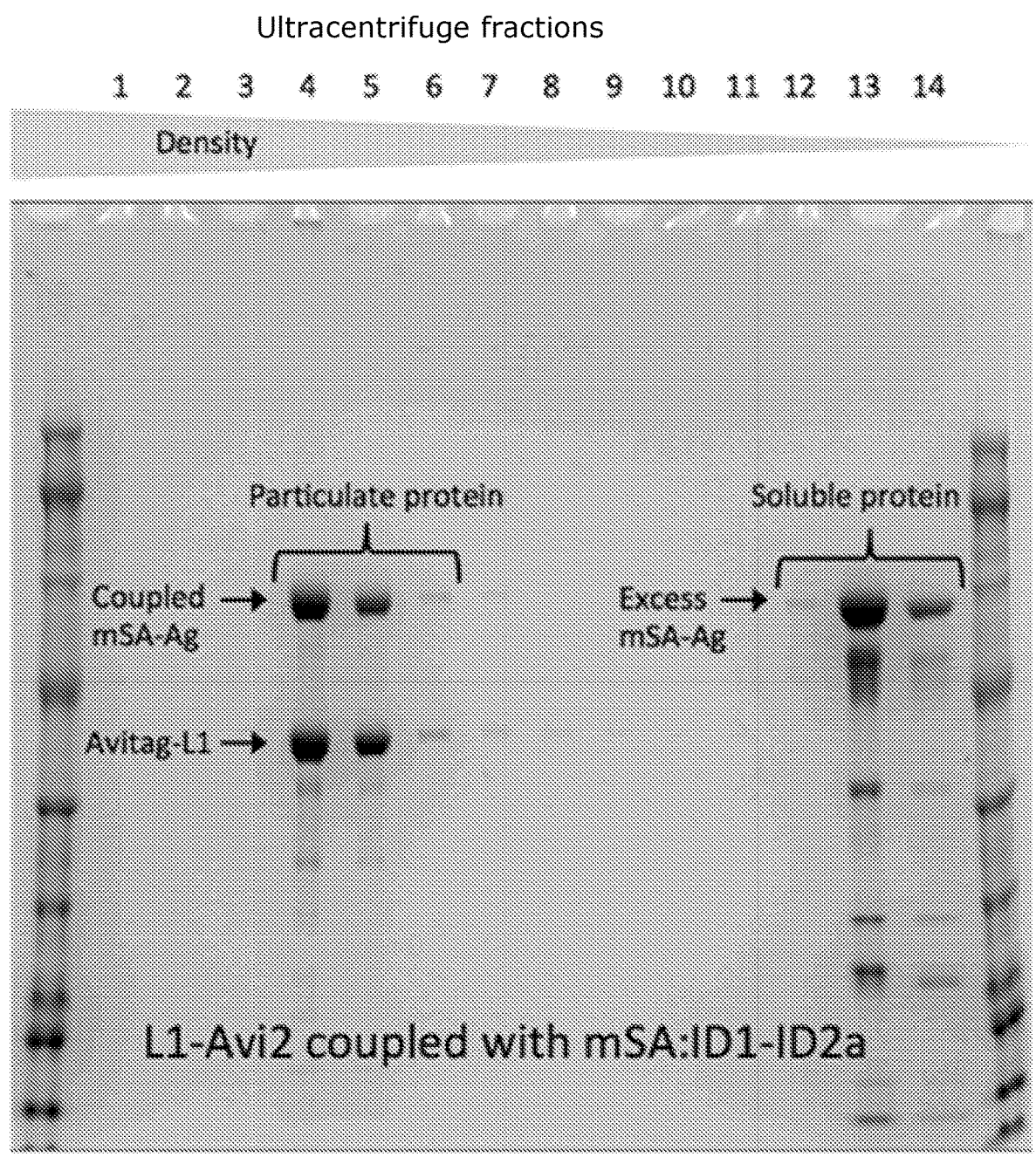
FIG. 3: VLP/mSA-antigen coupling efficiency. The figure shows SDS-PAGE gels (reduced conditions) with relative amounts of coupled mSA-antigens (mSA-ID1ID2a-HIS SEQ ID NO. 21; mSA-IL-5(C63T/C105T) SEQ ID NO. 19; HIS-GMZ2T:ggsmSA SEQ ID NO. 25; mSA-Her2-ECD|23-686 SEQ ID NO. 18) and AviTag-L1 protein (SEQ ID NO. 2). There is an estimated 0.8-1.0 mSA-antigen per AviTag-L1 protein in the VLP containing fractions.
Figure 3:
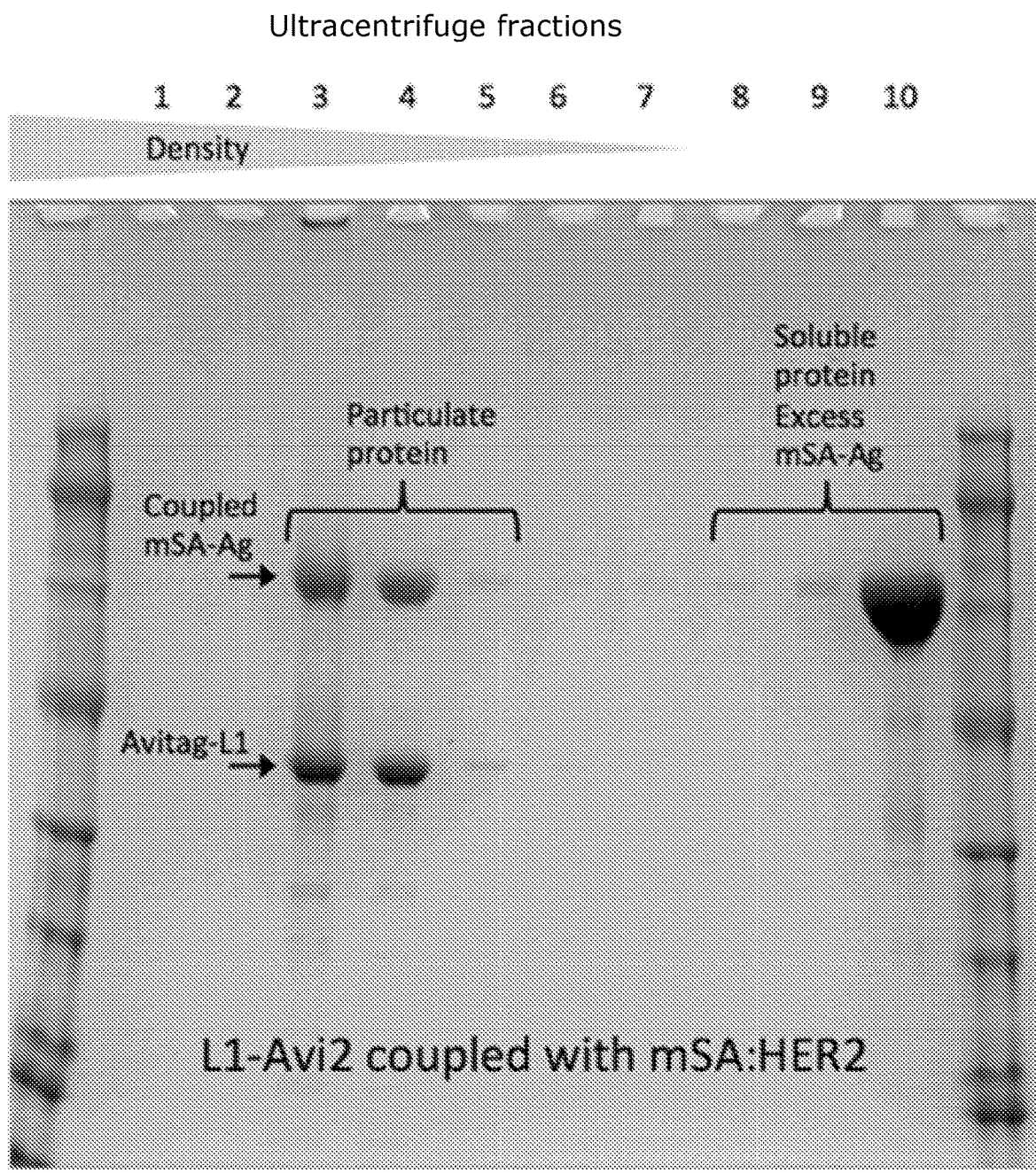
Figure 3:
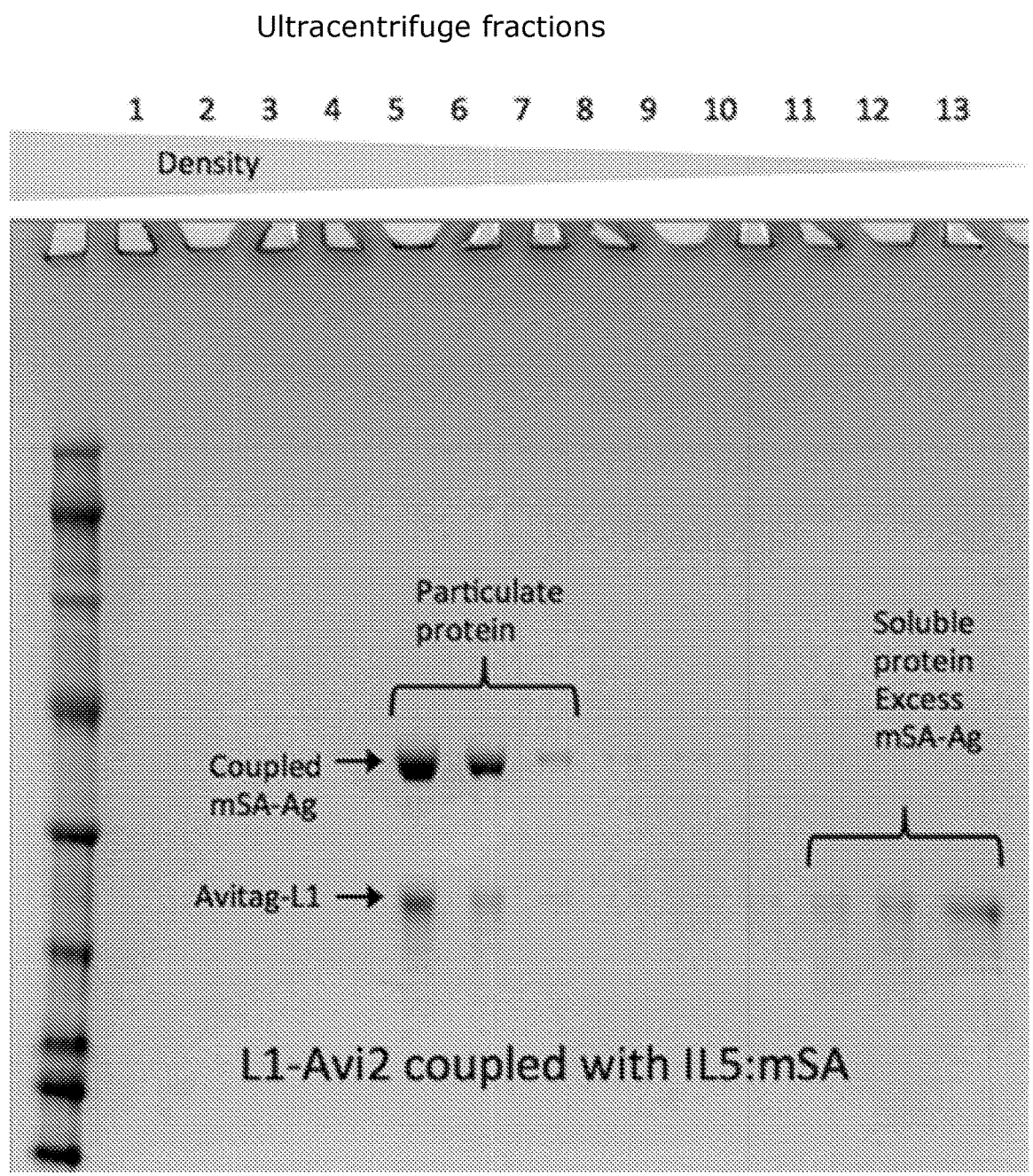
Figure 3:
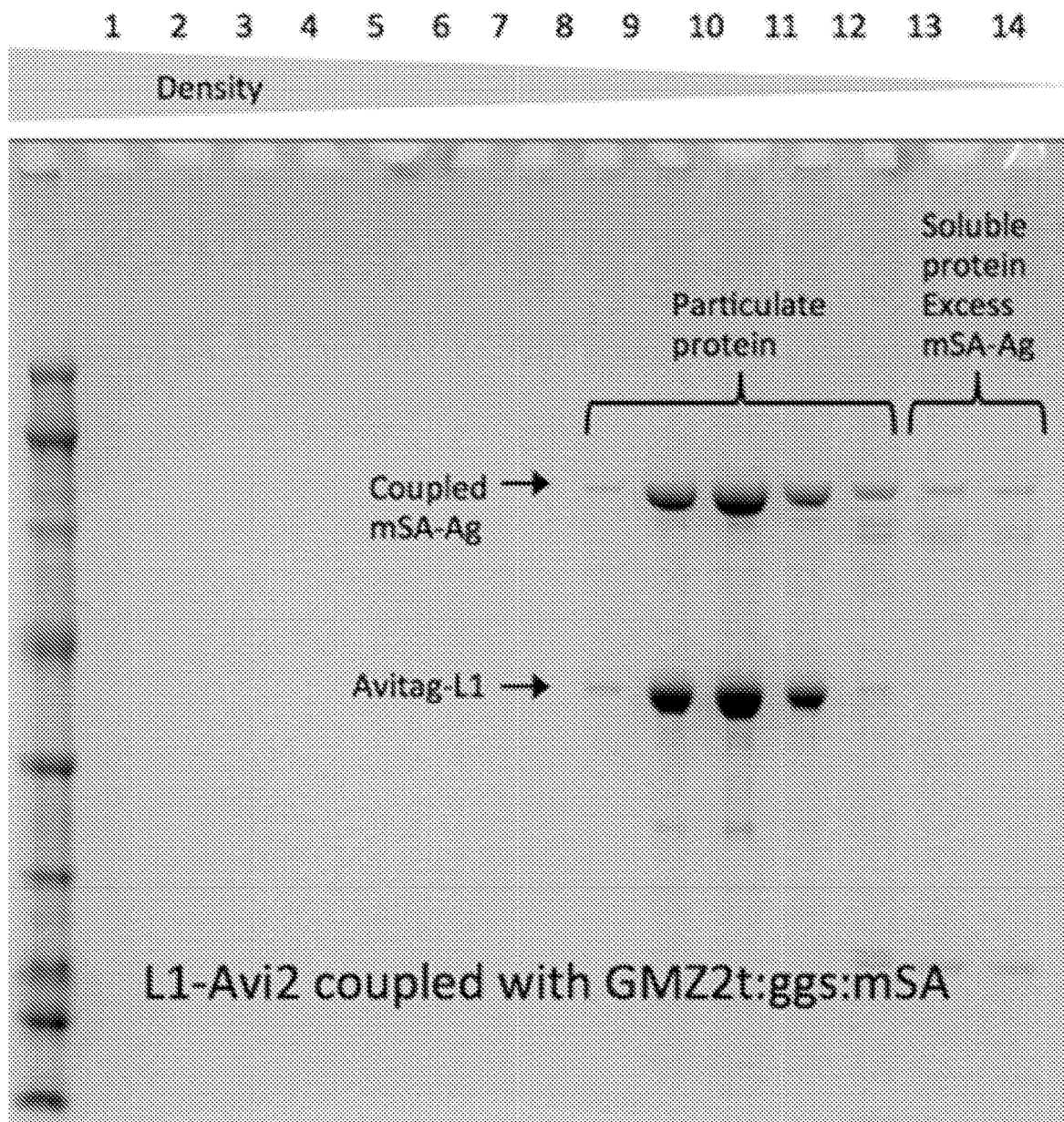
Figure 4:
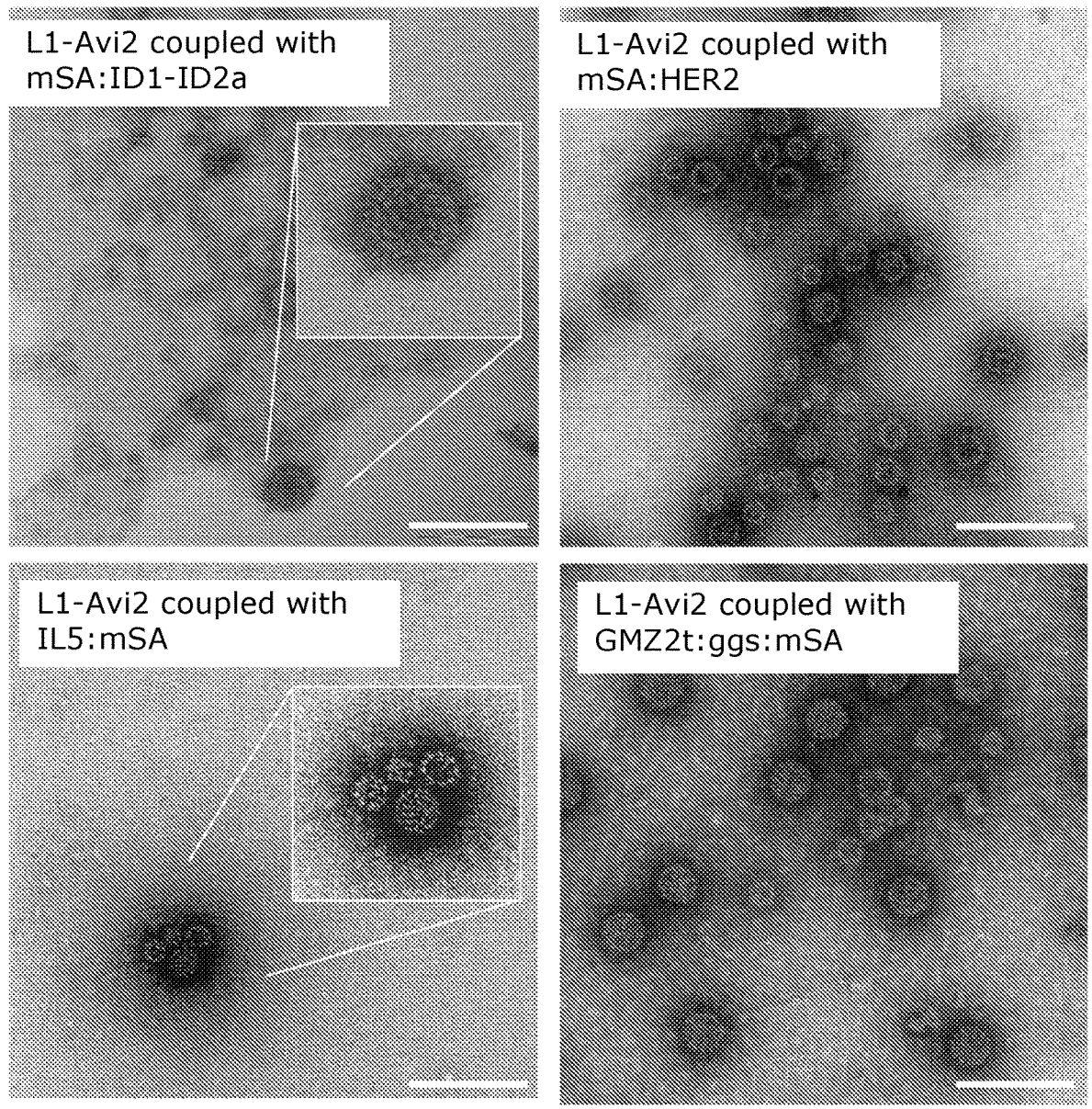
FIG. 4: Transmission electron microscopy of HPV AviTag-L1 virus-like particles coupled with different mSA-antigens (mSA-ID1ID2a-HIS SEQ ID NO. 21; mSA-IL-5 (C63T/C105T) SEQ ID NO. 19; HIS-GMZ2T:ggsmSA SEQ ID NO. 25; mSA-Her2-ECD|23-686 SEQ ID NO. 18) and AviTag-L1 protein (SEQ ID NO. 2). The TEM pictures shows non-aggregated VLPs assembled from biotinylated HPV16 L1-Avi (SEQ ID NO. 2) constructs, respectively. The apparent average size of the mSA-antigen coupled VLPs seems (~5-10 nm) larger than corresponding non-coupled VLPs. Scale bar=200 nm.

Example 7—Verification of the mSA-Antigen Coupling onto (Biotin Acceptor Site)—VLPs The overall amounts of antigen coupled onto the VLPs was estimated by comparing the relative amounts of antigen/HPV L1 protein on a reduced SDS-PAGE gel (FIG. 3). The material for this analysis was made by firstly mixing biotinylated VLPs with an excess amount of the mSA-antigen and then separating the mSA-antigen/VLP complexes from the excess mSA-antigen by density gradient ultracentrifugation. The VLPs were also examined by transmission electron microscopy to assess their integrity after coupling of different mSA-antigens (FIG. 4). Specifically, an aliquot of diluted particles (post mSA-coupling and removal of excess mSA-antigen) was placed on 200-mesh mica carbon-coated grids, negatively stained with 2% phosphotungstic acid (pH=7.0) and examined by transmission electron microscopy (TEM) using a CM 100 BioTWIN.

Example 8—Coupling of Antigens to VLPs

The inventors have partially tested the coupling of 7 different VLPs with 12 different antigen/monovalent streptavidin fusion proteins. The results have been obtained as described above and are summarized in table 3.

TABLE 3

Coupling of VLP1-7 and antigen/mSA A1-A11.
Sequences of the constructs are found in table 5.

| | VLP1 | VLP2 | VLP3 | VLP4 | VLP5 | VLP6 | VLP7 |
|---|---|---|---|---|---|---|---|
| A1 | No coupling | Yes | Yes | No VLPs | N/A | No VLPs | No VLPs |
| A2 | No coupling | Yes | Yes | No VLPs | N/A | No VLPs | No VLPs |
| A3 | No coupling | N/A | N/A | No VLPs | N/A | No VLPs | No VLPs |
| A4 | No coupling | Yes | Yes | No VLPs | N/A | No VLPs | No VLPs |
| A5 | No coupling | Yes | Yes | No VLPs | N/A | No VLPs | No VLPs |
| A6 | No coupling | Yes | Yes | No VLPs | N/A | No VLPs | No VLPs |
| A7 | No coupling | Yes | Yes | No VLPs | N/A | No VLPs | No VLPs |
| A8 | No coupling | Yes | Yes | No VLPs | N/A | No VLPs | No VLPs |
| A9 | No coupling | Yes | Yes | No VLPs | N/A | No VLPs | No VLPs |
| A10 | No coupling | Yes | Yes | No VLPs | N/A | No VLPs | No VLPs |
| A11 | No coupling | Yes | Yes | No VLPs | N/A | No VLPs | No VLPs |
| A12 | No coupling | Yes | N/A | No VLPs | N/A | No VLPs | No VLPs |

Example 9—Expression and Purification of VAR2CSA and mSA-VAR2CSA

The chimeric mSA-VAR2CSA gene sequence was designed with a small Gly-Gly-Ser linker separating the monomeric Streptavidin (mSA) [GenBank: 4JNJ_A] from the ID1-ID2a domains of VAR2CSA [FCR3 strain, GenBank: GU249598] (amino terminus). Both the VAR2CSA and mSA-VAR2CSA gene fragments were further modified to contain a C-terminal 6× histidine tag and flanking BamHI and NotI restriction sites used for sub-cloning into the Baculovirus vector, pAcGP67A (BD Biosciences). Linearized Bakpak6 Baculovirus DNA (BD Biosciences) was co-transfected with pAcGP67A-VAR2CSA or pAcGP67A-mSA-VAR2CSA into Sf9 insect cells for generation of recombinant virus particles. Histidine-tagged recombinant protein was purified on $Ni^{2+}$ sepharose columns from the supernatant of Baculovirus infected High-Five insect cells using an ÄKTAxpress purification system (GE-Healthcare).

Example 10—Conjugation and Purification of mSA-VAR2CSA to L1-Avi VLPs

For production of the VLP-VAR2CSA vaccine, biotinylated HPV16 Avi-L1 VLPs were mixed with 3× molar excess of mSA-VAR2CSA and the sample was incubated at 4° C. for 18-24 hours with gentle shaking. Unbound mSA-VAR2CSA was removed by ultracentrifugation over an Optiprep™ step gradient (27%, 33%, 39%) as previously described (Buck et al., 2004).

The VLP-VAR2CSA vaccine was dialyzed in PBS (0.32 M NaCl, 0.02% PS80) and the relative concentration of VLP-bound mSA-VAR2CSA was estimated by SDS-PAGE using a BSA standard dilution range. Post ultracentrifugation fractions were analyzed by SDS-PAGE or blotted onto a nitrocellulose membrane (GE-Healthcare RPN203E) for detection of L1 or mSA-VAR2CSA (via a 6× histidine tag) with CamVir-1 (AbD Serotec, Bio-Rad, 7135-2804) or Penta☐His HRP (QIAGEN, 34460) respectively.

Example 11—Anti-VAR2CSA Antibody Response Measured by ELISA

Recombinant VAR2CSA (1 µg/ml in PBS) was coated on Nunc MaxiSorp plates overnight at 4° C. Plates were incubated with blocking buffer for 1 hour at room temperature (RT) to inhibit non-specific binding to the plate. Plates were washed three times in between different steps. Serum samples were diluted in blocking buffer (1:100), added to the wells in three fold dilutions, and incubated for 1 hour at RT. Horseradish peroxidase (HRP)-conjugated polyclonal rabbit anti-mouse Ig (P260 DAKO, Denmark) was diluted 1:3000 in blocking buffer and incubated for 1 hour. Finally, color reactions were developed for 7 min by adding o-phenylenediamine substrate. The HRP enzymatic reaction was stopped by adding 2.5 M $H_2SO_4$ and the optical density was measured at 490 nm using an ELISA plate reader (VersaMax Molecular Devices).

Example 12—Parasite Culture

Parasites were maintained in culture as described (23). Briefly, parasites were cultured in 5% hematocrit of human blood (group 0+) in RPMI 1640 (Sigma) supplemented with 0.125 µg/ml Albumax II (Invitrogen) and 2% normal human serum. Atmospheric air was exchanged with a mixture of 1% oxygen and 5% carbon dioxide in nitrogen, whereafter incubation was done at 37° C. under static conditions with ad hoc change of culture medium. The FCR3 isolate was selected for binding to CSA by panning on BeWo cells as described (Haase et al., 2006). Parasite isolates tested negative for *mycoplasma* (Lonza) and were regularly genotyped using nested GLURP and MSP-2 primers in a single PCR step, as described (Snounou et al., 1999).

Example 13—Inhibition of Binding Assays

Parasite DNA was labeled with Tritium by overnight incorporation of titrated hypoxanthine. A 96 well plate (Falcon) was coated with 2 µg/ml of Decorin (Sigma-Aldrich) overnight and blocked with 2% bovine serum albumin (Sigma) as described (Nielsen et al., 2009). Tritium labeled late-stage IEs were MACS purified and added to the 96 well plate in a concentration of 200,000 cells per well. Titrations of serum were added in a total volume of 100 µl in triplicate wells. After incubation for 90 min at 37° C., unbound IEs were washed away by a pipetting robot (Beckman-Coulter). The remaining IEs were harvested onto a filter plate (Perkin-Elmer). After addition of scintillation fluid (Perkin-Elmer) the counts per minute (CPM) recording the number of non-inhibited IE was determined by liquid scintillation counting on a Topcount NXT (Perkin-Elmer). Data were adjusted to percentage of binding by dividing test result with the mean value of wells with IE incubated without serum.

Example 14—Generation of Biotinylated HPV Avi-L1 VLPs

Figure 5:
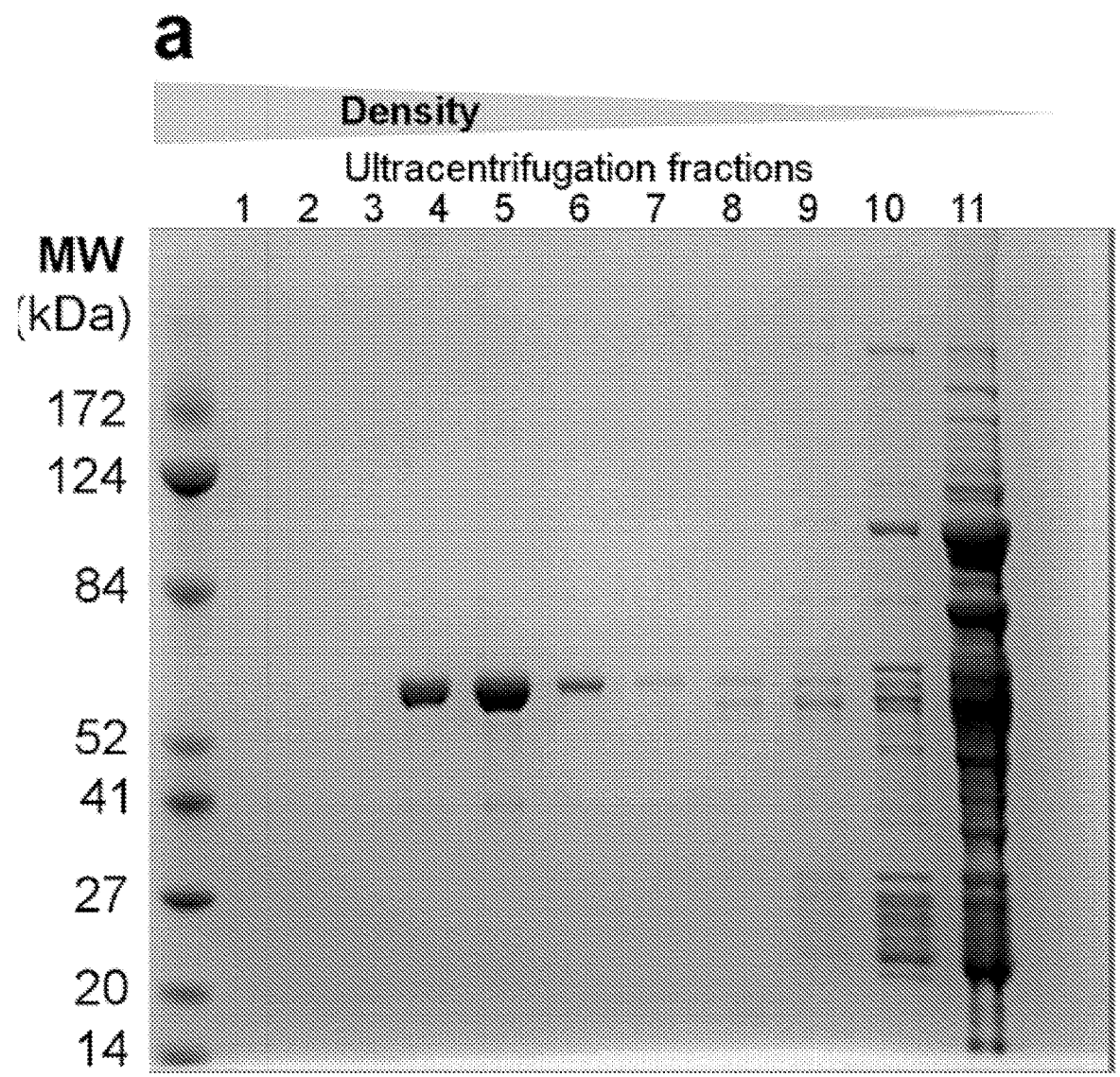
FIG. 5. Verification of self-assembly and subsequent in vitro biotinylation of HPV16 Avi-L1 VLPs a. Purification of HPV16 Avi-L1 VLPs (HI) VLPs was performed by ultracentrifugation (UC) on an iodixanol (Optiprep™) density-gradient (27%/33%/39%). Subsequent reduced SDS-PAGE analyses showed the presence of a 56 kDa protein band (theoretical size of Avi-L1) in the high-density UC fractions [4-6] containing particulate material. b. Transmission-electron microscopy (TEM) analysis of material representing UC fraction 4 post UC purification. To verify the integrity of the chimeric HPV16 Avi-L1 (HI) VLPs, an aliquot of diluted particles was placed on carbon-coated grids, negatively stained with 2% phosphotungstic acid (pH=7.0) and examined by transmission electron microscopy (TEM) using a CM 100 BioTWIN at magnification ×36,000 (Å), scale bar 80 nm. c. Western blot analysis of fraction 4 post UC purification. The blot demonstrates the presence of HPV16 Avi-L1 (56 kDa) detected by Camvir-1 (lane one) and successful biotinylation of HPV16 Avi-L1 using Strep-HRP to detect biotin (lane two).
Figure 5:
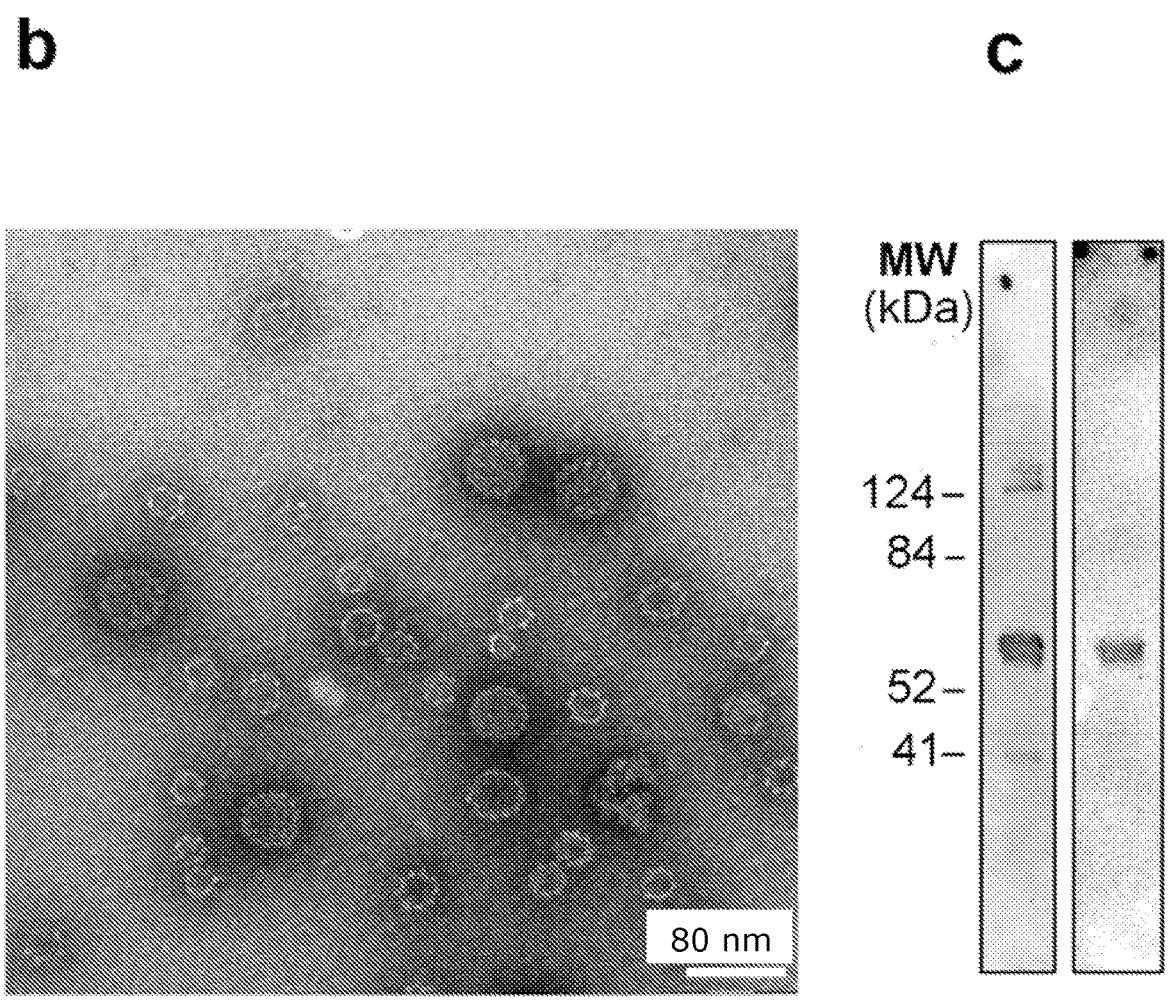

The biotin acceptor site (AviTag™) sequence was genetically inserted as described above at four different positions in the HPV16 L1 sequence, which based on the crystal structure of HPV16 L1 capsid protein, correspond to surface exposed loops in the assembled VLP structure. The chimeric Avi-L1 constructs were expressed in High-Five cells and allowed to assemble into VLPs (FIG. 1b). Formation of VLPs was confirmed by performing density gradient ultracentrifugation followed by SDS-PAGE analysis. This analysis indicated that three of the recombinant proteins, Avi-L1 (HI), Avi-L1 (DE) and Avi-L1 (H4-βJ coil) formed VLPs as the majority of the expressed protein were present in high molecular/density fractions 4-6 after ultracentrifugation (FIG. 5a). The Avi-L1 (FG) protein was exclusively found in the low density fractions containing non-particulate soluble protein, indicating that the AviTag™ insertion, in this case, prevented VLP assembly.

The identity of Avi-L1 proteins in the high-density fractions was confirmed by western blot analysis using a monoclonal anti-HPV16 L1 antibody (FIG. 5c). VLP assembly of the Avi-L1 constructs was verified by transmission electron microscopy (TEM) as described above showing a heterogeneous population of VLPs of different sizes (28-60 nm) (FIG. 5b), representing different icosahedral assembly symmetries of which roughly 30% had the size/appearance of native HPV16 L1 VLPs. The particles were subsequently biotinylated (FIG. 5c) and analyzed by TEM.

Example 15—Construction of the Displayed Antigen VAR2CSA

Figure 6:
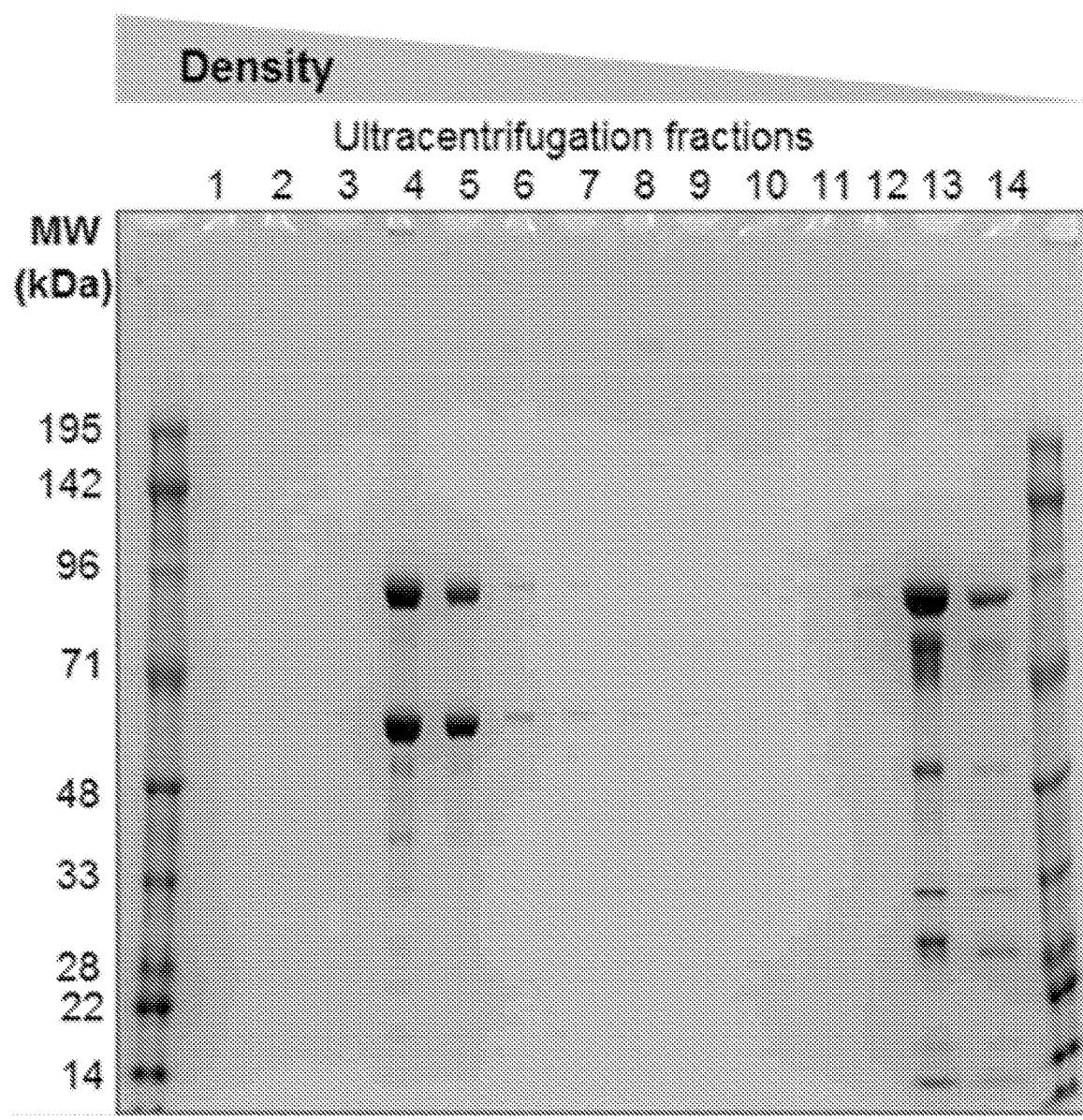
FIG. 6. HPV16 Avi-L1 VLP coupled to mSA-ID1-ID2a analyzed by ultracentrifugation followed by SDS-PAGE, Western blot and TEM analysis a After coupling of the mSA-ID1-ID2a antigen to the HPV16 Avi-L1 VLPs, excess antigen was removed by UC over an Optiprep™ gradient (27%/33%/39%). Reducing SDS-PAGE analysis showed the presence of two protein bands corresponding to the size of HPV16 Avi-L1 (56 kDa) and mSA-VAR2CSA (85 kDa), respectively, in the high-density fractions [4-6] post UC purification. Excess unbound mSA-VAR2CSA was present in the higher UC fractions [12-14] containing soluble proteins. b Transmission electron microscopy (TEM) analysis of material from UC fraction 4 containing HPV16 Avi-L1 VLPs coupled with mSA-VAR2CSA. An aliquot of diluted particles was placed on carbon-coated grids, negatively stained with 2% phosphotungstic acid (pH=7.0) and examined by transmission electron microscopy (TEM) using a CM 100 BioTWIN at magnification×36,000 (Å). Black scale bar 200 nm, enhanced section white scale bar 40 nm. c Western blot analysis of fraction 4 post UC purification of mixed HPV16 Avi-L1 and mSA-VAR2CSA. The blot confirms the presence of HPV16 Avi-L1 and mSA-VAR2CSA detected by Camvir-1 and α-PENTA HIS-tag, respectively.
Figure 6:
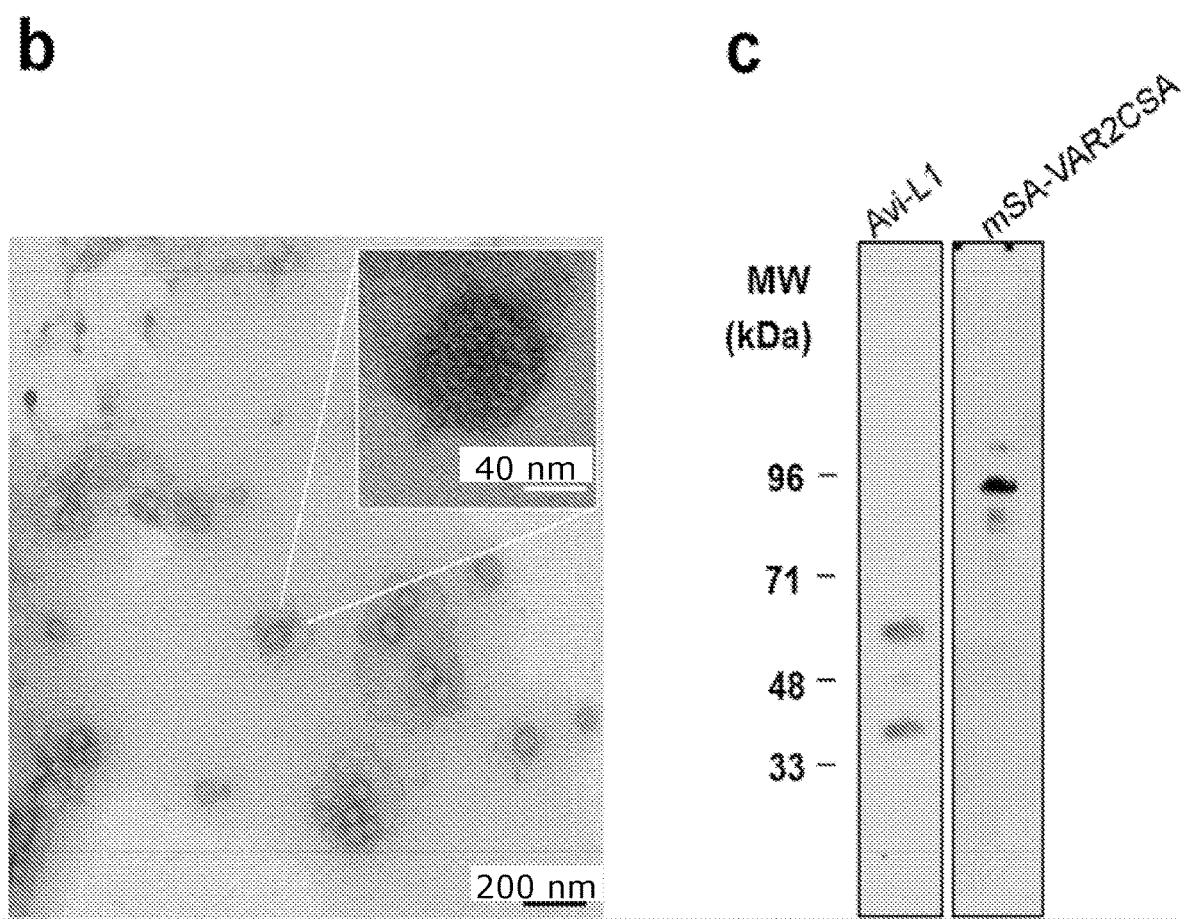
Figure 10:
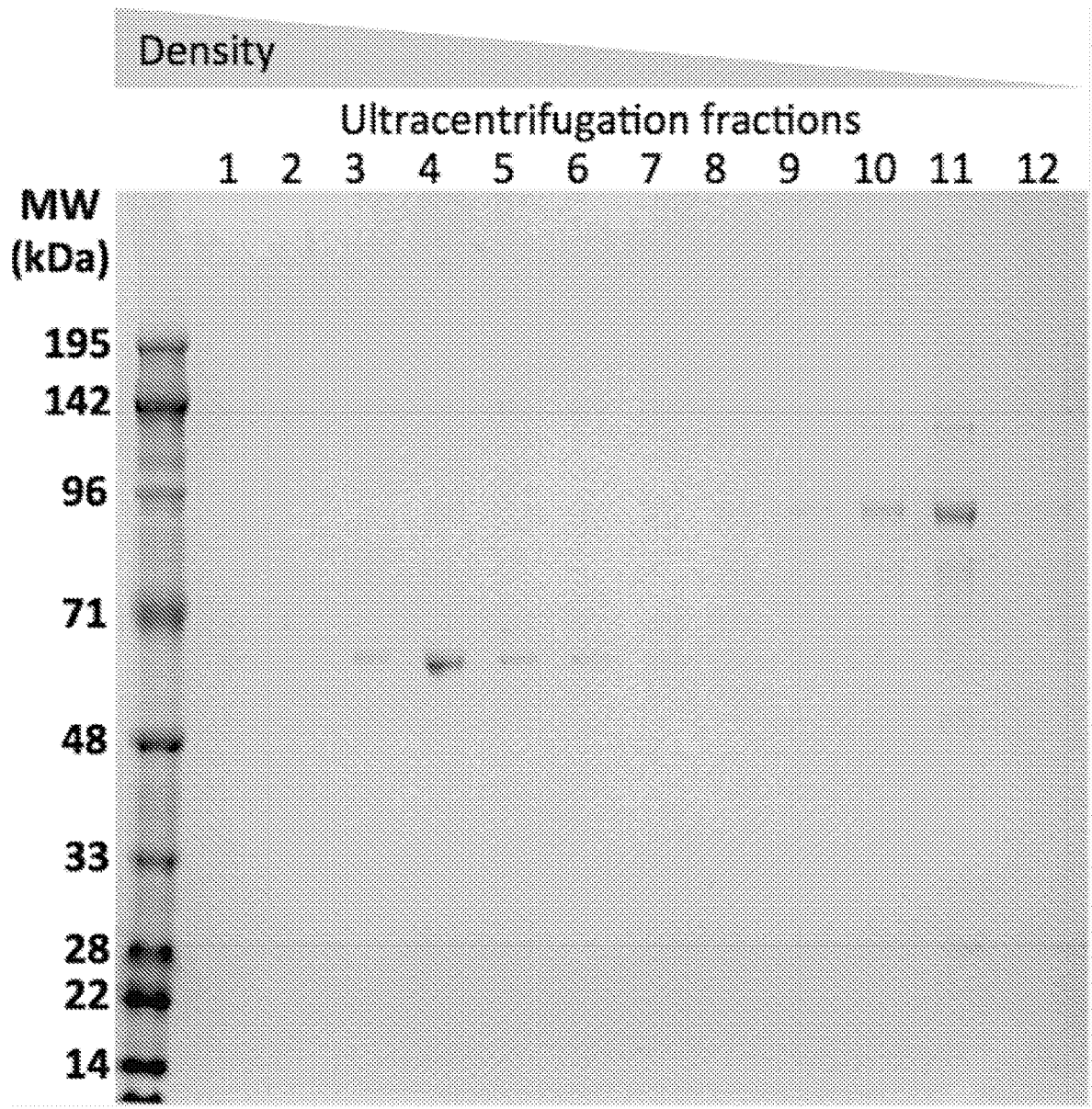
FIG. 10. Control experiment where unbiotinylated VLPs were mixed with mSA-VAR2CSA. SDS PAGE shows that ultracentrifugation efficiently separated soluble mSA-VAR2CSA from unbiotinylated VLPs.

The shortest truncated VAR2CSA polypeptide sequence that is able to bind CSA covers the ID1-ID2a region of the full-length protein (FIG. 1a). This construct (herein referred to as VAR2CSA) was genetically fused at the amino terminus to monomeric streptavidin (mSA) which can bind biotin with high affinity. To avoid VLP aggregation we used a monomeric form of streptavidin which is advantageous to native streptavidin as the latter contains four biotin binding sites. The chimeric construct expressed high levels of soluble protein and retained a structure capable of binding CSA (data not shown). Purified mSA-VAR2CSA was subsequently mixed with the biotinylated VLP (1:3 HPV L1/antigen), and examined by ultracentrifugation followed by SDS-PAGE and western blot analysis. High-density ultracentrifugation fractions [4-5] contained both mSA-VAR2CSA and Avi-L1 protein, which was estimated by densitometric analysis to be present at a 0.6:1 molar ratio. Excess mSA-VAR2CSA was present in the low-density fractions [12-14] (FIG. 6 a&c). The co-localization of Avi-L1 and mSA-VAR2CSA, indicated that the mSA-VAR2CSA antigen was bound to the surface of Avi-L1 VLPs at high density and that these large protein complexes had been separated from the excess soluble mSA-VAR2CSA (FIG. 6a). To confirm that co-localization of mSA-VAR2CSA and Avi-L1 VLPs was caused by the specific interaction between mSA and biotin, the procedure was repeated using unbiotinylated VLPs. This control experiment showed that ultracentrifugation efficiently separated soluble mSA-VAR2CSA from unbiotinylated VLPs (FIG. 10).

Antigen-coupled VLPs were further examined by TEM, showing particles of a comparably larger size (~70 nm) than the non-coupled VLPs (~30-60 nm) (FIG. 6b). This observation was further examined by dynamic light scattering (DLS) analysis, which confirmed that mixing of mSA-VAR2CSA with biotinylated Avi-L1 VLPs resulted in measurably larger particles with an average diameter of ~70 nm (12.9% Pd) compared to naked Avi-L1 VLPs (≤60 nm, 23.9% Pd). Importantly, this analysis also confirmed that such large complexes were not formed after mixing unbiotinylated VLPs with mSA-VAR2CSA, demonstrating that mSA-VAR2CSA is, in fact, bound to the surface of Avi-L1 VLPs via the specific affinity interaction between mSA and biotin.

Together, these results indicate that the produced mSA-VAR2CSA VLP vaccine consists of non-aggregated HPV16 Avi-L1 VLPs displaying dense, repetitive arrays of the mSA-VAR2CSA antigen presented in a consistent orientation, as illustrated schematically in FIG. 1b.

Example 16—Inserting AviTag™ into Other Coat Proteins Forming Papilloma VLP

Figure 7A:
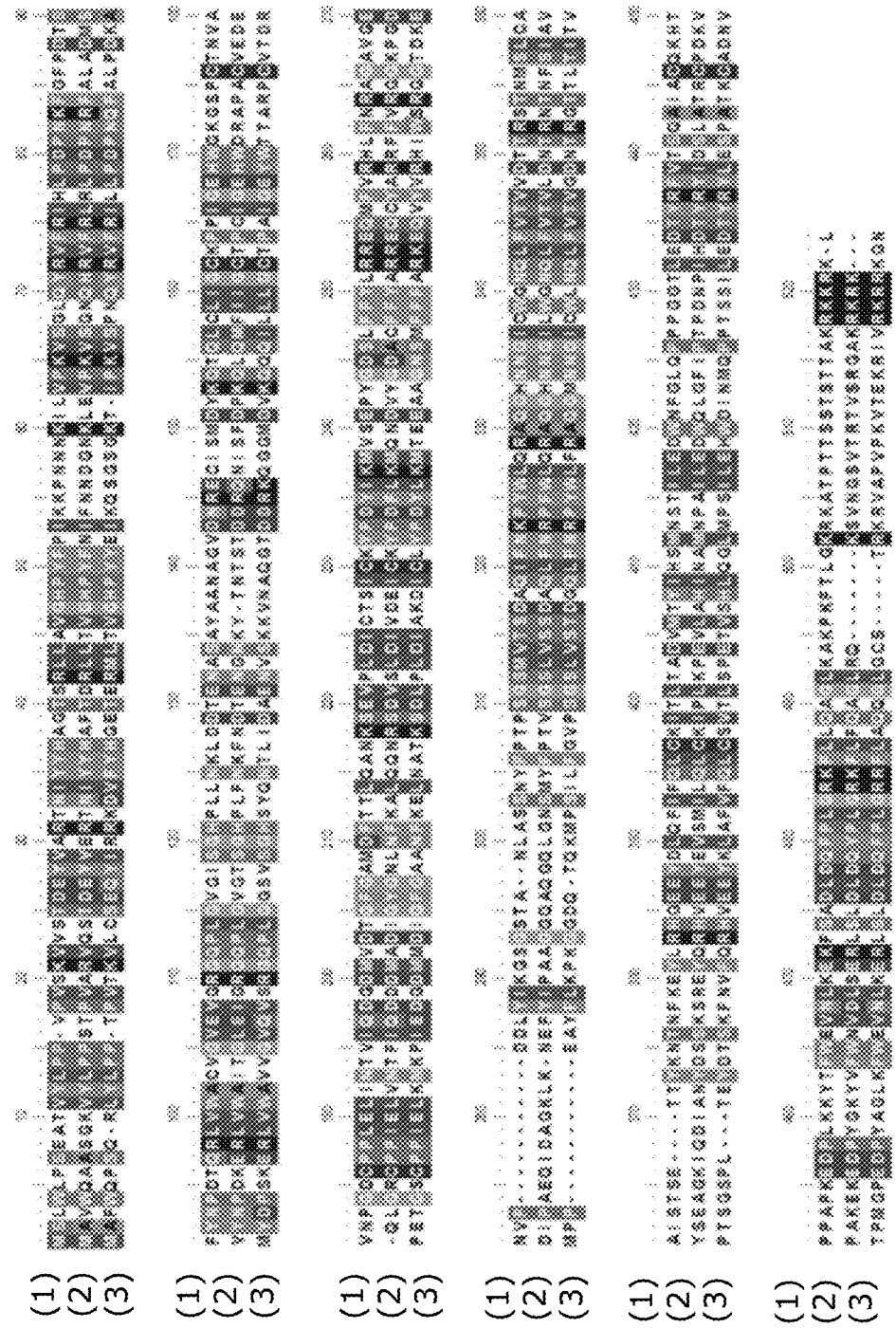
FIG. 7. Other PV VLPs with AviTag™ inserted in DE-loop. The HPV16 L1 VLP was used as VLP platform for proof of concept in this study. However, the AviTag™ can also be inserted into the DE loop of the major capsid protein from other papilloma viruses while retaining the ability to self-assemble into VLPs, as demonstrated in this figure. a Multiple sequence alignment of the HPV16 L1, HPV118 L1 and major capsid protein from European Elk (*Alces alces*) papilloma virus (PAPVE). b Purification of HPV118 Avi-L1 and PAPVE Avi-L1 VLPs were performed by UC over an Optiprep™ density gradient (27%/33%/39). Subsequent reduced SDS-PAGE analysis of high-density UC fractions [3-5] show the presence of a protein band of 56 kDa corresponding to the full-length Avi-L1 protein. These fractions also contain an intense protein band of approximately 43 kDa, which may represent a truncated Avi-L1 product.
Figure 7B:
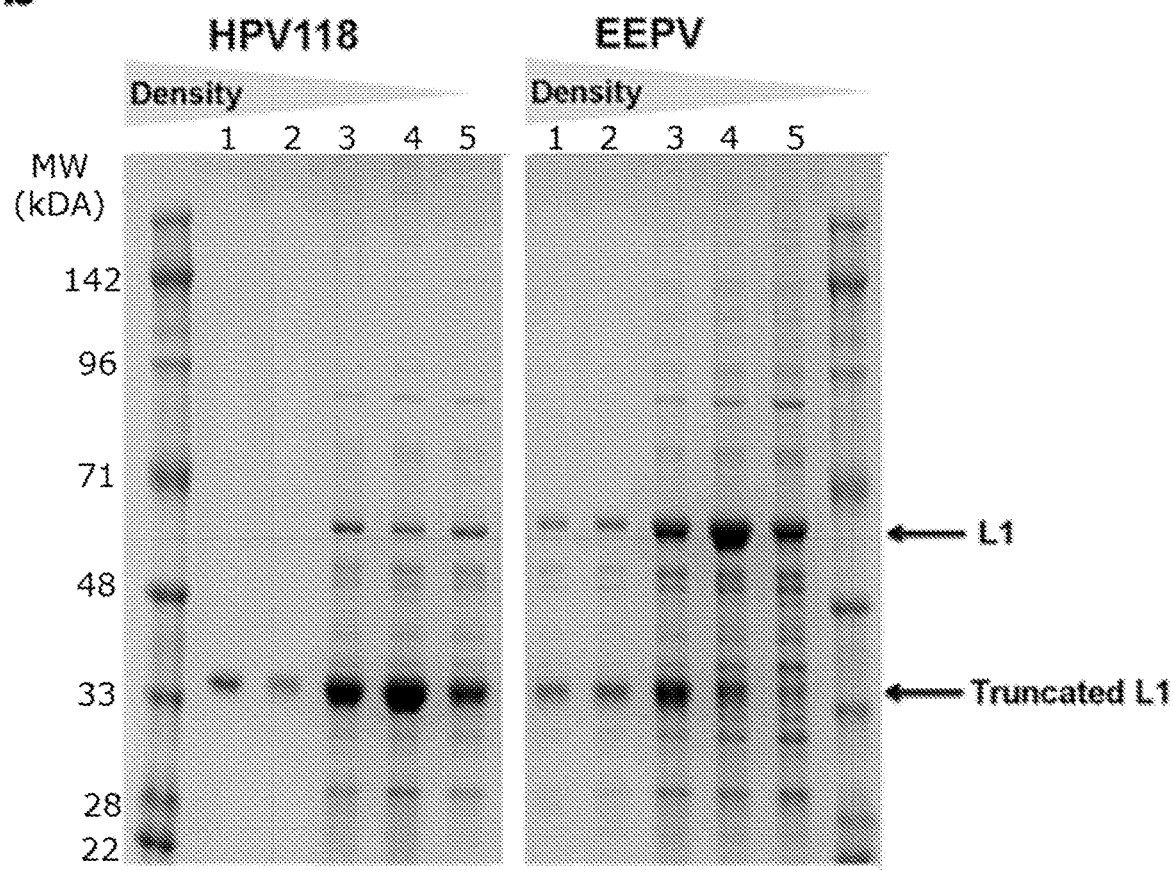

The HPV16 L1 genotype, used as VLP platform in this study, constitutes one of the most prevalent oncogenic HPV types. This genotype is included in all licensed HPV vaccines, which are being administered to millions of young women every year. Thus, the immunogenicity of this VLP platform could be impeded by pre-existing immunity towards the HPV L1 major capsid protein. We therefore examined whether insertion of the AviTag™ sequence was compatible with VLP formation in other HPV genotypes as well as in non-human PV. The AviTag™ sequence was inserted in the L1 major capsid protein of the European elk PV as well as in HPV genotype 118 at a position corresponding to the fusion site in the HPV16 Avi-L1 (DE) (FIG. 7a). The two protein sequences were expressed and purified as previously described. For both constructs a L1 band of the expected protein size (56 kDa) was found in the high-density ultracentrifugation fractions although the majority of protein present in these fractions was of a lower molecular size, possibly representing a L1 truncation (FIG. 7b).

These data indicate that insertion of the AviTag™ sequence into other PV types is a feasible strategy for avoiding the potential issue of pre-existing immunity.

Example 17—Immunization of Mice

Female C57BL/6 mice (Taconic, Denmark) were immunized by intramuscular injection with 5 µg VLP-coupled mSA-VAR2CSA, soluble mSA-VAR2CSA or soluble naked VAR2CSA on day 0 with no adjuvant. Two booster injections with 2.5 µg of the respective antigens were given on days 21 and 42. Immune-serum was collected on days 14, 35 and 56.

Figure 8:
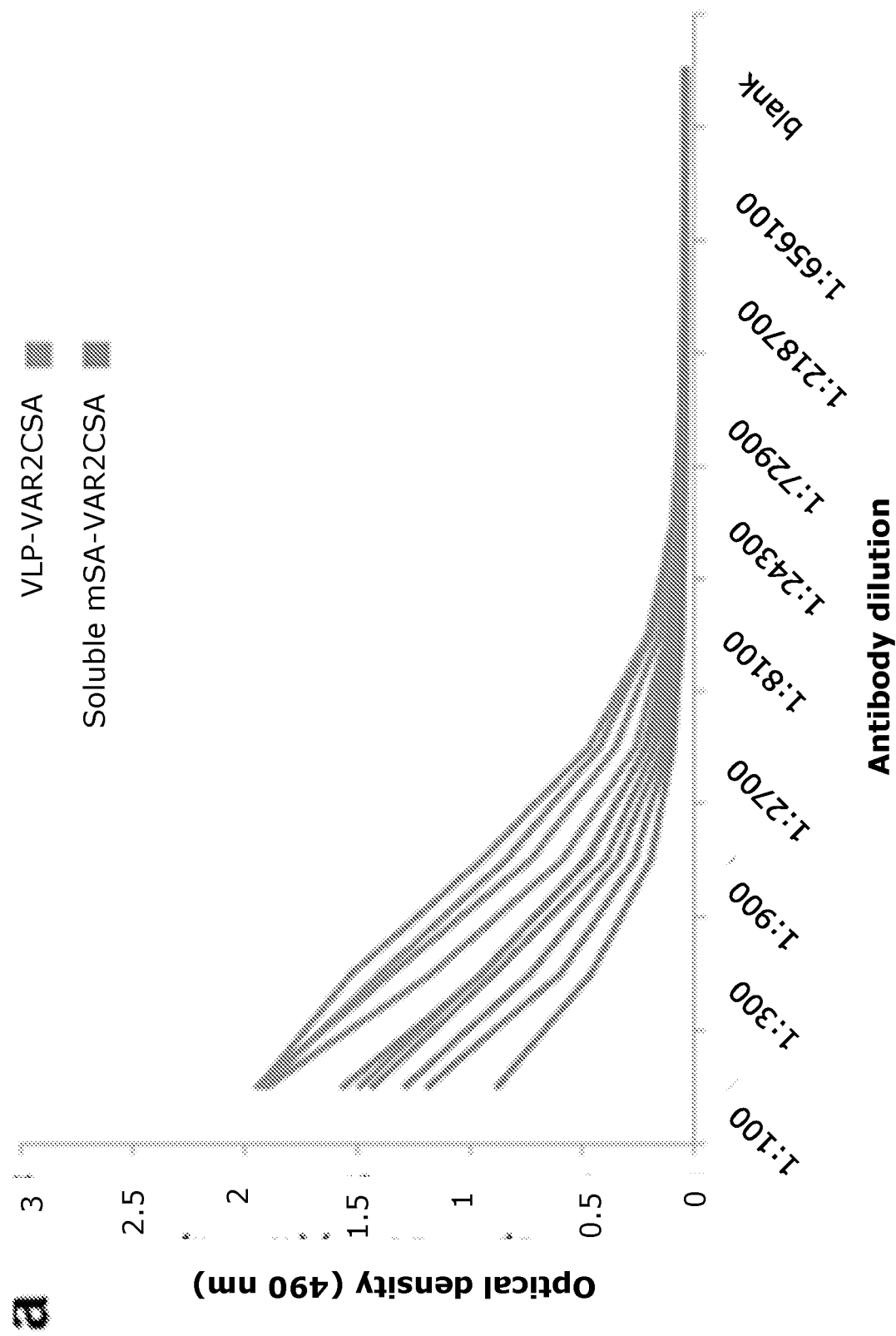
FIG. 8. Reactivity of sera from vaccinated mice by ELISA. C57BL/6 mice were immunized three times with three-week intervals. Serum samples were collected two weeks after each immunization. Total VAR2CSA-specific immunoglobulin was measured in a serial dilution of mouse anti-sera by ELISA using recombinant VAR2CSA as the solid phase capturing antigen. HRP conjugated anti-mouse Ig antibodies were used for detection by measuring absorbance at OD 490 nm. Serum reactivity from individual mice vaccinated with mSA-VAR2CSA coupled HPV16 Avi-L1 (HI) VLPs (blue) or uncoupled mSA-VAR2CSA (red) are shown after first (a), second (b) and third (c) immunization where each line shows the reactivity of one animal. Green curves represent sera from mice vaccinated with soluble naked VAR2CSA and is a pool of sera obtained after $2^{nd}$ and $3^{rd}$ bleed.
Figure 8:
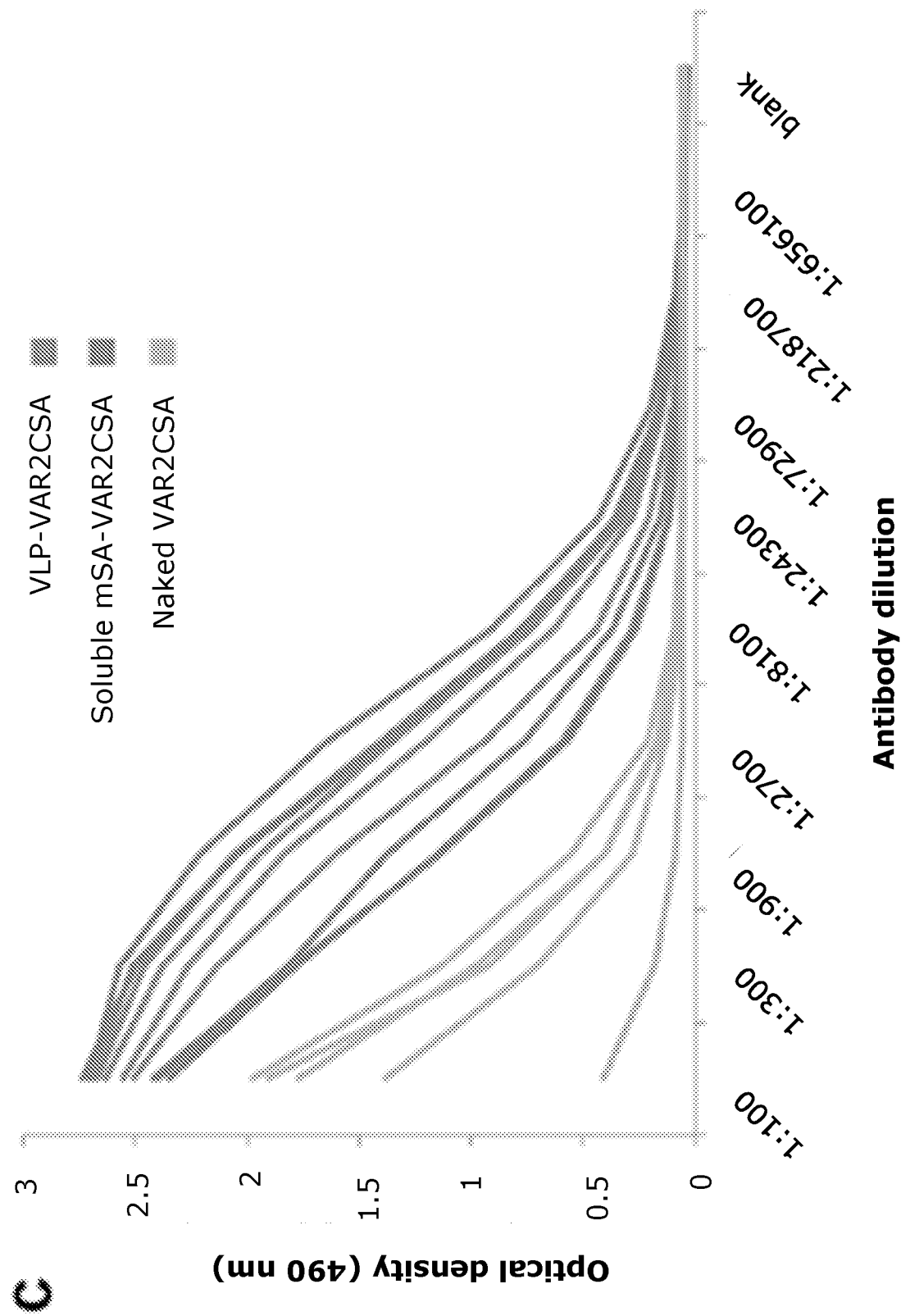
Figure 9:
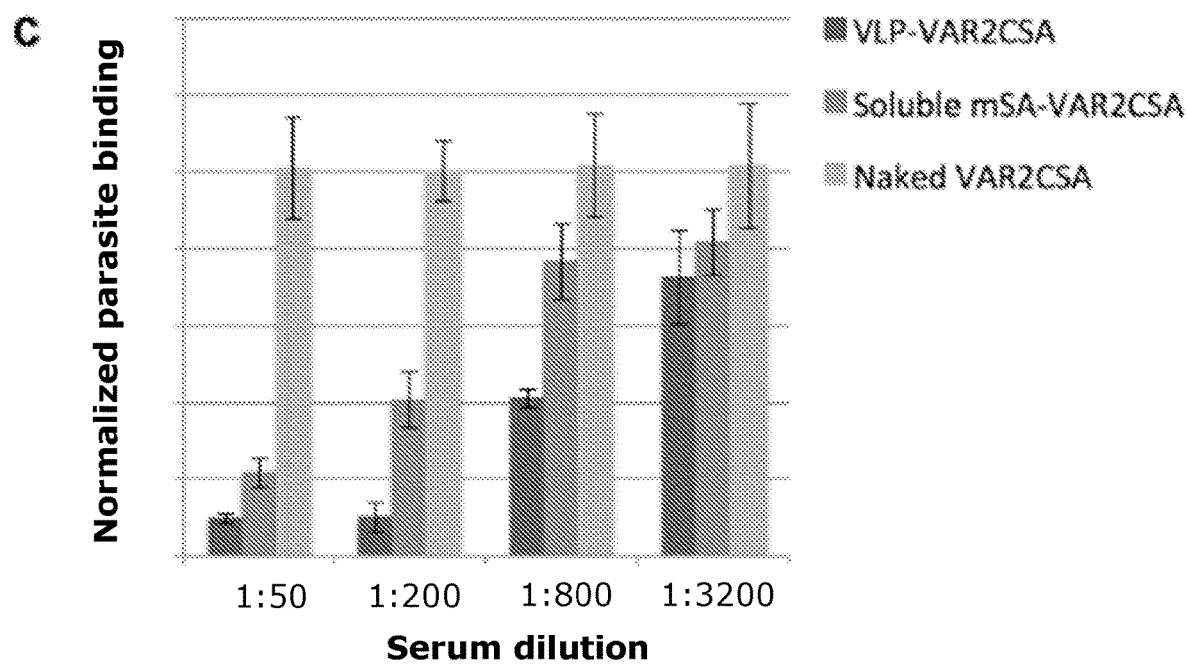
FIG. 9. Display of VAR2CSA on HPV16 L1-AviTag VLPs assessed by parasite inhibition assay. The functional antibody response was assessed by measuring the capacity of mouse anti-sera to inhibit binding between native VAR2CSA expressed on parasitized erythrocytes and CSA in a static binding-assay. *P. falciparum* (FCR3 genotype)-infected red blood cells, expressing the native VAR2CSA, were first incubated with mouse anti-serum (4 fold dilution series, starting from 1:50) and then allowed to incubate on decorin coated plates for 90 min. Unbound IE were washed away and the remaining IEs were quantified. Normalized parasite binding after incubation with pooled anti-sera from mice (n=5) vaccinated with mSA-VAR2CSA-coupled HPV16 Avi-L1 VLPs (blue) or soluble mSA-VAR2CSA (red) are shown after first (a), second (b) and third (c) immunization. The green piles in FIG. 6c represent anti-sera from mice vaccinated with soluble naked VAR2CSA and is a pool of sera from $2^{nd}$ and $3^{rd}$ bleed.

The immunogenicity of the mSA-VAR2CSA VLP vaccine was then tested. ELISA was used to measure total immunoglobulin (Ig) levels against VAR2CSA in sera obtained from mice immunized with mSA-VAR2CSA VLP, soluble mSA-VAR2CSA or soluble naked VAR2CSA (FIG. 8). After three immunizations the VAR2CSA specific Ig levels were higher in sera from mice immunized with the mSA-VAR2CSA Avi-L1 VLP vaccine than in sera from mice immunized with soluble naked VAR2CSA (FIG. 8c). After $1^{st}$ and $2^{nd}$ immunization sera from mSA-VAR2CSA Avi-L1 VLP immunized mice had statistically significantly higher Ig endpoint titers compared with sera from mice immunized with the soluble mSA-VAR2CSA vaccine (P=0.014 and P=0.018, respectively). This difference was, however, not statistically significant after the $3^{rd}$ immunization (P=0.058) (Table 4) where both vaccines seem to have reached a similar plateau.

by approximately 60%. By contrast, the soluble naked VAR2CSA vaccine failed to induce any binding-inhibitory antibodies (FIG. 9c).

These data show that the mSA-VAR2CSA VLP vaccine displays higher ability to inhibit binding between IE and CSA.

Example 19—Measurement of Antibody Avidity

The avidity values of serum antibodies (Ab) were determined by measuring the resistance of Ab-target complexes to 8 M urea by ELISA. Analyzed sera were obtained after the $2^{nd}$ immunization. Antibody titres of individual mouse sera were firstly normalized by dilution. After the serum incubation, triplicate wells were treated with either PBS or 8 M urea for 5 minutes. Subsequently, the wells were washed with PBS, and the ELISA was performed as previously described. The avidity value was calculated as the ratio of the mean OD value of urea-treated wells to PBS control wells multiplied by 100. A non-parametric two-sample Wilcoxon rank-sum (Mann-Whitney) test showed that sera from mice immunized with the VAR2CSA AviL1 VLP vaccine had significantly higher avidity values compared to mice immunized with soluble mSA-VAR2CSA (P value: 0.0275).

TABLE 4

Serum endpoint titers (median {25 and 75 percentiles}) obtained with the different immunogens

|  | After first immunization | After second immunization | After third immunization |
|---|---|---|---|
| 1. Soluble VAR2CSA | Not done | Not done | 8,100[a] {8,100:8,100} |
| 2. Soluble mSA-VAR2CSA | 24,300[a] {24,300:24,300} | 218,700[a] {72,900:218,700} | 218,700[a] {72,900:218,700} |
| 3. mSA-VAR2CSA Avi-L1 VLP | 72,900[a] {72,900:218,700} | 656,100[a] {656,100:656,100} | 218,700[a] {218,700:656,100} |
| P-Value[b] | 0.014 (2. vs 3.) | 0.018 (2. vs 3.) | 0.0072 (1. vs 2.) 0.0072 (1. vs 3.) 0.058 (2. vs 3.) |

[a]Endpoint titer, defined as the reciprocal of the highest serum dilution giving an OD measurement above the cutoff. The cutoff was set to be three standard deviations above the mean negative control reading.
[b]P values were calculated using Wilcoxon rank sum test.

Example 18—Functionality of the mSA-VAR2CSA VLP Vaccine Induced Anti-VAR2 Antibodies Antisera were examined for their ability to block the binding between native VAR2CSA expressed on the surface of parasite-infected erythrocytes and immobilized CSA. After first immunization, none of the three vaccines (mSA-VAR2CSA VLP, soluble mSA-VAR2CSA or soluble naked VAR2CSA) had induced efficient levels of functional binding-inhibitory antibodies, leading to full binding of parasites (FIG. 9a). However, after the second round of immunizations 1:50 diluted serum from mSA-VAR2CSA VLP immunized mice inhibited the binding between IE and CSA by approximately 70%. In comparison, the soluble mSA-VAR2CSA vaccine only inhibited approximately 20%, while no inhibition was seen for the soluble naked VAR2CSA vaccine (FIG. 9b). After three immunizations, 1:200 diluted serum from mice immunized with the mSA-VAR2CSA VLP vaccine showed roughly 90% binding-inhibition, while the sera from mice immunized with the soluble mSA-VAR2CSA vaccine inhibited parasite binding Statistical Analysis:

| Two-sample Wilcoxon rank-sum (Mann-Whitney) test | | | |
|---|---|---|---|
| group | obs | rank sum | expected |
| 1 | 4 | 29 | 20 |
| 2 | 5 | 16 | 25 |
| combined | 9 | 45 | 45 |
| unadjusted variance | | | 16.67 |
| adjustment for ties | | | 0.00 |
| adjusted variance | | | 16.67 |

Ho: reducall(group == 1) = reducall(group == 2)
z = 2.205
Prob > |z| = 0.0275

Example 20—Survivin

We wanted to examine if our virus-like particle (VLP) antigen presentation platform was able to overcome immune-tolerance to a cancer-associated self-antigen "Survivin". This was tested by coupling monovalent streptavidin (mSA)-Survivin fusion proteins to the surface of biotinylated HPV Avi-L1 (HI-loop) VLPs. Three mice were immunized with this VLP-based survivin vaccine. Negative control mice (n=2) were immunized with the same amount (5 μg) of mSA-Survivin, but mixed with unbiotinylated Avi-L1 (HI-loop) VLPs. Both vaccines were formulated using ALUM adjuvant. Mice were immunized three times at three week intervals and sera were obtained two weeks after each immunization.

The obtained anti-sera were tested in ELISA using naked survivin (no mSA) as the solid phase capturing antigen. In this way we could directly test what effect the VLP-display had on the ability of the mice to induce humoral immunity against the self-antigen.

Figure 11A:
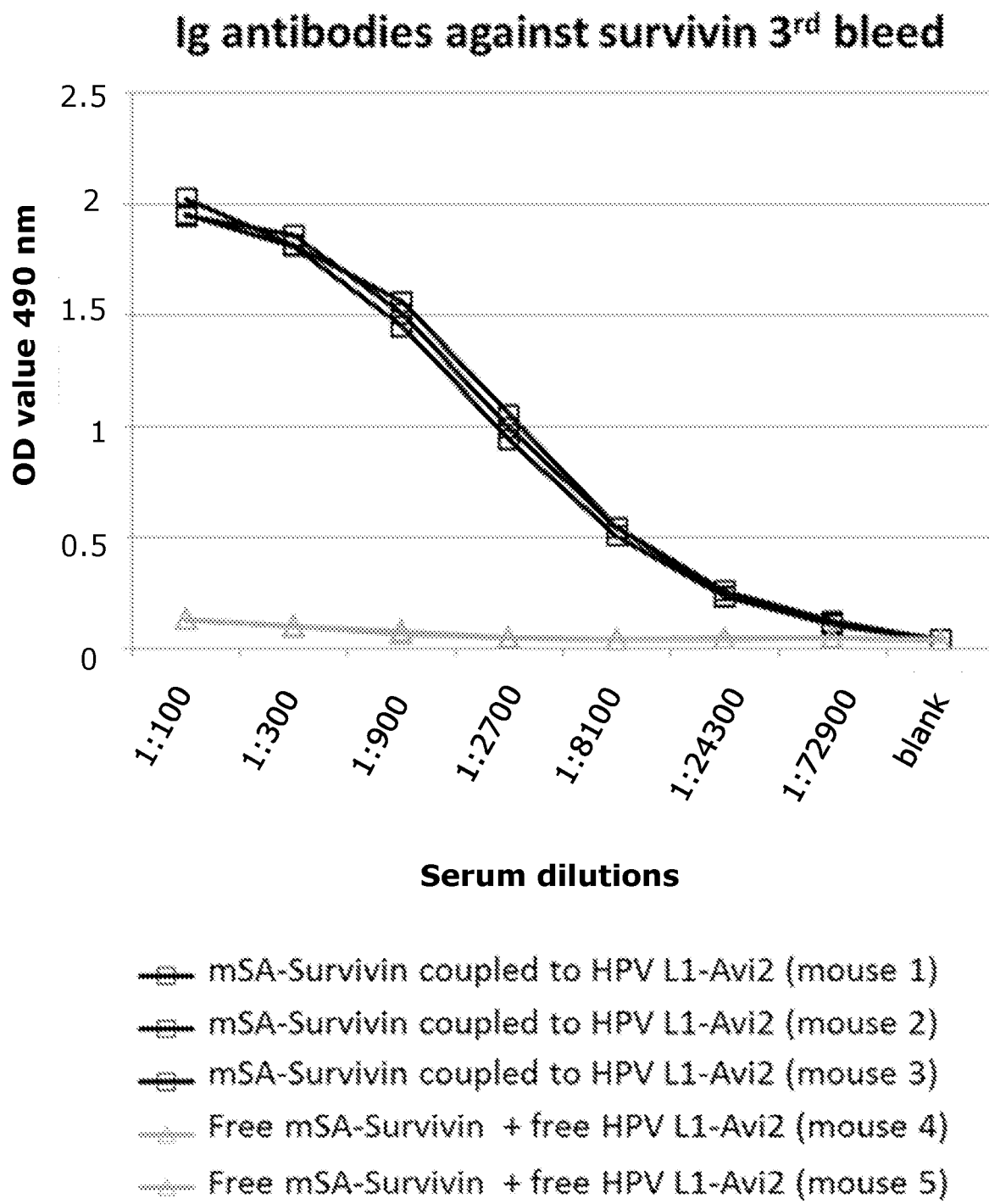
FIG. 11. Immuno-tolerance to a cancer-associated self-antigen "Survivin". a. All the survivin-VLP (mSA-Survivin coupled to HPV Avi-L1 (HI-LOOP)) immunized mice (n=3) induced high-titre antibody responses against the mSA-survivin self-antigen, whereas the negative control vaccine was not able to break immune-tolerance in the immunized mice (no sero-conversion). b. The same anti-sera in ELISA using the mSA-survivin as the solid phase capturing antigen, showing that the negative control mice did produce antibodies against the 'foreign' mSA part.

The results clearly show that all the survivin-VLP (mSA-Survivin coupled to HPV Avi-L1 (HI-LOOP)) immunized mice (n=3) induced high-titre antibody responses against the mSA-survivin self-antigen, whereas the negative control vaccine was not able to break immune-tolerance in the immunized mice (no sero-conversion) (FIG. 11a). The ability to break immune-tolerance thus relies solely on the virus-like display and is not a result of e.g. fusing the self-antigen to mSA.

Figure 11B:
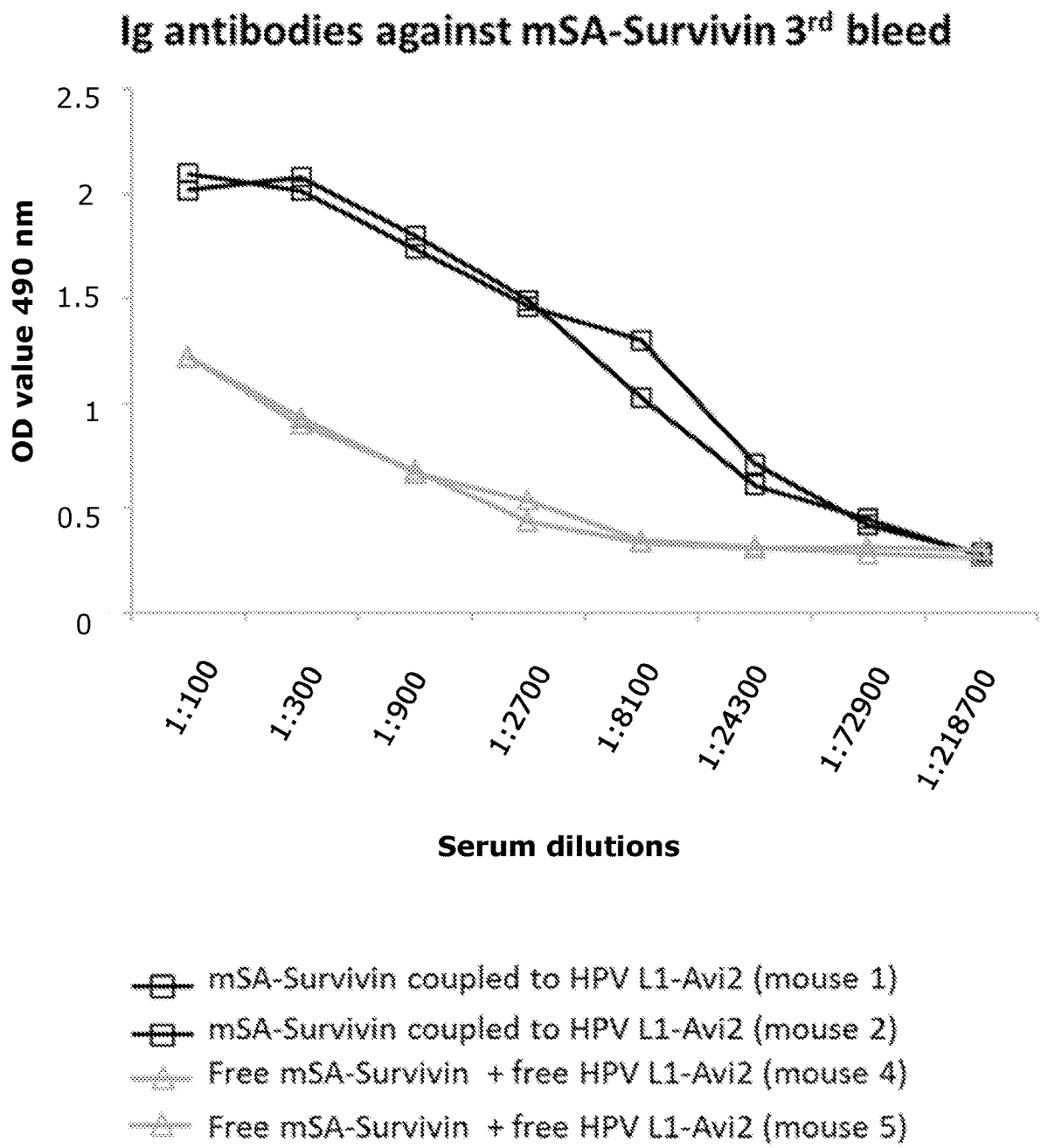

By testing the same anti-sera in ELISA using the mSA-survivin as the solid phase capturing antigen we could see the negative control mice did produce antibodies against the 'foreign' mSA part (FIG. 11b).

This experiment shows that after three immunizations mouse 1-3 (immunized with Survivin displayed on VLP) were able to break self-tolerance, whereas mouse 4 and 5 are unable to generate a response against soluble survivin.

Example 20—Testing of VLP:Avi Platform to Induce Humoral Immunity Against Self-Antigens To demonstrate the capacity of the VLP:Avi platform to break immune tolerance to self-antigens, associated with both cardiovascular disease (PCSK9), allergy (IL-5) and cancer (Her2), we will genetically fuse the self-antigens to the monovalent mSA and coupled them onto biotinylated (biotin acceptor site)-VLPs, as previously described. In some cases (IL-5) we will at first use the mouse gene homologues for the immunization of mice. Specifically, our working procedure will be to firstly couple HER2 (mSA: Her2-ECD|23-686|), and PCSK9(PCSK9|31-692|:mSA-HIS) to the (biotin acceptor site)-VLPs, immunize, and measure seroconversion of the animals in group a) mice immunized with conjugated VLPs and b) mice immunized with the non-coupled soluble antigen. The antigen specific Ig and IgG titer will be estimated in a 2 fold dilution series of the sera. A positive seroconversion is defined as ELISA OD measurements above 2× standard deviation of a mock immunized animal. Serum conversion and induction of specific antibodies to HER2 is further confirmed by western blotting using the sera and cell lysates from different cancerous cell lines (e.g. melanoma, prostate, breast and lung cancer).

Example 21—Testing of VLP:Avi Platform to Induce Cancer Inhibitory Antibodies

We are establishing animal models to study the effect of immunizing animals with tumor antigens on the growth of an established subcutaneous tumor. 100.000 tumor cells expressing HER2 and/or Survivin are injected into the left flank. This is being done in both vaccinated animals and mock immunized animals, to study the prophylactic effect of the vaccine. Tumor growth is monitored by measuring the size of the growing tumor as well as by scanning of the animal when using luciferase transfected cell lines. In another setup we are studying the therapeutic effect of the vaccine by immunizing animals with established tumors and monitoring tumor regression/progression by size measurements and/or by fluorescent scannings.

Example 22—Testing of VLP:Avi Platform to Induce Anti-PCSK9 Antibodies Capable of Lowering Plasma/Serum Cholesterol Levels The goal of making a VLP-based vaccine based on the PCSK9 antigen is to induce a humoral response capable of lowering blood cholesterol. Therefore, to test the VLP:avi platform we measure cholesterol levels in plasma and serum samples obtained from VLP-PCSK9 immunized mice and compare against the levels measured in mice immunized with the non-coupled PCSK9 antigen, as previously described. Cholesterol levels in plasma and serum samples are measured using a WAKO Cholesterol E Assay kit (Cat #439-17501) following the manufacturers' instructions. Dilutions of cholesterol standard or test plasma/serum samples (4 μl volume) are added to wells of a 96-well plate and 196 μl of prepared cholesterol reagent added. The plate is incubated for 5 minutes at 37° C. and the absorbance of the developed color read at 600 nm within 30 minutes.

Sequences

TABLE 5

Overview of the sequences disclosed in the present invention

| Seq ID NO protein (DNA) | | |
|---|---|---|
| | | (biotin acceptor site)/AviTag-VLPs: |
| 1 (11) | VLP1 | >L1avi1 (H4-loop, HPV16) |
| 2 (12) | VLP2 | >L1avi2 (HI-loop, HPV16) |
| 3 (13) | VLP3 | >L1avi3 (DE-loop, HPV16) |
| 4 (14) | VLP4 | >L1avi4 (FG-loop, HPV16) |
| 5 | | major capsid L1 protein [Human papillomavirus type 16] Protein |

TABLE 5-continued

Overview of the sequences disclosed in the present invention

| Seq ID NO protein (DNA) | | | |
|---|---|---|---|
| 6 (15) | VLP5 | >L1avi2 (HI-loop, HPV118) | |
| 7 (16) | VLP6 | >L1avi3 (DE-loop, HPV118) | |
| 8 | | L1 [Human papillomavirus type 118] | |
| 9 (17) | VLP7 | >PAPVE-L1avi3 | |
| 10 | | Major capsid protein L1 OS = European elk papillomavirus | |
| | | Antigens: | |
| 18 | A1 | >mSA-Her2-ECD\|23-686 | |
| 19 | A2 | >mSA-IL-5(C63T/C105T) | |
| 20 (29) | A3 | >PCSK9\|31-692\|:mSA:HIS | |
| 21 (30) | A4 | >mSA-ID1ID2a-HIS | |
| 22 (31) | A5 | >mSA-R0-HIS | |
| 23 (32) | A6 | >HIS-R0-mSA | |
| 24 (33) | A7 | >HIS-GMZ2ggsmSA | |
| 25 (34) | A8 | >HIS-GMZ2T:ggsmSA | |
| 26 35 | A9 | >mSA-PfRH5-HIS | |
| 27 | A10 | >mSA-Pfs25-HIS | |
| 28 | A11 | >HIS-PfCSP(aa92-397)-mSA | |
| 40 | A12 | >Survivin:mSA (*Homo Sapiens*) | |
| 41 | A13 | >mSA:Survivin (*Homo Sapiens*) | |
| 42 | A14 | >Survivin(F101A/L102A):mSA (*Homo Sapiens*) | |
| 43 | A15 | >mSA:Survivin(F101A/L102A) (*Homo Sapiens*) | |
| 44 (48) | A16 | >mSA:Survivin(F101A/L102A) (*Mus Musculus*) | |
| 45 (49) | A17 | >Survivin(F101A/L102A):mSA (*Mus Musculus*) | |
| 46 (50) | A18 | >mSA:Survivin (*Mus Musculus*) | |
| 47 (51) | A19 | >Survivin:mSA (*Mus Musculus*) | |
| 52 (53) | A20 | >mSA:CIDR1a-HIS | |
| | | Misc. | |
| 36 (39) | | Biotin acceptor site amino acid sequence | |
| 37 | | monovalent streptavidin | |

TABLE 5-continued

Overview of the sequences disclosed in the present invention

Seq ID NO protein (DNA)

38    BirA *Escherichia coli* (strain K12)
    GN = birA PE = 1 SV = 1

>SEQ ID NO: 1 [H4-loop, HPV genotype 16] L1Avi1 Protein
MSLWLPSEATVYLPPVPVSKVVSTDEYVARTNIYYHAGTSRLLAVGHPYFPIKKPNNN
KILVPKVSGLQYRVFRIHLPDPNKFGFPDTSFYNPDTQRLVWACVGVEVGRGQPLGV
GISGHPLLNKLDDTENASAYAANAGVDNRECISMDYKQTQLCLIGCKPPIGEHWGKG
SPCTNVAVNPGDCPPLELINTVIQDGDMVDTGFGAMDFTTLQANKSEVPLDICTSICK
YPDYIKMVSEPYGDSLFFYLRREQMFVRHLFNRAGAVGENVPDDLYIKGSGSTANLA
SSNYFPTPSGSMVTSDAQIFNKPYWLQRAQGHNNGICWGNQLFVTVVDTTRSTNMS
LCAAISTSETTYKNTNFKEYLRHGEEYDLQFIFQLCKITLTADVMTYIHSMNSTILEDWN
FGLQPPPGGTLEDTYRFVTSQAIACQKHGLNDIFEAQKIEWHETPPAPKEDPLKKYTF
WEVNLKEKFSADLDQFPLGRKFLLQAGLKAKPKFTLGKRKATPTTSSTSTTAKRKKRK
LELSGR >SEQ ID NO: 2 [HI-loop, HPV genotype 16] L1Avi2 Protein
MSLWLPSEATVYLPPVPVSKVVSTDEYVARTNIYYHAGTSRLLAVGHPYFPIKKPNNN
KILVPKVSGLQYRVFRIHLPDPNKFGFPDTSFYNPDTQRLVWACVGVEVGRGQPLGV
GISGHPLLNKLDDTENASAYAANAGVDNRECISMDYKQTQLCLIGCKPPIGEHWGKG
SPCTNVAVNPGDCPPLELINTVIQDGDMVDTGFGAMDFTTLQANKSEVPLDICTSICK
YPDYIKMVSEPYGDSLFFYLRREQMFVRHLFNRAGAVGENVPDDLYIKGXXWIYXXQ
XLASSNYFPTPSGSMVTSDAQIFNKPYWLQRAQGHNNGICWGNQLFVTVVDTTRST
NMSLCAAISTSGLNDIFEAQKIEWHEETTYKNTNFKEYLRHGEEYDLQFIFQLCKITLTA
DVMTYIHSMNSTILEDWNFGLQPPPGGTLEDTYRFVTSQAIACQKHTPPAPKEDPLKK
YTFWEVNLKEKFSADLDQFPLGRKFLLQAGLKAKPKFTLGKRKATPTTSSTSTTAKRK
KRKLELSGR >SEQ ID NO: 3 [DE-loop, HPV genotype 16] L1avi3 Protein
MSLWLPSEATVYLPPVPVSKVVSTDEYVARTNIYYHAGTSRLLAVGHPYFPIKKPNNN
KILVPKVSGLQYRVFRIHLPDPNKFGFPDTSFYNPDTQRLVWACVGVEVGRGQPLGV
GISGHPLLNKLDDTENASAGLNDIFEAQKIEWHEAGVDNRECISMDYKQTQLCLIGCK
PPIGEHWGKGSPCTNVAVNPGDCPPLELINTVIQDGDMVDTGFGAMDFTTLQANKSE
VPLDICTSICKYPDYIKMVSEPYGDSLFFYLRREQMFVRHLFNRAGAVGENVPDDLYIK
GSGSTANLASSNYFPTPSGSMVTSDAQIFNKPYWLQRAQGHNNGICWGNQLFVTVV
DTTRSTNMSLCAAISTSETTYKNTNFKEYLRHGEEYDLQFIFQLCKITLTADVMTYIHS
MNSTILEDWNFGLQPPPGGTLEDTYRFVTSQAIACQKHTPPAPKEDPLKKYTFWEVN
LKEKFSADLDQFPLGRKFLLQAGLKAKPKFTLGKRKATPTTSSTSTTAKRKKRKLEL >SEQ ID NO: 4 [FG-loop HPV genotype 16] L1avi4) Protein
MSLWLPSEATVYLPPVPVSKVVSTDEYVARTNIYYHAGTSRLLAVGHPYFPIKKPNNN
KILVPKVSGLQYRVFRIHLPDPNKFGFPDTSFYNPDTQRLVWACVGVEVGRGQPLGV
GISGHPLLNKLDDTENASAAGVDNRECISMDYKQTQLCLIGCKPPIGEHWGKGSPCT
NVAVNPGDCPPLELINTVIQDGDMVDTGFGAMDFTTLQANKSEVPLDICTSICKYPDYI
KMVSEPYGDSLFFYLRREQMFVRHLFNRAGAVGENVPDDLYIKGLNDIFEAQKIEWH
EASSNYFPTPSGSMVTSDAQIFNKPYWLQRAQGHNNGICWGNQLFVTVVDTTRSTN
MSLCAAISTSETTYKNTNFKEYLRHGEEYDLQFIFQLCKITLTADVMTYIHSMNSTILED
WNFGLQPPPGGTLEDTYRFVTSQAIACQKHTPPAPKEDPLKKYTFWEVNLKEKFSAD
LDQFPLGRKFLLQAGLKAKPKFTLGKRKATPTTSSTSTTAKRKKRKLELSGRF >SEQ ID NO: 5 gi|9627108|ref|NP_041332.1| major capsid L1 protein [Human
papillomavirus type 16] Protein
MSLWLPSEATVYLPPVPVSKVVSTDEYVARTNIYYHAGTSRLLAVGHPYFPIKKPNNN
KILVPKVSGLQYRVFRIHLPDPNKFGFPDTSFYNPDTQRLVWACVGVEVGRGQPLGV
GISGHPLLNKLDDTENASAYAANAGVDNRECISMDYKQTQLCLIGCKPPIGEHWGKG
SPCTNVAVNPGDCPPLELINTVIQDGDMVHTGFGAMDFTTLQANKSEVPLDICTSICK
YPDYIKMVSEPYGDSLFFYLRREQMFVRHLFNRAGTVGENVPDDLYIKGSGSTANLA
SSNYFPTPSGSMVTSDAQIFNKPYWLQRAQGHNNGICWGNQLFVTVVDTTRSTNMS
LCAAISTSETTYKNTNFKEYLRHGEEYDLQFIFQLCKITLTADVMTYIHSMNSTILEDWN
FGLQPPPGGTLEDTYRFVTQAIACQKHTPPAPKEDDPLKKYTFWEVNLKEKFSADLD
QFPLGRKFLLQAGLKAKPKFTLGKRKATPTTSSTSTTAKRKKRKL >SEQ ID NO: 6 L1Avi2 (HIloop, HPV118genotype) Protein
MAVWQAASGKVYLPPSTPVARVQSTDEYVERTNIYYHAFTDRLLTVGHPYFNIFNND
GNKLEVPKVSGNQHRVFRLRLPDPNRFALADMSVYNPDKERLVWAITGLEIGRGQPL
GVGTSGHPLFNKFNDTENGNKYTNTSTDDRQNISFDPKQLQMFIIGCTPCIGEHWDR
APACVEDEQLGRCPPIELVNTFIQDDDMADIGYGNLNFKALQQNRSDVSLDIVDEICKY
PDFLKMQNDVYGDACFFYARREQCYARRFFVRGGKPGDDIPAEQIDAGKLKNEFYIP
AAGGQAQGQLGNSMYFPTVSGSLVSSDAQLFNRPFWLQRAQGHNNGILWGNQLFV
TVLDNTRNTNFSIAVYSEGLNDIFEAQKIEWHEQDIANYDSSKSREYQRHVEEYEVSMI
LQLCKIPLKPEVLAHINAMNPAILEDWQLGFIPTPDNPIHDTYRYIDSLATRCPDKVPAK
EKEDPYGKYVFWNVDLSERLSLDLDQYPLGRKFLFQAGLRQKSVNGSVTRTVSRGA
KRKRKSGR TABLE 5-continued Overview of the sequences disclosed in the present invention Seq ID NO protein (DNA)

>SEQ ID NO: 7 L1avi3 (DEloop, HPV118genotype) Protein
MAVWQAASGKVYLPPSTPVARVQSTDEYVERTNIYYHAFTDRLLTVGHPYFNIFNND
GNKLEVPKVSGNQHRVFRLRLPDPNRFALADMSVYNPDKERLVWAITGLEIGRGQPL
GVGTSGHPLFNKFNDTENGNGLNDIFEAQKIEWHETSTDDDRQNISFDPKQLQMFIIGC
TPCIGEHWDRAPACVEDEQLGRCPPIELVNTFIQDDDMADIGYGNLNFKALQQNRSD
VSLDIVDEICKYPDFLKMQNDVYGDACFFYARREQCYARRFFVRGGKPGDDIPAEQID
AGKLKNEFYIPAAGGQAQGQLGNSMYFPTVSGSLVSSDAQLFNRPFWLQRAQGHNN
GILWGNQLFVTVLDNTRNTNFSIAVYSEQDIANYDSSKSREYQRHVEEYEVSMILQLC
KIPLKPEVLAHINAMNPAILEDWQLGFIPTPDNPIHDTYRYIDSLATRCPDKVPAKEKED
PYGKYVFWNVDLSERLSLDLDQYPLGRKFLFQAGLRQKSVNGSVTRTVSRGAKRKR
KSGRF >SEQ ID NO: 8 gi|256807737|gb|ACV30153.1| L1 [Human papillomavirus
type 118] Protein
MAVWQAASGKVYLPPSTPVARVQSTDEYVERTNIYYHAFTDRLLTVGHPYFNIFNND
GNKLEVPKVSGNQHRVFRLRLPDPNRFALADMSVYNPDKERLVWAITGLEIGRGQPL
GVGTSGHPLFNKFNDTENGNKYTNTSTDDRQNISFDPKQLQMFIIGCTPCIGEHWDR
APACVEDEQLGRCPPIELVNTFIQDDDMADIGYGNLNFKALQQNRSDVSLDIVDEICKY
PDFLKMQNDVYGDACFFYARREQCYARRFFVRGGKPGDDIPAEQIDAGKLKNEFYIP
AAGGQAQGQLGNSMYFPTVSGSLVSSDAQLFNRPFWLQRAQGHNNGILWGNQLFV
TVLDNTRNTNFSIAVYSEAGKIQDIANYDSSKSREYQRHVEEYEVSMILQLCKIPLKPE
VLAHINAMNPAILEDWQLGFIPTPDNPIHDTYRYIDSLATRCPDKVPAKEKEDPYGKYV
FWNVDLSERLSLDLDQYPLGRKFLFQAGLRQKSVNGSVTRTVSRGAKRKRK >SEQ ID NO: 9 Avi3 Europaeisk elg papillomavirus (DEloop) Protein
MAFWQPSQRLYLPPTPVTKVLCSEQYIRRKDVFYHGETERMLTVGHPYYEIKQSGSG
KTIPKVSPNQYRVFRILLPDPNQFALPDKAMYDPSKERLVWAVVGVQVSRGQPLGGS
VSGHSYQNTLIDAENVSGLNDIFEAQKIEWHEQGTDDRKQGGMDVKQQQILLLGCTP
AIGEYWTTARPCVTDRPETGSCPPIELKNKPIEDGDMMDIGFGAANFKELNATKSDLP
LDIAKDICLYPDYLKMTEEAAGNSMFFFARKEQVYVRHIWSRGGTDKEMPPEAYFLKP
KGGDQTQKMPSILFGVPSGSLVSTDGQLFNRPYWLFRAQGMNNGICWLNQLFVTVG
DNTRGTTLTITVPTSGSPLTEYDTSKFNVFQRHVEEYKLAFVFQLCSVTLSPETVSHLQ
GLMPSILEHWDINMQPPTSSILEDTYRYLESPATKCADNVTPMGPEDPYAGLKFWEV
NLKERLSLDLDQFPLGRRFLAQQGLGCSTRKRVAPVPKVTEKRIVRKRRKGN >SEQ ID NO: 10 sp|P11326|VL1_PAPVE Major capsid protein L1 OS = European
elk papillomavirus GN = L1 PE = 3 SV = 1 Protein
MAFWQPSQRLYLPPTPVTKVLCSEQYIRRKDVFYHGETERMLTVGHPYYEIKQSGSG
KTIPKVSPNQYRVFRILLPDPNQFALPDKAMYDPSKERLVWAVVGVQVSRGQPLGGS
VSGHSYQNTLIDAENVSKKVNAQGTDDRKQGGMDVKQQQILLLGCTPAIGEYWTTAR
PCVTDRPETGSCPPIELKNKPIEDGDMMDIGFGAANFKELNATKSDLPLDIAKDICLYP
DYLKMTEEAAGNSMFFFARKEQVYVRHIWSRGGTDKEMPPEAYFLKPKGGDQTQKM
PSILFGVPSGSLVSTDGQLFNRPYWLFRAQGMNNGICWLNQLFVTVGDNTRGTTLTIT
VPTSGSPLTEYDTSKFNVFQRHVEEYKLAFVFQLCSVTLSPETVSHLQGLMPSILEHW
DINMQPPTSSILEDTYRYLESPATKCADNVTPMGPEDPYAGLKFWEVNLKERLSLDLD
QFPLGRRFLAQQGLGCSTRKRVAPVPKVTEKRIVRKRRKGN >SEQ ID NO: 11 [H4-loop HPV genotype 16] L1Avi1] DNA
GATATCATGGAGATAATTAAAATGATAACCATCTCGCAAATAAATAAGTATTTTACT
GTTTTCGTAACAGTTTTGTAATAAAAAAACCTATAAATATTCCGGATTATTCATACC
GTCCCACCATCGGGCGCGGATCTCTACTAGTATGTCTCTGTGGCTGCCCTCTGAA
GCCACCGTCTACCTGCCCCCCGTCCCTGTCTCTAAGGTCGTCAGCACCGACGAAT
ACGTCGCCAGGACCAACATCTACTACCACGCCGGAACCTCTAGGCTGCTGGCCG
TCGGACACCCCTACTTCCCCATCAAGAAGCCCAACAACAACAAGATCCTGGTCCC
CAAGGTGTCCGGACTGCAGTACAGGGTGTTCAGGATCCACCTCCCCGACCCCAA
CAAGTTCGGATTCCCCGACACCCTCTTTCTACAACCCCGACACCCAGAGGCTCGTC
TGGGCCTGCGTCGGAGTCGAAGTCGGAAGGGGACAGCCCCTGGGAGTCGGAAT
CTCTGGACACCCCCTGCTGAACAAGCTGGACGACACCGAAAACGCCTCTGCCTA
CGCCGCCAACGCCGGTGTCGACAACAGGGAATGCATCTCTATGGACTACAAGCA
GACCCAGCTGTGCCTGATCGGATGCAAGCCCCCCATCGGAGAACACTGGGGAAA
GGGATCTCCCTGCACCAACGTCGCCGTCAACCCCGGCGACTGCCCCCCTCTGGA
ACTGATCAACACCGTCATCCAGGACGGCGACATGGTCGACACCGGATTCGGAGC
CATGGACTTCACCACCCTGCAGGCCAACAAGTCTGAAGTCCCCCTGGACATCTGC
ACCTCTATCTGCAAGTACCCCGACTACATCAAGATGGTGTCTGAACCCTACGGCG
ACTCTCTGTTCTTCTACCTGAGGCGCGAACAGATGTTCGTCAGGCACCTGTTCAA
CCGCGCCGGTGCCGTCGGAGAAAACGTCCCCGACGACCTGTACATCAAGGGATC
TGGATCTACCGCCAACCTGGCCTCTTCTAACTACTTCCCTACCCCTTCTGGATCTA
TGGTCACCTCTGACGCCCAGATCTTCAACAAGCCCTACTGGCTGCAGAGGGCCC
AGGGACACAACAACGGAATCTGCTGGGGAAACCAGCTGTTCGTCACCGTCGTCG
ACACCACCAGGTCTACCAACATGTCCCTGTGCGCCGCCATCTCTACCTCTGAAAC
CACCTACAAGAACACCAACTTCAAAGAATACCTGCGCCACGGCGAAGAATACGAC
CTGCAGTTCATCTTCCAGCTGTGCAAGATCACCCTGACCGCCGACGTCATGACCT
ACATCCACTCTATGAACTCTACCATCTTGGAGGACTGGAACTTCGGACTGCAGCC
CCCTCCCGGTGGAACCCTCGAGGACACCTACCGCTTCGTCACCAGCCAGGCTAT
CGCCTGCCAGAAGCACGGACTGAACGACATCTTCGAAGCCCAAAAGATCGAATG
GCACGAAACCCCCCCTGCCCCCAAAGAGGACCCCCTGAAGAAGTACACCTTCTG TABLE 5-continued Overview of the sequences disclosed in the present invention Seq ID NO protein (DNA)

GGAAGTCAACCTGAAAGAAAAGTTCTCTGCCGACCTGGACCAGTTCCCCCTGGGA
CGCAAGTTCCTGCTGCAAGCCGGACTGAAGGCCAAGCCCAAGTTCACCCTGGGA
AAGAGGAAGGCCACCCCCACCACCTCTTCTACCTCTACCACCGCCAAGAGGAAG
AAGCGCAAGCTGGAACTGTAAAGCGGCCGC

>SEQ ID NO: 12 L1avi2 (HI-loop, HPV16) DNA
GATATCATGGAGATAATTAAAATGATAACCATCTCGCAAATAAATAAGTATTTTACT
GTTTTCGTAACAGTTTTGTAATAAAAAAACCTATAAATATTCCGGATTATTCATACC
GTCCCACCATCGGGCGCGGATCTCTACTAGTATGTCTCTGTGGCTGCCCTCTGAA
GCCACCGTCTACCTGCCCCCCGTCCCTGTCTCTAAGGTCGTCAGCACCGACGAAT
ACGTCGCCAGGACCAACATCTACTACCACGCCGGAACCTCTAGGCTGCTGGCCG
TCGGACACCCCTACTTCCCCATCAAGAAGCCCAACAACAACAAGATCCTGGTCCC
CAAGGTGTCCGGACTGCAGTACAGGGTGTTCAGGATCCACCTCCCCGACCCCAA
CAAGTTCGGATTCCCCGACACCTCTTTCTACAACCCCGACACCCAGAGGCTCGTC
TGGGCCTGCGTCGGAGTCGAAGTCGGAAGGGGACAGCCCCTGGGAGTCGGAAT
CTCTGGACACCCCCTGCTGAACAAGCTGGACGACACCGAAAACGCCTCTGCCTA
CGCCGCCAACGCCGGTGTCGACAACAGGGAATGCATCTCTATGGACTACAAGCA
GACCCAGCTGTGCCTGATCGGATGCAAGCCCCCCATCGGAGAACACTGGGGAAA
GGGATCTCCCTGCACCAACGTCGCCGTCAACCCCGGCGACTGCCCCCCTCTGGA
ACTGATCAACACCGTCATCCAGGACGGCGACATGGTCGACACCGGATTCGGAGC
CATGGACTTCACCACCCTGCAGGCCAACAAGTCTGAAGTCCCCCTGGACATCTGC
ACCTCTATCTGCAAGTACCCCGACTACATCAAGATGGTGTCTGAACCCTACGGCG
ACTCTCTGTTCTTCTACCTGAGGCGCGAACAGATGTTCGTCAGGCACCTCTTCAA
CAGGGCCGGTGCCGTCGGAGAAAACGTCCCCGACGACCTGTACATCAAGGGATC
TGGATCTACCGCCAACCTGGCCTCTTCTAACTACTTCCCTACCCCTTCTGGATCTA
TGGTCACCTCTGACGCCCAGATCTTCAACAAGCCCTACTGGCTGCAGAGGGCCC
AGGGACACAACAACGGAATCTGCTGGGGAAACCAGCTGTTCGTCACCGTCGTCG
ACACCACCAGGTCTACCAACATGTCCCTGTGCGCCGCCATCTCTACCTCTGGACT
GAACGACATCTTCGAGGCCCAAAAGATCGAATGGCACGAGGAAACCACCTACAAG
AACACCAACTTCAAAGAATACCTGCGCCACGGCGAAGAATACGACCTGCAGTTCA
TCTTCCAGCTGTGCAAGATCACCCTGACCGCCGACGTCATGACCTACATCCACTC
TATGAACTCTACCATCTTGGAGGATTGGAACTTCGGACTGCAGCCCCCTCCCGGT
GGAACCCTCGAGGACACCTACCGCTTCGTCACCAGCCAGGCTATCGCCTGCCAG
AAGCACACCCCCCTGCCCCCAAAGAGGACCCCCTGAAGAAGTACACCTTCTGG
GAAGTCAACCTGAAAGAAAAGTTCTCTGCCGACCTGGACCAGTTCCCCCTGGGAC
GCAAGTTCCTGCTGCAAGCCGGACTGAAGGCCAAGCCCAAGTTCACCCTGGGAA
AGAGGAAGGCCACCCCCACCACCTCTTCTACCTCTACCACCGCCAAGAGGAAGA
AGCGCAAGCTGGAACTGTAAAGCGGCCGC >SEQ ID NO: 13 L1avi3 (DE-loop, HPV16)
GATATCATGGAGATAATTAAAATGATAACCATCTCGCAAATAAATAAGTATTTTACT
GTTTTCGTAACAGTTTTGTAATAAAAAAACCTATAAATATTCCGGATTATTCATACC
GTCCCACCATCGGGCGCGGATCTCTACTAGTATGTCTCTGTGGCTGCCCTCTGAA
GCCACCGTCTACCTGCCCCCCGTCCCTGTCTCTAAGGTCGTCAGCACCGACGAAT
ACGTCGCCAGGACCAACATCTACTACCACGCCGGAACCTCTAGGCTGCTGGCCG
TCGGACACCCCTACTTCCCCATCAAGAAGCCCAACAACAACAAGATCCTGGTCCC
CAAGGTGTCCGGACTGCAGTACAGGGTGTTCAGGATCCACCTCCCCGACCCCAA
CAAGTTCGGATTCCCCGACACCTCTTTCTACAACCCCGACACCCAGAGGCTCGTC
TGGGCCTGCGTCGGAGTCGAAGTCGGAAGGGGACAGCCCCTGGGAGTCGGAAT
CTCTGGACACCCCCTGCTGAACAAGCTGGACGACACCGAAAACGCCTCTGCCGG
ACTGAACGACATCTTCGAGGCCCAAAAGATCGAATGGCACGAGGCCGGTGTCGA
CAACAGGGAATGCATCTCTATGGACTACAAGCAGACCCAGCTGTGCCTGATCGGA
TGCAAGCCCCCCATCGGAGAACACTGGGGAAAGGGATCTCCCTGCACCAACGTC
GCCGTCAACCCCGGCGACTGCCCCCCTCTGGAACTGATCAACACCGTCATCCAG
GACGGCGACATGGTCGACACCGGATTCGGAGCCATGGACTTCACCACCCTGCAG
GCCAACAAGTCTGAAGTCCCCCTGGACATCTGCACCTCTATCTGCAAGTACCCCG
ACTACATCAAGATGGTGTCTGAACCCTACGGCGACTCTCTGTTCTTCTACCTGAG
GCGCGAACAGATGTTCGTCAGGCACCTCTTCAACAGGGCCGGTGCCGTCGGAGA
AAACGTCCCCGACGACCTGTACATCAAGGGATCTGGATCTACCGCCAACCTGGCC
TCTTCTAACTACTTCCCTACCCCTTCTGGATCTATGGTCACCTCTGACGCCCAGAT
CTTCAACAAGCCCTACTGGCTGCAGAGGGCCCAGGGACACAACAACGGAATCTG
CTGGGGAAACCAGCTGTTCGTCACCGTCGTCGACACCACCAGGTCTACCAACATG
TCCCTGTGCGCCGCCATCTCTACCTCTGAAACCACCTACAAGAACACCAACTTCA
AAGAATACCTGCGCCACGGCGAAGAATACGACCTGCAGTTCATCTTCCAGCTGTG
CAAGATCACCCTGACCGCCGACGTCATGACCTACATCCACTCTATGAACTCTACC
ATCTTGGAGGATTGGAACTTCGGACTGCAGCCCCCTCCCGGTGGAACCCTCGAG
GACACCTACCGCTTCGTCACCAGCCAGGCTATCGCCTGCCAGAAGCACACCCCC
CTGCCCCCAAAGAGGACCCCCTGAAGAAGTACACCTTCTGGGAAGTCAACCTGA
AAGAAAAGTTCTCTGCCGACCTGGACCAGTTCCCCCTGGGACGCAAGTTCCTGCT
GCAAGCCGGACTGAAGGCCAAGCCCAAGTTCACCCTGGGAAAGAGGAAGGCCAC
CCCCACCACCTCTTCTACCTCTACCACCGCCAAGAGGAAGAAGCGCAAGCTGGAA
CTGTAAAGCGGCCGC TABLE 5-continued Overview of the sequences disclosed in the present invention Seq ID NO protein (DNA)

>SEQ ID NO: 14 L1avi4 (FG-loop, HPV16)
GATATCATGGAGATAATTAAAATGATAACCATCTCGCAAATAAATAAGTATTTTACT
GTTTTCGTAACAGTTTTGTAATAAAAAAACCTATAAATATTCCGGATTATTCATACC
GTCCCACCATCGGGCGCGGATCTCTACTAGTATGTCTCTGTGGCTGCCCTCTGAA
GCCACCGTCTACCTGCCCCCCGTCCCTGTCTCTAAGGTCGTCAGCACCGACGAAT
ACGTCGCCAGGACCAACATCTACTACCACGCCGGAACCTCTAGGCTGCTGGCCG
TCGGACACCCCTACTTCCCCATCAAGAAGCCCAACAACAACAAGATCCTGGTCCC
CAAGGTGTCCGGACTGCAGTACAGGGTGTTCAGGATCCACCTCCCCGACCCCAA
CAAGTTCGGATTCCCCGACACCTCTTTCTACAACCCCGACACCCAGAGGCTCGTC
TGGGCCTGCGTCGGAGTCGAAGTCGGAAGGGGACAGCCCCTGGGAGTCGGAAT
CTCTGGACACCCCCTGCTGAACAAGCTGGACGACACCGAAAACGCCTCTGCCTA
CGCCGCCAACGCCGGTGTCGACAACAGGGAATGCATCTCTATGGACTACAAGCA
GACCCAGCTGTGCCTGATCGGATGCAAGCCCCCCATCGGAGAACACTGGGGAAA
GGGATCTCCCTGCACCAACGTCGCCGTCAACCCCGGCGACTGCCCCCCTCTGGA
ACTGATCAACACCGTCATCCAGGACGGCGACATGGTCGACACCGGATTCGGAGC
CATGGACTTCACCACCCTGCAGGCCAACAAGTCTGAAGTCCCCCTGGACATCTGC
ACCTCTATCTGCAAGTACCCCGACTACATCAAGATGGTGTCTGAACCCTACGGCG
ACTCTCTGTTCTTCTACCTGAGGCGCGAACAGATGTTCGTCAGGCACCTCTTCAA
CAGGGCCGGTGCCGTCGGAGAAAACGTCCCCGACGACCTGTACATCAAGGGACT
GAACGACATCTTCGAGGCCCAAAAGATCGAATGGCACGAGGCCTCTTCTAACTAC
TTCCCTACCCCTTCTGGATCTATGGTCACCTCTGACGCCCAGATCTTCAACAAGCC
CTACTGGCTGCAGAGGGCCCAGGGACACAACAACGGAATCTGCTGGGGAAACCA
GCTGTTCGTCACCGTCGTCGACACCACCAGGTCTACCAACATGTCCCTGTGCGCC
GCCATCTCTACCTCTGAAACCACCTACAAGAACACCAACTTCAAAGAATACCTGCG
CCACGGCGAAGAATACGACCTGCAGTTCATCTTCCAGCTGTGCAAGATCACCCTG
ACCGCCGACGTCATGACCTACATCCACTCTATGAACTCTACCATCTTGGAGGATT
GGAACTTCGGACTGCAGCCCCTCCCGGTGGAACCCTCGAGGACACCTACCGCT
TCGTCACCAGCCAGGCTATCGCCTGCCAGAAGCACACCCCCCCTGCCCCCAAAG
AGGACCCCCTGAAGAAGTACACCTTCTGGGAAGTCAACCTGAAAGAAAAGTTCTC
TGCCGACCTGGACCAGTTCCCCCTGGGACGCAAGTTCCTGCTGCAAGCCGGACT
GAAGGCCAAGCCCAAGTTCACCCTGGGAAAGAGGAAGGCCACCCCCACCACCTC
TTCTACCTCTACCACCGCCAAGAGGAAGAAGCGCAAGCTGGAACTGTAAAGCGG
CCGC >SEQ ID NO: 15 L1avi2 (HI-loop, HPV118)
GATATCATGGAGATAATTAAAATGATAACCATCTCGCAAATAAATAAGTATTTTACT
GTTTTCGTAACAGTTTTGTAATAAAAAAACCTATAAATATTCCGGATTATTCATACC
GTCCCACCATCGGGCGCGGATCTCTACTAGTATGGCCGTCTGGCAGGCCGCCTC
TGGAAAGGTCTACCTGCCCCCCTCTACCCCCGTCGCCAGGGTCCAGTCTACCGA
CGAATACGTCGAAAGGACCAACATCTACTACCACGCCTTCACCGACAGGCTGCTG
ACCGTCGGACACCCCTACTTCAACATCTTCAACAACGACGGAAACAAGCTCGAAG
TCCCCAAGGTGTCCGGAAACCAGCACAGGGTGTTCAGGCTGAGGCTGCCCGACC
CCAACCGCTTCGCCCTGGCCGACATGTCTGTCTACAACCCCGACAAAGAAAGGCT
CGTCTGGGCCATCACCGGACTGGAAATCGGAAGGGGACAGCCCCTGGGAGTCG
GAACCTCTGGACACCCCCTGTTCAACAAGTTCAACGACACCGAAAACGGCAACAA
GTACACCAACACCTCCACCGACGACAGGCAGAACATCTCTTTCGACCCCAAGCAG
CTGCAGATGTTCATCATCGGATGCACCCCCTGCATCGGAGAACACTGGGACAGG
GCCCCTGCCTGCGTCGAGGACGAACAGCTGGGAAGGTGCCCCCCCATCGAACTG
GTCAACACCTTCATCCAGGACGACGACATGGCCGACATCGGATACGGAAACCTGA
ACTTCAAGGCCCTGCAGCAGAACCGCTCTGACGTGTCCCTGGACATCGTCGACG
AAATCTGCAAGTACCCCGACTTCCTGAAGATGCAGAACGACGTCTACGGCGACGC
CTGCTTCTTCTACGCTAGGCGCGAACAGTGCTACGCCAGGCGCTTCTTCGTCCGC
GGAGGAAAGCCCGGCGACGACATCCCCGCCGAACAGATCGACGCCGGAAAGCT
GAAGAACGAATTCTACATCCCTGCCGCCGGTGGACAGGCCCAGGGACAGCTCGG
AAACTCTATGTACTTCCCCACCGTCAGCGGATCTCTCGTCAGCTCTGACGCCCAG
CTGTTCAACAGGCCCTTCTGGCTGCAGCGCGCTCAGGGACACAACAACGGAATC
CTGTGGGGAAACCAGTTGTTCGTCACCGTCCTGGACAACACCCGCAACACCAACT
TCTCTATCGCCGTCTACTCTGAGGGACTGAACGACATCTTCGAAGCCCAAAAGAT
CGAATGGCACGAGCAGGACATTGCCAACTACGACTCTTCTAAGTCTAGGGAATAC
CAGCGCCACGTCGAAGAGTACGAAGTCTCTATGATCCTGCAGCTGTGCAAGATCC
CCCTGAAGCCCGAAGTCCTGGCCCACATCAACGCCATGAACCCCGCCATCTTGG
AGGACTGGCAGCTGGGATTCATCCCCACCCCCGACAACCCCATCCACGACACCT
ACCGCTACATCGACTCCCTGGCCACCAGGTGCCCTGACAAGGTCCCCGCCAAAG
AAAAAGAGGACCCCTACGGCAAATACGTGTTCTGGAACGTCGACCTGTCTGAAAG
GCTGTCTCTGGACCTGGACCAGTACCCCCTGGGACGCAAGTTCCTGTTCCAAGC
CGGACTGAGGCAGAAGTCTGTCAACGGATCTGTCACCAGGACCGTCAGCAGGGG
AGCCAAGAGGAAGCGCAAGTAAAGCGGCCGC >SEQ ID NO: 16 L1avi3 (DE-loop, HPV118)
GATATCATGGAGATAATTAAAATGATAACCATCTCGCAAATAAATAAGTATTTTACT
GTTTTCGTAACAGTTTTGTAATAAAAAAACCTATAAATATTCCGGATTATTCATACC
GTCCCACCATCGGGCGCGGATCTCTACTAGTATGGCCGTCTGGCAGGCCGCCTC
TGGAAAGGTCTACCTGCCCCCCTCTACCCCCGTCGCCAGGGTCCAGTCTACCGA
CGAATACGTCGAAAGGACCAACATCTACTACCACGCCTTCACCGACAGGCTGCTG
ACCGTCGGACACCCCTACTTCAACATCTTCAACAACGACGGAAACAAGCTCGAAG
TCCCCAAGGTGTCCGGAAACCAGCACAGGGTGTTCAGGCTGAGGCTGCCCGACC TABLE 5-continued Overview of the sequences disclosed in the present invention Seq ID NO protein (DNA)

```
CCAACCGCTTCGCCCTGGCCGACATGTCTGTCTACAACCCCGACAAAGAAAGGCT
CGTCTGGGCCATCACCGGACTGGAAATCGGAAGGGGACAGCCCCTGGGAGTCG
GAACCTCTGGACACCCCCTGTTCAACAAGTTCAACGACACCGAAAACGGCAACGG
ACTGAACGACATCTTTCGAAGCCCAAAAGATCGAATGGCACGAGACCTCCACCGAC
GACAGGCAGAACATCTCTTTCGACCCCAAGCAGCTGCAGATGTTCATCATCGGAT
GCACCCCCTGCATCGGAGAACACTGGGACAGGGCCCCTGCCTGCGTCGAGGAC
GAACAGCTGGGAAGGTGCCCCCCCATCGAACTGGTCAACACCTTCATCCAGGAC
GACGACATGGCCGACATCGGATACGGAAACCTGAACTTCAAGGCCCTGCAGCAG
AACCGCTCTGACGTGTCCCTGGACATCGTCGACGAAATCTGCAAGTACCCCGACT
TCCTGAAGATGCAGAACGACGTCTACGGCGACGCCTGCTTCTTCTACGCTAGGCG
CGAACAGTGCTACGCCAGGCGCTTCTTCGTCCGCGGAGGAAAGCCCGGCGACGA
CATCCCCGCCAACAGATCGACGCCGGAAAGCTGAAGAACGAATTCTACATCCCT
GCCGCCGGTGGACAGGCCCAGGGACAGCTCGGAAACTCTATGTACTTCCCCACC
GTCAGCGGATCTCTCGTCAGCTCTGACGCCCAGCTGTTCAACAGGCCCTTCTGGC
TGCAGCGCGCTCAGGGACACAACAACGGAATCCTGTGGGGAAACCAGTTGTTCG
TCACCGTCCTGGACAACACCCGCAACACCAACTTCTCTATCGCCGTCTACTCTGA
GGCCGGAAAGATCCAGGACATTGCCAACTACGACTCTTCTAAGTCTAGGGAATAC
CAGCGCCACGTCGAAGAGTACGAAGTCTCTATGATCCTGCAGCTGTGCAAGATCC
CCCTGAAGCCCGAAGTCCTGGCCCACATCAACGCCATGAACCCCGCCATCTTGG
AGGACTGGCAGCTGGGATTCATCCCCACCCCCGACAACCCCATCCACGACACCT
ACCGCTACATCGACTCCCTGGCCACCAGGTGCCCTGACAAGGTCCCCGCCAAAG
AAAAAGAGGACCCCTACGCAAATACGTGTTCTGGAACGTCGACCTGTCTGAAAG
GCTGTCTCTGGACCTGGACCAGTACCCCTGGGACGCAAGTTCCTGTTCCAAGC
CGGACTGAGGCAGAAGTCTGTCAACGGATCTGTCACCAGGACCGTCAGCAGGGG
AGCCAAGAGGAAGCGCAAGTAAAGCGGCCGC
```

>SEQ ID NO: 17 PAPVE-L1 avi3
```
GATATCATGGAGATAATTAAAATGATAACCATCTCGCAAATAAATAAGTATTTTACT
GTTTTCGTAACAGTTTTGTAATAAAAAAACCTATAAATATTCCGGATTATTCATACC
GTCCCACCATCGGGCGCGGATCTCTACTAGTATGGCCTTCTGGCAGCCCTCTCAG
CGTCTGTACCTGCCCCCCACCCCCGTCACCAAGGTCCTGTGCTCTGAACAGTACA
TCAGGCGCAAGGACGTGTTCTACCACGGCGAAACCGAAAGGATGCTGACCGTCG
GACACCCCTACTACGAAATCAAGCAGTCTGGATCTGGAAAGACCATCCCCAAGGT
GTCCCCCAACCAGTACAGGGTGTTCAGGATCCTGCTGCCCGACCCTAACCAGTTC
GCCCTGCCCGACAAGGCTATGTACGACCCCTCTAAGGAAAGGCTCGTCTGGGCC
GTCGTCGGAGTCCAGGTGTCCGTGGACAGCCTCTGGGAGGATCTGTCTCTGGA
CACTCTTACCAGAACACCCTGATCGACGCCGAAAACGTGTCCGGACTGAACGACA
TCTTCGAAGCCCAAAAGATCGAATGGCACGAACAGGGAACCGACGACCGCAAGC
AGGGTGGAATGGACGTCAAGCAGCAGCAGATCCTGCTCCTGGGATGCACCCCCG
CCATCGGAGAATACTGGACCACCGCCAGGCCCTGCGTCACCGACAGGCCCGAAA
CCGGATCTTGCCCCCCATCGAACTGAAGAACAAGCCCATCGAGGACGGCGACA
TGATGGACATCGGATTCGGAGCCGCCAACTTCAAGGAACTGAACGCCACCAAGTC
TGACCTGCCCCTGGACATCGCCAAGGACATCTGCCTGTACCCCGACTACCTGAAG
ATGACCGAAGAAGCCGCCGGAAACTCTATGTTCTTCTTCGCCCGCAAGGAACAGG
TCTACGTCCGCCACATCTGGTCCCGCGGAGGAACCGACAAGGAAATGCCCCCG
AAGCCTACTTCCTGAAGCCCAAGGGTGGCGACCAGACCCAGAAGATGCCCTCTAT
CCTGTTCGGAGTCCCCTCTGGATCTCTCGTCAGCACCGACGGACAGCTGTTCAAC
AGGCCCTACTGGCTGTTCAGGGCCCAGGGAATGAACAACGGAATCTGCTGGCTG
AACCAGCTGTTCGTCACCGTCGGAGACAACACCAGGGGAACCACCCTGACCATC
ACCGTCCCCACCTCTGGATCCCCCCTGACCGAATACGACACCTCCAAGTTCAACG
TGTTCCAGAGGCACGTCGAAGAGTACAAGCTGGCCTTCGTGTTCCAGCTGTGCTC
TGTCACCCTGTCTCCCGAAACCGTCAGCCACCTCCAGGGACTGATGCCTTCCATC
CTGGAACACTGGGACATCAACATGCAGCCCCCCACCTCTTCTATCCTCGAGGACA
CCTACCGCTACCTGGAATCTCCTGCCACCAAGTGCGCCGACAACGTCACCCCCAT
GGGACCCGAGGACCCCTACGCCGGACTGAAGTTCTGGGAAGTCAACCTGAAGGA
ACGCCTGTCCCTGGACCTGGACCAGTTCCCCCTGGGAAGGCGCTTCCTGGCCCA
GCAGGGACTGGGATGCTCTACCCGCAAGAGGGTCGCCCCCGTCCCTAAGGTCAC
CGAAAAGAGGATCGTCCGCAAGAGGCGCAAGGGAAACTAAAGCGGCCGCTAA
```

>SEQ ID NO: 18 A1 >mSA- Her2-ECD|23-686
```
AEAGITGTWYNQHGSTFTVTAGADGNLTGQYENRAQGTGCQNSPYTLTGRYNGTKL
EWRVEWNNSTENCHSRTEWRGQYQGGAEARINTQWNLTYEGGSGPATEQGQDTF
TKVKGGSTQVCTGTDMKLRLPASPETHLDMLRHLYQGCQVVQGNLELTYLPTNASLS
FLQDIQEVQGYVLIAHNQVRQVPLQRLRIVRGTQLFEDNYALAVLDNGDPLNNTTPVT
GASPGGLRELQLRSLTEILKGGVLIQRNPQLCYQDTILWKDIFHKNNQLALTLIDTNRS
RACHPCSPMCKGSRCWGESSEDCQSLTRTVCAGGCARCKGPLPTDCCHEQCAAG
CTGPKHSDCLACLHFNHSGICELHCPALVTYNTDTFESMPNPEGRYTFGASCVTACP
YNYLSTDVGSCTLVCPLHNQEVTAEDGTQRCEKCSKPCARVCYGLGMEHLREVRAV
TSANIQEFAGCKKIFGSLAFLPESFDGDPASNTAPLQPEQLQVFETLEEITGYLYISAW
PDSLPDLSVFQNLQVIRGRILHNGAYSLTLQGLGISWLGLRSLRELGSGLALIHHNTHL
CFVHTVPWDQLFRNPHQALLHTANRPEDECVGEGLACHQLCARGHCWGPGPTQCV
NCSQFLRGQECVEECRVLQGLPREYVNARHCLPCHPECQPQNGSVTCFGPEADQC
VACAHYKDPPFCVARCPSGVKPDLSYMPIWKFPDEEGACQPCPINCTHSCVDLDDK
GCPAEQRASPLTSIISAVVGILLVVVLGVVFGILIKRRQQKIRKYTHHHHHH
```

TABLE 5-continued

Overview of the sequences disclosed in the present invention

Seq ID NO protein (DNA)

>SEQ ID NO: 19 A2 >mSA-IL-5(C63T/C105T)
AEAGITGTWYNQHGSTFTVTAGADGNLTGQYENRAQGTGCQNSPYTLTGRYNGTKL
EWRVEWNNSTENCHSRTEWRGQYQGGAEARINTQWNLTYEGGSGPATEQGQDTF
TKVKGGSIPTEIPTSALVKETLALLSTHRTLLIANETLRIPVPVHKNHQLTTEEIFQGIGTL
ESQTVQGGTVERLFKNLSLIKKYIDGQKKKTGEERRRVNQFLDYLQEFLGVMNTEWII
ES*SGRK

>SEQ ID NO: 20 A3 >PCSK9|31-692|:mSA:HIS
QEDEDGDYEELVLALRSEEDGLAEAPEHGTTATFHRCAKDPWRLPGTYVVVLKEETH
LSQSERTARRLQAQAARRGYLTKILHVFHGLLPGFLVKMSGDLLELALKLPHVDYIEED
SSVFAQSIPWNLERITPPRYRADEYQPPDGGSLVEVYLLDTSIQSDHREIEGRVMVTD
FENVPEEDGTRFHRQASKCDSHGTHLAGVVSGRDAGVAKGASMRSLRVLNCQGKG
TVSGTLIGLEFIRKSQLVQPVGPLVVLLPLAGGYSRVLNAACQRLARAGVVLVTAAGN
FRDDACLYSPASAPEVITVGATNAQDQPVTLGTLGTNFGRCVDLFAPGEDIIGASSDC
STCFVSQSGTSQAAAHVAGIAAMMLSAEPELTLAELRQRLIHFSAKDVINEAWFPEDQ
RVLTPNLVAALPPSTHGAWGWQLFCRTVWSAHSGPTRMATAVARCAPDEELLSCSSF
SRSGKRRGERMEAQGGKLVCRAHNAFGGEGVYAIARCCLLPQANCSVHTAPPAEAS
MGTRVHCHQQGHVLTGCSSHWEVEDLGTHKPPVLRPRGQPNQCVGHREASIHASC
CHAPGLECKVKEHGIPAPQEQVTVACEEGWTLTGCSALPGTSHVLGAYAVDNTCVV
RSRDVSTTGSTSEGAVTAVAICCRSRHLAQASQELQGGSAEAGITGTWYNQHGSTFT
VTAGADGNLTGQYENRAQGTGCQNSPYTLTGRYNGTKLEWRVEWNNSTENCHSRT
EWRGQYQGGAEARINTQWNLTYEGGSGPATEQGQDTFTKVKHHHHHH

>SEQ ID NO: 21 A4 >mSA-ID1ID2a-HIS
AEAGITGTWYNQHGSTFTVTAGADGNLTGQYENRAQGTGCQNSPYTLTGRYNGTKL
EWRVEWNNSTENCHSRTEWRGQYQGGAEARINTQWNLTYEGGSGPATEQGQDTF
TKVKGGSNYIKGDPYFAEYATKLSFILNPSDANNPSGETANHNDEACNCNESGISSVG
QAQTSGPSSNKTCITHSSIKTNKKKECKDVKLGVRENDKDLKICVIEDTSLSGVDNCC
CQDLLGILQENCSDNKRGSSSNDSCDNKNQDECQKKLEKVFASLTNGYKCDKCKSG
TSRSKKKWIWKKSSGNEEGLQEEYANTIGLPPRTQSLYLGNLPKLENVCEDVKDINFD
TKEKFLAGCLIVSFHEGKNLKKRYPQNKNSGNKENLCKALEYSFADYGDLIKGTSIWD
NEYTKDLELNLQNNFGKLFGKYIKKNNTAEQDTSYSSLDELRESWWNTNKKYIWTAM
KHGAEMNITTCNADGSVTGSGSSCDDIPTIDLIPQYLRFLQEWVENFCEQRQAKVKDV
ITNCKSCKESGNKCKTECKTKCKDECEKYKKFIEACGTAGGGIGTAGSPWSKRWDQI
YKRYSKHIEDAKRNRKAGTKNCGTSSTTNAAASTDENKCVQSDIDSFFKHLIDIGLTTP
SSYLSNVLDDNICGADKAPWTTYTTYTTTEKCNKERDKSKSQSSDTLVVVNVPSPLG
NTPYRYKYACQCKIPTNEETCDDRKEYMNQWSCGSARTMKRGYKNDNYELCKYNG
VDVKPTTVRSNSSKLDHHHHHH

>SEQ ID NO: 22 A5 >mSA-RO-HIS
AEAGITGTWYNQHGSTFTVTAGADGNLTGQYENRAQGTGCQNSPYTLTGRYNGTKL
EWRVEWNNSTENCHSRTEWRGQYQGGAEARINTQWNLTYEGGSGPATEQGQDTF
TKVKGGSTSENRNKRIGGPKLRGNVTSNIKFPSDNKGKIIRGSNDKLNKNSEDVLEQS
EKSLVSENVPSGLDIDDIPKESIFIQEDQEGQTHSELNPETSEHSKDLNNNGSKNESSD
IISENNKSNKVQNHFESLSDLELLENSSQDNLDKDTISTEPFPNQKHKDLQQDLNDEPL
EPFPTQIHKDYKEKNLINEEDSEPFPRQKHKKVDNHNEEKNVFHENGSANGNQGSLK
LKSFDEHLKDEKIENEPLVHENLSIPNDPIEQILNQPEQETNIQEQLYNEKQNVEEKQN
SQIPSLDLKEPTNEDILPNHNPLENIKQSESEINHVQDHALPKENIIDKLDNQKEHIDQS
QHNINVLQENNINNHQLEPQEKPNIESFEPKNIDSEIILPENVETEEIIDDVPSPKHSNHE
TFEEETSESEHEEAVSEKNAHETVEHEETVSQESNPEKADNDGNVSQNSNNELNEN
EFVESEKSEHEARSKAKEASSYDYILGWEFGGGVPEHKKEENMLSHLYVSSKDKENI
SKENDDVLDEKEEEAEETEEEELEEKNEEETESEISEDEEEEEEEEEKEEENDKKKEQ
EKEQSNENNDQKKDMEAQNLISKNQNNNEKNVKEAAESIMKTLAGLIKGNNQIDSTLK
DLVEELSKYFKNHRSHHHHHH

>SEQ ID NO: 23 A6 >HIS-RO-mSA
GSTSENRNKRIGGPKLRGNVTSNIKFPSDNKGKIIRGSNDKLNKNSEDVLEQSEKSLV
SENVPSGLDIDDIPKESIFIQEDQEGQTHSELNPETSEHSKDLNNNGSKNESSDIISEN
NKSNKVQNHFESLSDLELLENSSQDNLDKDTISTEPFPNQKHKDLQQDLNDEPLEPFP
TQIHKDYKEKNLINEEDSEPFPRQKHKKVDNHNEEKNVFHENGSANGNQGSLKLKSF
DEHLKDEKIENEPLVHENLSIPNDPIEQILNQPEQETNIQEQLYNEKQNVEEKQNSQIP
SLDLKEPTNEDILPNHNPLENIKQSESEINHVQDHALPKENIIDKLDNQKEHIDQSQHNI
NVLQENNINNHQLEPQEKPNIESFEPKNIDSEIILPENVETEEIIDDVPSPKHSNHETFEE
ETSESEHEEAVSEKNAHETVEHEETVSQESNPEKADNDGNVSQNSNNELNENEFVE
SEKSEHEAGGSGAEAGITGTWYNQHGSTFTVTAGADGNLTGQYENRAQGTGCQNS
PYTLTGRYNGTKLEWRVEWNNSTENCHSRTEWRGQYQGGAEARINTQWNLTYEGG
SGPATEQGQDTFTKVK

>SEQ ID NO: 24 A7 >HIS-GMZ2ggsmSA
GSTSENRNKRIGGPKLRGNVTSNIKFPSDNKGKIIRGSNDKLNKNSEDVLEQSEKSLV
SENVPSGLDIDDIPKESIFIQEDQEGQTHSELNPETSEHSKDLNNNGSKNESSDIISEN
NKSNKVQNHFESLSDLELLENSSQDNLDKDTISTEPFPNQKHKDLQQDLNDEPLEPFP
TQIHKDYKEKNLINEEDSEPFPRQKHKKVDNHNEEKNVFHENGSANGNQGSLKLKSF
DEHLKDEKIENEPLVHENLSIPNDPIEQILNQPEQETNIQEQLYNEKQNVEEKQNSQIP
SLDLKEPTNEDILPNHNPLENIKQSESEINHVQDHALPKENIIDKLDNQKEHIDQSQHNI
NVLQENNINNHQLEPQEKPNIESFEPKNIDSEIILPENVETEEIIDDVPSPKHSNHETFEE TABLE 5-continued Overview of the sequences disclosed in the present invention Seq ID NO protein (DNA)

ETSESEHEEAVSEKNAHETVEHEETVSQESNPEKADNDGNVSQNSNNELNENEFVE
SEKSEHEARSKAKEASSYDYILGWEFGGGVPEHKKEENMLSHLYVSSKDKENISKEN
DDVLDEKEEEAEETEEEELEEKNEEETESEISEDEEEEEEEEEKEEENDKKKEQEKEQ
SNENNDQKKDMEAQNLISKNQNNNEKNVKEAAESIMKTLAGLIKGNNQIDSTLKDLVE
ELSKYFKNHGGSGAEAGITGTWYNQHGSTFTVTAGADGNLTGQYENRAQGTGCQN
SPYTLTGRYNGTKLEWRVEWNNSTENCHSRTEWRGQYQGGAEARINTQWNLTYEG
GSGPATEQGQDTFTKVK

>SEQ ID NO:25 A8 >HIS-GMZ2T:ggsmSA
GSTSENRNKRIGGPKLRGNVTSNIKFPSDNKGKIIRGSNDKLNKNSEDVLEQSEKSLV
SENVPSGLDIDDIPKESIFIQEDQEGQTHSELNPETSEHSKDLNNNGSKNESSDIISEN
NKSNKVQNHFESLSDLELLENSSQDNLDKDTISTEPFPNQKHKDLQQDLNDEPLEPFP
TQIHKDYKEKNLINEEDSEPFPRQKHKKVDNHNEEKNVFHENGSANGNQGSLKLKSF
DEHLKDEKIENEPLVHENLSIPNDPIEQILNQPEQETNIQEQLYNEKQNVEEKQNSQIP
SLDLKEPTNEDILPNHNPLENIKQSESEINHVQDHALPKENIIDKLDNQKEHIDQSQHNI
NVLQENNINNHQLEPQEKPNIESFEPKNIDSEIILPENVETEEIIDDVPSPKHSNHETFEE
ETSESEHEEAVSKTKEYAEKAKNAYQKANQAVLKAKEASSYDYILGWEFGGG
VPEHKKEENMLSHLYVSSKDKENISKENDDVLDEKEEEAEETEEEELEGGSGAEAGIT
GTWYNQHGSTFTVTAGADGNLTGQYENRAQGTGCQNSPYTLTGRYNGTKLEWRVE
WNNSTENCHSRTEWRGQYQGGAEARINTQWNLTYEGGSGPATEQGQDTFTKVK >SEQ ID NO: 26 A9 >mSA-PfRH5-HIS
AEAGITGTWYNQHGSTFTVTAGADGNLTGQYENRAQGTGCQNSPYTLTGRYNGTKL
EWRVEWNNSTENCHSRTEWRGQYQGGAEARINTQWNLTYEGGSGPATEQGQDTF
TKVKGGSLSFENAIKKTKNQENNLTLLPIKSTEEEKDDIKNGKDIKKEIDNDKENIKTNN
AKDHSTYIKSYLNTNVNDGLKYLFIPSHNSFIKKYSVFNQINDGMLLNEKNDVKNNEDY
KNVDYKNVNFLQYHPKELSNYNIANSIDILQEKEGHLDFVIIPHYTFLDYYKHLSYNSIYH
KYSTYGKYIAVDAFIKKINETYDKVKSKCNDIKNDLIATIKKLEHPYDINNKNDDSYRYDI
SEEIDDKSEETDDETEEVEDSIQDTDSNHTPSNKKKNDLMNRTFKKMMDEYNTKKKK
LIKCIKNHENDFNKICMDMKNYGTNLFEQLSCYNNNFCNTNGIRFHYDEYIHKLILSVKS
KNLNKDLSDMTNILQQSELLLTNLNKKMGSYIYIDTIKFIHKEMKHIFNRIEYHTKIINDKT
KIIQDKIKLNIWRTFQKDELLKRILDMSNEYSLFITSDHLRQMLYNTFYSKEKHLNNIFHH
LIYVLQMKFNDVPIKMEYFQTYKKNKPLTQHHHHHH >SEQ ID NO: 27 A10 >mSA-Pfs25-HIS
AEAGITGTWYNQHGSTFTVTAGADGNLTGQYENRAQGTGCQNSPYTLTGRYNGTKL
EWRVEWNNSTENCHSRTEWRGQYQGGAEARINTQWNLTYEGGSGPATEQGQDTF
TKVKGGSNKLYSLFLFLFIQLSIKYNNAKVTVDTVCKRGFLIQMSGHLECKCENDLVLV
NEETCEEKVLKCDEKTVNKPCGDFSKCIKIDGNPVSYACKCNLGYDMVNNVCIPNEC
KNVTCGNGKCILDTSNPVKTGVCSCNIGKVPNVQDQNKCSKDGETKCSLKCLKENET
CKAVDGIYKCDCKDGFIIDNESSICTAFSAYNILNLSIMFILFSVCFFIM >SEQ ID NO: 28 A11 >HIS-PfCSP(aa92-397)-mSA
KLKQPADGNPDPNANPNVDPNANPNVDPNANPNVDPNANPNANPNANPNANPNAN
PNANPNANPNANPNANPNANPNANPNANPNANPNANPNANPNANPNVDPNA
NPNANPNANPNANPNANPNANPNANPNANPNANPNANPNANPNANPNANPN
ANPNANPNANPNANPNKNNQGNGQGHNMPNDPNRNVDENANANSAVKNNNNEEP
SDKHIKEYLNKIQNSLSTEWSPCSVTCGNGIQVRIKPGSANKPKDELDYANDIEKKICK
MEKCSSVFNVVNSSIGLIMVLSFLFLNGGSAEAGITGTVVYNQHGSTFTVTAGADGNLT
GQYENRAQGTGCQNSPYTLTGRYNGTKLEWRVEWNNSTENCHSRTEWRGQYQGG
AEARINTQWNLTYEGGSGPATEQGQDTFTKVK >SEQ ID NO: 29 A3 >PCSK9|31-692|:mSA:HIS DNA
TTTCATATGCCAAGTACGCCCCCTATTGACGTCAATGACGGTAAATGGCCCGCCT
GGCATTATGCCCAGTACATGACCTTATGGGACTTTCCTACTTGGCAGTACATCTAC
GTATTAGTCATCGCTATTACCATGGTGATGCGGTTTTGGCAGTACATCAATGGGC
GTGGATAGCGGTTTGACTCACGGGGATTTCCAAGTCTCCACCCCATTGACGTCAA
TGGGAGTTTGTTTTGGCACCAAAATCAACGGGACTTTCCAAAATGTCGTAACAACT
CCGCCCCATTGACGCAAATGGGCGGTAGGCGTGTACGGTGGGAGGTCTATATAA
GCAGAGCTCTCTGGCTAACTAGAGAACCCACTGCTTACTGGCTTATCGAAATTAAT
ACGACTCACTATAGGGAGACCCAAGCTGGCTAGCGTTTAAACTTAAGCTTAGCGC
AGAGGCTTGGGGCAGCCGAGCGGCAGCCAGGCCCCGGCCCGGCCCTCGGTTCC
AGAAGGGAGAGGAGCCCGCCAAGGCGCGCAAGAGAGCGGGCTGCCTCGCAGTC
CGAGCCGGAGAGGGAGCGCGAGCCGCGCCGGCCCCGGACGGCCTCCGAAACC
ATGCAGGAAGATGAGGACGGCGACTACGAGGAACTGGTGCTGGCCCTGCGGAG
CGAAGAGGATGGACTGGCCGAGGCCCCTGAGCACGGCACCACCGCCACCTTCC
ACAGATGCGCCAAGGACCCTTGGCGGCTGCCCGGCACATACGTGGTGGTGCTGA
AAGAGGAAACCCACCTGAGCCAGAGCGAGCGGACCGCCAGAAGGCTGCAGGCC
CAGGCCGCCAGAAGAGGCTACCTGACCAAGATCCTGCACGTGTTCCACGGCCTG
CTGCCCGGCTTCCTGGTGAAAATGAGCGGCGACCTGCTGGAACTGGCCCTGAAG
CTGCCCCACGTGGACTACATCGAAGAGGACAGCAGCGTGTTCGCCCAGAGCATC
CCCTGGAACCTGGAACGGATCACCCCCCCCAGATACCGGGCCGACGAGTACCAG
CCTCCTGACGGCGGCAGCCTGGTGGAAGTGTACCTGCTGGACACCAGCATCCAG
AGCGACCACCGCGAGATCGAGGGCAGAGTGATGGTGACAGACTTCGAGAACGTG
CCCGAAGAGGACGGCACCCGGTTCCACAGACAGGCCAGCAAGTGCGACAGCCA TABLE 5-continued Overview of the sequences disclosed in the present invention Seq ID NO protein (DNA)

CGGCACACATCTGGCCGGCGTGGTGTCTGGCAGAGATGCCGGCGTGGCCAAGG
GCGCCAGCATGAGAAGCCTGCGGGTGCTGAACTGCCAGGGCAAGGGCACCGTG
TCCGGCACCCTGATCGGCCTGGAATTCATCCGGAAGTCCCAGCTGGTGCAGCCC
GTGGGCCCTCTGGTGGTGCTGCTGCCCTCTGGCTGGCGGCTACAGCAGAGTGCTG
AACGCCGCCTGCCAGAGACTGGCCAGAGCTGGCGTGGTGCTGGTGACAGCCGC
CGGAAACTTCCGGGACGACGCCTGCCTGTACAGCCCCGCCTCTGCCCCCGAAGT
GATCACCGTGGGCGCCACCAACGCCCAGGACCAGCCTGTGACACTGGGCACCCT
GGGCACAAACTTCGGCAGATGCGTGGACCTGTTCGCCCCTGGCGAGGACATCAT
CGGCGCCAGCAGCGACTGCAGCACCTGTTTCGTGTCCCAGAGCGGCACCAGCCA
GGCCGCTGCCCATGTGGCCGGAATCGCCGCCATGATGCTGAGCGCCGAGCCTG
AGCTGACCCTGGCCGAGCTGCGGCAGCGGCTGATCCACTTCTCCGCCAAGGACG
TGATCAACGAGGCCTGGTTCCCCGAGGACCAGAGAGTGCTGACCCCCAACCTGG
TGGCCGCCCTGCCTCCTTCTACACACGGCGCTGGCTGGCAGCTGTTCTGCAGGA
CAGTGTGGTCCGCCCACAGCGGCCCCACCAGAATGGCCACAGCCGTGGCCAGAT
GCGCCCCTGATGAGGAACTGCTGAGCTGCAGCAGCTTCTCCAGAAGCGGCAAGC
GGAGAGGCGAGCGGATGGAAGCCCAGGGCGGCAAGCTCGTGTGCAGAGCCCAC
AATGCCTTCGGCGGCGAGGGCGTGTACGCCATTGCCAGATGCTGCCTGCTGCCT
CAGGCCAACTGCAGCGTGCACACAGCCCCTCCAGCCGAGGCCAGCATGGGCAC
CAGAGTGCACTGCCACCAGCAGGGCCACGTGCTGACCGGCTGTAGCAGCCACTG
GGAGGTGGAAGATCTGGGCACCCACAAGCCCCCGTGCTGAGGCCCAGAGGCC
AGCCTAATCAGTGCGTGGGCCACAGAGAGGCCTCCATCCACGCCAGCTGTTGCC
ACGCCCCTGGCCTGGAATGCAAAGTGAAAGAGCACGGCATCCCTGCCCCCCAGG
AACAGGTCACAGTGGCCTGCGAGGAAGGCTGGACCCTGACAGGCTGTTCCGCCC
TGCCAGGCACCTCTCACGTGCTGGGCGCCTACGCCGTGGACAATACCTGCGTCG
TGCGCAGCCGGGACGTGTCCACAACCGGCTCTACAAGCGAGGGCGCCGTGACC
GCCGTGGCCATCTGCTGCAGAAGCAGACACCTGGCCCAGGCCTCCCAGGAACTG
CAGGGCGGATCTGCCGAGGCCGGCATCACCGGCACCTGGTACAATCAGCACGG
CAGCACCTTCACCGTGACCGCTGGCGCCGACGGCAACCTGACCGGCCAGTACGA
GAACAGAGCCCAGGGCACCGGCTGCCAGAACAGCCCTTACACCCTGACCGGCAG
ATACAACGGCACCAAGCTGGAATGGCGGGTGGAATGGAACAACAGCACCGAGAA
CTGCCACAGCCGGACCGAGTGGCGGGGACAGTATCAGGGCGGAGCCGAGGCCC
GGATCAACACCCAGTGGAACCTGACCTACGAGGGCGGCTCTGGCCCTGCCACAG
AGCAGGGACAGGACACCTTCACCAAAGTGAAGCACCACCACCATCACCACTAAGC
GGCCGCTTTT

>SEQ ID NO: 30 A4 >mSA-ID1ID2a-HIS DNA
CCATGGGCGGTGCAGAAGCAGGTATTACCGGCACCTGGTATAATCAGCATGGTA
GCACCTTTACCGTTACCGCAGGCGCAGATGGTAATCTGACAGGTCAGTATGAAAA
TCGTGCACAGGGCACCGGTTGTCAGAATAGCCCGTATACCCTGACCGGTCGTTAT
AATGGCACCAAACTGGAATGGCGTGTTAATGGAATAATAGCACCGAAAATTGTC
ATAGCCGTACCGAATGGCGTGGTCAGTATCAGGGTGGTGCAGAAGCCCGTATTAA
TACCCAGTGGAATCTGACCTATGAAGGTGGTAGCGGTCCGGCAACCGAACAGGG
TCAGGATACCTTTACCAAAGTTAAAGGTGGCAGCAACTATATCAAAGGCGATCCGT
ATTTTGCAGAGTATGCAACCAAACTGAGCTTTATTCTGAATCCGAGTGATGCAAAT
AATCCGAGCGGTGAAACCGCAAATCACAATGATGAAGCCTGTAATTGTAACGAAA
GCGGTATTAGCAGCGTTGGTCAGGCACAGACCAGCGGTTCCGAGCAGCAATAAAA
CCTGTATTACCCATAGCAGCATTAAAACCAATAAAAAGAAAGAATGCAAAGATGTG
AAACTGGGCGTGCGCGAAAATGATAAAGATCTGAAAATTTGCGTGATCGAGGATA
CCAGCCTGAGCGGTGTTGATAATTGTTGTTGTCAGGATCTGCTGGGTATTCTGCA
AGAAAATTGCAGCGATAATAAACGTGGTAGCAGCAGCAATGATAGCTGCGATAAC
AAAAAATCAGGATGAATGCCAGAAAAAACTGGAAAAAGTTTTTGCCAGCCTGACGAA
TGGTTACAAATGCGATAAATGTAAAAGCGGCACCAGCCGCAGCAAAAAGAAATGG
ATTTGGAAAAAAGCAGCGGCAATGAAGAAGGTCTGCAAGAGGAATATGCAAATA
CCATTGGTCTGCCTCCGCGTACCCAGAGCCTGTATCTGGGTAATCTGCCGAAACT
GGAAAATGTGTGTGAAGATGTGAAAGATATCAATTTTGATACCAAAGAAAAATTTCT
GGCAGGCTGCCTGATTGTGAGCTTTCATGAAGGTAAAAACCTGAAAAAACGCTAT
CCGCAGAATAAAAACAGCGGTAACAAAGAAAATCTGTGCAAAGCACTGGAATACA
GCTTTGCAGATTATGGCGATCTGATTAAAGGCACCAGCATTTGGGATAACGAGTAT
ACCAAAGATCTGGAACTGAATCTGCAGAACAATTTCGGTAAACTGTTCGGCAAATA
TATCAAAAAAACAATACCGCAGAGCAGGATACCAGCTATAGCAGCCTGGATGAA
CTGCGTGAAAGTTGGTGGAATACCAACAAAAATACATTTGGACCGCCATGAAAC
ATGGTGCCGAAATGAATATTACCACCTGTAATGCAGATGGTAGCGTTACCGGTAG
CGGTAGCAGCTGTGATGATATTCCGACCATTGATCTGATTCCGCAGTATCTGCGTT
TTCTGCAAGAATGGGTTGAAAACTTTTGTGAACAGCGTCAGGCGAAAGTGAAAGA
TGTTATTACCAATTGCAAAAGCTGCAAAGAAAGCGGCAATAAATGCAAAACCGAGT
GCAAAACCAATGCAAAGACGAGTGCGAGAAATACAAAAAATTCATTGAAGCATGT
GGTACAGCCGGTGGTGGTATTGGCACCGCAGGTAGCCCGTGGTCAAAACGTTGG
GATCAGATCTATAAACGCTACAGCAAACACATCGAAGATGCCAAACGTAATCGTAA
AGCAGGCACCAAAAATTGTGGCACCAGCAGCACCACCAATGCAGCAGCAAGCAC
CGATGAAAACAAATGTGTTCAGAGCGATATCGATAGCTTCTTCAAACATCTGATTG
ATATTGGTCTGACCACCCCGAGCAGCTATCTGAGCAATGTTCTGGATGATAACATT
TGCGGTGCAGATAAAGCACCGTGGACCACCTATACCACATATACCACCACAGAAA
AATGCAACAAAGAGCGCGATAAAGCAAAAGCCAGAGCAGCGATACCCTGGTTGT
TGTTAATGTTCCGAGTCCGCTGGGTAATACCCCGTATCGTTATAAGTATGCCTGCC
AGTGTAAAATCCCGACCAATGAAGAAACCTGTGATGATCGCAAAGAATACATGAAT
CAGTGGTCATGTGGTAGCGCACGTACCATGAAACGTGGCTATAAAAACGATAATT

TABLE 5-continued

Overview of the sequences disclosed in the present invention

Seq ID NO protein (DNA)

ATGAACTGTGCAAATATAACGGCGTGGATGTTAAACCGACCACCGTTCGTAGCAA
TAGCAGCAAACTGGATCATCATCATCACCATCATTAAGGATCC

>SEQ ID NO: 31 A5 >mSA-RO-HIS DNA
CCATGGGCGGTGCAGAAGCAGGTATTACCGGCACCTGGTATAATCAGCATGGTA
GCACCTTTACCGTTACCGCAGGCGCAGATGGTAATCTGACAGGTCAGTATGAAA
TCGTGCACAGGGCACCGGTTGTCAGAATAGCCCGTATACCCTGACCGGTCGTTAT
AATGGCACCAAACTGGAATGGCGTGTTGAATGGAATAATAGCACCGAAAATTGTC
ATAGCCGTACCGAATGGCGTGGTCAGTATCAGGGTGGTGCAGAAGCCCGTATTAA
TACCCAGTGGAATCTGACCTATGAAGGTGGTAGCGGTCCGGCAACCGAACAGGG
TCAGGATACCTTTACCAAAGTTAAAGGTGGCAGCACAAGTGAGAATAGAAATAAAC
GAATCGGGGTCCTAAATTAAGGGGTAATGTTACAAGTAATATAAAGTTCCCATCA
GATAACAAAGGTAAAATTATAAGAGGTTCGAATGATAAACTTAATAAAAACTCTGAA
GATGTTTTAGAACAAAGCGAAAAATCGCTTGTTTCAGAAAATGTTCCTAGTGGATT
AGATATAGATGATATCCCTAAAGAATCTATTTTTATTCAAGAAGATCAAGAAGGTCA
AACTCATTCTGAATTAAATCCTGAAACATCAGAACATAGTAAAGATTTAAATAATAA
TGGTTCAAAAAATGAATCTAGTGATATTATTTCAGAAAATAATAAATCAAATAAAGT
ACAAAATCATTTTGAATCATTATCAGATTTAGAATTACTTGAAAATTCCTCACAAGAT
AATTTAGACAAAGATACAATTTCAACAGAACCTTTTCCTAATCAAAAACATAAAGAC
TTACAACAAGATTTAAATGATGAACCTTTAGAACCCTTTCCTACACAAATACATAAA
GATTATAAAGAAAAAATTTAATAAATGAAGAAGATTCAGAACCATTTCCCAGACAA
AAGCATAAAAAGGTAGACAATCATAATGAAGAAAAAAACGTATTTCATGAAAATGG
TTCTGCAAATGGTAATCAAGGAAGTTTGAAACTTAAATCATTCGATGAACATTTAAA
AGATGAAAAAATAGAAAATGAACCACTTGTTCATGAAAATTTATCCATACCAAATGA
TCCAATAGAACAAATATTAAATCAACCTGAACAAGAAACAAATATCCAGGAACAATT
GTATAATGAAAAACAAAATGTTGAAGAAAAACAAAATTCTCAAATACCTTCGTTAGA
TTTAAAAGAACCAACAAATGAAGATATTTTACCAAATCATAATCCATTAGAAAATAT
AAAACAAAGTGAATCAGAAATAAATCATGTACAAGATCATGCGCTACCAAAAGAGA
ATATAATAGACAAACTTGATAATCAAAAAGAACACATCGATCAATCACAACATAATA
TAAATGTATTACAAGAAAATAACATAAACAATCACCAATTAGAACCTCAAGAGAAAC
CTAATATTGAATCGTTTGAACCTAAAAATATAGATTCAGAAATTATTCTTCCTGAAA
ATGTTGAAACAGAAGAAATAATAGATGATGTGCCTTCCCCTAAACATTCTAACCAT
GAAACATTTGAAGAAGAAACAAGTGAATCTGAACATGAAGAAGCCGTATCTGAAAA
AAATGCCCACGAAACTGTCGAACATGAAGAAACTGTGTCTCAAGAAAGCAATCCT
GAAAAAGCTGATAATGATGGAAATGTATCTCAAAACAGCAACAACGAATTAAATGA
AAATGAATTCGTTGAATCGGAAAAAAAGCGAGCATGAAGCAAGATCCAAAGCAAAA
GAAGCTTCTAGTTATGATTATATTTTAGGTTGGGAATTTGGAGGAGGCGTTCCAGA
ACACAAAAAAGAAGAAAATATGTTATCACATTTATATGTTTCTTCAAAGGATAAGGA
AAATATATCTAAGGAAAATGATGATGTATTAGATGAGAAGGAAGAAGAGGCAGAAG
AAACAGAAGAAGAAGAACTTGAAGAAAAAAATGAAGAAGAAACAGAATCAGAAATA
AGTGAAGATGAAGAAGAAGAAGAAGAAGAAGAAGAAAAGGAAGAAGAAAATGACA
AAAAAAAAGAACAAGAAAAAGAACAAAGTAATGAAAATAATGATCAAAAAAAAGATA
TGGAAGCACAGAATTTAATTTCTAAAAACCAGAATAATAATGAGAAAAACGTAAAA
GAAGCTGCTGAAAGCATCATGAAAACTTTAGCTGGTTTAATCAAGGGAAATAATCA
AATAGATTCTACCTTAAAAGATTTAGTAGAAGAATTATCCAAATATTTTAAAAATCAT
AGATCTCATCACCATCATCACCATTAGggatcctttt >SEQ ID NO:32 A6 >HIS-RO-mSA DNA
GGATCCACAAGTGAGAATAGAAATAAACGAATCGGGGTCCTAAATTAAGGGGTA
ATGTTACAAGTAATATAAAGTTCCCATCAGATAACAAAGGTAAAATTATAAGAGGTT
CGAATGATAAACTTAATAAAAACTCTGAAGATGTTTTAGAACAAAGCGAAAAATCG
CTTGTTTCAGAAAATGTTCCTAGTGGATTAGATATAGATGATATCCCTAAAGAATCT
ATTTTTATTCAAGAAGATCAAGAAGGTCAAACTCATTCTGAATTAAATCCTGAAACA
TCAGAACATAGTAAAGATTTAAATAATAATGGTTCAAAAAATGAATCTAGTGATATT
ATTTCAGAAAATAATAAATCAAATAAAGTACAAAATCATTTTGAATCATTATCAGATT
TAGAATTACTTGAAAATTCCTCACAAGATAATTTAGACAAAGATACAATTTCAACAG
AACCTTTTCCTAATCAAAAACATAAAGACTTACAACAAGATTTAAATGATGAACCTT
TAGAACCCTTTCCTACACAAATACATAAAGATTATAAAGAAAAAATTTAATAAATG
AAGAAGATTCAGAACCATTTCCCAGACAAAAGCATAAAAAGGTAGACAATCATAAT
GAAGAAAAAAACGTATTTCATGAAAATGGTTCTGCAAATGGTAATCAAGGAAGTTT
GAAACTTAAATCATTCGATGAACATTTAAAAGATGAAAAAATAGAAAATGAACCACT
TGTTCATGAAAATTTATCCATACCAAATGATCCAATAGAACAAATATTAAATCAACC
TGAACAAGAAACAAATATCCAGGAACAATTGTATAATGAAAAACAAAATGTTGAAG
AAAAACAAAATTCTCAAATACCTTCGTTAGATTTAAAAGAACCAACAAATGAAGATA
TTTTACCAAATCATAATCCATTAGAAAATATAAAACAAAGTGAATCAGAAATAAATC
ATGTACAAGATCATGCGCTACCAAAAGAGAATATAATAGACAAACTTGATAATCAA
AAAGAACACATCGATCAATCACAACATAATATAAATGTATTACAAGAAAATAACATA
AACAATCACCAATTAGAACCTCAAGAGAAACCTAATATTGAATCGTTTGAACCTAAA
AATATAGATTCAGAAATTATTCTTCCTGAAATGTTGAAACAGAAGAAATAATAGAT
GATGTGCCTTCCCCTAAACATTCTAACCATGAAACATTTGAAGAAGAAACAAGTGA
ATCTGAACATGAAGAAGCCGTATCTGAAAAAAATGCCCACGAAACTGTCGAACAT
GAAGAAACTGTGTCTCAAGAAAGCAATCCTGAAAAAGCTGATAATGATGGAAATGT
ATCTCAAAACAGCAACAACGAATTAAATGAAATGAATTCGTTGAATCGGAAAAAA
GCGAGCATGAAGCAGGTGGTAGCGGTGCAGAAGCAGGTATTACCGGCACCTGGT
ATAATCAGCATGGTAGCACCTTTACCGTTACCGCAGGCGCAGATGGTAATCTGAC
AGGTCAGTATGAAAATCGTGCACAGGGCACCGGTTGTCAGAATAGCCCGTATACC TABLE 5-continued Overview of the sequences disclosed in the present invention Seq ID NO protein (DNA)

CTGACCGGTCGTTATAATGGCACCAAACTGGAATGGCGTGTTGAATGGAATAATA
GCACCGAAAATTGTCATAGCCGTACCGAATGGCGTGGTCAGTATCAGGGTGGTG
CAGAAGCCCGTATTAATACCCAGTGGAATCTGACCTATGAAGGTGGTAGTGGTCC
GGCAACCGAACAGGGTCAGGATACCTTTACCAAAGTGAAATAAcatatg >SEQ ID NO: 33 A7 >HIS-GMZ2ggsmSA3
GGATCCACAAGTGAGAATAGAAATAAACGAATCGGGGGTCCTAAATTAAGGGGTA
ATGTTACAAGTAATATAAAGTTCCCATCAGATAACAAAGGTAAAATTATAAGAGGTT
CGAATGATAAACTTAATAAAAACTCTGAAGATGTTTTAGAACAAAGCGAAAAATCG
CTTGTTTCAGAAAATGTTCCTAGTGGATTAGATATAGATGATATCCCTAAAGAATCT
ATTTTTATTCAAGAAGATCAAGAAGGTCAAACTCATTCTGAATTAAATCCTGAAACA
TCAGAACATAGTAAAGATTTAAATAATAATGGTTCAAAAAATGAATCTAGTGATATT
ATTTCAGAAAATAATAAATCAAATAAAGTACAAAATCATTTTGAATCATTATCAGATT
TAGAATTACTTGAAAATTCCTCACAAGATAATTTAGACAAAGATACAATTTCAACAG
AACCTTTTCCTAATCAAAAACATAAAGACTTACAACAAGATTTAAATGATGAACCTT
TAGAACCCTTTCCTACACAAATACATAAAGATTATAAAGAAAAAAATTTAATAAATG
AAGAAGATTCAGAACCATTTCCCAGACAAAAGCATAAAAAGGTAGACAATCATAAT
GAAGAAAAAACGTATTTCATGAAAATGGTTCTGCAAATGGTAATCAAGGAAGTTT
GAAACTTAAATCATTCGATGAACATTTAAAAGATGAAAAAATAGAAAATGAACCACT
TGTTCATGAAAATTTATCCATACCAAATGATCCAATAGAACAAATATTAAATCAACC
TGAACAAGAAACAAATATCCAGGAACAATTGTATAATGAAAAACAAATGTTGAAG
AAAAACAAAATTCTCAAATACCTTCGTTAGATTTAAAAGAACCAACAAATGAAGATA
TTTTACCAAATCATAATCCATTAGAAAATATAAAACAAAGTGAATCAGAAATAAATC
ATGTACAAGATCATGCGCTACCAAAAGAGAATATAATAGACAAACTTGATAATCAA
AAAGAACACATCGATCAATCACAACATAATATAAATGTATTACAAGAAAATAACATA
AACAATCACCAATTAGAACCTCAAGAGAAACCTAATATTGAATCGTTTGAACCTAAA
AATATAGATTCAGAAATTATTCTTCCTGAAAATGTTGAAACAGAAGAAATAATAGAT
GATGTGCCTTCCCCTAAACATTCTAACCATGAAACATTTGAAGAAGAAACAAGTGA
ATCTGAACATGAAGAAGCCGTATCTGAAAAAAATGCCCACGAAACTGTCGAACAT
GAAGAAACTGTGTCTCAAGAAAGCAATCCTGAAAAAGCTGATAATGATGGAAATGT
ATCTCAAAACAGCAACAACGAATTAAATGAAAATGAATTCGTTGAATCGGAAAAAA
GCGAGCATGAAGCAAGATCCAAAGCAAAAGAAGCTTCTAGTTATGATTATATTTTA
GGTTGGGAATTTGGAGGAGGCGTTCCAGAACACAAAAAAGAAGAAAATATGTTAT
CACATTTATATGTTTCTTCAAAGGATAAGGAAAATATATCTAAGGAAAATGATGATG
TATTAGATGAGAAGGAAGAAGAGGCAGAAGAAACAGAAGAAGAAGAACTTGAAGA
AAAAAATGAAGAAGAAACAGAATCAGAAATAAGTGAAGATGAAGAAGAAGAAGAA
GAAGAAGAAGAAAAGGAAGAAGAAAATGACAAAAAAAAAGAACAAGAAAAAGAAC
AAAGTAATGAAAATAATGATCAAAAAAAAGATATGGAAGCACAGAATTTAATTTCTA
AAAACCAGAATAATAATGAGAAAAACGTAAAAGAAGCTGCTGAAAGCATCATGAAA
ACTTTAGCTGGTTTAATCAAGGGAAATAATCAAATAGATTCTACCTTAAAAGATTTA
GTAGAAGAATTATCCAAATATTTTAAAAATCATGGTGGTAGCGGTGCAGAAGCAGG
TATTACCGGCACCTGGTATAATCAGCATGGTAGCACCTTTACCGTTACCGCAGGC
GCAGATGGTAATCTGACAGGTCAGTATGAAAATCGTGCACAGGGCACCGGTTGTC
AGAATAGCCCGTATACCCTGACCGGTCGTTATAATGGCACCAAACTGGAATGGCG
TGTTGAATGGAATAATAGCACCGAAAATTGTCATAGCCGTACCGAATGGCGTGGT
CAGTATCAGGGTGGTGCAGAAGCCCGTATTAATACCCAGTGGAATCTGACCTATG
AAGGTGGTAGTGGTCCGGCAACCGAACAGGGTCAGGATACCTTTACCAAAGTGAA
ATAAcatatg >SEQ ID NO: 34 A8 >HIS-GMZ2T:ggsmSA DNA
GGATCCACAAGTGAGAATAGAAATAAACGAATCGGGGGTCCTAAATTAAGGGGTA
ATGTTACAAGTAATATAAAGTTCCCATCAGATAACAAAGGTAAAATTATAAGAGGTT
CGAATGATAAACTTAATAAAAACTCTGAAGATGTTTTAGAACAAAGCGAAAAATCG
CTTGTTTCAGAAAATGTTCCTAGTGGATTAGATATAGATGATATCCCTAAAGAATCT
ATTTTTATTCAAGAAGATCAAGAAGGTCAAACTCATTCTGAATTAAATCCTGAAACA
TCAGAACATAGTAAAGATTTAAATAATAATGGTTCAAAAAATGAATCTAGTGATATT
ATTTCAGAAAATAATAAATCAAATAAAGTACAAAATCATTTTGAATCATTATCAGATT
TAGAATTACTTGAAAATTCCTCACAAGATAATTTAGACAAAGATACAATTTCAACAG
AACCTTTTCCTAATCAAAAACATAAAGACTTACAACAAGATTTAAATGATGAACCTT
TAGAACCCTTTCCTACACAAATACATAAAGATTATAAAGAAAAAAATTTAATAAATG
AAGAAGATTCAGAACCATTTCCCAGACAAAAGCATAAAAAGGTAGACAATCATAAT
GAAGAAAAAACGTATTTCATGAAAATGGTTCTGCAAATGGTAATCAAGGAAGTTT
GAAACTTAAATCATTCGATGAACATTTAAAAGATGAAAAAATAGAAAATGAACCACT
TGTTCATGAAAATTTATCCATACCAAATGATCCAATAGAACAAATATTAAATCAACC
TGAACAAGAAACAAATATCCAGGAACAATTGTATAATGAAAAACAAATGTTGAAG
AAAAACAAAATTCTCAAATACCTTCGTTAGATTTAAAAGAACCAACAAATGAAGATA
TTTTACCAAATCATAATCCATTAGAAAATATAAAACAAAGTGAATCAGAAATAAATC
ATGTACAAGATCATGCGCTACCAAAAGAGAATATAATAGACAAACTTGATAATCAA
AAAGAACACATCGATCAATCACAACATAATATAAATGTATTACAAGAAAATAACATA
AACAATCACCAATTAGAACCTCAAGAGAAACCTAATATTGAATCGTTTGAACCTAAA
AATATAGATTCAGAAATTATTCTTCCTGAAAATGTTGAAACAGAAGAAATAATAGAT
GATGTGCCTTCCCCTAAACATTCTAACCATGAAACATTTGAAGAAGAAACAAGTGA
ATCTGAACATGAAGAAGCCGTATCTGAAAAAAATGCCCACGAAACTGTCGAACAT
GAAGAAACTGTGTCTCAAGAAAGCAATCCTGAAAAAGCTGATAATGATGGAAATGT
ATCTCAAAACAGCAACAACGAATTAAATGAAAATGAATTCGTTGAATCGGAAAAAA
GCGAGCATGAAGCAAGATCCAAAACAAAAGAATATGCTGAAAAAGCAAAAAATGC TABLE 5-continued Overview of the sequences disclosed in the present invention Seq ID NO protein (DNA)

TTATGAAAAGGCAAAAAATGCTTATCAAAAAGCAAACCAAGCTGTTTTAAAAGCAA
AAGAAGCTTCTAGTTATGATTATATTTTAGGTTGGGAATTTGGAGGAGGCGTTCCA
GAACACAAAAAGAAGAAAATATGTTATCACATTTATATGTTTCTTCAAAGGATAAG
GAAAATATATCTAAGGAAAATGATGATGTATTAGATGAGAAGGAAGAAGAGGCAGA
AGAAACAGAAGAAGAAGAACTTGAAGGTGGTAGCGGTGCAGAAGCAGGTATTACC
GGCACCTGGTATAATCAGCATGGTAGCACCTTTACCGTTACCGCAGGCGCAGATG
GTAATCTGACAGGTCAGTATGAAAATCGTGCACAGGGCACCGGTTGTCAGAATAG
CCCGTATACCCTGACCGGTCGTTATAATGGCACCAAACTGGAATGGCGTGTTGAA
TGGAATAATAGCACCGAAAATTGTCATAGCCGTACCGAATGGCGTGGTCAGTATC
AGGGTGGTGCAGAAGCCCGTATTAATACCCAGTGGAATCTGACCTATGAAGGTGG
TAGTGGTCCGGCAACCGAACAGGGTCAGGATACCTTTACCAAAGTGAAATAAcatat
g >SEQ ID NO: 35 A9 >mSA-PfRH5-HIS DNA
gaattcGGTGCAGAAGCAGGTATTACCGGCACCTGGTATAATCAGCATGGTAGCACC
TTTACCGTTACCGCAGGCGCAGATGGTAATCTGACAGGTCAGTATGAAAATCGTG
CACAGGGCACCGGTTGTCAGAATAGCCCGTATACCCTGACCGGTCGTTATAATGG
CACCAAACTGGAATGGCGTGTTGAATGGAATAATAGCACCGAAAATTGTCATAGC
CGTACCGAATGGCGTGGTCAGTATCAGGGTGGTGCAGAAGCCCGTATTAATACCC
AGTGGAATCTGACCTATGAAGGTGGTAGCGGTCCGGCAACCGAACAGGGTCAGG
ATACCTTTACCAAAGTTAAAGGTGGCAGCCTGTCCTTCGAGAACGCCATCAAGAA
GACCAAGAACCAGGAAAACAACCTGACCCTGCTGCCCATCAAGTCCACCGAGGA
AGAGAAGGACGACATCAAGAACGGCAAGGATATCAAGAAGGAAATCGACAACGA
CAAGGAAAACATCAAGACCAACAACGCCAAGGACCACTCCACCTACATCAAGTCT
TACCTGAACACCAACGTGAACGACGGCCTGAAGTACCTGTTCATCCCATCCCACA
ACAGCTTCATCAAGAAGTACTCCGTTTTCAACCAGATCAACGACGGCATGCTGCT
GAACGAGAAGAACGACGTGAAGAACAACGAGGACTACAAGAACGTCGACTACAA
GAACGTGAACTTCCTGCAGTACCACTTCAAGGAACTGTCCAACTACAACATCGCC
AACTCCATCGACATCCTGCAAGAAAAGGAAGGCCACCTGGACTTCGTGATCATCC
CCCACTACACTTTCTTGGACTACTACAAGCACCTGTCCTACAACAGCATCTACCAC
AAGTACAGCACCTACGGCAAGTACATCGCTGTGGACGCTTTCATCAAGAAGATCA
ACGAGACTTACGACAAAGTGAAGTCCAAGTGTAACGATATCAAGAACGACCTGAT
CGCCACCATCAAGAAGCTCGAGCACCCCTACGACATCAACAACAAGAACGACGAC
AGCTACCGCTACGACATCTCCGAAGAGATCGACGACAAGTCCGAGGAAACCGAC
GACGAGACTGAGGAAGTCGAGGACTCCATCCAGGACACCGACTCCAACCACACC
CCCTCCAACAAGAAGAAGAACGATCTGATGAACCGCACCTTCAAGAAGATGATGG
ACGAGTACAACACTAAGAAGAAGAAGCTGATCAAGTGCATCAAGAACCACGAGAA
CGACTTCAACAAGATCTGCATGGACATGAAGAACTACGGCACCAACCTGTTCGAG
CAGCTGTCCTGCTACAACAACAACTTCTGCAACACTAACGGCATCCGCTTCCACTA
CGATGAGTACATCCACAAGCTGATCCTGTCCGTCAAGAGCAAGAACCTGAACAAG
GACCTGAGCGACATGACCAACATCCTCCAGCAGTCCGAGCTGCTGCTGACCAACT
TGAACAAGAAGATGGGCTCCTACATCTACATCGACACTATCAAGTTCATCCACAAG
GAAATGAAGCACATCTTCAACCGCATCGAGTACCACACCAAGATCATCAACGATAA
GACTAAGATCATCCAAGACAAGATCAAGCTGAACATCTGGCGCACTTTCCAAAAG
GACGAACTGCTGAAGCGTATCCTGGACATGTCTAACGAGTACTCCCTCTTCATCA
CCTCCGACCACCTGAGGCAGATGCTGTACAACACCTTCTACTCCAAGGAAAAGCA
CCTCAACAACATCTTCCACCACCTGATCTACGTGCTGCAGATGAAGTTCAACGAC
GTCCCCATCAAGATGGAATACTTCCAGACCTACAAGAAGAACAAGCCCCTGACCC
AGCATCATCACCACCACCAC >SEQ ID NO: 36 (biotin acceptor site)
GLNDIFEAQKIEWHE >SEQ ID NO: 37 monovalent streptavidin
AEAGITGTWYNQHGSTFTVTAGADGNLTGQYENRAQGTGCQNSPYTLTGRYNGTKL
EWRVEWNNSTENCHSRTEWRGQYQGGAEARINTQWNLTYEGGSGPATEQGQDTF
TKVK >SEQ ID NO: 38 BirA OS = *Escherichia coli* (strain K12) GN = birA PE = 1
SV = 1
MKDNTVPLKLIALLANGEFHSGEQLGETLGMSRAAINKHIQTLRDWGVDVFTVPGKGY
SLPEPIQLLNAKQILGQLDGGSVAVLPVIDSTNQYLLDRIGELKSGDACIAEYQQAGRG
RRGRKWFSPFGANLYLSMFWRLEQGPAAAIGLSLVIGIVMAEVLRKLGADKVRVKWP
NDLYLQDRKLAGILVELTGKTGDAAQIVIGAGINMAMRRVEESVVNQGWITLQEAGINL
DRNTLAAMLIRELRAALELFEQEGLAPYLSRWEKLDNFINRPVKLIIGDKEIFGISRGIDK
QGALLLEQDGIIKPWMGGEISLRSAEK >SEQ ID NO: 39 DNA sequence of the biotin binding site
GGTCTGAACGACATCTTCGAGGCTCAGAAAATCGAATGGCACGAA >SEQ ID NO: 40 >Survivin:mSA (*Homo Sapiens*)
MGAPTLPPAWQPFLKDHRISTFKNWPFLEGCACTPERMAEAGFIHCPTENEPDLAQC
FFCFKELEGWEPDDDPIEEHKKHSSGCAFLSVKKQFEELTLGEFLKDRERAKNKIAK
ETNNKKKEFEETAKKVRRAIEQLAAMDggsGAEAGITGTWYNQHGSTFTVTAGADGNL
TGQYENRAQGTGCQNSPYTLTGRYNGTKLEWRVEWNNSTENCHSRTEWRGQYQG
GAEARINTQWNLTYEGGSGPATEQGQDTFTKVK TABLE 5-continued Overview of the sequences disclosed in the present invention Seq ID NO protein (DNA)

>SEQ ID NO: 41 >mSA:Survivin (*Homo Sapiens*)
MAEAGITGTWYNQHGSTFTVTAGADGNLTGQYENRAQGTGCQNSPYTLTGRYNGT
KLEWRVEWNNSTENCHSRTEWRGQYQGGAEARINTQWNLTYEGGSGPATEQGQD
TFTKVKggsGAPTLPPAWQPFLKDHRISTFKNWPFLEGCACTPERMAEAGFIHCPTEN
EPDLAQCFFCFKELEGWEPDDDPIEEHKKHSSGCAFLSVKKQFEELTLGEFLKLDRER
AKNKIAKETNNKKKEFEETAKKVRRAIEQLAAMD >SEQ ID NO: 42 >Survivin(F101A/L102A):mSA (*Homo Sapiens*)
MGAPTLPPAWQPFLKDHRISTFKNWPFLEGCACTPERMAEAGFIHCPTENEPDLAQC
FFCFKELEGWEPDDDPIEEHKKHSSGCAFLSVKKQFEELTLGEAAKLDRERAKNKIAK
ETNNKKKEFEETAKKVRRAIEQLAAMDggsGAEAGITGTWYNQHGSTFTVTAGADGNL
TGQYENRAQGTGCQNSPYTLTGRYNGTKLEWRVEWNNSTENCHSRTEWRGQYQG
GAEARINTQWNLTYEGGSGPATEQGQDTFTKVK >SEQ ID NO: 43 >mSA:Survivin(F101A/L102A) (*Homo Sapiens*)
MAEAGITGTWYNQHGSTFTVTAGADGNLTGQYENRAQGTGCQNSPYTLTGRYNGT
KLEWRVEWNNSTENCHSRTEWRGQYQGGAEARINTQWNLTYEGGSGPATEQGQD
TFTKVKggsGAPTLPPAWQPFLKDHRISTFKNWPFLEGCACTPERMAEAGFIHCPTEN
EPDLAQCFFCFKELEGWEPDDDPIEEHKKHSSGCAFLSVKKQFEELTLGEAAKLDRE
RAKNKIAKETNNKKKEFEETAKKVRRAIEQLAAMD >SEQ ID NO: 44 >mSA:Survivin(F101A/L102A) (*Mus Musculus*)
MAEAGITGTVVYNQHGSTFTVTAGADGNLTGQYENRAQGTGCQNSPYTLTGRYNGT
KLEWRVEWNNSTENCHSRTEWRGQYQGGAEARINTQWNLTYEGGSGPATEQGQD
TFTKVKGGSGAPALPQIWQLYLKNYRIATFKNWPFLEDCACTPERMAEAGFIHCPTEN
EPDLAQCFFCFKELEGWEPDDNPIEEHRKHSPGCAFLTVKKQMEELTVSEAAKLDRQ
RAKNKIAKETNNKQKEFEETAKTTRQSIEQLAASGRF >SEQ ID NO: 45 >Survivin (F101A/L102A):mSA (*Mus Musculus*)
GAPALPQIWQLYLKNYRIATFKNWPFLEDCACTPERMAEAGFIHCPTENEPDLAQCFF
CFKELEGWEPDDNPIEEHRKHSPGCAFLTVKKQMEELTVSEAAKLDRQRAKNKIAKE
TNNKQKEFEETAKTTRQSIEQLAAggsAEAGITGTWYNQHGSTFTVTAGADGNLTGQY
ENRAQGTGCQNSPYTLTGRYNGTKLEWRVEWNNSTENCHSRTEWRGQYQGGAEA
RINTQWNLTYEGGSGPATEQGQDTFTKVK >SEQ ID NO: 46 >mSA:Survivin (*Mus Musculus*)
MAEAGITGTWYNQHGSTFTVTAGADGNLTGQYENRAQGTGCQNSPYTLTGRYNGT
KLEWRVEWNNSTENCHSRTEWRGQYQGGAEARINTQWNLTYEGGSGPATEQGQD
TFTKVKGGSGAPALPQIWQLYLKNYRIATFKNWPFLEDCACTPERMAEAGFIHCPTEN
EPDLAQCFFCFKELEGWEPDDNPIEEHRKHSPGCAFLTVKKQMEELTVSEFLKLDRQ
RAKNKIAKETNNKQKEFEETAKTTRQSIEQLAASGRF >SEQ ID NO: 47 >Survivin:mSA (*Mus Musculus*)
GAPALPQIWQLYLKNYRIATFKNWPFLEDCACTPERMAEAGFIHCPTENEPDLAQCFF
CFKELEGWEPDDNPIEEHRKHSPGCAFLTVKKQMEELTVSEFLKLDRQRAKNKIAKET
NNKQKEFEETAKTTRQSIEQLAAGGSAEAGITGTWYNQHGSTFTVTAGADGNLTGQY
ENRAQGTGCQNSPYTLTGRYNGTKLEWRVEWNNSTENCHSRTEWRGQYQGGAEA
RINTQWNLTYEGGSGPATEQGQDTFTKVK >SEQ ID NO: 48 >mSA:Survivin(F101A/L102A) (*Mus Musculus*) DNA
ATGGCAGAAGCAGGTATTACCGGCACCTGGTATAATCAGCATGGTAGCACCTTTA
CCGTTACCGCAGGCGCAGATGGTAATCTGACAGGTCAGTATGAAAATCGTGCACA
GGGCACCGGTTGTCAGAATAGCCCGTATACCCTGACCGGTCGTTATAATGGCACC
AAACTGGAATGGCGTGTTGAATGAATAATAGCACCGAAAATTGTCATAGCCGTA
CCGAATGGCGTGGTCAGTATCAGGGTGGTGCAGAAGCCCGTATTAATACCCAGT
GGAATCTGACCTATGAAGGTGGTAGCGGTCCGGCAACCGAACAGGGTCAGGATA
CCTTTACCAAAGTTAAAGGTGGCAGCGGTGCACCGGCACTGCCGCAGATTTGGC
AGCTGTATCTGAAAAACTATCGTATCGCCACCTTTAAAAACTGGCCGTTTCTGGAA
GATTGTGCATGTACACCGGAACGTATGGCAGAAGCAGGTTTTATTCATTGTCCGA
CCGAAAATGAACCGGATCTGGCACAGTGTTTTTTTGCTTTAAAGAACTGGAAGGT
TGGGAGCCGGATGATAATCCGATTGAAGAACATCGTAAACATAGTCCGGGTTGTG
CATTTCTGACCGTGAAAAAACAAATGGAAGAACTGACCGTTAGCGAGGCAGCAAA
ACTGGATCGTCAGCGTGCCAAAAACAAAATTGCAAAAGAAACCAATAACAAACAGA
AAGAATTCGAAGAAACCGCCAAAACCACCCGTCAGAGCATTGAACAGCTGGCAGC
Aagcggccgcttt >SEQ ID NO: 49 >Survivin (F101A/L102A):mSA (*Mus Musculus*) DNA
GGTGCACCGGCACTGCCGCAGATTTGGCAGCTGTATCTGAAAAACTATCGTATCG
CCACCTTTAAAAACTGGCCGTTTCTGGAAGATTGTGCATGTACACCGGAACGTAT
GGCAGAAGCAGGTTTTATTCATTGTCCGACCGAAAATGAACCGGATCTGGCACAG
TGTTTTTTTGCTTTAAAGAACTGGAAGGTTGGGAGCCGGATGATAATCCGATTGA
AGAACATCGTAAACATAGTCCGGGTTGTGCATTTCTGACCGTGAAAAAACAAATGG
AAGAACTGACCGTTAGCGAGGCAGCAAACTGGATCGTCAGCGTGCCAAAAACAA
AATTGCAAAAGAAACCAATAACAAACAGAAAGAATTCGAAGAAACCGCCAAAACCA
CCCGTCAGAGCATTGAACAGCTGGCAGCAGGTGGCAGCGCAGAAGCAGGTATTA TABLE 5-continued Overview of the sequences disclosed in the present invention Seq ID NO protein (DNA)

```
CCGGCACCTGGTATAATCAGCATGGTAGCACCTTTACCGTTACCGCAGGCGCAGA
TGGTAATCTGACAGGTCAGTATGAAAATCGTGCACAGGGCACCGGTTGTCAGAAT
AGCCCGTATACCCTGACCGGTCGTTATAATGGCACCAAACTGGAATGGCGTGTTG
AATGGAATAATAGCACCGAAAATTGTCATAGCCGTACCGAATGGCGTGGTCAGTA
TCAGGGTGGTGCAGAAGCCCGTATTAATACCCAGTGGAATCTGACCTATGAAGGT
GGTAGCGGTCCGGCAACCGAACAGGGTCAGGATACCTTTACCAAAGTTAAA

>SEQ ID NO: 50 >mSA:Survivin (Mus Musculus) DNA
ATGGCAGAAGCAGGTATTACCGGCACCTGGTATAATCAGCATGGTAGCACCTTTA
CCGTTACCGCAGGCGCAGATGGTAATCTGACAGGTCAGTATGAAAATCGTGCACA
GGGCACCGGTTGTCAGAATAGCCCGTATACCCTGACCGGTCGTTATAATGGCACC
AAACTGGAATGGCGTGTTGAATGGAATAATAGCACCGAAAATTGTCATAGCCGTA
CCGAATGGCGTGGTCAGTATCAGGGTGGTGCAGAAGCCCGTATTAATACCCAGT
GGAATCTGACCTATGAAGGTGGTAGCGGTCCGGCAACCGAACAGGGTCAGGATA
CCTTTACCAAAGTTAAAGGTGGCAGCGGTGCACCGGCACTGCCGCAGATTTGGC
AGCTGTATCTGAAAAACTATCGTATCGCCACCTTTAAAAACTGGCCGTTTCTGGAA
GATTGTGCATGTACACCGGAACGTATGGCAGAAGCAGGTTTTATTCATTGTCCGA
CCGAAAATGAACCGGATCTGGCACAGTGTTTTTTTTGCTTTAAAGAACTGGAAGGT
TGGGAGCCGGATGATAATCCGATTGAAGAACATCGTAAACATAGTCCGGGTTGTG
CATTTCTGACCGTGAAAAAACAAATGGAAGAACTGACCGTTAGCGAGTTTCTGAAA
CTGGATCGTCAGCGTGCCAAAAACAAAATTGCAAAAGAAACCAATAACAAACAGAA
AGAATTCGAAGAAACCGCCAAAACCACCCGTCAGAGCATTGAACAGCTGGCAGCA
agcggccgcttt >SEQ ID NO: 51 >Survivin: mSA (Mus Musculus) DNA
GGTGCACCGGCACTGCCGCAGATTTGGCAGCTGTATCTGAAAAACTATCGTATCG
CCACCTTTAAAAACTGGCCGTTTCTGGAAGATTGTGCATGTACACCGGAACGTAT
GGCAGAAGCAGGTTTTATTCATTGTCCGACCGAAAATGAACCGGATCTGGCACAG
TGTTTTTTTTGCTTTAAAGAACTGGAAGGTTGGGAGCCGGATGATAATCCGATTGA
AGAACATCGTAAACATAGTCCGGGTTGTGCATTTCTGACCGTGAAAAAACAAATGG
AAGAACTGACCGTTAGCGAGTTTCTGAAACTGGATCGTCAGCGTGCCAAAAACAA
AATTGCAAAAGAAACCAATAACAAACAGAAAGAATTCGAAGAAACCGCCAAAACCA
CCCGTCAGAGCATTGAACAGCTGGCAGCAGGTGGCAGCGCAGAAGCAGGTATTA
CCGGCACCTGGTATAATCAGCATGGTAGCACCTTTACCGTTACCGCAGGCGCAGA
TGGTAATCTGACAGGTCAGTATGAAAATCGTGCACAGGGCACCGGTTGTCAGAAT
AGCCCGTATACCCTGACCGGTCGTTATAATGGCACCAAACTGGAATGGCGTGTTG
AATGGAATAATAGCACCGAAAATTGTCATAGCCGTACCGAATGGCGTGGTCAGTA
TCAGGGTGGTGCAGAAGCCCGTATTAATACCCAGTGGAATCTGACCTATGAAGGT
GGTAGCGGTCCGGCAACCGAACAGGGTCAGGATACCTTTACCAAAGTTAAA >SEQ ID NO: 52 >mSA:CIDR1a-HIS
GAEAGITGTWYNQHGSTFTVTAGADGNLTGQYENRAQGTGCQNSPYTLTGRYNGTK
LEWRVEWNNSTENCHSRTEWRGQYQGGAEARINTQWNLTYEGGSGPATEQGQDT
FTKVKGGSKITSFDEFFDFWVRKLLIDTIKWETELTYCINNTDVTDCNKCNKNCVCFDK
WVKQKEDEWTNIMKLFTNKHDIPKKYYLNINDLFDSFFFQVIYKFNEGEAKWNELKEN
LKKQIASSKANNGTKDSEAAIKVLFNHIKEIATICKDNNTN >SEQ ID NO: 53 >mSA:CIDR1a-HIS DNA
GCAGAAGCAGGTATTACCGGCACCTGGTATAATCAGCATGGTAGCACCTTT
ACCGTTACCGCAGGCGCAGATGGTAATCTGACAGGTCAGTATGAAAATCGT
GCACAGGGCACCGGTTGTCAGAATAGCCCGTATACCCTGACCGGTCGTTAT
AATGGCACCAAACTGGAATGGCGTGTTGAATGGAATAATAGCACCGAAAAT
TGTCATAGCCGTACCGAATGGCGTGGTCAGTATCAGGGTGGTGCAGAAGCC
CGTATTAATACCCAGTGGAATCTGACCTATGAAGGTGGTGGTCCGGCA
ACCGAACAGGGTCAGGATACCTTTACCAAAGTTAAAGGTGGCAGCAAAATAAC
GTCATTTGATGAATTTTTTGATTTTTGGGTTAGAAAATTATTAATAGACACTATAAAGTGGGAAACCGAA
CTTACGTATTGTATAAATAATACTGATGTCACGGATTGTAATAAATGTAACAAAAATTGCGTATGTTTTG
ACAAATGGGTTAAACAAAAGAAGACGAATGGACAAATATAATGAAACTATTCACAAACAAACACGAT
ATACCGAAAAAATATTATCTTAATATTAATGATCTTTTTGATAGTTTTTTTTTCCAAGTTATATATAAGTTT
AACGAAGGAGAAGCAAAATGGAATGAACTTAAAGAAAATTTAAAAAAGCAAATTGCGTCTTCCAAAGC
AAATAACGGAACCAAAGATTCAGAAGCTGCAATAAAAGTGTTGTTTAATCACATAAAAGAAATTGCAA
CAATATGCAAAGATAATAATACAAAC
```

REFERENCES

Bachmann, M F. and Jennings, Gary T. Vaccine delivery: a matter of size, geometry, kinetics and molecular patterns. Nat Rev Immunol 10(11), 787-796. 2010.

Bachmann M F, Zinkernagel, R M. Neutralizing antiviral B cell responses. Annual review of immunology 15: 235-270. 1997.

Bachmann, M F. et al. The influence of antigen organization on B cell responsiveness. Science. 262(5138), 1448-1451. 1993.

Bachmann, M. F., Jennings, G. T., 2004a. Virus-like particles: combining innate and adaptive immunity for effective vaccination. In: Kaufmann, P.D.S.H.E. (Ed.), Novel Vaccination Strategies. Wiley-VCH Verlag GmbH & Co, pp. 415-432.

Buck, Christopher B. and Thompson, Cynthia D. Production of Papillomavirus-Based Gene Transfer Vectors. Current Protocols in Cell Biology. 2001.

Buck C B, Pastrana D V, Lowy D R, Schiller J T. Efficient intracellular assembly of papillomaviral vectors. J Virol. 2004; 78(2):751-7.

Buck C B, Thompson C D, Pang Y-YS, Lowy D R, Schiller J T. Maturation of papillomavirus capsids. J Virol. 2005; 79(5):2839-46.

Buck C B, Thompson C D. Production of papillomavirus-based gene transfer vectors. Curr Protoc Cell Biol. 2007; Chapter 26:Unit 26.1.

Chackerian, B. et al. Induction of autoantibodies to mouse CCR5 with recombinant papillomavirus particles. PNAS. (5) 2373-2378. 1999.

Chackerian, B. Virus-like particles: flexible platforms for vaccine development. Expert Review of Vaccines. 6(3), 381-390. 2007.

Grgacic, Elizabeth V. L. and Anderson, David A. Virus-like particles: Passport to immune recognition. Particle-based Vaccines. Methods 40(1), 60-65. 2006.

Kouskoff, V. et al. T Cell-Independent Rescue of B Lymphocytes from Peripheral Immune Tolerance. Science 287 (5462). 2501-2503. 2000.

Lim K H, Huang H, Pralle A, Park S. Engineered streptavidin monomer and dimer with improved stability and function. Biochemistry. 2011; 50(40):8682-91.

Murray K. Application of recombinant DNA techniques in the development of viral vaccines. Vaccine. 6:164-74. 1988.

Nielsen M A, Pinto V V., Resende M, Dahlbäck M, Ditlev S B, Theander T G, et al. Induction of adhesion-inhibitory antibodies against placental *Plasmodium falciparum* parasites by using single domains of VAR2CSA. Infect Immun. 2009; 77(6):2482-7.

Haase R N, Megnekou R, Lundquist M, Ofori M F, Hviid L, Staalsoe T. *Plasmodium falciparum* parasites expressing pregnancy-specific variant surface antigens adhere strongly to the choriocarcinoma cell line BeWo. Infect Immun. 2006; 74(5):3035-8.

Snounou G, Zhu X, Siripoon N, Jarra W, Thaithong S, Brown K N, et al. Biased distribution of msp1 and msp2 allelic variants in *Plasmodium falciparum* populations in Thailand. Trans R Soc Trop Med Hyg. 1999; 93(4):369-74.

Plotkin, S A. Vaccines: past, present and future. Nat Med. 5-4-2005.

Pumpens, P. and Grens, E. HBV Core Particles as a Carrier for B Cell/T Cell Epitopes. Intervirology 44(2-3), 98-114. 2001.

Raja, Krishnaswami S. et al. Icosahedral Virus Particles as Polyvalent Carbohydrate Display Platforms. ChemBioChem 4(12), 1348-1351. 2003.

---

The invention claimed is:

1. A vaccine comprising:
   i) a papilloma virus (PV) L1 protein containing a biotin acceptor site, and
   ii) a biotin molecule enzymatically conjugated to said biotin acceptor site, and
   iii) an antigen fused to a monovalent streptavidin,
   wherein the PV L1 protein containing the biotin acceptor site comprises an amino acid sequence selected from the group consisting of SEQ ID NO: 3 [DE-loop, HPV genotype 16], and SEQ ID NO: 2 [HI-loop, HPV gemotype 16],
   wherein the antigen and PV L1 protein are linked via interaction between the monovalent streptavidin and the biotin molecule enzymatically conjugated to the biotin acceptor site of the PV L1 protein, and wherein several PV L1 proteins containing the biotin acceptor site are able to form a virus like particle form a virus like particle displaying said antigen.

2. The vaccine according to claim 1, wherein the PV L1 protein is from a virus infecting mammals.

3. The vaccine according to claim 1, wherein the PV L1 protein is from human PV genotype 16 and/or 118.

4. The vaccine according to claim 1, wherein the biotin acceptor site comprises amino acid sequence SEQ ID NO: 36.

5. The vaccine according to claim 1, wherein the biotin acceptor site is fused into a loop of the PV L1 protein, the loop selected from the group consisting of: a DE-loop and an HI-loop of the PV L1 protein.

6. The vaccine according to claim 1, wherein the PV L1 protein containing the biotin acceptor site is a PV L1 protein derived from the human PV genotype 16, the PV L1 protein containing the biotin acceptor site having a PV L1 amino acid sequence wherein residues 134-137 are deleted compared to a wild-type PV L1 amino acid sequence, and wherein the PV L1 protein contains the biotin acceptor site in a DE-loop at position 133/138 in the amino acid sequence of said PV L1 protein (SEQ ID NO: 3).

7. The vaccine according to claim 1, wherein the PV L1 protein containing the biotin acceptor site is a PV L1 protein derived from human PV genotype 16 and contains the biotin acceptor site in an HI-loop at position 351/352 in the amino acid sequence of said PV L1 protein.

8. The vaccine according to claim 1, wherein the PV L1 protein containing the biotin acceptor site comprises:
   i) a polypeptide having an amino acid sequence selected from the group consisting of SEQ ID NO: 3 [DE-loop, HPV genotype 16], SEQ ID NO: 2 [HI-loop, HPV genotype 16], and SEQ ID NO: 6 [HI-loop, HPV118], or
   ii) a biologically active sequence variant of said polypeptide, wherein the biologically active sequence variant has at least 95% sequence identity to SEQ ID NO: 3 [DE-loop, HPV genotype 16], SEQ ID NO: 2 [HI-loop, HPV genotype 16], or SEQ ID NO: 6 [HI-loop, HPV118].

9. The vaccine according to claim 1, wherein said antigen is a protein, peptide and/or an antigenic fragment from the group consisting of cancer-specific polypeptides, polypeptides specific for cardiovascular diseases, polypeptides specific for asthma, polypeptides specific for nasal polyposis, polypeptides specific for atopic dermatitis, polypeptides specific for eosinophilic esophagitis, polypeptides specific for hypereosinophilic syndrome, polypeptides specific for Churg-Strauss syndrome and/or polypeptides specific for pathogenic organisms.

10. The vaccine according to claim 1, wherein the ratio of PV L1 proteins, biotin molecules, and antigens is 1:1:1.

11. The vaccine according to claim 1, wherein the antigen fused to the monovalent streptavidin further comprises a polyhistidine tag.

12. The vaccine according to claim 1, wherein the monovalent streptavidin comprises amino acid sequence SEQ ID NO 37.

13. The vaccine according to claim 1, wherein the monovalent streptavidin is fused to the antigen in a position selected from the group consisting of an N-terminal end of the antigen, a C-terminal end of the antigen, and/or wherein the sequence coding for the monovalent streptavidin is inserted in-frame into a coding sequence of the antigen.

14. The vaccine according to claim 1, wherein the monovalent streptavidin fused to the antigen comprises:
   i) a polypeptide having a sequence selected from the group consisting of SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, and SEQ ID NO: 28, or
   ii) a sequence variant of said polypeptide sequence, wherein the sequence variant has at least 95% sequence identity to the sequences comprising SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, and SEQ ID NO: 28.

15. A method of manufacturing a pharmaceutical composition comprising a vaccine according to claim 1, wherein the method comprises the steps of:
   i) obtaining a first polypeptide; a PV L1 protein containing a biotin acceptor site according to claim 1, and
   ii) obtaining a second polypeptide; a biotin ligase, according to claim 1, capable of biotinylating the biotin acceptor site, and
   iii) obtaining a third polypeptide; an antigen fused to a monovalent streptavidin according to any one of the preceding claims, and
   iv) subjecting the first polypeptide to conditions which enable formation of virus like particles, and
   v) enabling enzymatic biotinylation of the biotin acceptor site of said virus like particles using said second polypeptide, and
   vi) obtaining a vaccine by linkage of the third polypeptide and said virus like particles via the interaction between the monovalent streptavidin and the biotin molecule enzymatically conjugated to the biotin acceptor site of said virus like particles, and
   vii) generating a composition comprising said vaccine according to any one of the preceding claims,
   thereby obtaining a pharmaceutical composition.

* * * * *